(12) United States Patent
Seo et al.

(10) Patent No.: US 9,620,723 B2
(45) Date of Patent: Apr. 11, 2017

(54) ORGANIC SEMICONDUCTOR MATERIAL AND LIGHT-EMITTING ELEMENT, LIGHT-EMITTING DEVICE, LIGHTING SYSTEM, AND ELECTRONIC DEVICE USING THE SAME

(71) Applicant: Semiconductor Energy Laboratory Co., Ltd., Kanagawa-ken (JP)

(72) Inventors: Satoshi Seo, Kanagawa (JP); Sachiko Kawakami, Kanagawa (JP); Hiroko Nomura, Fukuoka (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 746 days.

(21) Appl. No.: 13/728,313

(22) Filed: Dec. 27, 2012

(65) Prior Publication Data
US 2013/0112961 A1    May 9, 2013

Related U.S. Application Data

(63) Continuation of application No. 12/554,508, filed on Sep. 4, 2009, now Pat. No. 8,343,639.

(30) Foreign Application Priority Data

Sep. 5, 2008  (JP) ................................. 2008-228660
Sep. 5, 2008  (JP) ................................. 2008-228805
Sep. 5, 2008  (JP) ................................. 2008-229129

(51) Int. Cl.
*H01L 51/00*    (2006.01)
*C07D 263/56*    (2006.01)
(Continued)

(52) U.S. Cl.
CPC ........ *H01L 51/0071* (2013.01); *C07D 263/57* (2013.01); *C07D 271/07* (2013.01);
(Continued)

(58) Field of Classification Search
CPC .. C07D 263/57; C07D 271/07; C07D 413/10; C07D 417/10; C09K 11/06;
(Continued)

(56) References Cited

U.S. PATENT DOCUMENTS 5,869,929 A   2/1999  Eida et al.
6,344,283 B1  2/2002  Inoue et al.
(Continued)

FOREIGN PATENT DOCUMENTS

CN   101030624     9/2007
EP   0 891 121 A1   1/1999
(Continued)

OTHER PUBLICATIONS

Office Action re Chinese application No. CN 200980135836.X, dated Jan. 18, 2013 (with English translation).
(Continued)

*Primary Examiner* — Dawn Garrett
(74) *Attorney, Agent, or Firm* — Husch Blackwell LLP

(57) ABSTRACT

Disclosed is a novel organic semiconductor material which has a twisted quaterphenylene skeleton as a central unit and simultaneously possesses a skeleton having an electron-transporting property and a skeleton having a hole-transporting property at the terminals of the quaterphenylene skeleton. Specifically, the organic semiconductor material has a [1,1':2',1":2",1'"]quaterphenyl-4-4'"-diyl group, and one of the terminals of the [1,1':2',1":2",1'"]quaterphenyl-4-4'"-diyl group is bonded to a skeleton having an electron-transporting property such as a benzoxazole group or an oxadiazole group. A skeleton having a hole-transporting
(Continued)

property such as diarylamino group is introduced at the other terminal. This structure allows the formation of a compound having a bipolar property, a high molecular weight, an excellent thermal stability, a large band gap, and high triplet excitation energy.

19 Claims, 45 Drawing Sheets

(51) Int. Cl.
  C07D 271/10 (2006.01)
  C07D 263/57 (2006.01)
  C07D 271/07 (2006.01)
  C07D 413/10 (2006.01)
  C07D 417/10 (2006.01)
  C09K 11/06 (2006.01)
  H05B 33/10 (2006.01)
  H05B 33/14 (2006.01)
  H01L 51/50 (2006.01)

(52) U.S. Cl.
  CPC ......... *C07D 413/10* (2013.01); *C07D 417/10* (2013.01); *C09K 11/06* (2013.01); *H01L 51/0061* (2013.01); *H01L 51/0072* (2013.01); *H05B 33/10* (2013.01); *H05B 33/14* (2013.01); *C09K 2211/1007* (2013.01); *C09K 2211/1011* (2013.01); *C09K 2211/1029* (2013.01); *C09K 2211/1033* (2013.01); *H01L 51/5016* (2013.01); *H01L 2051/0063* (2013.01)

(58) Field of Classification Search
  CPC .... C09K 2211/1007; C09K 2211/1011; C09K 2211/1029; C09K 2211/1033; H01L 2051/0063; H01L 51/0061; H01L 51/0071; H01L 51/0072; H01L 51/5016; H05B 33/10; H05B 33/14
  See application file for complete search history.

(56) References Cited

U.S. PATENT DOCUMENTS

| | | | |
|---|---|---|---|
| 6,623,872 | B2 | 9/2003 | Inoue et al. |
| 7,097,918 | B2 | 8/2006 | Inoue et al. |
| 8,293,921 | B2 * | 10/2012 | Nomura et al. ........... 548/267.2 |
| 8,334,061 | B2 * | 12/2012 | Nomura et al. ............. 428/690 |
| 8,343,639 | B2 | 1/2013 | Seo et al. |
| 8,389,735 | B2 | 3/2013 | Murata et al. |
| 8,686,159 | B2 | 4/2014 | Murata et al. |
| 2002/0102434 | A1 | 8/2002 | Inoue et al. |
| 2004/0110030 | A1 | 6/2004 | Inoue et al. |
| 2004/0227764 | A1 * | 11/2004 | Endo ............................ 345/534 |
| 2007/0196692 | A1 | 8/2007 | Ise et al. |
| 2009/0295278 | A1 | 12/2009 | Lee et al. |

FOREIGN PATENT DOCUMENTS

| | | |
|---|---|---|
| JP | 04-298596 A | 10/1992 |
| JP | 2003-7467 | 1/2003 |
| JP | 2005-166680 | 6/2005 |
| JP | 2005-320277 | 11/2005 |
| JP | 2006-032599 A | 2/2006 |
| JP | 2007-197429 A | 8/2007 |
| JP | 2007-227658 | 9/2007 |
| JP | 2009-10181 | 1/2009 |
| JP | 5399173 B2 | 1/2014 |
| WO | WO 2007/074893 A1 | 7/2007 |
| WO | WO 2010/027004 A1 | 3/2010 |

OTHER PUBLICATIONS

Ge et al., "Spin-Coated Highly Efficient Phosphorescent Organic Light-Emitting Diodes Based on Bipolar Triphenylamine-Benzimidazole Derivatives," Adv. Funct. Mater., 2008, vol. 18, No. 4, pp. 584-590.
Search Report re European application No. 09811529.8, dated Feb. 8, 2013.
Ide, N. et al., "Organic Light-Emitting Diode (OLED) and its Application to Lighting Devices," Proceedings of SPIE—Organic Light Emitting Materials and Devices X, vol. 6333, 2006, pp. 63330M-1-6330M-10.
Tanaka, D. et al., "High Luminous Efficiency Blue Organic Light-Emitting Devices Using High Triplet Excited Energy Materials," Japanese Journal of Applied Physics, vol. 46, No. 5, Feb. 25, 2007, pp. L117-L119.
Zhang, T. et al., "Synthesis and Photoelectricity of Bipolar Stilbenyl Derivatives with Triphenylamino and Benzoxazole as Charge-transporting Groups," Journal of Materials Science & Engineering, Oct. 1, 2007, vol. 25, No. 5, pp. 704-708.
Choy, W.C.H. et al., "Oxadiazole-Triphenylamine Derivatives for OLEDs," Proceedings of SPIE, 2005, vol. 5937, pp. 59371L-1-59371L-10.
Kim, O.-K. et al., "New Class of Light-Emitting Polymers/Oligomers," Proceedings of SPIE, 2000, vol. 3955, pp. 134-140.
Goldsmith, C.R. et al., "C-H Bond Activation by a Ferric Methoxide Complex: Modeling the Rate-Determining Step in the Mechanism of Lipoxygenase," J. Am. Chem. Soc., vol. 124, No. 1, 2002, pp. 83-96.
Onishi.T et al, "A Method of Measuring an Energy Level," *High Molecular EL Materials Development of Light-Emitting High Molecular Compounds*, Kyoritsu Shuppan, Dec. 25, 2004, p. 64-67 (with English translation, pp. 1-3).
Agata, Y. et al, "Syntheses and Properties of Novel Quarterphenylene-Based Materials for Blue Organic Light-Emitting Devices," Chemistry Letters, vol. 36, No. 2, 2007, pp. 316-317.
International Search Report re application No. PCT/JP2009/065373, dated Oct. 6, 2009.
Written Opinion re application No. PCT/JP2009/065373, dated Oct. 6, 2009.

* cited by examiner

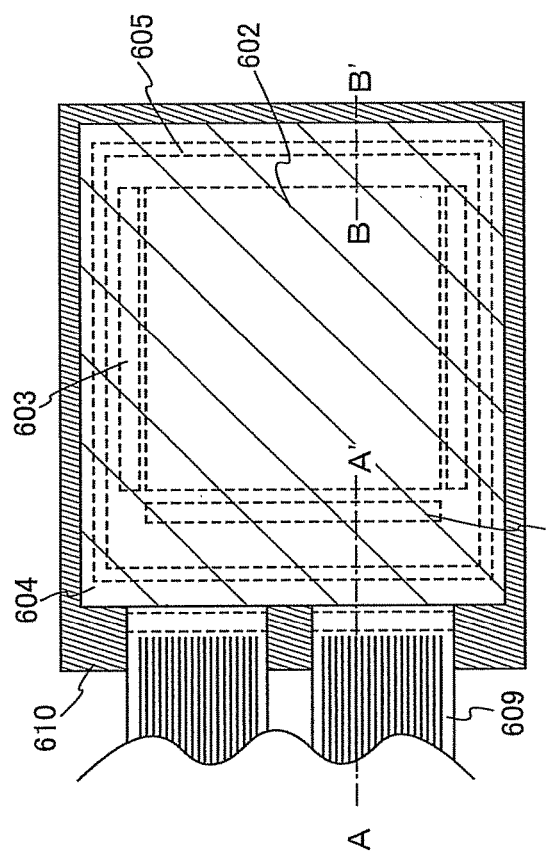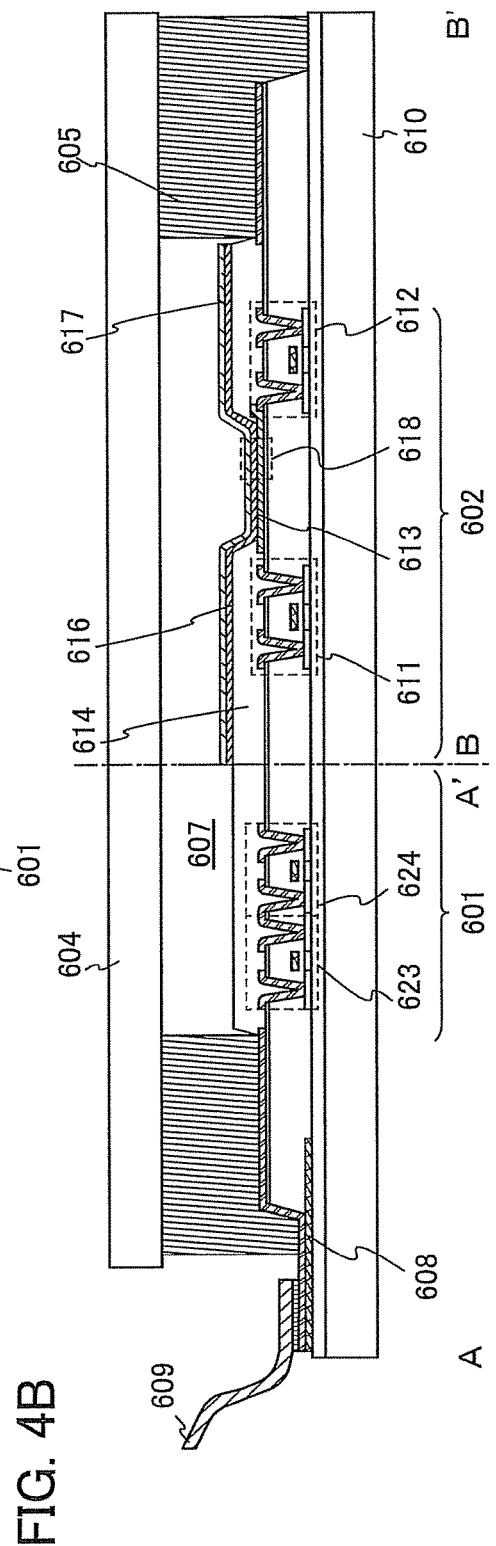
FIG. 4A
FIG. 4B

ORGANIC SEMICONDUCTOR MATERIAL AND LIGHT-EMITTING ELEMENT, LIGHT-EMITTING DEVICE, LIGHTING SYSTEM, AND ELECTRONIC DEVICE USING THE SAME

This application is a continuation of co-pending U.S. application Ser. No. 12/554,508 filed on Sep. 4, 2009.

TECHNICAL FIELD

The present invention relates to an organic semiconductor. The present invention also relates to a light-emitting element, a light-emitting device, a lighting system, and an electronic device in each of which any of the above materials is used.

BACKGROUND ART

An organic compound can take various structures in comparison with an inorganic compound, and it is possible to synthesize a material having various functions by appropriate molecular design of an organic compound. Owing to those advantages, electronics utilizing a functional organic material has been attracting attention in recent years.

For example, a solar cell, a light-emitting element, an organic transistor, and the like are given as examples of an electronic device utilizing an organic compound as a functional material. Those are devices taking advantage of electric properties and optical properties of the organic compound. Among them, in particular, a light-emitting element has been remarkably developed.

It is said that the light emission mechanism of a light-emitting element is as follows: by application of voltage between a pair of electrodes with a light-emitting layer interposed therebetween, electrons injected from a cathode and holes injected from an anode are recombined in the light-emitting layer to form molecular excitons and when the molecular excitons relax to a ground state, energy is released to emit light. Singlet excitation (S*) and triplet excitation (T*) are known as excited states. Light emission is considered possible through either singlet excitation or triplet excitation. Further, the statistical generation ratio thereof in a light-emitting element is considered to be S*:T*=1:3.

As for a compound in which a singlet excited state is converted to light emission (hereinafter, such a compound is referred to as a "fluorescent compound"), light emission from a triplet excited state (phosphorescence) is not observed but only light emission from a singlet excited state (fluorescence) is observed at a room temperature. Accordingly, the internal quantum efficiency (the ratio of generated photons to injected carriers) in a light-emitting element using a fluorescent compound is assumed to have a theoretical limit of 25% based on the relationship of S*:T*=1:3.

On the other hand, when a compound in which a triplet excited state is converted into light emission (hereinafter, such a compound is referred to as a "phosphorescent compound") is used, internal quantum efficiency can be theoretically 75% to 100%. In other words, emission efficiency that is 3 times to 4 times as much as that of the fluorescence compound can be achieved. For those reasons, in order to achieve a highly efficient light-emitting element, a light-emitting element in which a phosphorescent compound is used has been actively developed recently.

When a light-emitting layer of a light-emitting element is formed using the above phosphorescent compound, in order to suppress concentration quenching of the phosphorescent compound or quenching due to triplet-triplet annihilation (T-T annihilation), the light-emitting layer is often formed so that the phosphorescent compound is dispersed in a matrix of another substance. In the above case, the substance, which serves as a matrix, is referred to as a host material, and the substance, like a phosphorescent substance, which is dispersed in a matrix, is referred to as a guest material.

In the case where a phosphorescent compound is used as a guest material, a host material is required to have a large energy gap (a difference between the highest occupied molecular orbital level (HOMO level) and the lowest unoccupied molecular orbital level (LUMO level)) or higher triplet excitation energy (a difference in energy between a ground state and a triplet excited state) than that of the phosphorescent compound. Therefore, a substance having such characteristics has been developed.

For example, in Non Patent Document 1, a material which has a quaterphenylene skeleton is used as a host material of a phosphorescent compound which exhibits blue light emission and as a hole-transporting layer.

NON PATENT DOCUMENT 1

J. Kido et. al., *Chemistry Letters*, Vol. 36, No. 2, 316-317 (2007)

DISCLOSURE OF INVENTION

As is clear from the fact that the host material described in Non Patent Document 1 is used for the hole-transporting layer, the host material exhibits a hole-transporting property. Therefore, it is expected that holes penetrate a light-emitting layer in the case where the material described in Non Patent Document 1 is used as a host material of the light-emitting layer. In Non Patent Document 1, it is considered that an electron-transporting layer is formed using t-BuTAZ which is a hole-blocking material on the cathode side of the light-emitting layer in order that holes are prevented from penetrating the light-emitting layer. As described above, since the host material of the light-emitting layer has a hole-transporting property, a light-emitting region could exist close to an interface between the light-emitting layer and the electron-transporting layer (a hole-blocking layer).

When the light-emitting region locally exists, quenching due to triplet-triplet annihilation (T-T annihilation) or dispersion of excitons into a layer adjacent to the light-emitting layer (the hole-transporting layer, the electron-transporting layer, or the hole-blocking layer) arises, which results in decrease of luminous efficiency.

Thus, the host material is required to have a bipolar property which enables oxidation and reduction and to be stable against repetitive oxidation and reduction cycles. However, when a skeleton having an electron-transporting property and a skeleton having a hole-transporting property are directly bonded, decrease in a band gap is caused, which makes it difficult to synthesize a material having high triplet excitation energy. In addition, when a substituent is introduced between the skeleton having an electron-transporting property and the skeleton having a hole-transporting property to expand a conjugation system, problems such as decrease in a band gap and triplet excitation energy occur.

In view of the above problems, it is an object of an embodiment of the present invention to provide a novel material having a bipolar property.

It is another object of the present invention to reduce driving voltage of a light-emitting element. It is still another object to improve emission efficiency of a light-emitting element.

It is yet another object to reduce power consumption of a light-emitting element, a light-emitting device, and an electronic device.

The present inventors have found out that a material, in which a skeleton having an electron-transporting property and a skeleton having a hole-transporting property are bonded through a twisted quaterphenylene skeleton that inhibits extension of conjugation, has a large energy gap and an electron-transporting property and a hole-transporting property (that is, a bipolar property).

Specifically, they have found out that a material represented by General Formula (G1) in which a [1,1':2',1":2", 1"']quaterphenyl-4-4"'-diyl group is applied as a quaterphenylene skeleton has a large energy gap and an electron-transporting property and a hole-transporting property.

In some cases, even if a compound has a skeleton having an electron-transporting property and a skeleton having a hole-transporting property, it does not have a bipolar property. However, an organic semiconductor material of an embodiment of the present invention has a twisted quaterphenylene skeleton, in which a conjugation hardly extends, in the center; thus, the organic semiconductor material is considered to have a limited intramolecular interaction between a skeleton having an electron-transporting property and a skeleton having a hole-transporting property, which contributes to realization of a bipolar property.

Thus, an embodiment of the present invention is an organic semiconductor material represented by General Formula (G1).

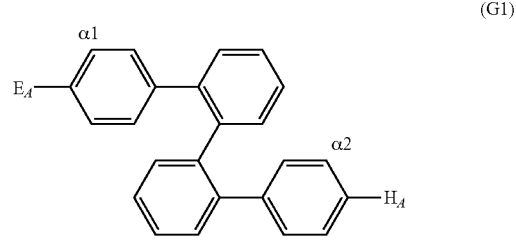

(G1)

In the formula, $E_A$ represents an electron-accepting unit, $H_A$ represents a hole-accepting unit; carbon of α1 and $E_A$ may be bonded to form a ring; and carbon of α2 and $H_A$ may be bonded to form a ring.

In the above structure, the electron affinity and ionization potential of the electron-accepting unit are greater than those of the hole-accepting unit. Note that the electron-accepting unit is the skeleton having an electron-transporting property, and the hole-accepting unit is the skeleton having a hole-transporting property.

Specifically, an embodiment of the present invention is an organic semiconductor material represented by General Formula (G1).

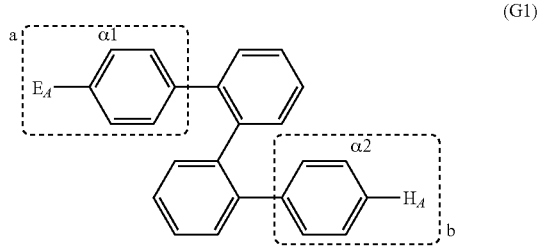

(G1)

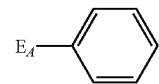

(G2A)

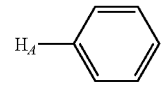

(G2B)

In the formula, $E_A$ and $H_A$ are each a substituent; carbon of α1 and $E_A$ may be bonded to form a ring; and carbon of α2 and $H_A$ may be bonded to form a ring. In addition, a compound represented by General Formula (G2A) which corresponds to a partial structure a has greater electron affinity and ionization potential than a compound represented by General Formula (G2B) which corresponds to a partial structure b.

In the above structure, the electron affinity of the compound represented by General Formula (G2A) is preferably greater than or equal to 2.0 eV and less than or equal to 4.0 eV and the ionization potential of the compound represented by General Formula (G2B) is preferably greater than or equal to 4.5 eV and less than or equal to 6.5 eV. In particular, in the case of being used for a light-emitting element, the electron affinity of the compound represented by General Formula (G2A) is preferably greater than or equal to 2.0 eV and less than or equal to 3.0 eV and the ionization potential of the compound represented by General Formula (G2B) is preferably greater than or equal to 5.0 eV and less than or equal to 6.0 eV.

In the above structure, as the substituent represented by $E_A$, a nitrogen-containing 6-membered aromatic ring group, a 1,2-azole group, a 1,3-azole group, a polyazole group, and the like are given.

In the above structure, as the substituent represented by $H_A$, a π-electron rich heteroaromatic substituent group, a diarylamino group, and the like are given.

In the organic semiconductor material represented by General Formula (G1), a benzoxazole skeleton can be selected as a skeleton having an electron-transporting property ($E_A$).

Thus, an embodiment of the present invention is a benzoxazole derivative represented by General Formula (BOX 1).

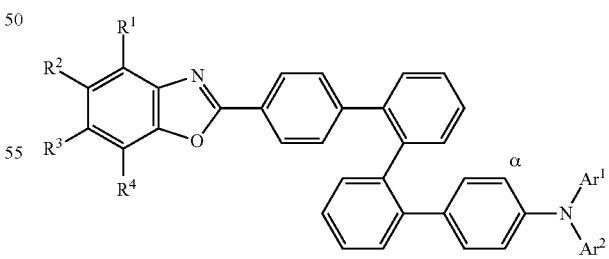

(BOX1)

In the formula, $Ar^1$ and $Ar^2$ each independently represent a substituted or unsubstituted aryl group having 6 to 13 carbon atoms; and $R^1$ to $R^4$ each independently represent any of hydrogen, an alkyl group having 1 to 4 carbon atoms, an unsubstituted aryl group having 6 to 10 carbon atoms, or halogen. $Ar^1$ and carbon of α, or $Ar^1$ and $Ar^2$ may be bonded directly or through sulfur, oxygen, or nitrogen.

Further, an embodiment of the present invention is a benzoxazole derivative represented by General Formula (BOX2).

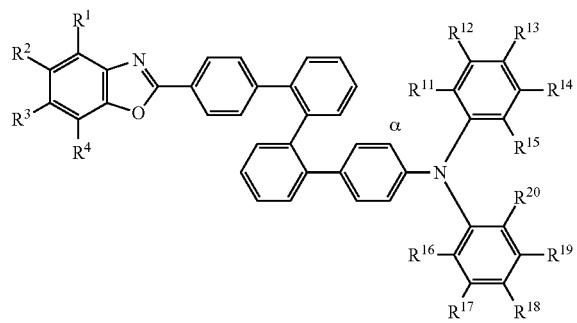
(BOX2)

In the formula, $R^1$ to $R^4$ each independently represent any of hydrogen, an alkyl group having 1 to 4 carbon atoms, an unsubstituted aryl group having 6 to 10 carbon atoms, or halogen; and $R^{11}$ to $R^{20}$ each independently represent any of hydrogen, alkyl group having 1 to 4 carbon atoms, or a substituted or unsubstituted aryl group having 6 to 13 carbon atoms. A carbon atom of the benzene ring which is bonded to $R^{11}$ and carbon of α, or a carbon atom of the benzene ring which is bonded to $R^{15}$ and a carbon atom of the benzene ring which is bonded to $R^{20}$ may be directly bonded.

Further, an embodiment of the present invention is a benzoxazole derivative represented by General Formula (BOX2).

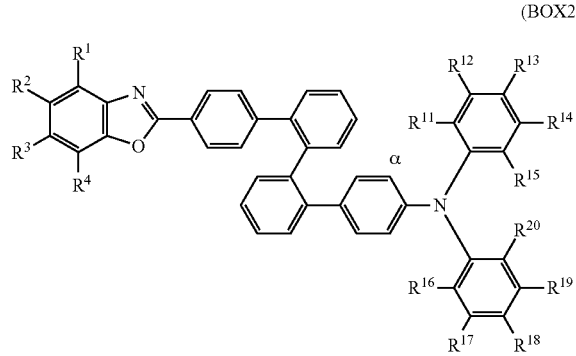
(BOX2)

In the formula, $R^1$ to $R^4$ each independently represent any of hydrogen, an alkyl group having 1 to 4 carbon atoms, an unsubstituted aryl group having 6 to 10 carbon atoms, or halogen; and $R^{11}$ to $R^{20}$ each independently represent any of hydrogen, alkyl group having 1 to 4 carbon atoms, or a substituted or unsubstituted aryl group having 6 to 13 carbon atoms. A carbon atom of the benzene ring which is bonded to $R^{11}$ and carbon of α, or a carbon atom of the benzene ring which is bonded to $R^{15}$ and a carbon atom of the benzene ring which is bonded to $R^{20}$ may be directly bonded to form a carbazole skeleton.

Further, an embodiment of the present invention is a benzoxazole derivative represented by General Formula (BOX3).

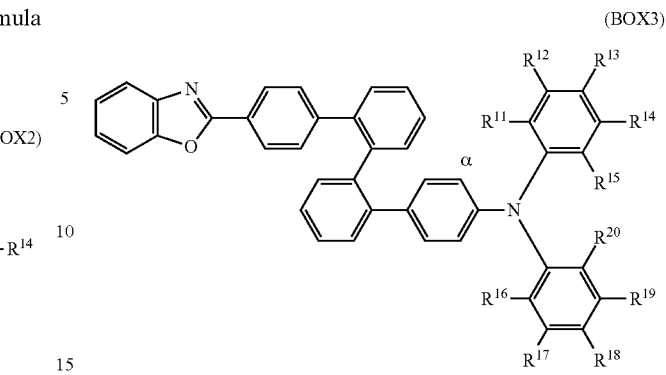
(BOX3)

In the formula, $R^{11}$ to $R^{20}$ each independently represent any of hydrogen, an alkyl group having 1 to 4 carbon atoms, or a substituted or unsubstituted aryl group having 6 to 13 carbon atoms. A carbon atom of the benzene ring which is bonded to $R^{11}$ and carbon of α, or a carbon atom of the benzene ring which is bonded to $R^{15}$ and a carbon atom of the benzene ring which is bonded to $R^{20}$ may be directly bonded to form a carbazole skeleton.

Further, in the organic semiconductor material represented by General Formula (G1), an oxadiazole skeleton can be selected as a skeleton having an electron-transporting property $(E_A)$.

Thus, an embodiment of the present invention is an oxadiazole derivative represented by General Formula (OXD1).

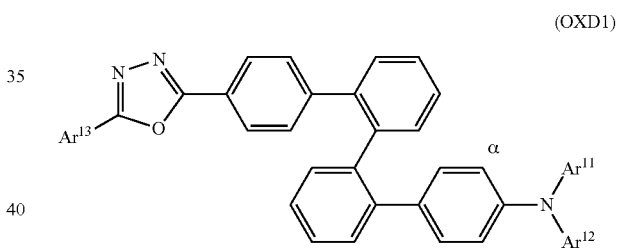
(OXD1)

In the formula, $Ar^{11}$, $Ar^{12}$, and $Ar^{13}$ each represent a substituted or unsubstituted aryl group having 6 to 13 carbon atoms. In addition, $Ar^{11}$ and carbon of α, or $Ar^{11}$ and $Ar^{12}$ may be bonded directly or through any of oxygen, sulfur, or nitrogen.

The oxadiazole derivative represented by General Formula (OXD1) is preferably an oxadiazole derivative represented by General Formula (OXD2).

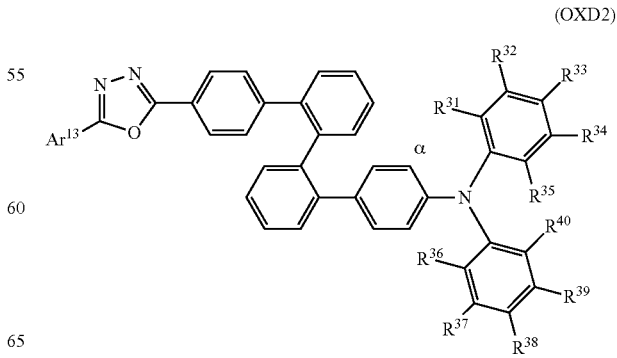
(OXD2)

In the formula, $R^{31}$ to $R^{40}$ each represent any of hydrogen, an allyl group having 1 to 4 carbon atoms, or an unsubstituted aryl group having 6 to 13 carbon atoms; and $Ar^{13}$ represents a substituted or unsubstituted aryl group having 6 to 13 carbon atoms. In addition, a carbon atom of the benzene ring which is bonded to $R^{31}$ and carbon of α, or a carbon atom of the benzene ring which is bonded to $R^{35}$ and a carbon atom of the benzene ring which is bonded to $R^{40}$ may be directly bonded to form a carbazole skeleton.

Further, in the oxadiazole derivative represented by General Formula (OXD2), $Ar^{13}$ preferably represents any of a substituted or unsubstituted phenyl group or a substituted or unsubstituted naphthyl group, and $Ar^{13}$ more preferably represents any of an unsubstituted phenyl group, an unsubstituted 1-naphthyl group, or an unsubstituted 2-naphthyl group.

Since the above organic semiconductor material has a bipolar property, it can be favorably used for a light-emitting element or an organic device such as an organic transistor.

Thus, an embodiment of the present invention is a light-emitting element in which the above organic semiconductor material is used.

In particular, since the above organic semiconductor material has high triplet excitation energy, it has more prominent effect in the case of being used for a light-emitting element together with a phosphorescent compound.

Thus, an embodiment of the present invention is a light-emitting element in which the above organic semiconductor material is included between a pair of electrodes and a phosphorescent compound is included in a light-emitting layer.

Further, the above organic semiconductor material has a bipolar property, and thus is preferably used for a light-emitting layer.

Moreover, an embodiment of the present invention also includes, in its category, a light-emitting device having the above light-emitting element.

Note that the light-emitting device in this specification includes, in its category, an image display device, a light-emitting device, and a light source (including a lighting system). Further, the following are all included in the category of the light-emitting device: a module in which a connector, for example, a flexible printed circuit (FPC), a tape automated bonding (TAB) tape, or a tape carrier package (TCP) is attached to a panel provided with a light-emitting element; a module provided with a printed wiring board at the end of the TAB tape or the TCP; and a module in which an IC (integrated circuit) is directly mounted to a light-emitting element by a chip on glass (COG) method.

Further, an embodiment of the present invention also includes, in its category, an electronic device in which the above light-emitting element is used for a display portion. Therefore, the electronic device of an embodiment of the present invention has a display portion in which the above light-emitting element is used.

Effect of the Invention

The organic semiconductor material of an embodiment of the present invention is a novel bipolar material.

In addition, the benzoxazole derivative of an embodiment of the present invention is a novel bipolar material.

Moreover, the oxadiazole derivative of an embodiment of the present invention is a novel bipolar material.

Further, application of an embodiment of the present invention makes it possible to reduce driving voltage of a light-emitting element. In addition, emission efficiency of a light-emitting element can be improved.

Further, application of an embodiment of the present invention makes it possible to reduce power consumption of a light-emitting element, a light-emitting device, and an electronic device.

BRIEF DESCRIPTION OF DRAWINGS

In the accompanying drawings:

FIGS. 4A and 4B illustrate a light-emitting device of an embodiment of the present invention;

BEST MODE FOR CARRYING OUT THE INVENTION

Figure 1:
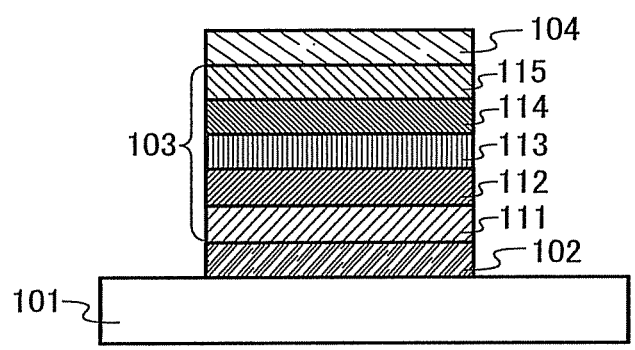
FIG. 1 illustrates a light-emitting element of an embodiment of the present invention.

Hereinafter, Embodiments and Examples of the present invention will be described with reference to the accompanying drawings. Note that it is easily understood by those skilled in the art that the present invention can be carried out in many different modes, and the modes and details disclosed herein can be modified in various ways without departing from the spirit and scope of the present invention. Therefore, the present invention should not be construed as being limited to the description below of the embodiments and examples.

Embodiment 1

In Embodiment 1, an organic semiconductor material of an embodiment of the present invention will be described.

An organic semiconductor material of Embodiment 1 has a Z quaterphenylene skeleton ([1,1':2',1":2",1'"]quaterphenyl-4-4'"-diyl group). An electron-accepting unit is bonded to a para position of a terminal benzene ring of the Z quaterphenylene skeleton, and a hole-accepting unit is bonded to a para position of the other terminal benzene ring.

Specifically, the organic semiconductor material of Embodiment 1 is an organic semiconductor material represented by General Formula (G1).

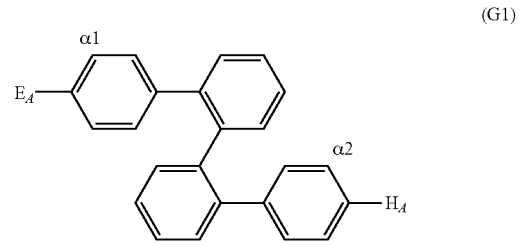

In the formula, $E_A$ represents an electron-accepting unit, $H_A$ represents a hole-accepting unit, carbon of α1 and $E_A$ may be bonded to form a ring, and carbon of α2 and $H_A$ may be bonded to form a ring.

An organic semiconductor material having such a structure has an electron-accepting unit and a hole-accepting unit in its molecule, and thus is a bipolar material which can transport both electrons and holes.

In some cases, even if a compound has a skeleton having an electron-accepting unit and a hole-accepting unit in its molecule, it does not have a bipolar property. However, the organic semiconductor material of Embodiment 1 has two ortho-linked benzene rings in the center; thus, the organic semiconductor material is considered to have a limited intramolecular interaction between the electron-accepting unit and the hole-accepting unit, which contributes to realization of a bipolar property.

Specifically, in General Formula (G1) shown below, a benzene ring 2 and a benzene ring 3 are bonded at their ortho positions. Those two benzene rings bonded at the ortho positions are considered to limit interaction between the substituents bonded to the terminal benzene rings. Thus, an organic semiconductor material having a bipolar property can be obtained.

Further, the organic semiconductor material represented by General Formula (G1) below is considered to have a twisted structure due to the two ortho-linked benzene rings, which suppresses the extension of conjugation. Thus, the organic semiconductor material can have a large energy gap while having a high molecular weight. Accordingly, the organic semiconductor material can be favorably used as a host material in a light-emitting layer of a light-emitting element. In addition, the organic semiconductor material has high triplet excitation energy, and thus can be favorably used for a light-emitting element together with a phosphorescent compound.

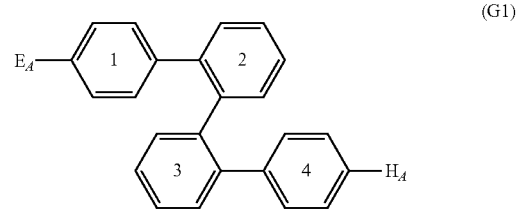

Note that increase in the number of the ortho-linked benzene rings makes a synthesis method complicated, which results in decrease in yield. In addition, increase in the number of benzene rings increases the distance between the electron-accepting unit and the hole-accepting unit. Moreover, since increase in the number of benzene rings increases proportion of portions other than the units which accept carriers, the hopping distance of carriers is increased, which results in decrease in a carrier-transporting property. Thus, an embodiment of the present invention provides, in view of those problems, a bipolar semiconductor material with an optimal structure.

Note that the electron-accepting unit has higher electron affinity and ionization potential than the hole-accepting unit.

In practice, it is difficult to evaluate the electron affinity and the ionization potential of a substituent itself. Therefore, in the specification, the electron affinity and the ionization potential of the electron-accepting unit are evaluated using a compound represented by General Formula (G2A) which corresponds to a partial structure a of the organic semiconductor material represented by General Formula (G1). In addition, the electron affinity and the ionization potential of the hole-accepting unit are evaluated using a compound represented by General Formula (G2B) which corresponds to a partial structure b of the organic semiconductor material represented by General Formula (G1).

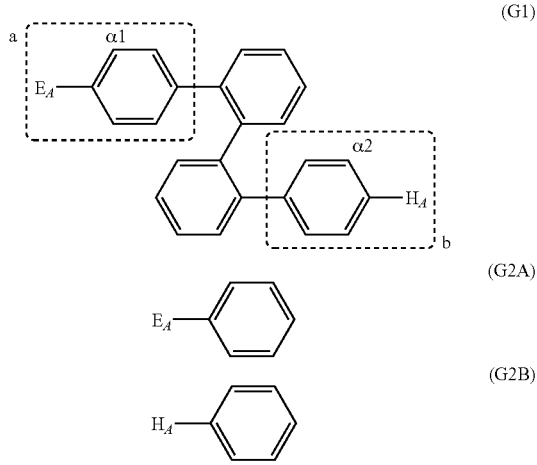

In other words, the organic semiconductor material of Embodiment 1 is represented by General Formula (G1), and the compound represented by General Formula (G2A) which corresponds to a partial structure a of General Formula (G1) has higher electron affinity and ionization potential than the compound represented by General Formula (G2B) which corresponds to a partial structure b of General Formula (G1).

Further, the organic semiconductor material of Embodiment 1 has the ortho-linked benzene rings in the center and limited intramolecular interaction between the electron-accepting unit and the hole-accepting unit. Therefore, the electron affinity of the organic semiconductor material represented by General Formula (G1) and that of the compound represented by General Formula (G2A) are almost the same. Thus, the electron affinity of the compound represented by General Formula (G2A) is preferably greater than or equal to 2.0 eV and less than or equal to 4.0 eV. In particular, in the case where the organic semiconductor material represented by General Formula (G1) is used for a light-emitting element, in consideration of the electron affinity of a general organic material used for a light-emitting element, the electron affinity of the compound represented by General Formula (G2A) is more preferably greater than or equal to 2.0 eV and less than or equal to 3.0 eV.

Similarly, the ionization potential of the organic semiconductor material represented by General Formula (G1) is almost the same as that of the ionization potential of the compound represented by General Formula (G2B). Thus, the ionization potential of the compound represented by General Formula (G2B) is preferably greater than or equal to 4.5 eV and less than or equal to 6.5 eV. In particular, in the case where the organic semiconductor material represented by General Formula (G1) is used for a light-emitting element, in consideration of the ionization potential of a general organic material used for a light-emitting element, the ionization potential of the compound represented by General Formula (G2B) is more preferably greater than or equal to 5.0 eV and less than or equal to 6.0 eV.

The above structure makes it possible to obtain an organic semiconductor material having a large band gap.

As the electron-accepting unit $E_A$, a π-electron deficient heteroaromatic substituent is preferable so that the electron-accepting unit $E_A$ has high electron affinity. As the π-electron deficient heteroaromatic substituent, the following can be given: a nitrogen-containing 6-membered aromatic ring group (note that the nitrogen-containing 6-membered aromatic ring includes a condensed aromatic hydrocarbon and a nitrogen-containing 6-membered condensed aromatic ring), a 1,2-azole group (note that the 1,2-azole includes a condensed aromatic hydrocarbon and a nitrogen-containing 6-membered condensed aromatic ring), a 1,3-azole group (note that the 1,3-azole includes a condensed aromatic hydrocarbon and a nitrogen-containing 6-membered condensed aromatic ring), a polyazole group (note that the polyazole includes a condensed aromatic hydrocarbon and a nitrogen-containing 6-membered condensed aromatic ring), and the like. In particular, the nitrogen-containing 6-membered aromatic ring group, the 1,3-azole group, and the polyazole group are preferable because they are stable against repetitive reduction-oxidation processes and exhibits a high electron-transporting property as well as having relatively high electron affinity.

As the nitrogen-containing 6-membered aromatic ring, the following can be given for example: a substituted or unsubstituted pyridyl group, a substituted or unsubstituted pyrazinyl group, a substituted or unsubstituted pyrimidinyl group, a substituted or unsubstituted pyridazinyl group, a substituted or unsubstituted 1,2,4-triazinyl group, a substituted or unsubstituted 1,3,5-triazinyl group, a substituted or unsubstituted quinolyl group, a substituted or unsubstituted isoquinolyl group, a substituted or unsubstituted 1,5-naphthyridinyl group, a substituted or unsubstituted 1,6-naphthyridinyl group, a substituted or unsubstituted 1,7-naphthyridinyl group, a substituted or unsubstituted 1,8-naphthyridinyl group, a substituted or unsubstituted 2,6-naphthyridinyl group, a substituted or unsubstituted 2,7-naphthyridinyl group, a substituted or unsubstituted quinoxalinyl group, a substituted or unsubstituted quinazolinyl group, a substituted or unsubstituted phthalazinyl group, a substituted or unsubstituted cinnolinyl group, a substituted or unsubstituted phenanthridinyl group, a substituted or unsubstituted 1,10-phenanthrolinyl group, and the like.

Further, as the 1,2-azole group, the following can be given, for example: a substituted or unsubstituted pyrazolyl group, a substituted or unsubstituted isoxazolyl group, a substituted or unsubstituted isothiazolyl group, a substituted or unsubstituted indazolyl group, a substituted or unsubstituted 1,2-benzoisoxazolyl group, a substituted or unsubstituted 1,2-benzoisothiazolyl group, a substituted or unsubstituted 2,1-benzoisoxazolyl group, a substituted or unsubstituted 2,1-benzoisothiazolyl group, and the like.

Further, as the 1,3-azole group, the following can be given, for example: a substituted or unsubstituted imidazolyl group, a substituted or unsubstituted oxazolyl group, a substituted or unsubstituted thiazolyl group, a substituted or unsubstituted 1H-benzoimidazolyl group, a substituted or unsubstituted benzoxazolyl group, a substituted or unsubstituted benzothiazolyl group, an imidazo[1,2-a]pyridyl group, and the like.

Further, as the polyazole group, the following can be given, for example: a substituted or unsubstituted 1H-1,2,3-triazolyl group, a substituted or unsubstituted 1,2,5-oxadiazolyl group, a substituted or unsubstituted 1,2,5-thiadiazolyl group, a substituted or unsubstituted 1H-1,2,4-triazolyl group, a substituted or unsubstituted 4H-1,2,4-triazolyl group, a substituted or unsubstituted 1,2,4-oxadiazolyl group, a substituted or unsubstituted 1,2,4-thiadiazolyl group, a substituted or unsubstituted 1,3,4-oxadiazolyl group, a substituted or unsubstituted 1,3,4-thiadiazolyl group, a substituted or unsubstituted 1H-benzotriazolyl group, a substituted or unsubstituted 2H-benzotriazolyl group, a substituted or unsubstituted 2,1,3-benzoxadiazolyl group, a substituted or unsubstituted 2,1,3-benzothiadiazolyl group, and the like.

Note that in the case where the above nitrogen-containing 6-membered aromatic ring group, 1,2-azole group, 1,3-azole group, and polyazole group each have another substituent, the following can be given as the substituent: an aryl group such as a phenyl group, a tolyl group, or a naphthyl group; a heteroaromatic group such as a pyridyl group, a quinolyl group, or an isoquinolyl group; an alkyl group such as a methyl group, an ethyl group, an isopropyl group, a tert-butyl group; and the like.

The above electron-accepting unit $E_A$ is selected as appropriate, whereby the partial structure represented by a can be formed.

As specific examples of the partial structure a in the case where the nitrogen-containing 6-membered aromatic ring group (note that the nitrogen-containing 6-membered aromatic ring includes a condensed aromatic hydrocarbon and a nitrogen-containing 6-membered condensed aromatic ring) is applied as the electron-accepting unit $E_A$, the following can be given: a 4-(2-pyridyl)phenyl group, a 4-(5-methyl-2-pyridyl)phenyl group, a 4-(6-methyl-2-pyridyl)phenyl group, a 4-(3-phenyl-2-pyridyl)phenyl group, a 4-(6-phenyl-2-pyridyl)phenyl group, a 4-(3-pyridyl)phenyl group, a 4-(6-methyl-3-pyridyl)phenyl group, a 4-(2,2':6',2''-terpyridin-4'-yl)phenyl group, a 4-(3-phenylpyrazin-2-yl)phenyl group, a 4-(3,5,6-triphenylpyrazin-2-yl)phenyl group, a 4-(pyrimidin-4-yl)phenyl group, a 4-(6-methylpyrimidin-4-yl)phenyl group, a 4-(6-phenylpyrimidin-4-yl)phenyl group, a 4-(pyrimidin-5-yl)phenyl group, 4-(2,4,6-triphenylpyrimidin-5-yl)phenyl group, a 4-(6-phenylpyridazin-3-yl)phenyl group, a 4-(3-methyl-1,2,4-triazin-6-yl)phenyl group, a 4-(4,6-diphenyl-1,3,5-triazin-2-yl)phenyl group, a 4-(3-quinolyl)phenyl group, a 4-(8-quinolyl)phenyl group, a 4-(2,4-dimethyl-8-quinolyl)phenyl group, a 4-(4-isoquinolyl)phenyl group, a 4-(1,5-naphthyridin-3-yl)phenyl group, a 4-(1,6-naphthyridin-4-yl)phenyl group, a 4-(5,7-dimethyl-1,6-naphthyridin-4-yl)phenyl group, a 4-(5-methyl-1,6-naphthyridin-2-yl)phenyl group, a 4-(1,7-naphthyridin-8-yl)phenyl group, a 4-(1,8-naphthyridin-2-yl)phenyl group, a 4-(3-methyl-1,8-naphthyridin-2-yl)phenyl group, a 4-(1,8-naphthyridin-3-yl)phenyl group, a 4-(2-methyl-1,8-naphthyridin-3-yl)phenyl group, 4-(1,8-naphthyridin-4-yl)phenyl group, a 4-(2,6-naphthyridin-1-yl)phenyl group, 4-(2,7-naphthyridin-3-yl)phenyl group, a 4-(quinoxalin-2-yl)phenyl group, 4-(3-methylquinoxalin-2-yl)phenyl group, a 4-(3-isopropylquinoxalin-2-yl)phenyl group, a 4-(3-phenylquinoxalin-2-yl)phenyl group, a 4-(quinazolin-4-yl)phenyl group, a 4-(phthalazin-1-yl)phenyl group, 4-(3-phenylcinnolin-4-yl)phenyl group, 4-(phenanthridin-6-yl)phenyl group, 4-(1,10-phenanthrolin-2-yl)phenyl group, 4-(1,10-phenanthrolin-3-yl)phenyl group, and the like.

Further, as specific examples of the partial structure a in the case where the 1,2-azole group (note that the 1,2-azole includes a condensed aromatic hydrocarbon and a nitrogen-containing 6-membered condensed aromatic ring) is applied as the electron-accepting unit $E_A$, the following can be given: a 4-(3,5-diphenyl-1H-pyrazol-1-yl)phenyl group, a 4-(1,5-diphenyl-1H-pyrazol-3-yl)phenyl group, a 4-(5-phenylisoxazol-3-yl)phenyl group, a 4-(5-phenylisothiazol-3-yl)phenyl group, a 4-(3-methyl-1,2-benzoisoxazol-5-yl)phenyl group, a 4-(3-methyl-1,2-benzoisothiazol-5-yl)phenyl group, a 4-(2,1-benzoisoxazol-3-yl)phenyl group, a 4-(2,1-benzoisothiazol-3-yl)phenyl group, and the like.

Further, as specific examples of the partial structure a in the case where the 1,3-azole group (note that the 1,3-azole includes a condensed aromatic hydrocarbon and a nitrogen-containing 6-membered condensed aromatic ring) is applied as the electron-accepting unit $E_A$, the following can be given: a 4-(2,4-diphenyl-1H-imidazol-1-yl)phenyl group, a 4-(2-phenyloxazol-4-yl)phenyl group, a 4-(2-phenylthiazol-4-yl)phenyl group, a 4-(1-methyl-1H-benzoimidazol-2-yl)phenyl group, a 4-(1-ethyl-1H-benzoimidazol-2-yl)phenyl group, a 4-(1-phenyl-1H-benzoimidazol-2-yl)phenyl group, a 4-(2-phenyl-1H-benzoimidazol-1-yl)phenyl group, a 4-(benzoxazol-2-yl)phenyl group, a 4-(5-phenylbenzoxazol-2-yl)phenyl group, a 4-[5-(p-tolyl)benzoxazol-2-yl]phenyl group, a 4-(benzothiazol-2-yl)phenyl group, a 4-(5-phenyl benzothiazol-2-yl)phenyl group, a 4-[5-(p-tolyl)benzothiazol-2-yl]phenyl group, a 4-(imidazo[1,2-a]pyridin-2-yl) phenyl group, a 4-(5-phenylimidazo[1,2-a]pyridin-2-yl)phenyl group, and the like.

Further, as specific examples of the partial structure a in the case where the polyazole group (note that the polyazole includes a condensed aromatic hydrocarbon and a nitrogen-containing 6-membered condensed aromatic ring) is applied as the electron-accepting unit $E_A$, the following can be given: a 4-(1-phenyl-1H-1,2,3-triazol-4-yl)phenyl group, a 4-(4-phenyl-1,2,5-oxadiazol-3-yl)phenyl group, a 4-(4-phenyl-1,2,5-thiadiazol-3-yl)phenyl group, a 4-(5-methyl-1-phenyl-1H-1,2,4-triazol-3-yl)phenyl group, a 4-(4,5-diphenyl-4H-1,2,4-triazol-3-yl)phenyl group, a 4-[4-(4-sec-butylphenyl)-5-phenyl-4H-1,2,4-triazol-3-yl]phenyl group, a 4-(3,5-diphenyl-4H-1,2,4-triazol-4-yl)phenyl group, a 4-[4-phenyl-5-(2-pyridyl)-4H-1,2,4-triazol-3-yl]phenyl group, a 4-[5-(2-pyridyl)-4-(4-pyridyl)-4H-1,2,4-triazol-3-yl]phenyl group, a 4-[5-phenyl-4-(8-quinolyl)-4H-1,2,4-triazol-3-yl]phenyl group, a 4-(3-phenyl-1,2,4-oxadiazol-5-yl) phenyl group, a 4-(3-phenyl-1,2,4-thiadiazol-5-yl)phenyl group, a 4-(5-phenyl-1,3,4-oxadiazol-2-yl)phenyl group, a 4-[5-(4-tert-butylphenyl)-1,3,4-oxadiazol-2-yl]phenyl group, a 4-[5-(2-naphthyl)-1,3,4-oxadiazol-2-yl]phenyl group, a 4-{5-[4-(1-naphthyl)phenyl]-1,3,4-oxadiazol-2-yl}phenyl group, a 4-{5-[4-(2-naphthyl)phenyl]-1,3,4-oxadiazol-2-yl}phenyl group, a 4-(5-phenyl-1,3,4-thiadiazol-2-yl)phenyl group, a 4-[5-(4-tert-butylphenyl)-1,3,4-thiadiazol-2-yl]phenyl group, a 4-[5-(2-naphthyl)-1,3,4-thiadiazol-2-yl]phenyl group, a 4-{5-[4-(1-naphthyl)

phenyl]-1,3,4-thiadiazol-2-yl}phenyl group, a 4-{5-[4-(2-naphthyl)phenyl]-1,3,4-thiadiazol-2-yl}phenyl group, and the like.

Note that in the partial structure a, the electron-accepting unit $E_A$ may be bonded to carbon of α1 to form a ring. A specific example of that case is described below. As shown below, when a 3-phenylpyrazin-2-yl group is selected as the electron-accepting unit $E_A$, the partial structure a becomes a 4-(3-phenylpyrazin-2-yl)phenyl group (Structural Formula (II)). In this 4-(3-phenylpyrazin-2-yl)phenyl group (Structural Formula (II)), when the electron-accepting unit $E_A$ and carbon of α1 are bonded, the partial structure a becomes a dibenzo[f,h]quinoxalin-7-yl group (Structural Formula (12)). Thus, the partial structure a of Embodiment 1 includes the dibenzo[f,h]quinoxalin-7-yl group. This is just an example, and the same modification can be applied to the cases where other electron-accepting units $E_A$ are selected.

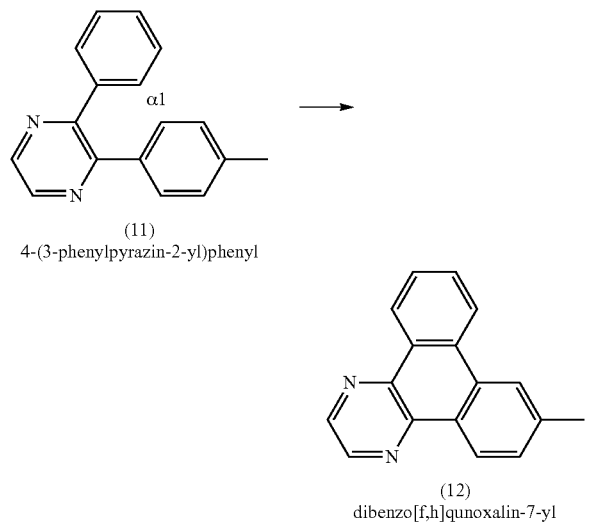

(11)
4-(3-phenylpyrazin-2-yl)phenyl

(12)
dibenzo[f,h]qunoxalin-7-yl

As the hole-accepting unit, a π-electron rich heteroaromatic substituent or a diarylamino group is preferable so that the hole-accepting unit has small ionization potential. Note that as for the diarylamino group, aryl groups may be directly bonded to form a carbazole ring or they may be bonded through nitrogen, oxygen, or sulfur to form a ring. In particular, the diarylamino group (including the case where aryl groups are directly bonded to form a carbazole ring or they are bonded through nitrogen, oxygen, or sulfur to form a ring) is preferable because it is stable against repetitive oxidation-reduction cycles and exhibits a high hole-transporting property as well as having relatively small ionization potential.

As the π-electron rich heteroaromatic substituent, a monohetero 5-membered aromatic ring group (note that the monohetero 5-membered aromatic ring includes a condensed aromatic hydrocarbon and a nitrogen-containing 6-membered condensed aromatic ring) is given. Specifically, the following can be given: a substituted or unsubstituted pyrrolyl group, a substituted or unsubstituted furyl group, a substituted or unsubstituted thienyl group, a substituted or unsubstituted indolyl group, a substituted or unsubstituted benzofuryl group, a substituted or unsubstituted benzothienyl group, a substituted or unsubstituted isoindolyl group, a substituted or unsubstituted isobenzofuryl group, a substituted or unsubstituted isobenzothienyl group, and the like.

Further, as the diarylamino group, the following can be given: a substituted or unsubstituted diphenylamino group, a substituted or unsubstituted N-(1-naphthyl)-N-phenylamino group, a substituted or unsubstituted N-(2-naphthyl)-N-phenylamino group, and the like. Furthermore, as for the diarylamino group, aryl groups may be directly bonded to form a carbazole ring or they may be bonded through nitrogen, oxygen, or sulfur to form a ring. A hole-accepting unit in that case is a substituted or unsubstituted 9H-carbazol-9-yl group, a substituted or unsubstituted 10H-phenoxazin-10-yl group, a substituted or unsubstituted 10H-phenothiazin-10-yl group, a substituted or unsubstituted 5,10-dihydrophenazin-5-yl group.

Note that in the case where the above monohetero 5-membered aromatic ring group and diarylamino group each have another substituent, the following can be given as the substituent: an aryl group such as a phenyl group, tolyl group, or a naphthyl group; a heteroaryl group such as a pyridyl group, a quinolyl group, or an isoquinolyl group; an alkyl group such as a methyl group, an ethyl group, an isopropyl group, a tert-butyl group; and the like.

The above hole-accepting unit is selected as appropriate, whereby the partial structure represented by b can be formed.

As specific examples of the partial structure b in the case where the monohetero 5-membered aromatic ring group (note that monohetero 5-membered aromatic ring includes a condensed aromatic hydrocarbon and a nitrogen-containing 6-membered condensed aromatic ring) is applied as the hole-accepting unit $H_A$, the following can be given: 4-(1-methyl-5-phenyl-1H-pyrrol-2-yl)phenyl group, 4-(1,5-diphenyl-1H-pyrrol-2-yl)phenyl group, 4-(2,5-diphenyl-1H-pyrrol-1-yl)phenyl group, 4-(5-phenyl-2-furyl)phenyl group, 4-(5-phenyl-2-thienyl)phenyl group, 4-(1H-indol-1-yl)phenyl group, 4-(2-methyl-1H-indol-1-yl)phenyl group, 4-(2-phenyl-1H-indol-1-yl)phenyl group, 4-(1-phenyl-1H-indol-2-yl)phenyl group, 4-(2-benzofuryl)phenyl group, 4-(2-benzothienyl)phenyl group, 4-(2,3-diphenylisoindol-1-yl)phenyl group, 4-(3-phenylisofuryl)phenyl group, 4-(3-phenylisothienyl)phenyl group, and the like.

As specific examples of the partial structure b in the case where the diarylamino group (a case where aryl groups are directly bonded to form a carbazole ring or a case where aryl groups are bonded through nitrogen, oxygen, or sulfur is included) is applied as the hole-accepting unit $H_A$, the following can be given: 4-(diphenylamino)phenyl group, a 4-[N-(biphenyl-4-yl)-N-phenylamino]phenyl group, a 4-{N-[4-(1-naphthyl)phenyl]-N-phenylamino}phenyl group, a 4-{N-[4-(2-naphthyl)phenyl]-N-phenylamino}phenyl group, a 4-{N,N-bis[4-(1-naphthyl)phenyl]amino}phenyl group, a 4-[N-(1-naphthyl)-N-phenylamino]phenyl group, a 4-(9H-carbazol-9-yl)phenyl group, a 4-(3-phenyl-9H-carbazol-9-yl)phenyl group, a 4-[3-(1-naphthyl)-9H-carbazol-9-yl]phenyl group, a 4-[3-(2-naphthyl)-9H-carbazol-9-yl]phenyl group, a 4-(10-phenyl-5,10-dihydrophenazin-5-yl)phenyl group, a 4-(10H-phenoxazin-10-yl)phenyl group, a 4-(10H-phenothiazin-10-yl)phenyl group, and the like.

Note that in the partial structure b, the hole-accepting unit $H_A$ may be bonded to carbon of α2 to form a ring. A specific example of that case is described below. As shown below, when a diphenylamino group is selected as the hole-accepting unit $H_A$, the partial structure b becomes a 4-(diphenylamino)phenyl group (Structural Formula (21)). In this 4-(diphenylamino)phenyl group (Structural Formula (21)), when the hole-accepting unit $H_A$ and carbon of α2 are bonded, the partial structure b becomes a 9-phenyl-9H-carbazol-3-yl group (Structural Formula (22)). Thus, the partial structure b of Embodiment 1 includes the 9-phenyl-9H-carbazol-3-yl group. This is just an example, and the same modification can be applied to the cases where other hole-accepting units $H_A$ are selected.

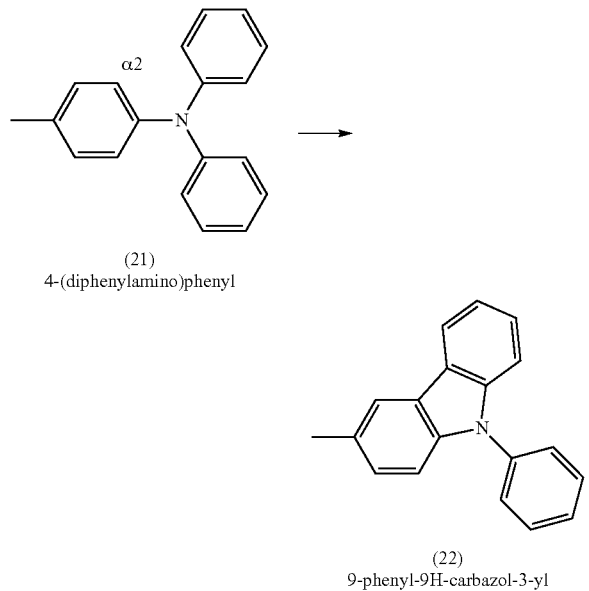

(21)
4-(diphenylamino)phenyl

(22)
9-phenyl-9H-carbazol-3-yl

The organic semiconductor material of Embodiment 1 has a bipolar property having both an electron-transporting property and a hole-transporting property. Thus, in the case where the organic semiconductor material is applied to a light-emitting element, driving voltage can be reduced. In the case where the organic semiconductor material is applied especially to a light-emitting layer, a prominent effect can be obtained.

Further, in the case where the organic semiconductor material of Embodiment 1 is used as a host material of a light-emitting layer, localization of a light-emitting region can be suppressed, and concentration quenching of a substance having a high light-emitting property or quenching due to triplet-triplet annihilation (T-T annihilation) can be suppressed. Accordingly, high emission efficiency can be realized.

Further, since the organic semiconductor material of Embodiment 1 has two ortho-linked benzene rings in the center, it has a sterically bulky structure. The sterically bulky structure makes it difficult for the organic semiconductor material to be crystallized in the case of being formed as a film. Thus, the organic semiconductor material of Embodiment 1 easily keeps an amorphous state in a thin film state, and thus is suitable for a light-emitting element.

In addition, the organic semiconductor material of Embodiment 1 has high triplet excitation energy. Thus, the organic semiconductor material can be used for a light-emitting element together with a phosphorescent compound. Especially in the case where the organic semiconductor material is used together with a phosphorescent compound which exhibits light emission of a short wavelength, a prominent effect can be obtained.

Moreover, the organic semiconductor material of Embodiment 1 has a large energy gap (a difference between the highest occupied molecular orbital (HOMO level) and the lowest unoccupied molecular orbital level (LUMO level)). Thus, the organic semiconductor material can be used for a light-emitting element together with a fluorescent compound. Especially in the case where the organic semiconductor material is used together with a fluorescent compound which exhibits light emission of a short wavelength, a prominent effect can be obtained.

Furthermore, in the organic semiconductor material of Embodiment 1, the electron-accepting unit and the hole-accepting unit are bonded with a twisted quaterphenylene skeleton whose conjugation is hardly extended therebetween; thus, the molecular weight can be increased without decrease in triplet excitation energy, and at the same time a sterically bulky molecular skeleton can be structured. In addition, the organic semiconductor material can have a large band gap. Such a material is used for a light-emitting element, whereby the film quality can be stabilized.

Embodiment 2

In Embodiment 2, a benzoxazole derivative having the structure represented by General Formula (G1) will be described as an example of the organic semiconductor material of an embodiment of the present invention described in Embodiment 1.

A benzoxazole derivative according to Embodiment 2 is a benzoxazole derivative represented by General Formula (BOX1).

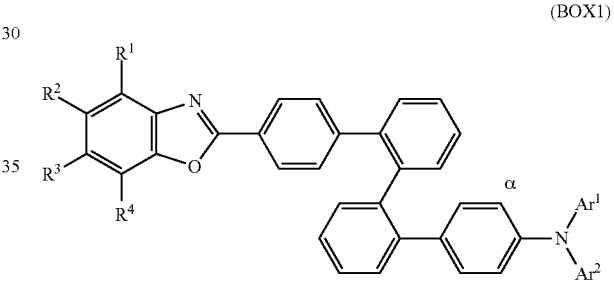

(BOX1)

In the formula, $Ar^1$ and $Ar^2$ each independently represent a substituted or unsubstituted aryl group having 6 to 13 carbon atoms, and $R^1$ to $R^4$ each independently represent any of hydrogen, an alkyl group having 1 to 4 carbon atoms, an unsubstituted aryl group having 6 to 10 carbon atoms, or halogen. $Ar^1$ and carbon of α, or $Ar^1$ and $Ar^2$ may be bonded directly or through sulfur, oxygen, or nitrogen.

The benzoxazole derivative according to Embodiment 2 is a benzoxazole derivative represented by General Formula (BOX2).

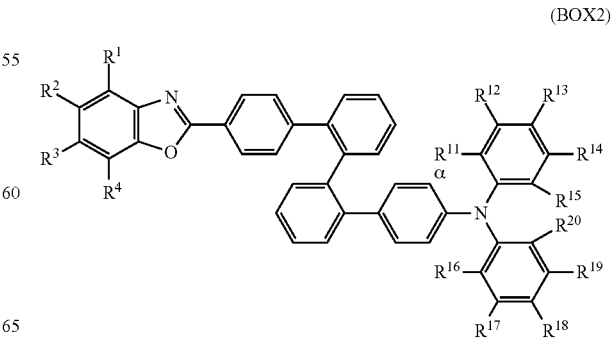

(BOX2)

In the formula, $R^1$ to $R^4$ each independently represent any of hydrogen, an alkyl group having 1 to 4 carbon atoms, an unsubstituted aryl group having 6 to 10 carbon atoms, or halogen, and $R^{11}$ to $R^{20}$ each independently represent any of hydrogen, an alkyl group having 1 to 4 carbon atoms, or a substituted or unsubstituted aryl group having 6 to 13 carbon atoms. A carbon atom of the benzene ring which is bonded to $R^{11}$ and carbon of α, or a carbon atom of the benzene ring which is bonded to $R^{15}$ and a carbon atom of the benzene ring which is bonded to $R^{20}$ may be directly bonded.

The benzoxazole derivative according to Embodiment 2 is a benzoxazole derivative represented by General Formula (BOX2).

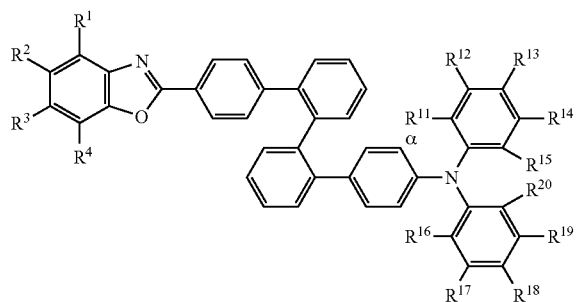

(BOX2)

In the formula, $R^1$ to $R^4$ each independently represent any of hydrogen, an alkyl group having 1 to 4 carbon atoms, an unsubstituted aryl group having 6 to 10 carbon atoms, or halogen, and $R^{11}$ to $R^{20}$ each independently represent any of hydrogen, an alkyl group having 1 to 4 carbon atoms, a substituted or unsubstituted aryl group having 6 to 13 carbon atoms. A carbon atom of the benzene ring which is bonded to $R^{11}$ and carbon of α, or a carbon atom of the benzene ring which is bonded to $R^{15}$ and a carbon atom of the benzene ring which is bonded to $R^{20}$ may be directly bonded to form a carbazole skeleton.

The benzoxazole derivative according to Embodiment 2 is a benzoxazole derivative represented by General Formula (BOX3).

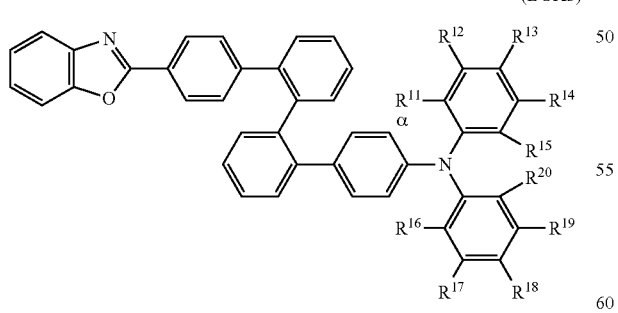

(BOX3)

In the formula, $R^{11}$ to $R^{20}$ each independently represent any of hydrogen, an alkyl group having 1 to 4 carbon atoms, or a substituted or unsubstituted aryl group having 6 to 13 carbon atoms. A carbon atom of the benzene ring which is bonded to $R^{11}$ and carbon of α, or a carbon atom of the benzene ring which is bonded to $R^{15}$ and a carbon atom of the benzene ring which is bonded to $R^{20}$ may be directly bonded to form a carbazole skeleton.

Note that the number of carbon atoms of the aryl group or the arylene group described in this specification represents the number of carbon atoms which form a ring of the main skeleton, and the number of carbon atoms of a substituent bonded to the main skeleton is not included therein. As a substituent bonded to the aryl group or the arylene group, an alkyl group having 1 to 4 carbon atoms, an aryl group having 6 to 13 carbon atoms, or a haloalkyl group having 1 carbon atom can be given. Specifically, a methyl group, an ethyl group, a propyl group, a butyl group, a phenyl group, a naphthyl group, a fluorenyl group, a trifluoromethyl group, and the like are given. Further, the number of substituents included in the aryl group or the arylene group may be either single or plural. In the case where the aryl group or the arylene group has two substituents, the substituents may be bonded to each other to form a ring. For example, when the aryl group is a fluorenyl group, carbon at the 9-position may have two phenyl groups, and the two phenyl groups may be bound to each other to form a spiro ring structure.

In General Formulae (BOX1) to (BOX3), the aryl group having 6 to 13 carbon atoms may have a substituent, and in the case where the aryl group has a plurality of substituents, the substituents may be bonded to form a ring. In addition, also in the case where one carbon atom has two substituents, the substituents may be bonded to form a spiro ring. For example, substituents represented by Structural Formulae (11-1) to (11-22) are given as specific examples of the groups represented by $Ar^1$ and $Ar^2$.

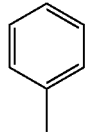

(11-1)

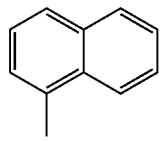

(11-2)

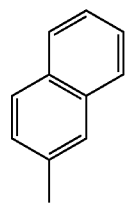

(11-3)

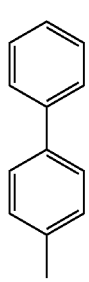

(11-4)

(11-5) 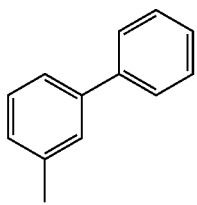
(11-6) 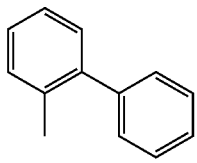
(11-7) 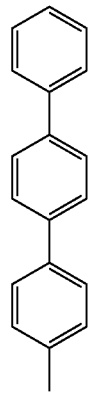
(11-8) 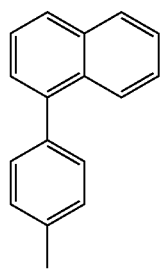
(11-9) 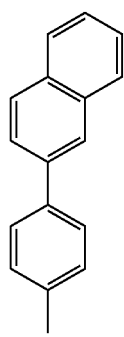
(11-10) 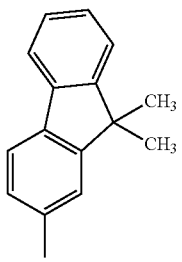
(11-11) 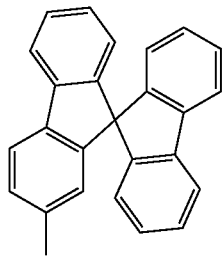
(11-12) 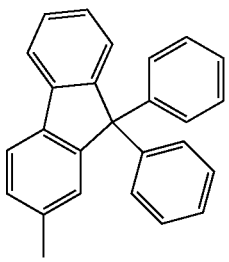
(11-13) 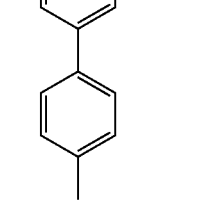
(11-14) 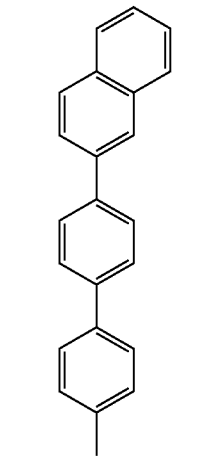

(11-15)
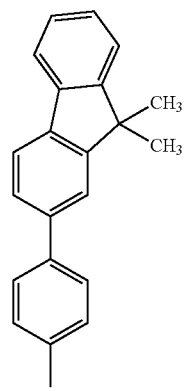
(11-16)
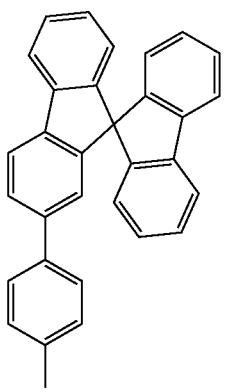
(11-17)
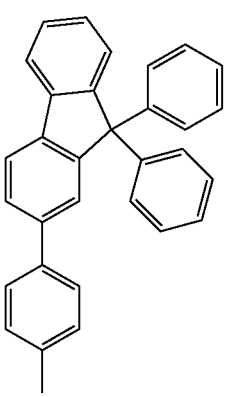
(11-18)
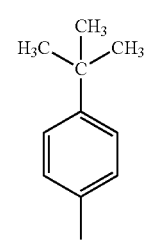
(11-19)
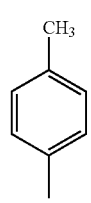
(11-20)
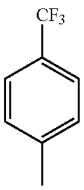
(11-21)
(11-22)
For example, substituents represented by Structural Formulae (13-1) to (13-16) are given as specific examples of the groups represented by $R^1$ to $R^4$ and $R^{11}$ to $R^{20}$.
(13-1)
(13-2)
(13-3)

(13-4)
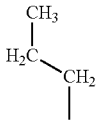
(13-5)

(13-6)
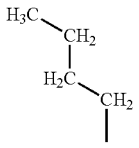
(13-7)
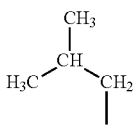
(13-8)
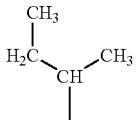

(13-9) 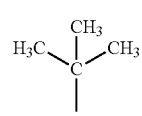
(13-10) 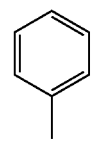
(13-11) 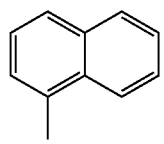
(13-12) 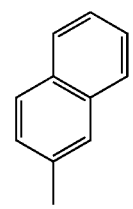
(13-13) Br|
(13-14) I|
(13-15) F|
(13-16) Cl|
For example, substituents represented by Structural Formulae (14-1) to (14-18) are given as specific examples of the groups represented by $R^{11}$ to $R^{20}$.
(14-1) H|
(14-2) CH₃|
(14-3) 
(14-4) 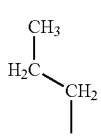
(14-5) 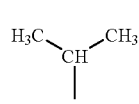
(14-6) 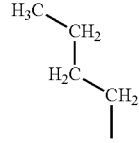
(14-7) 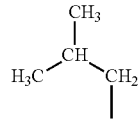
(14-8) 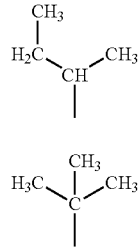
(14-9) 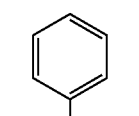
(14-10) 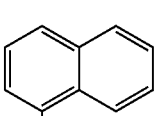
(14-11) 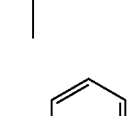
(14-12) 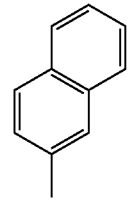
(14-13)

(14-14)
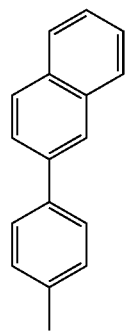

(14-15)
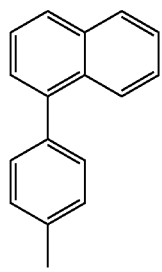

(14-16)
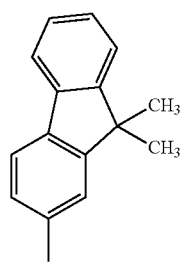

(14-17)
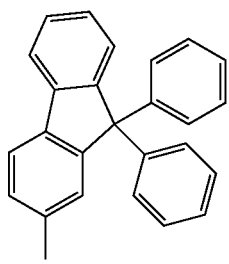

(14-18)
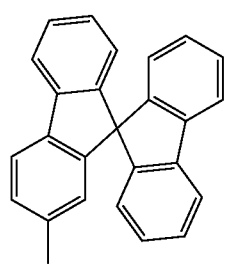

Further, in the benzoxazole derivatives represented by General Formulae (BOX1) to (BOX3), $Ar^1$ and $Ar^2$ are preferably a phenyl group in terms of easiness of synthesis and purification.

As specific examples of the benzoxazole derivatives represented by General Formulae (BOX1) to (BOX3), benzoxazole derivatives represented by Structural Formulae (101) to (194), Structural Formulae (201) to (294), and Structural Formulae (301) to (383) can be given. However, the present invention is not limited thereto.

(101)
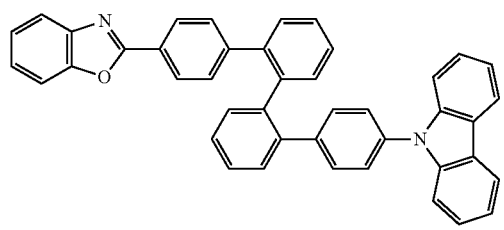

(102)
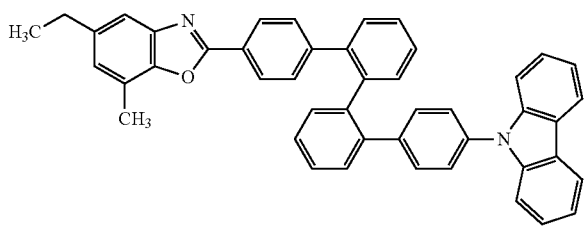

(103)
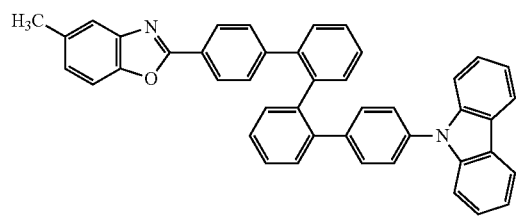

(104)
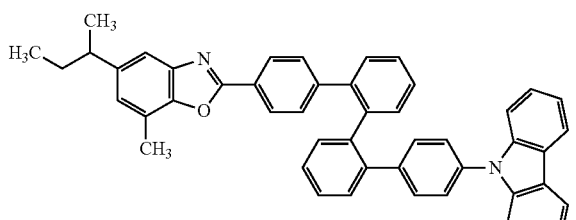

-continued
(105)
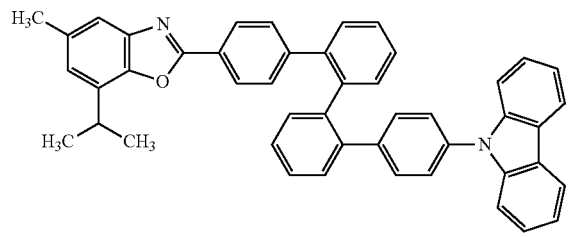
(106)
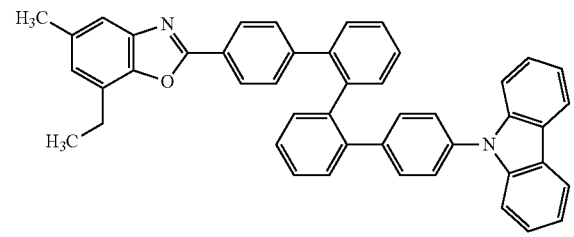
(107)
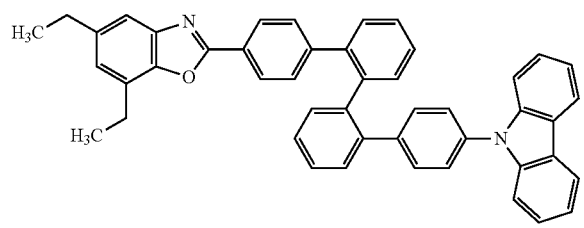
(108)
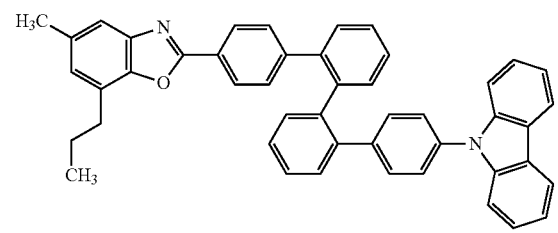
(109)
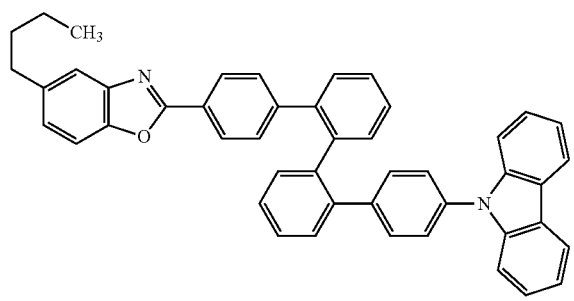
(110)
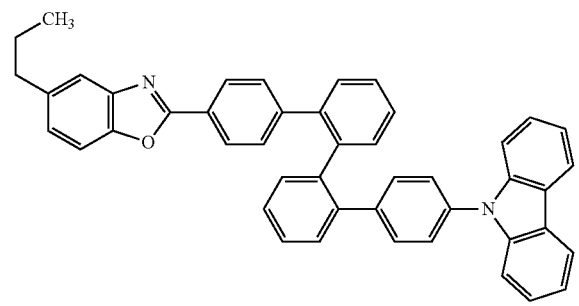
(111)
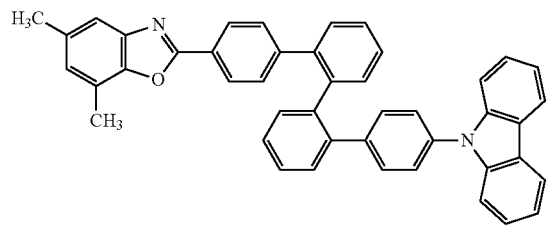
(112)
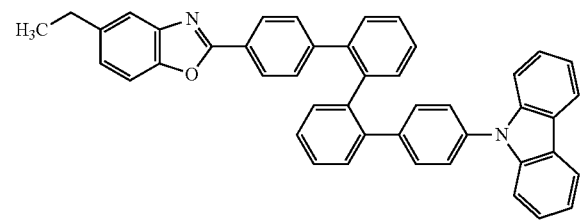
(113)
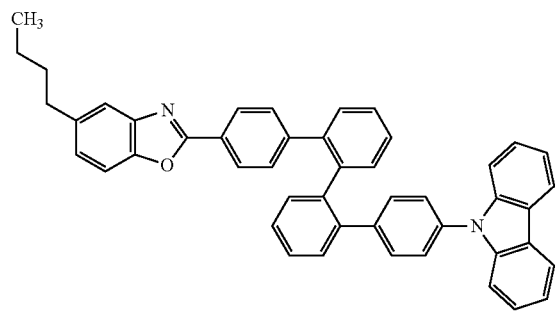
(114)
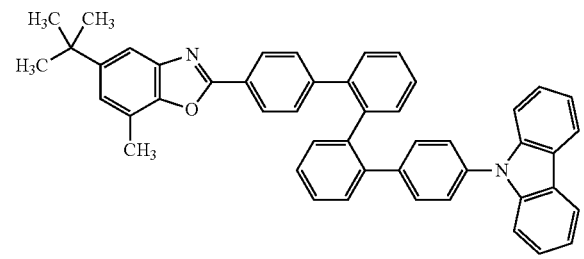

-continued
(115)
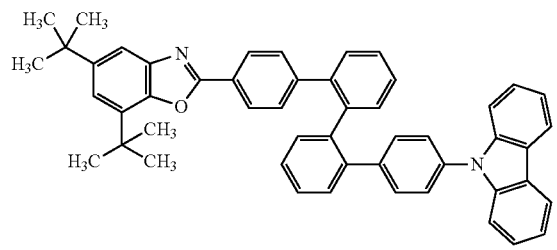
(116)
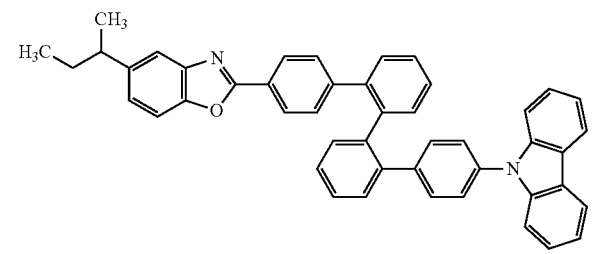
(117)
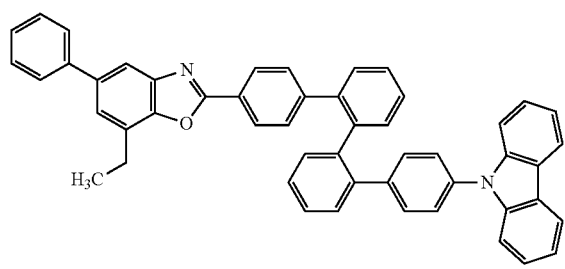
(118)
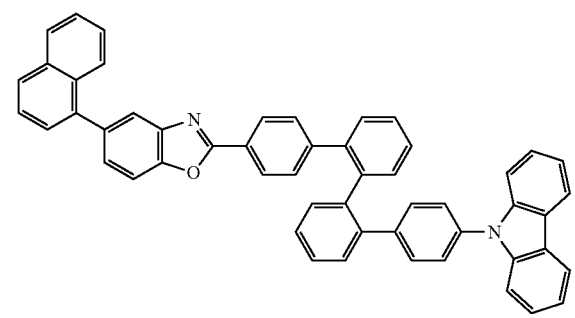
(119)
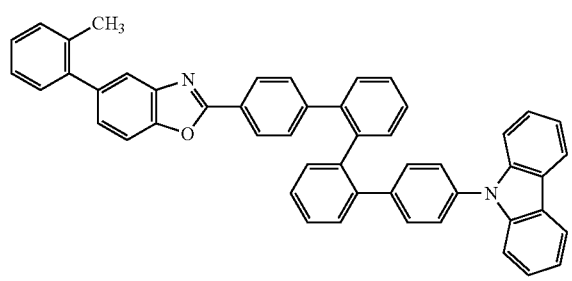
(120)
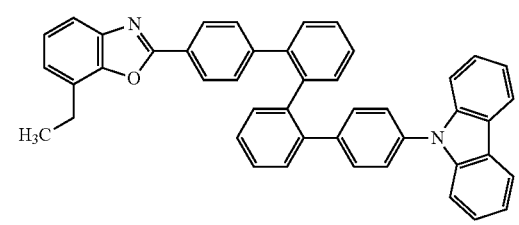
(121)
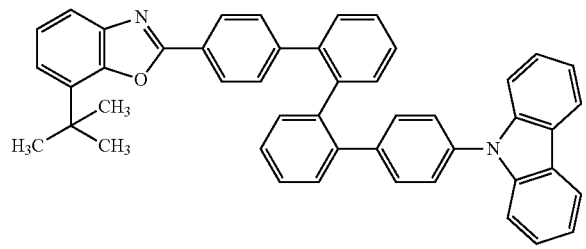
(122)
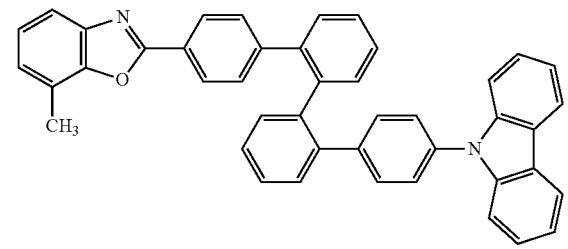
(123)
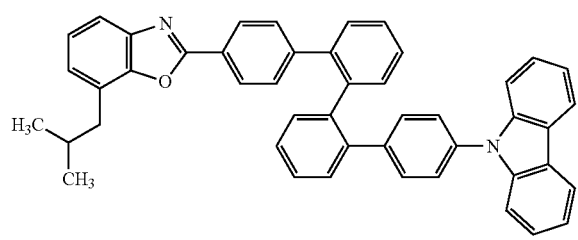
(124)
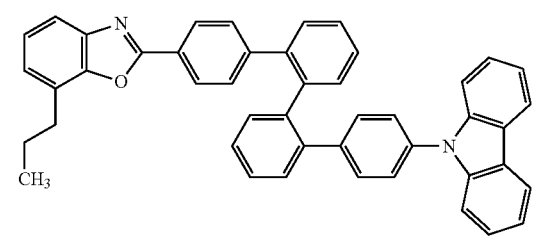

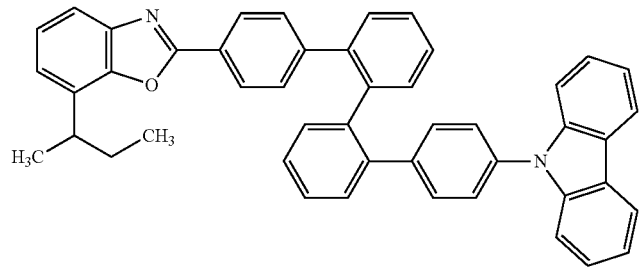
(125)
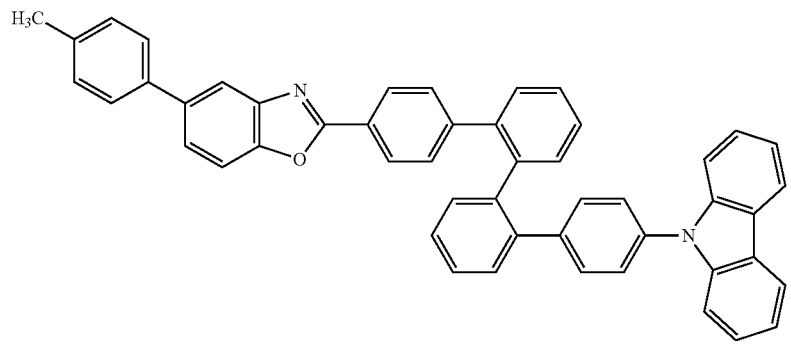
(126)
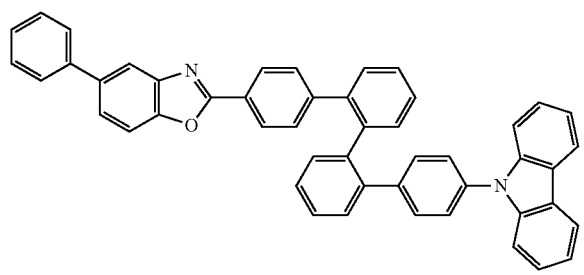
(127)
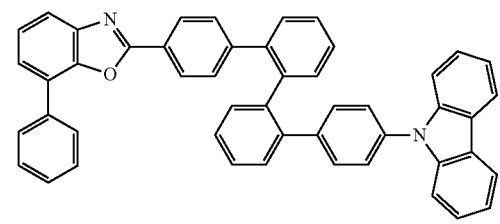
(128)
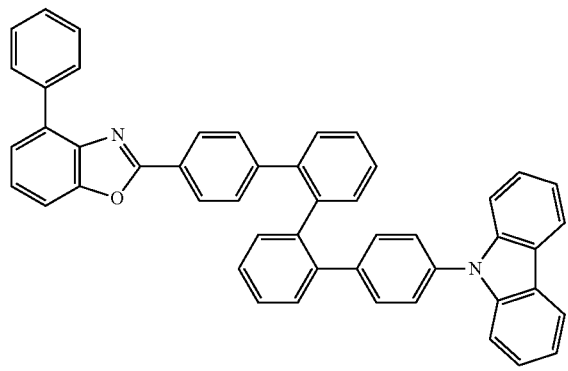
(129)
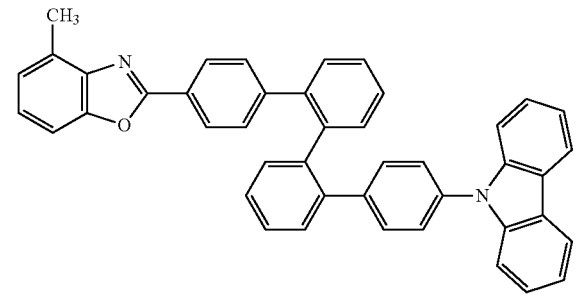
(130)

-continued
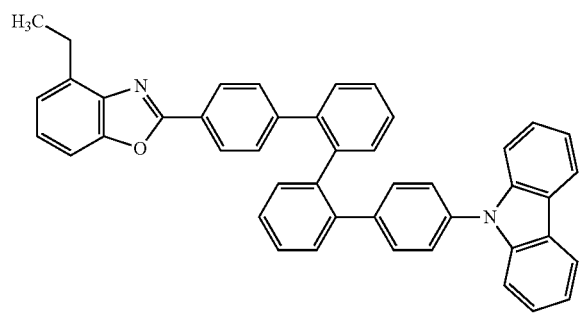
(131)
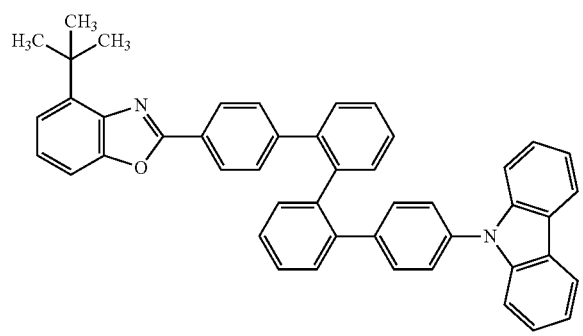
(132)
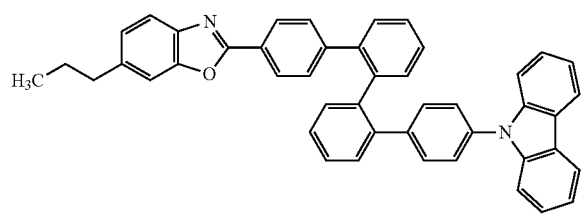
(133)
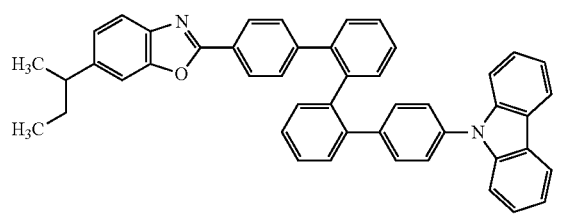
(134)
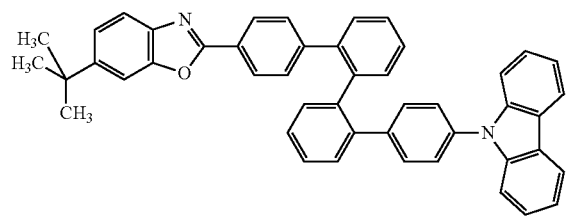
(135)
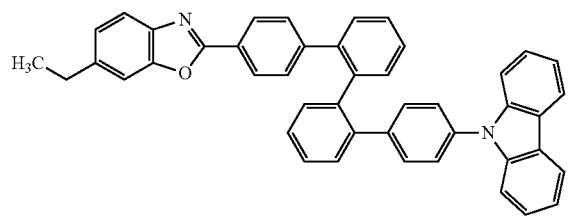
(136)
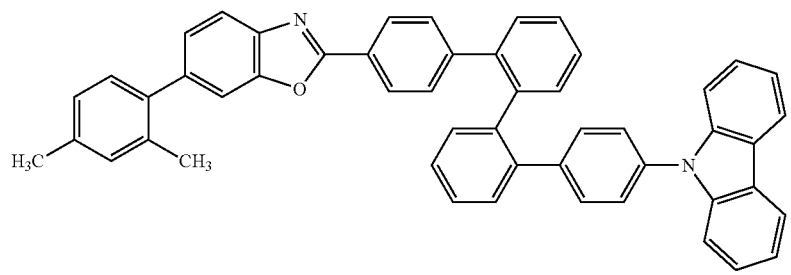
(137)
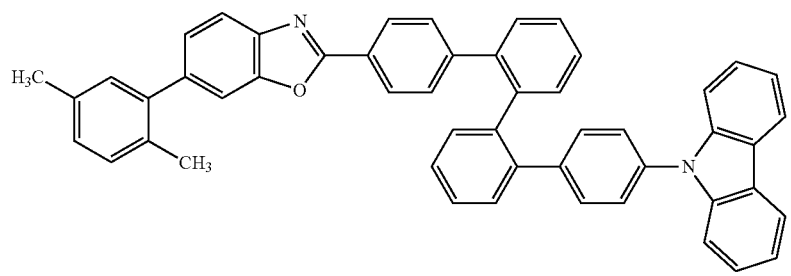
(138)

-continued
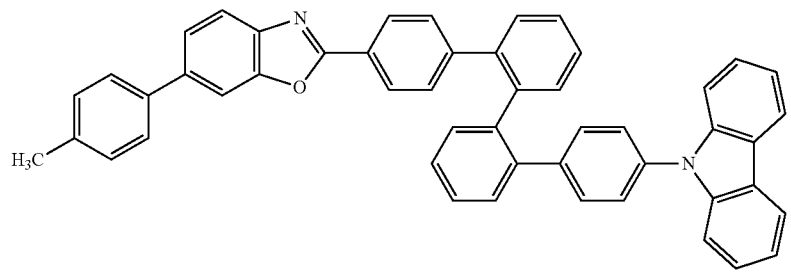
(139)
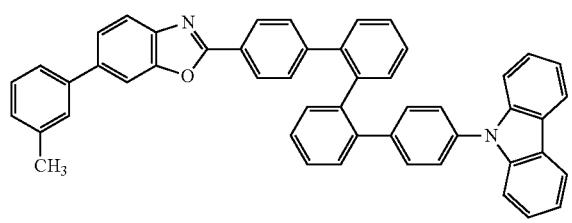
(140)
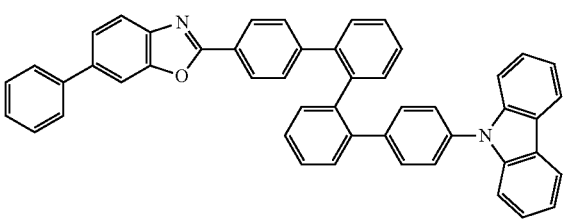
(141)
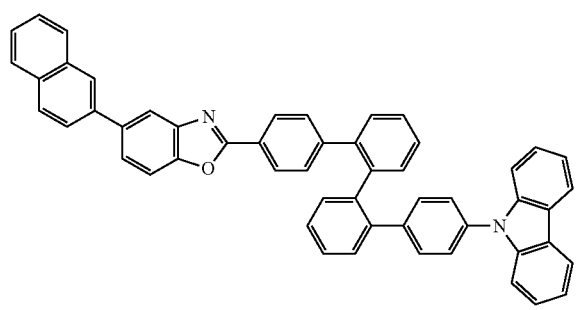
(142)
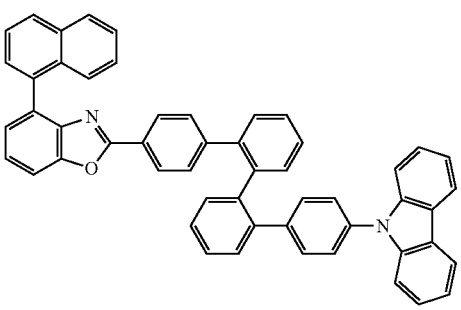
(143)
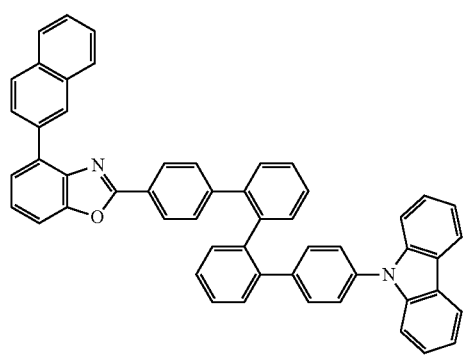
(144)
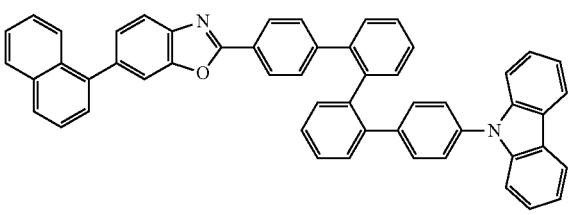
(145)
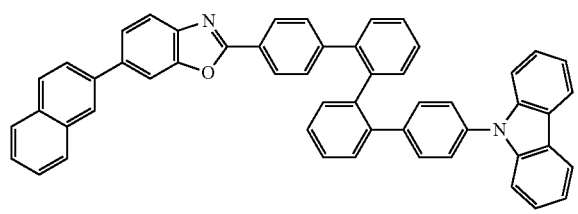
(146)
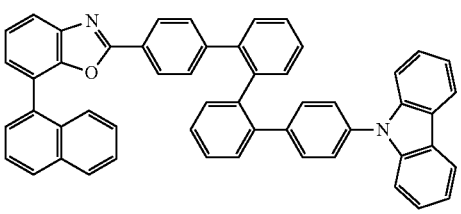
(147)

-continued
(148)
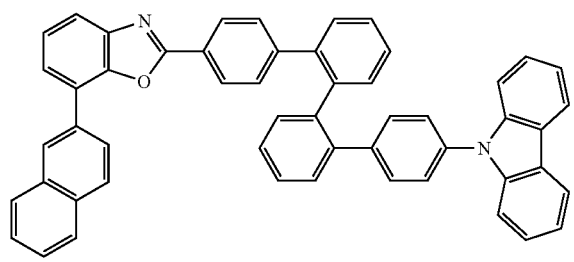
(149)
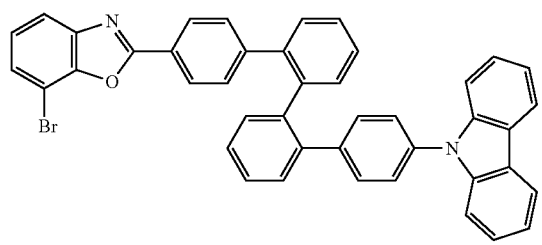
(150)
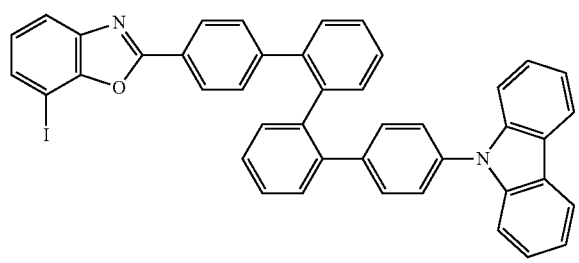
(151)
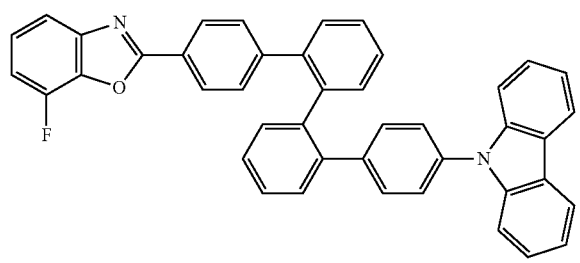
(152)
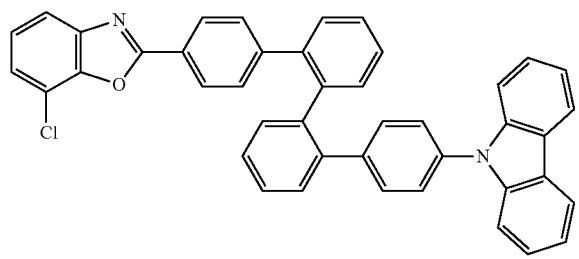
(153)
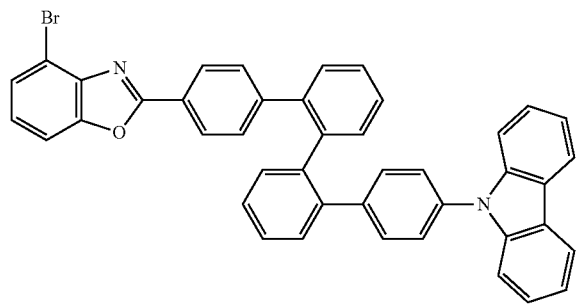
(154)
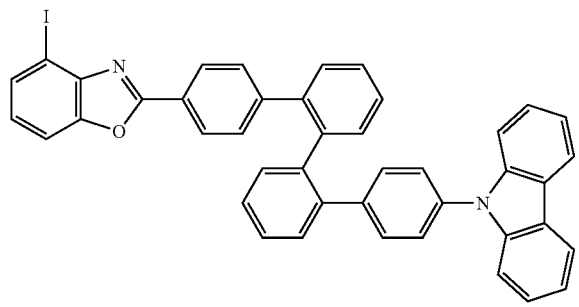
(155)
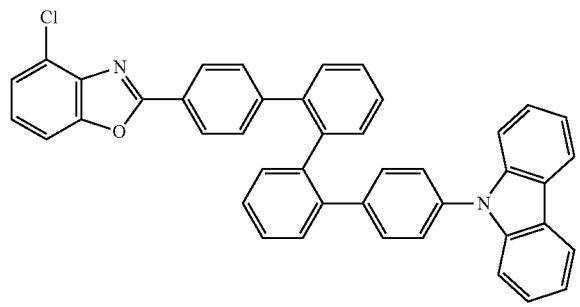
(156)
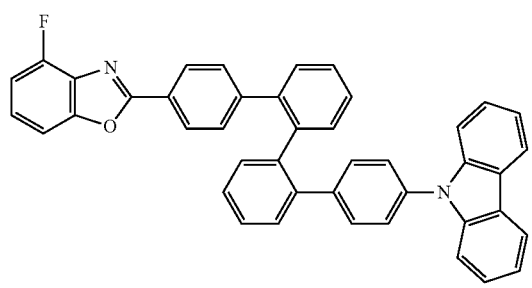
(157)
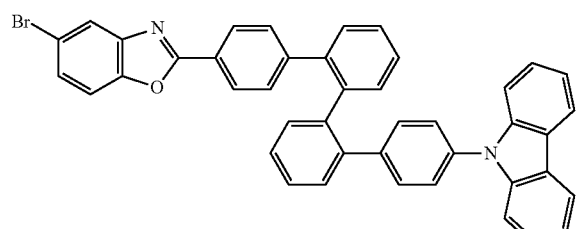

-continued
(158)
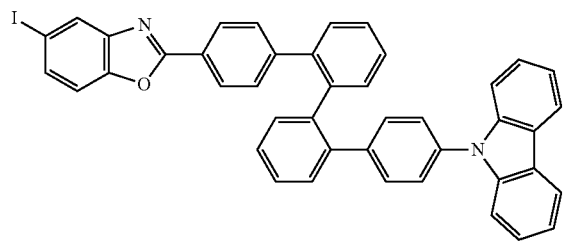
(159)
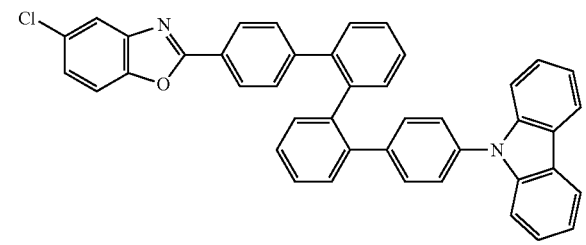
(160)
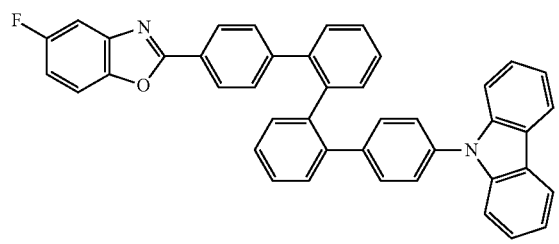
(161)
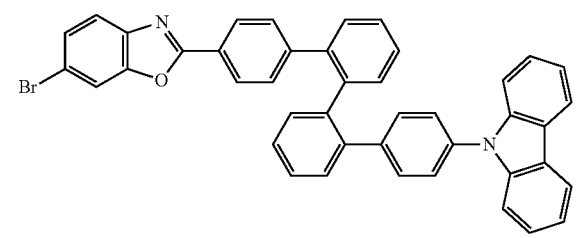
(162)
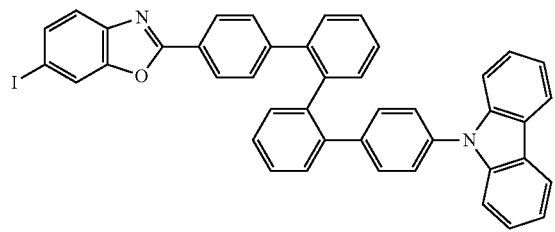
(163)
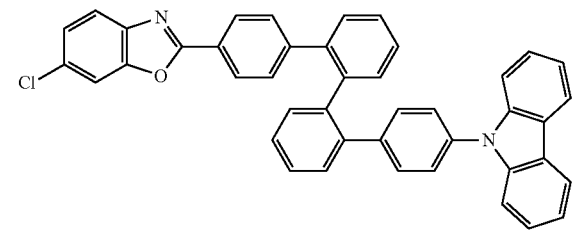
(164)
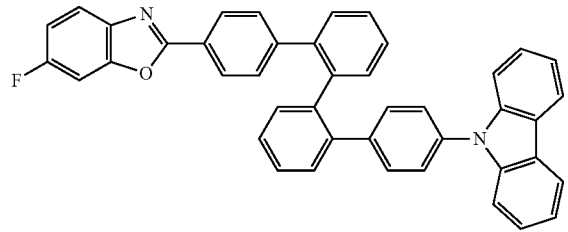
(165)
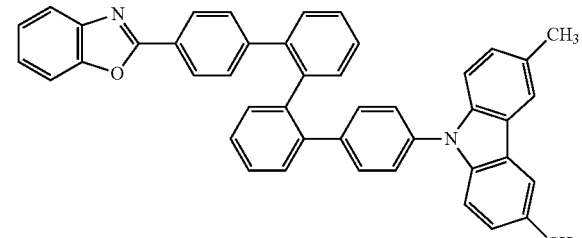
(166)
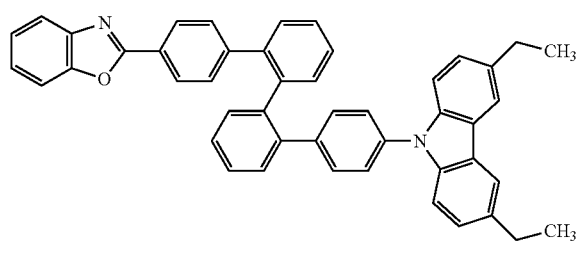
(167)
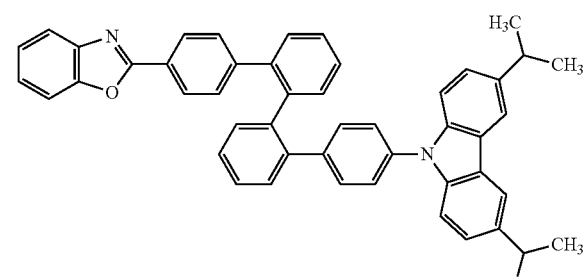

-continued
(168)
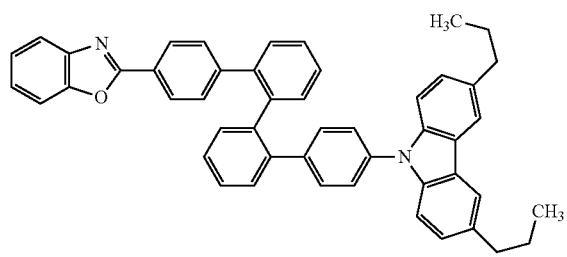
(169)
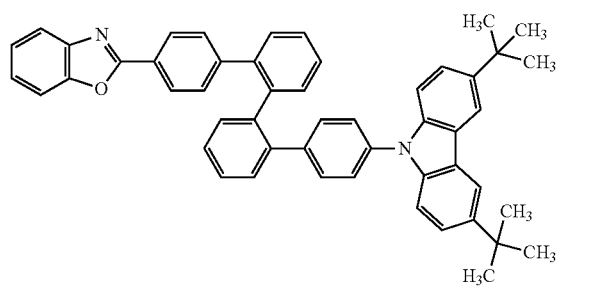
(170)
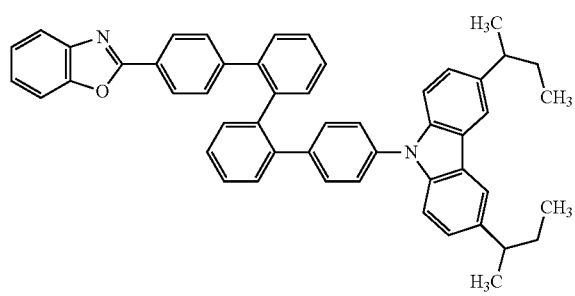
(171)
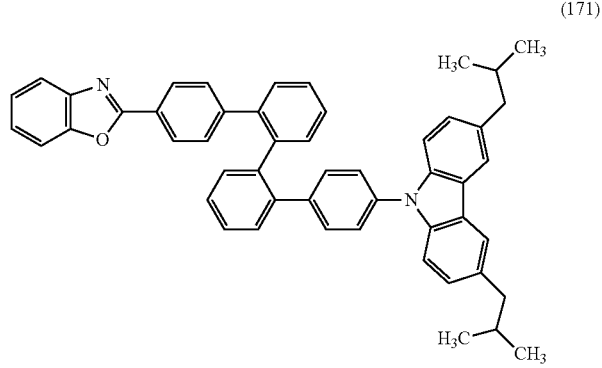
(172)
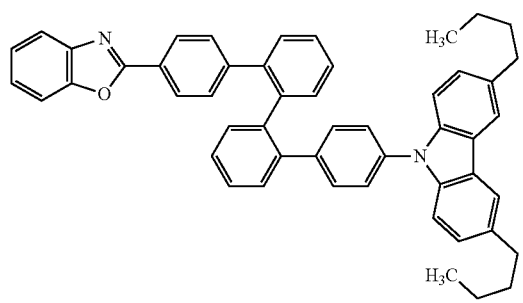
(173)
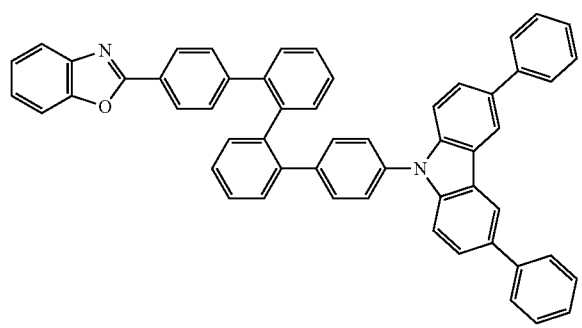
(174)
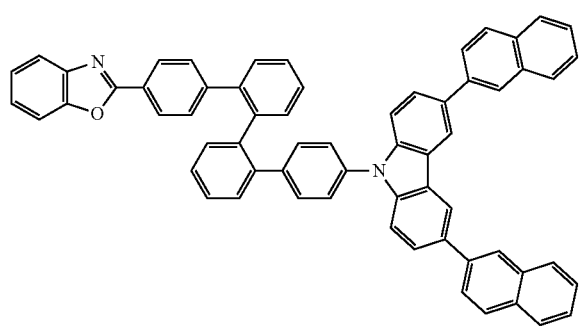
(175)
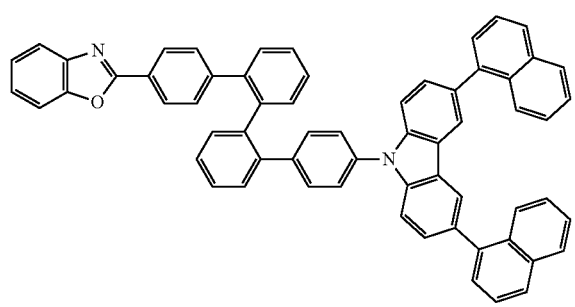

(176)
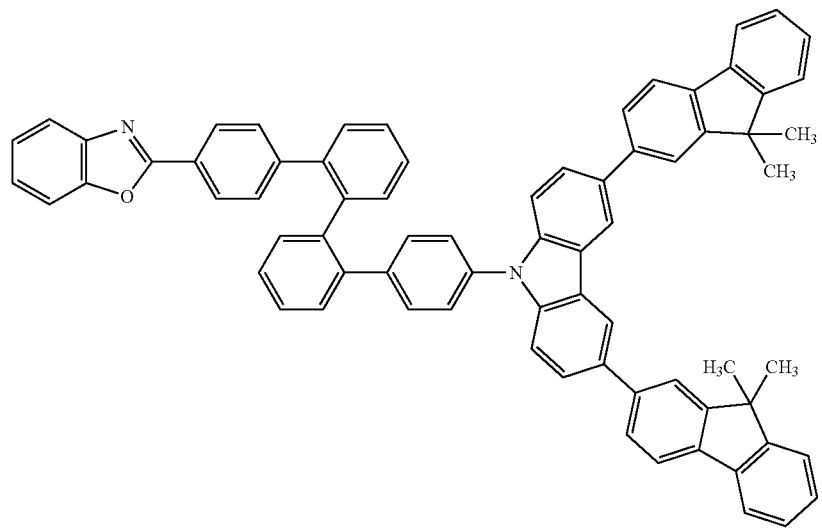
(177)
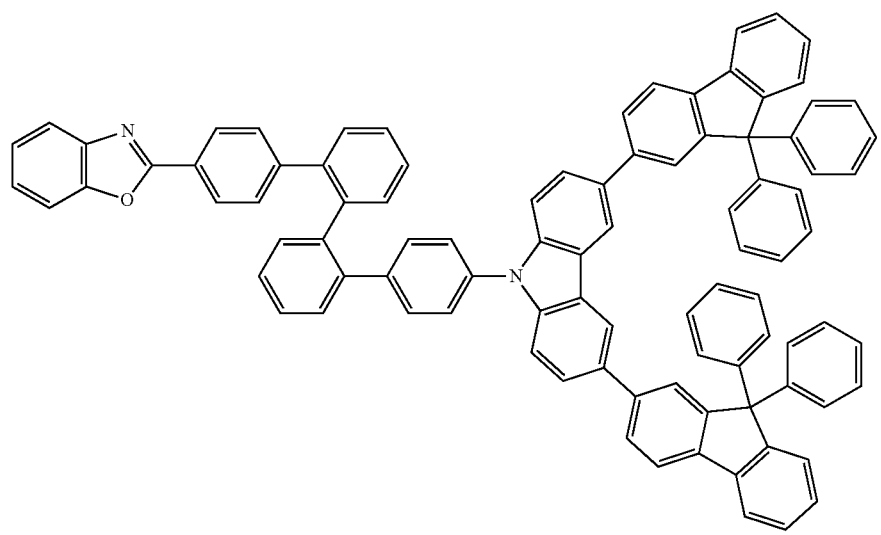
(178)
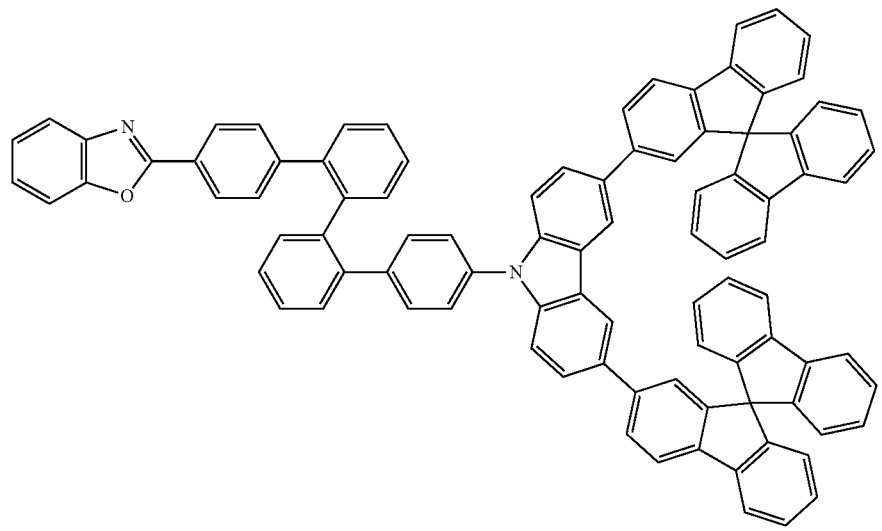

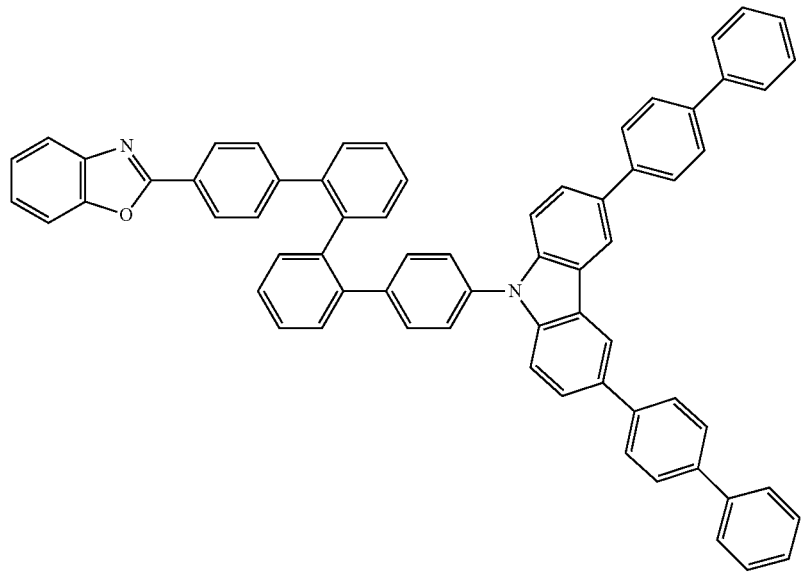
(179)
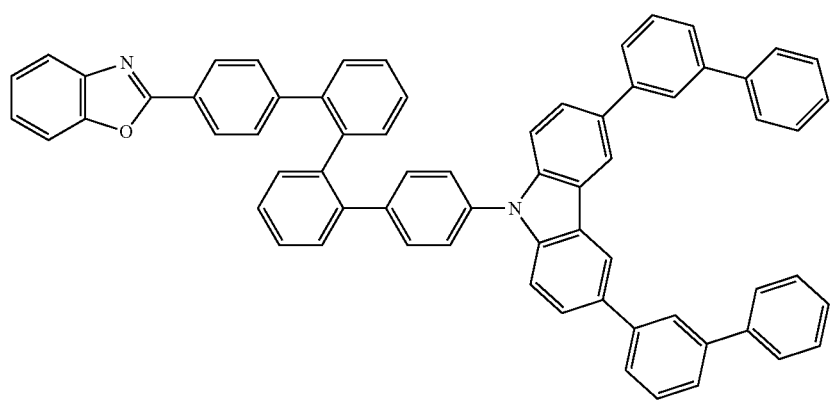
(180)
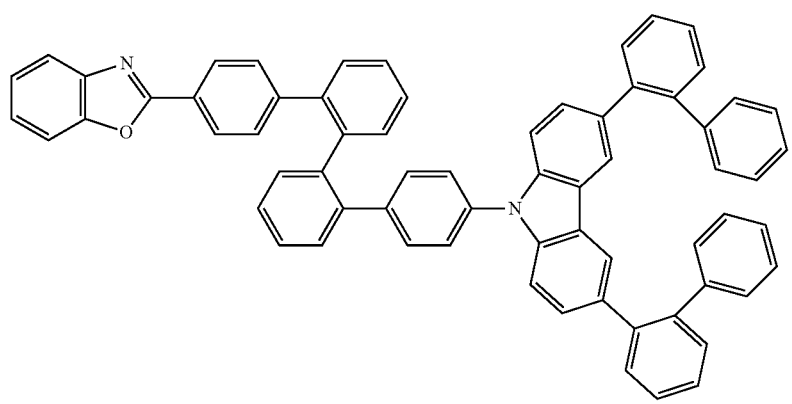
(181)

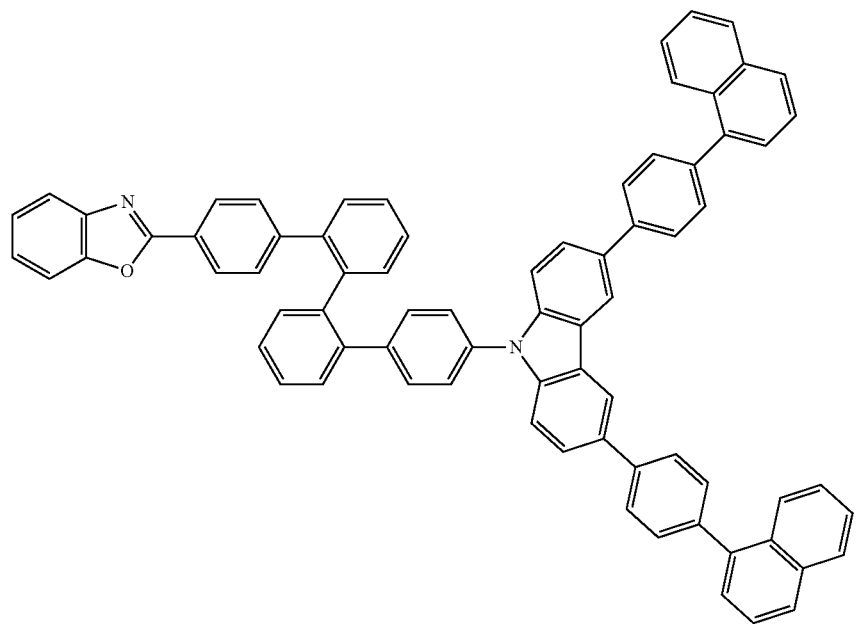
(182)
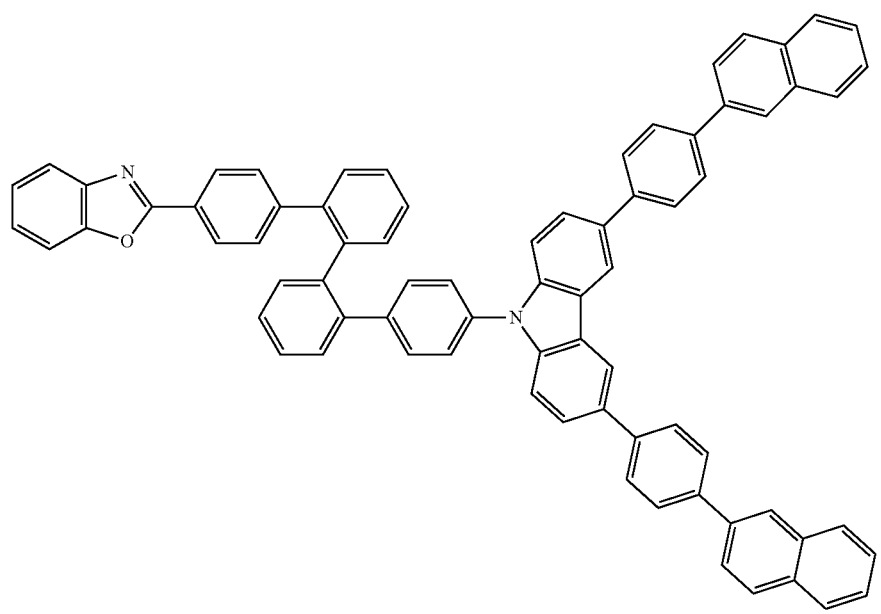
(183)
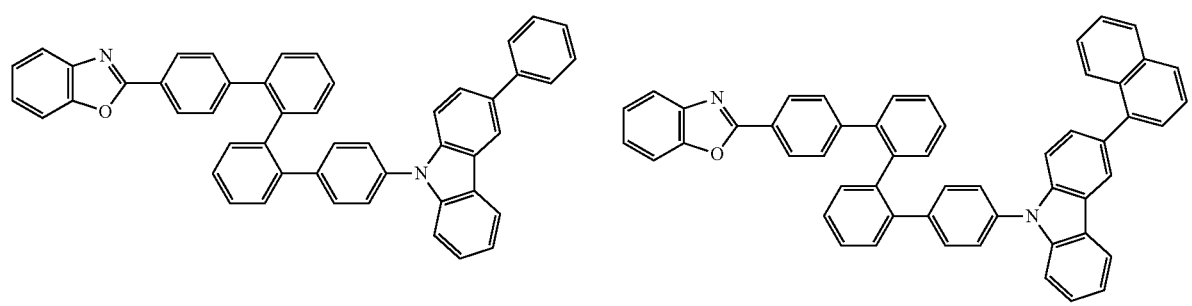
(184) (185)

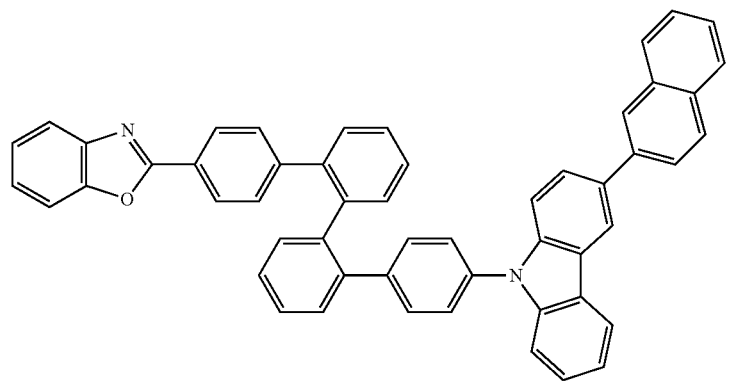
(186)
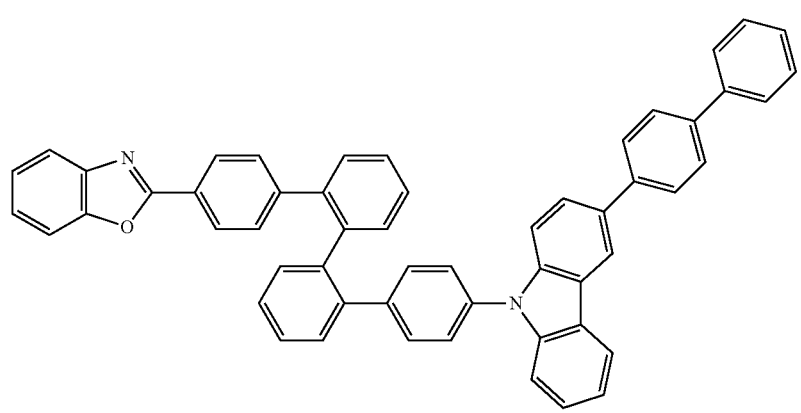
(187)
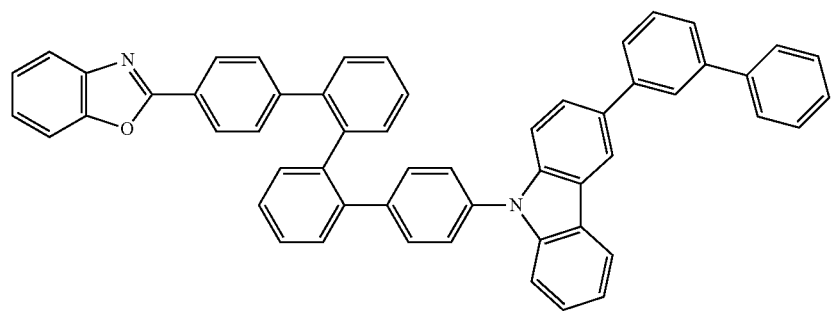
(188)
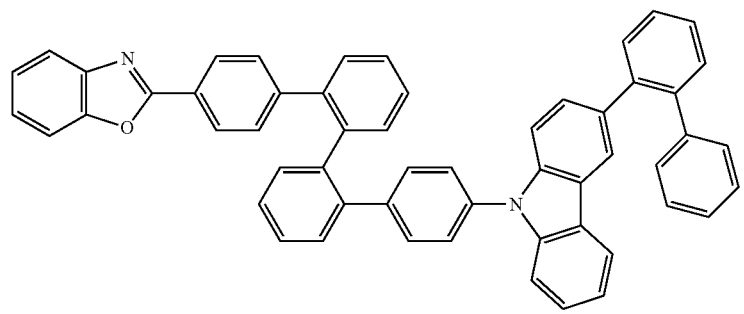
(189)

-continued
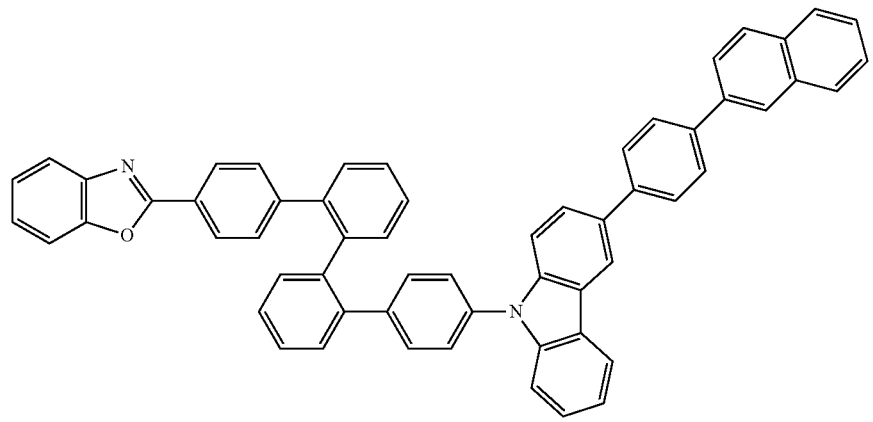
(190)
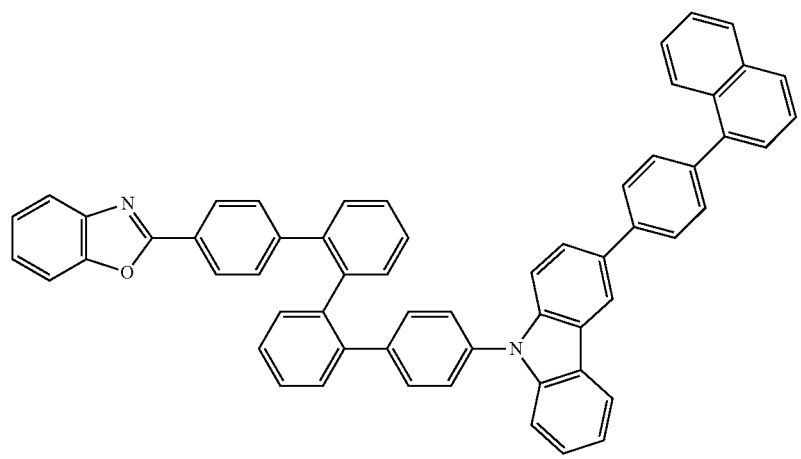
(191)
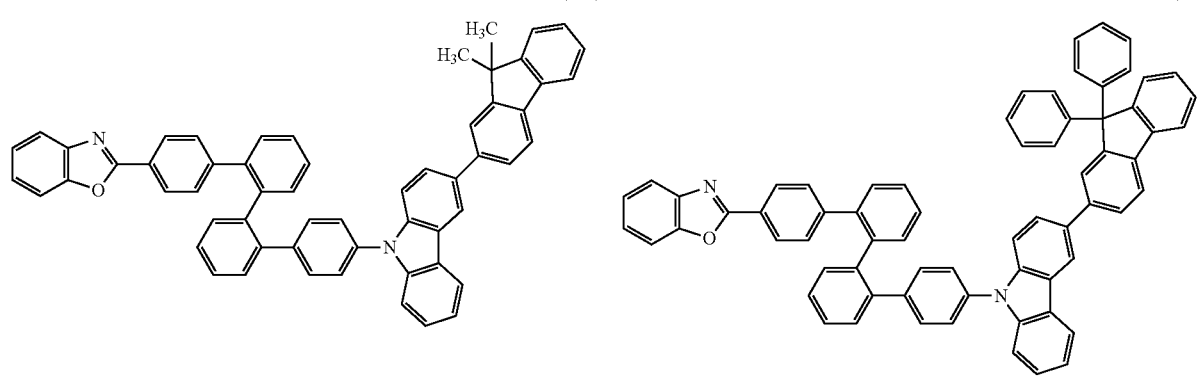
(192) (193)
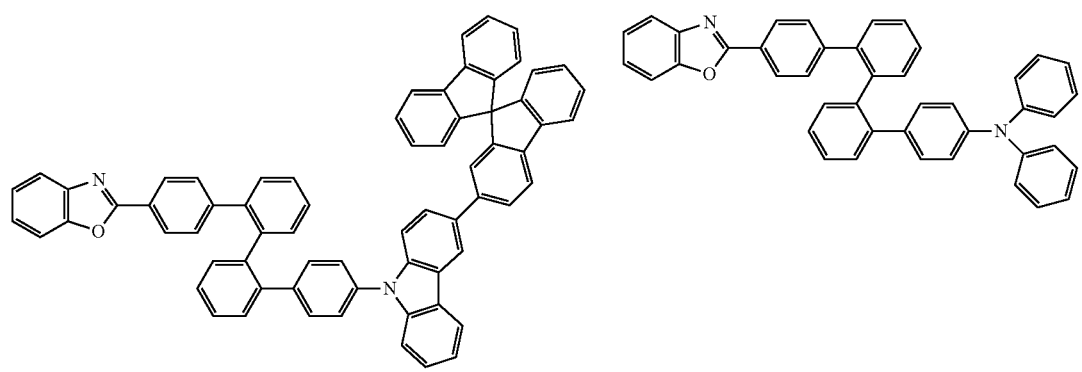
(194) (201)

-continued
(202)
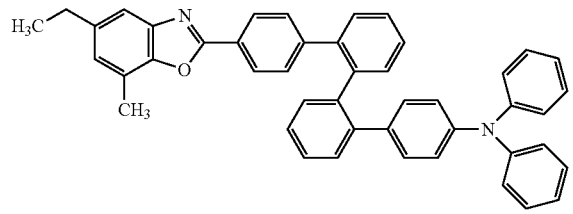
(203)
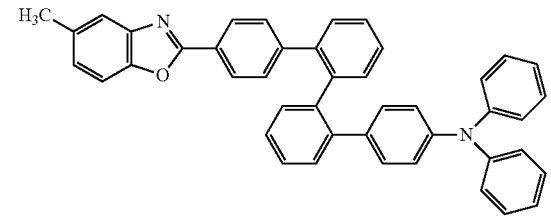
(204)
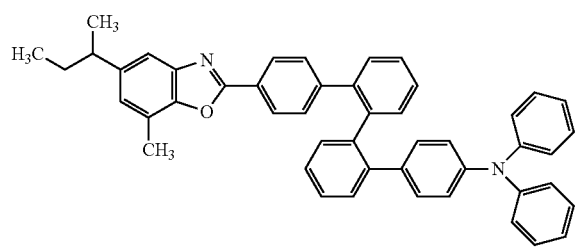
(205)
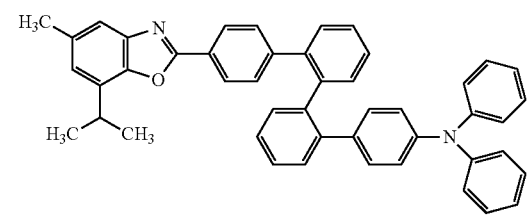
(206)
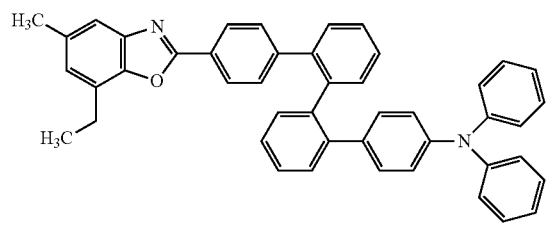
(207)
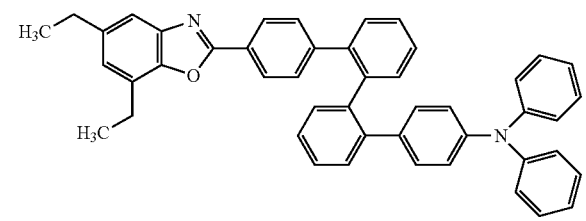
(208)
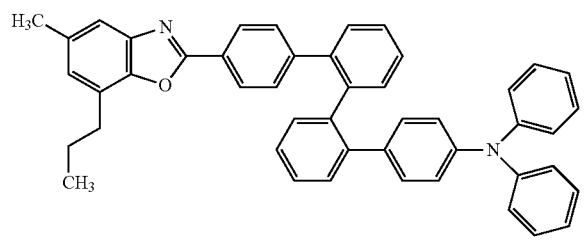
(209)
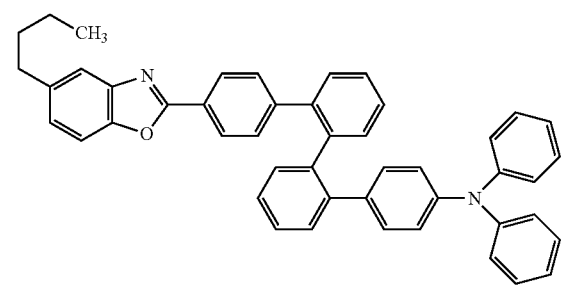
(210)
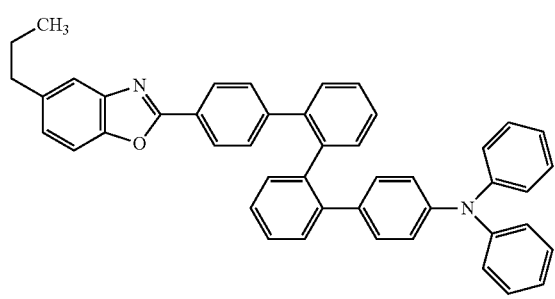
(211)
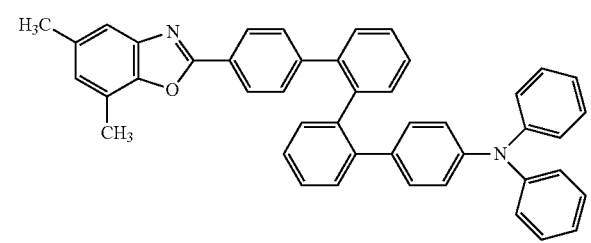

-continued
(212)
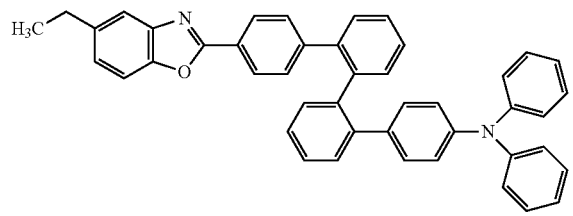
(213)
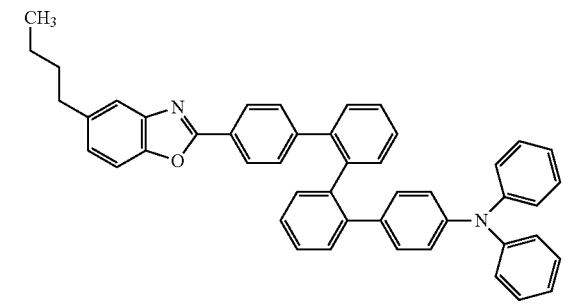
(214)
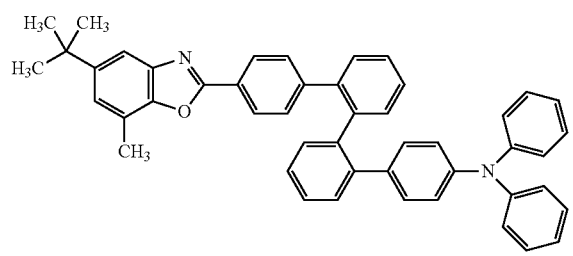
(215)
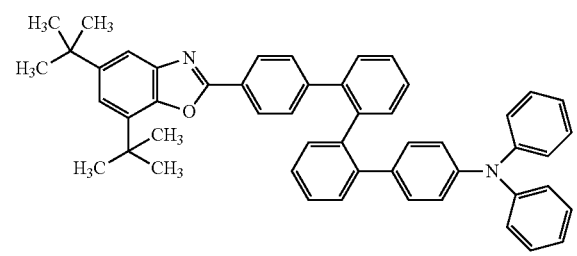
(216)
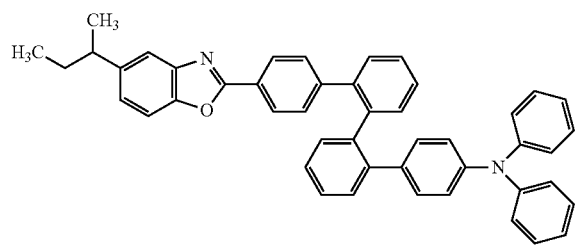
(217)
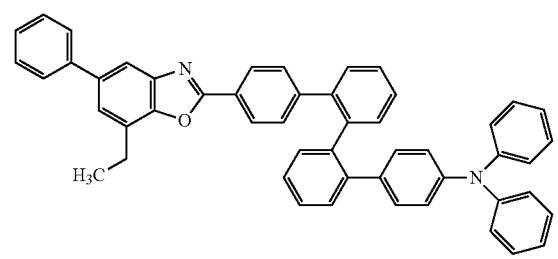
(218)
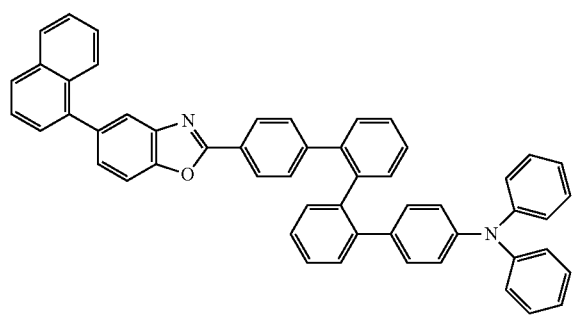
(219)
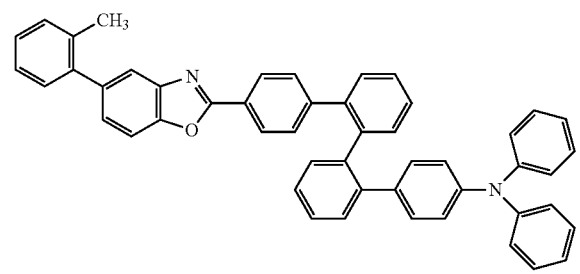
(220)
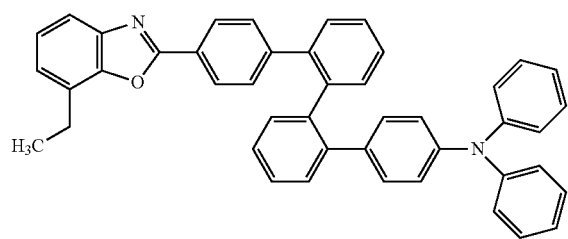
(221)
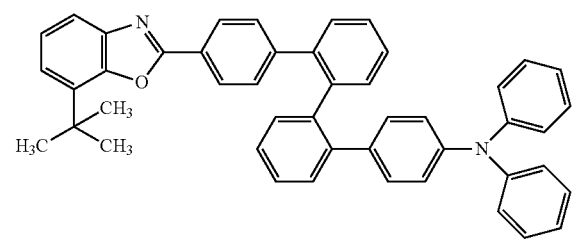

-continued
(222)
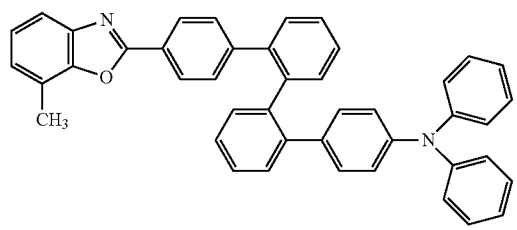
(223)
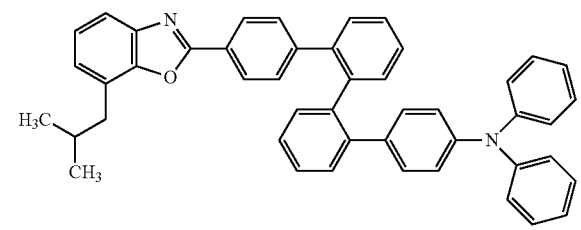
(224)
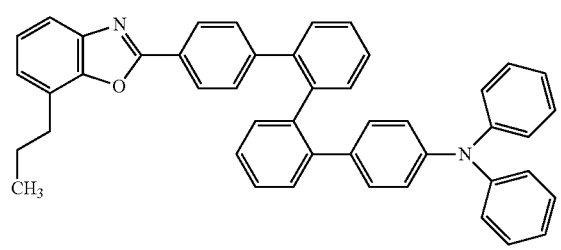
(225)
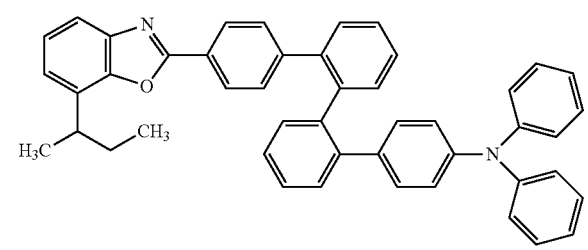
(226)
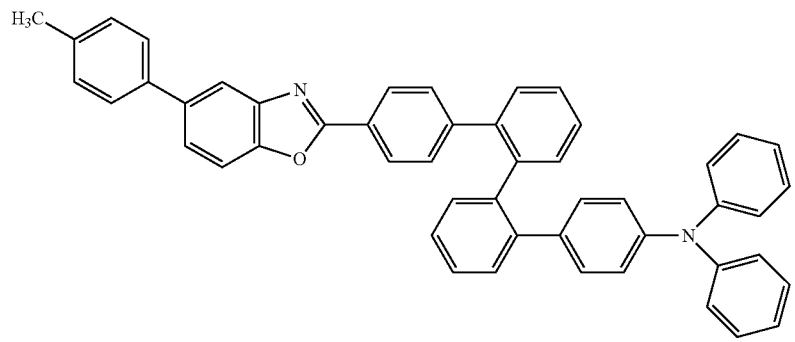
(227)
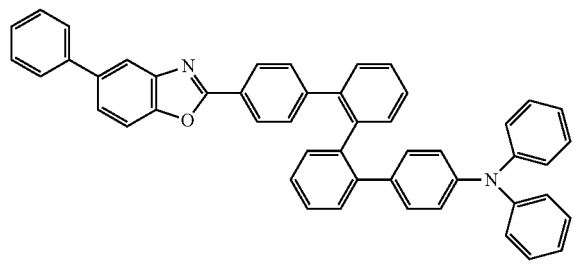
(228)
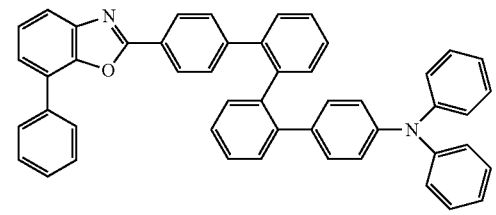
(229)
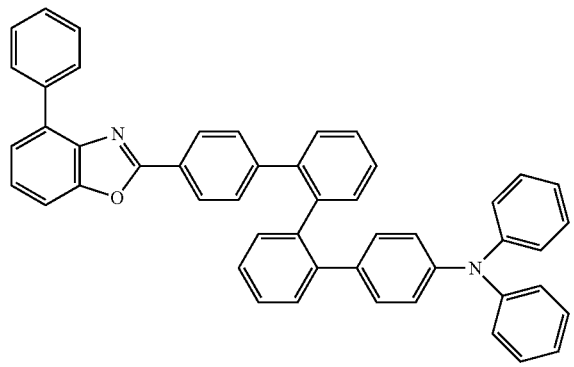
(230)
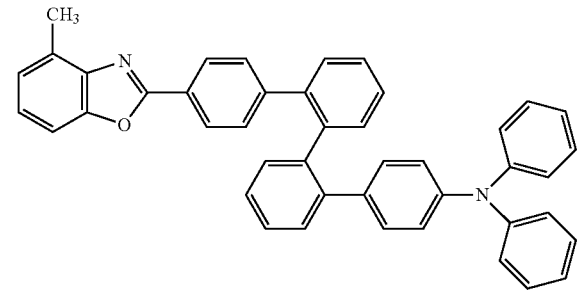

-continued
(231)
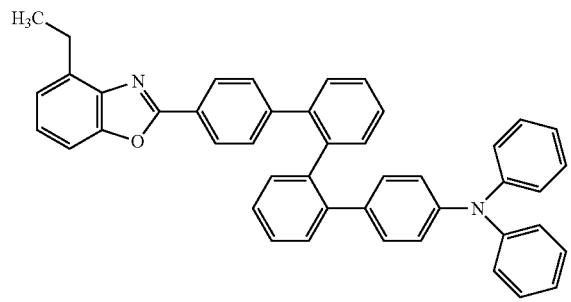
(232)
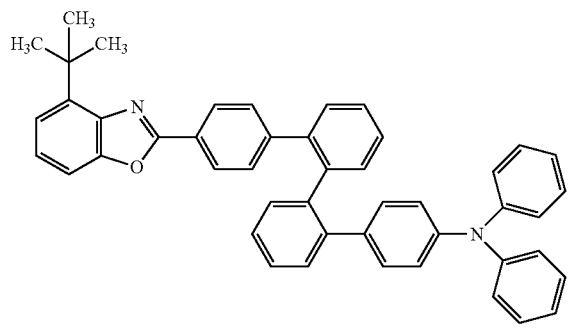
(233)
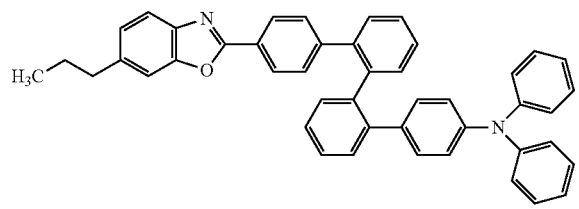
(234)
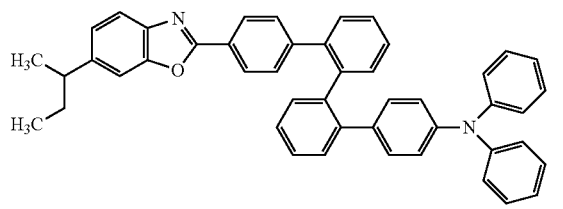
(235)
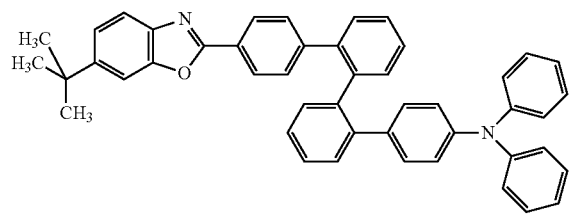
(236)
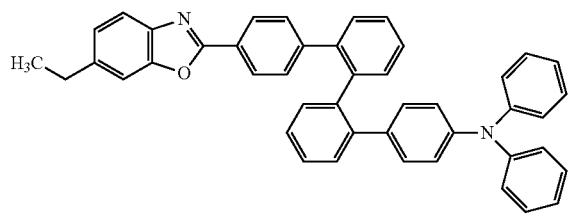
(237)
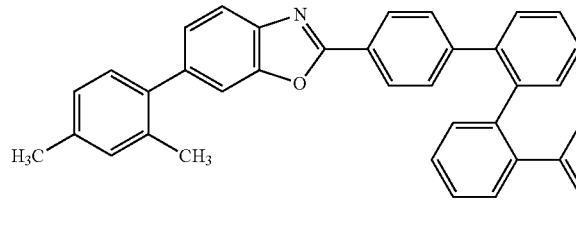
(238)
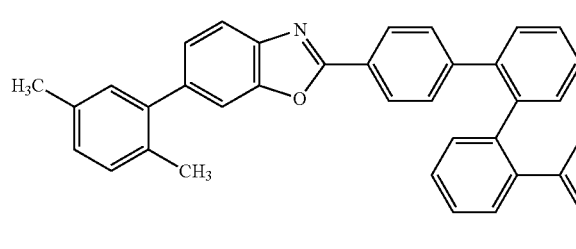
(239)
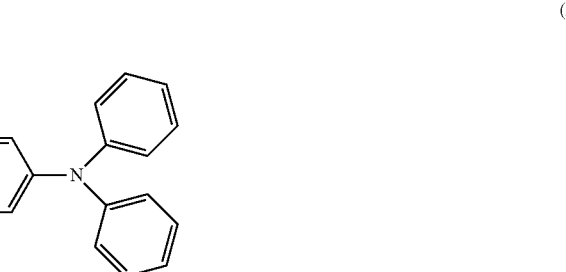

-continued
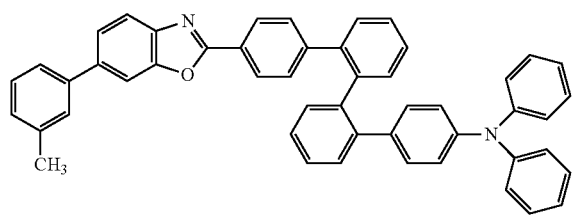
(240)
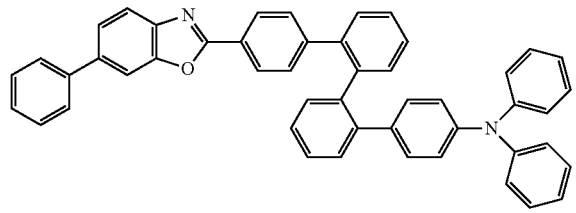
(241)
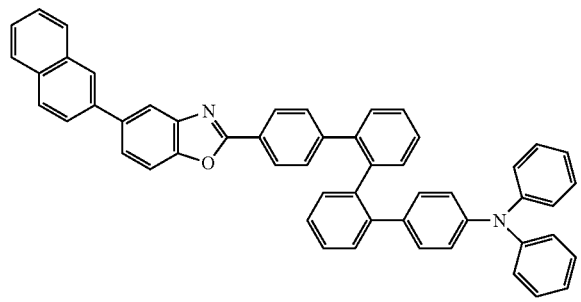
(242)
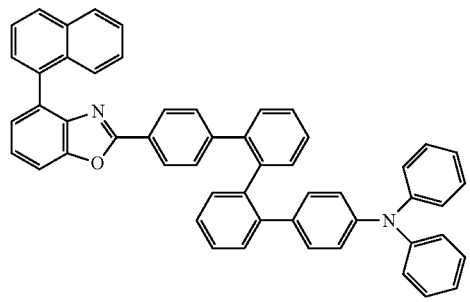
(243)
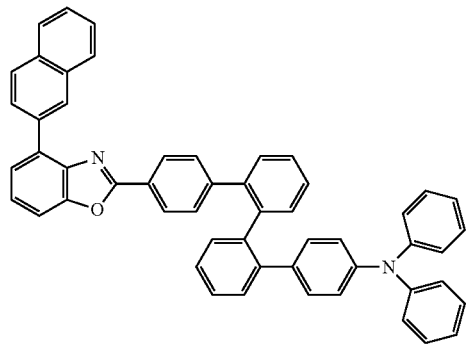
(244)
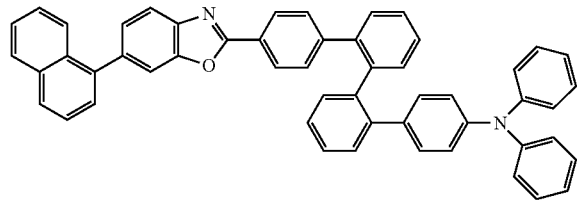
(245)
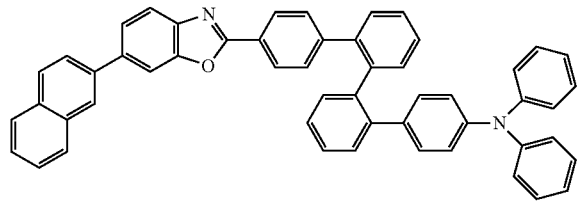
(246)
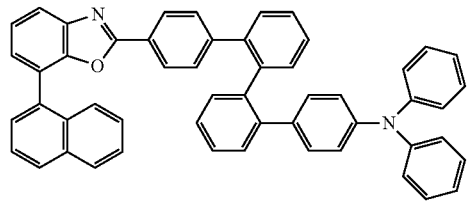
(247)
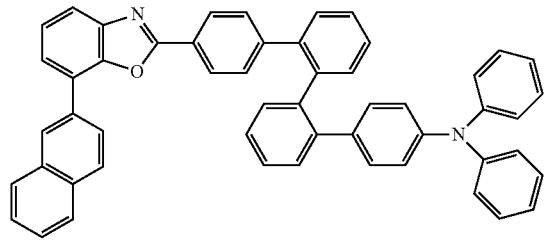
(248)
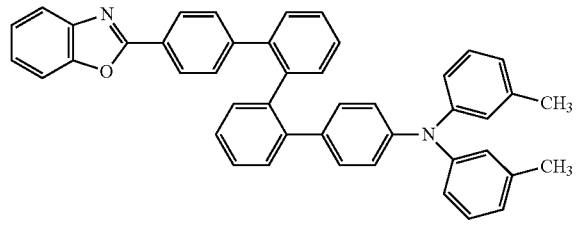
(249)

-continued
(250)
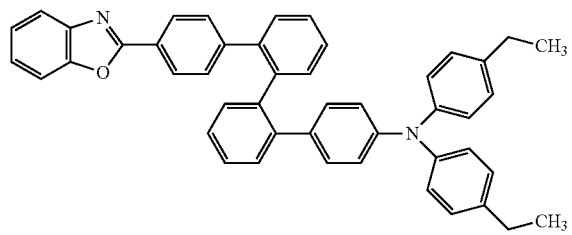
(251)
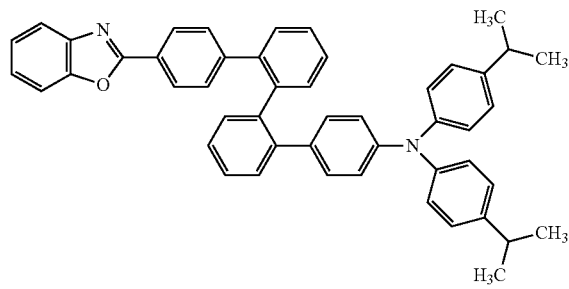
(252)
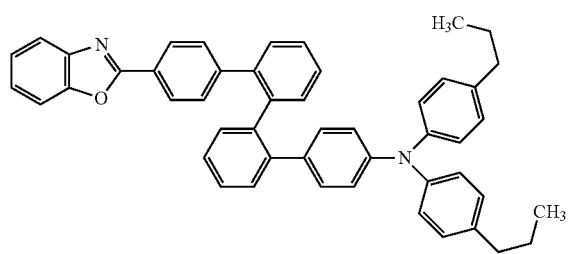
(253)
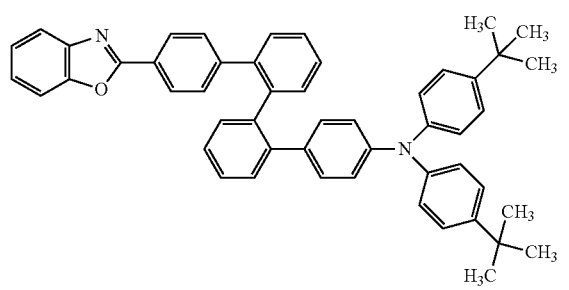
(254)
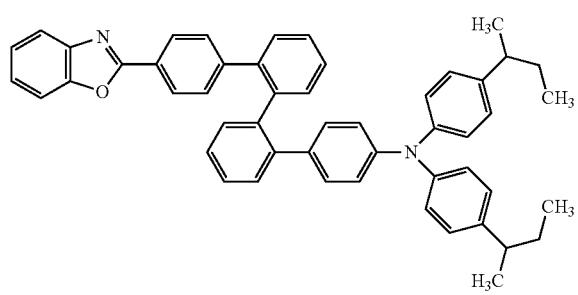
(255)
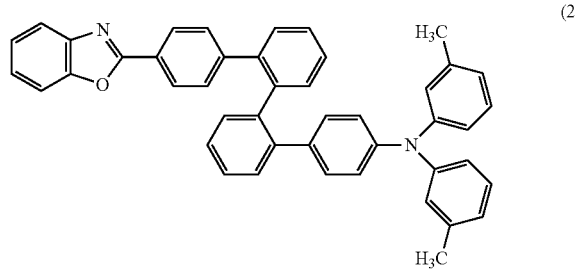
(256)
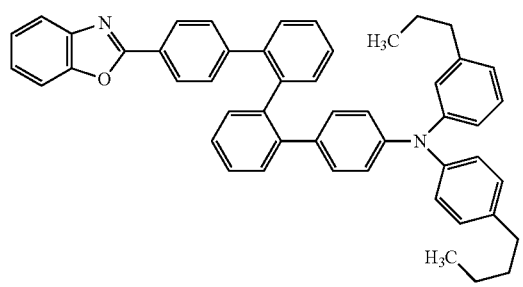
(257)
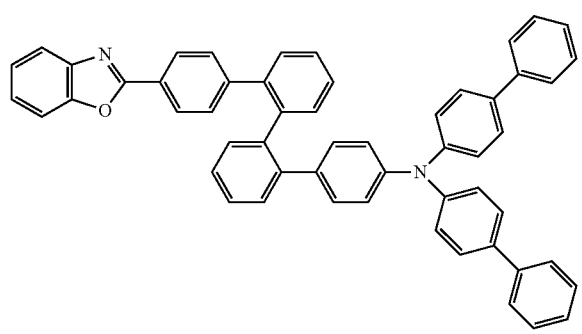
(258)
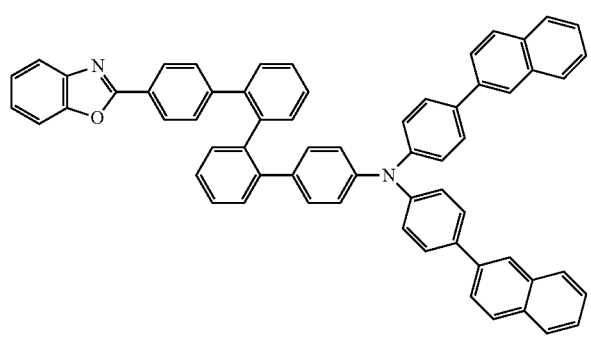
(259)
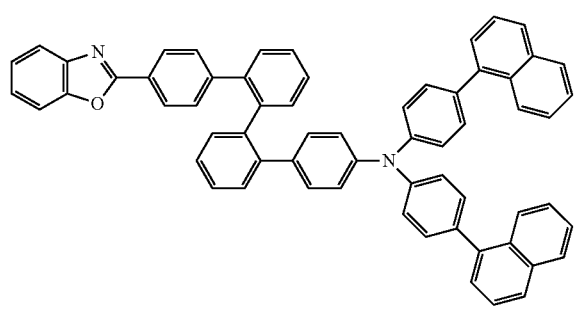

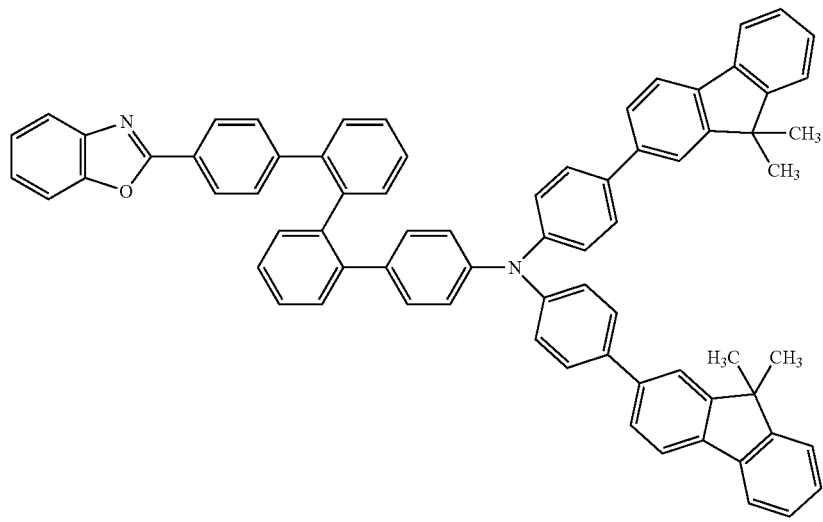
(260)
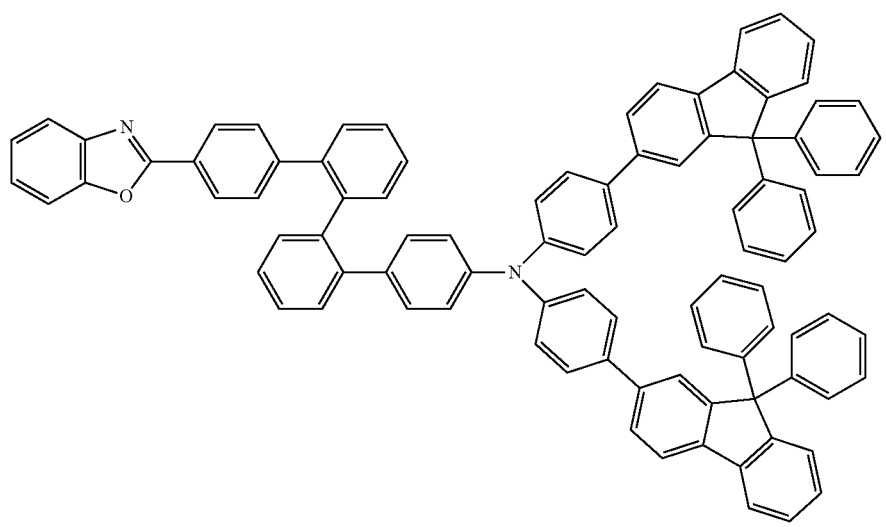
(261)
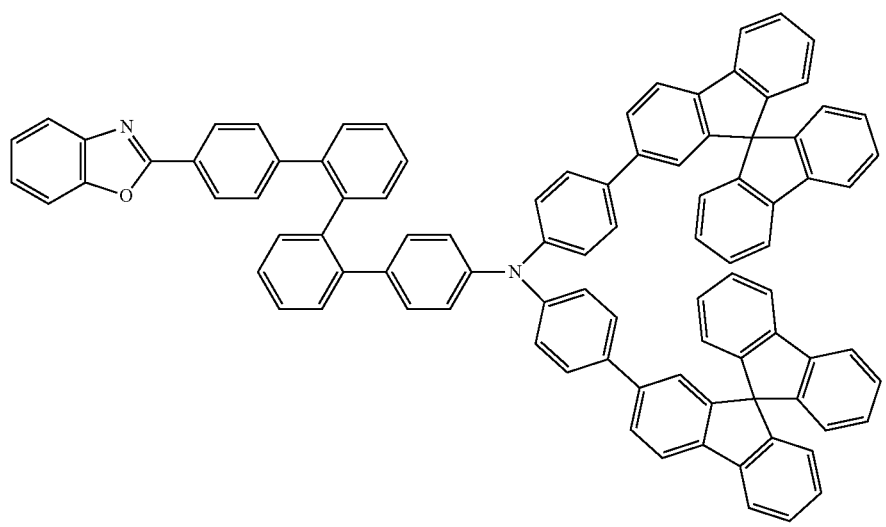
(262)

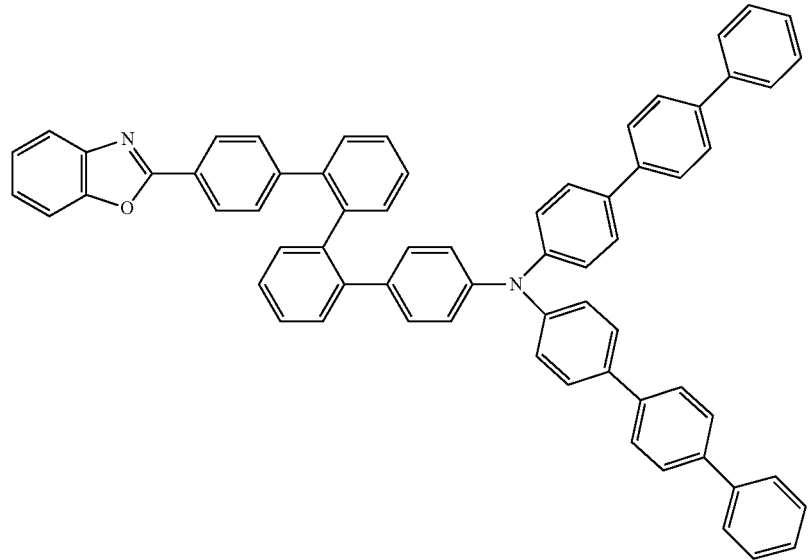
(263)
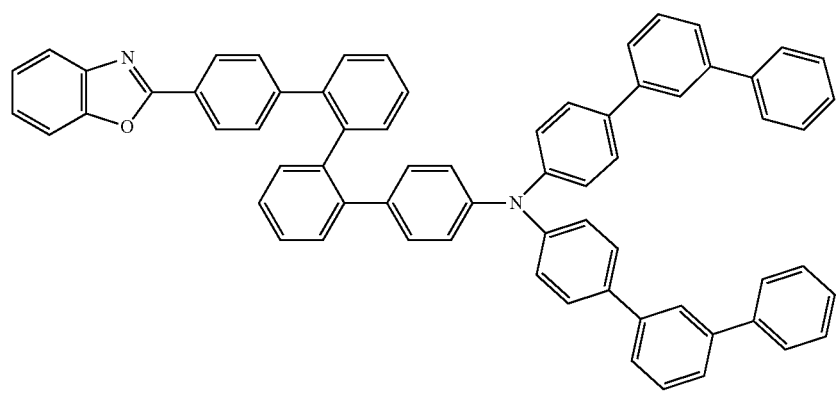
(264)
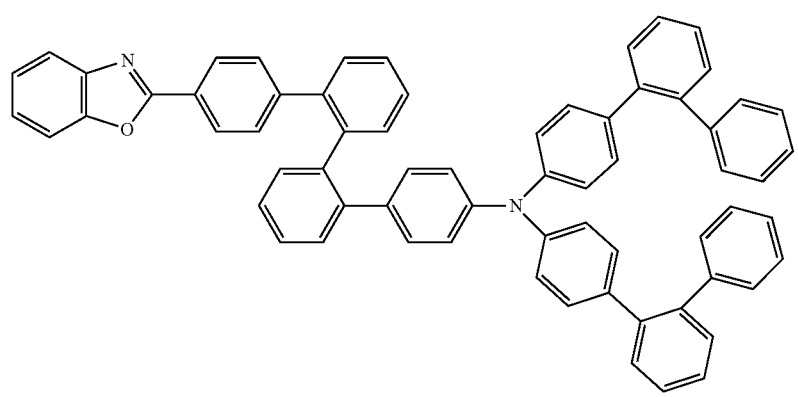
(265)

-continued
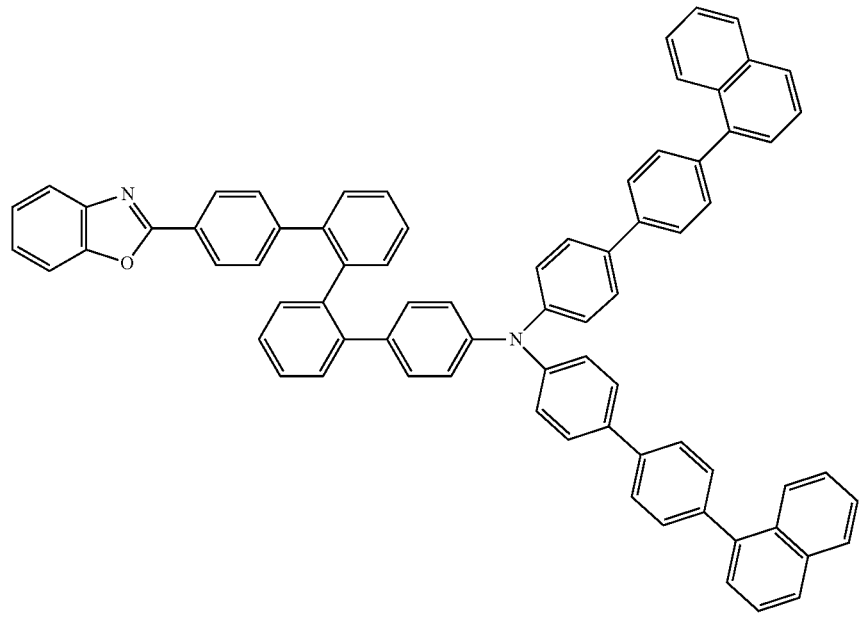
(266)
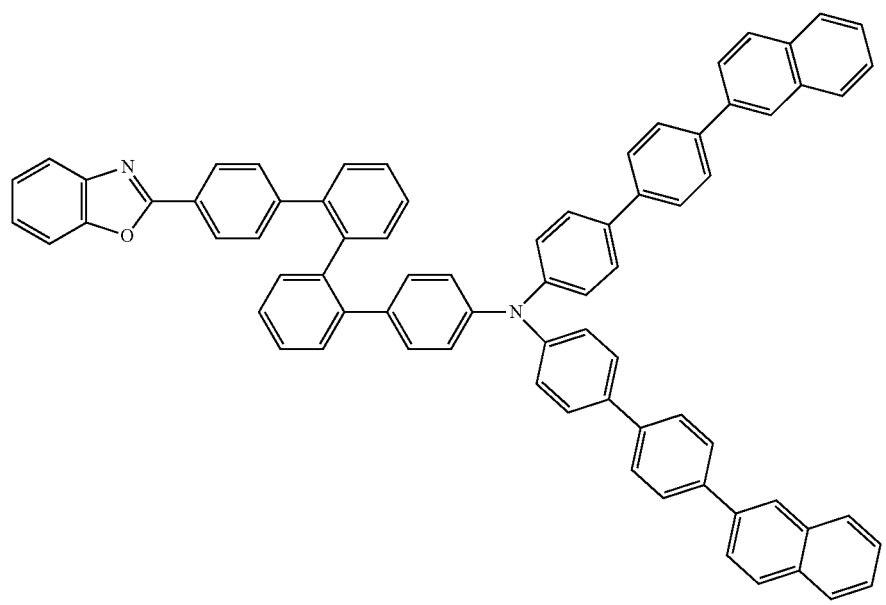
(267)
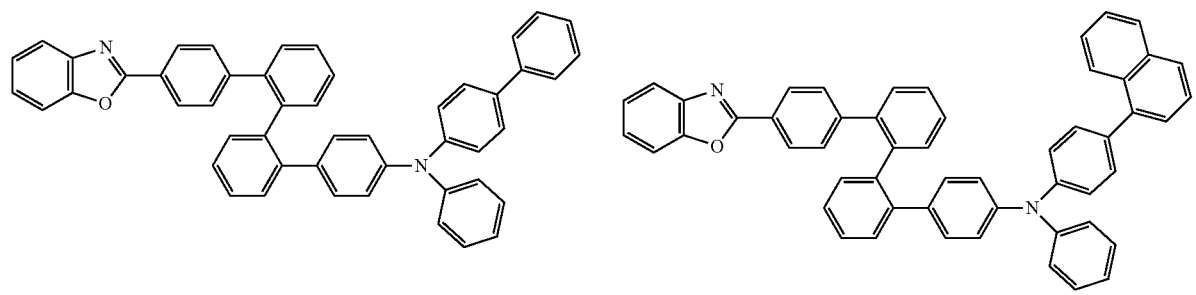
(268)
(269)

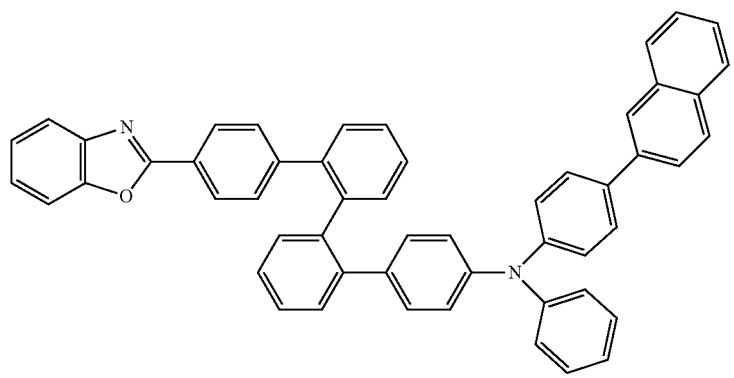
(270)
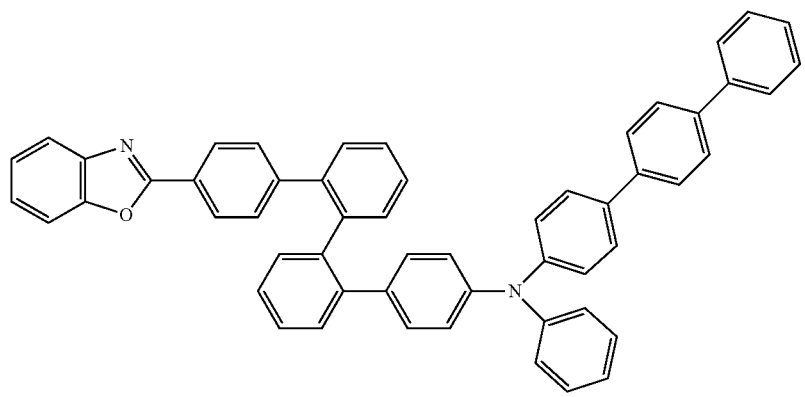
(271)
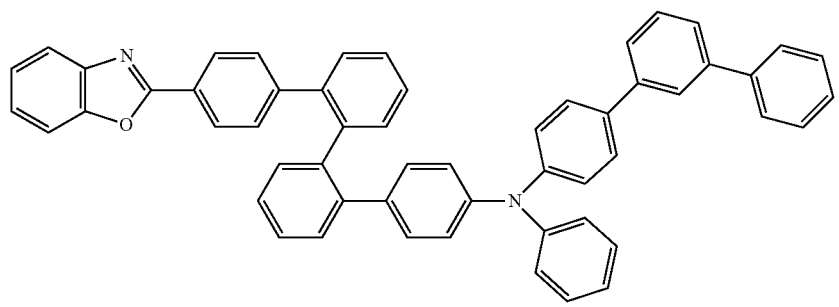
(272)
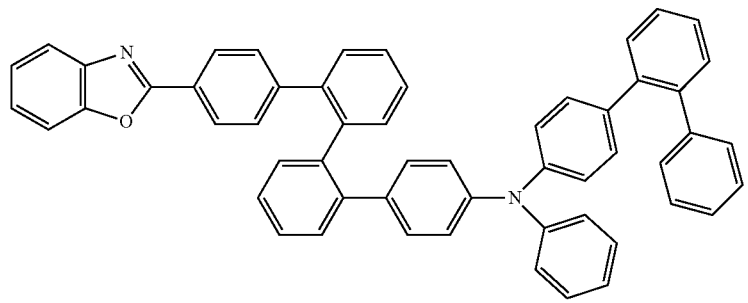
(273)

(274)
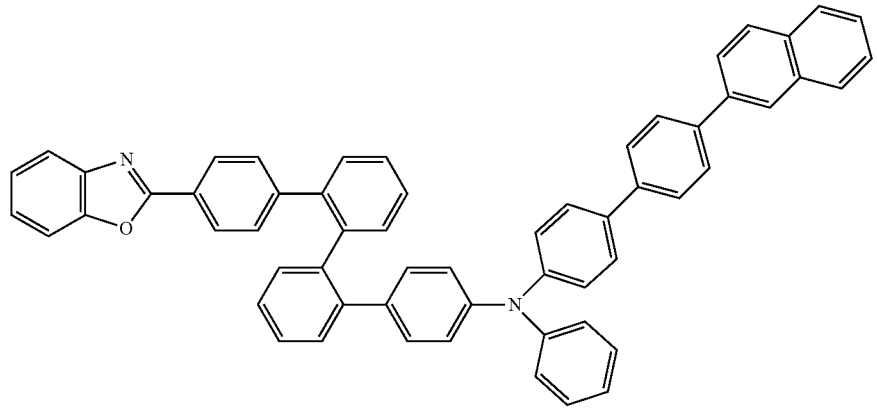
(275)
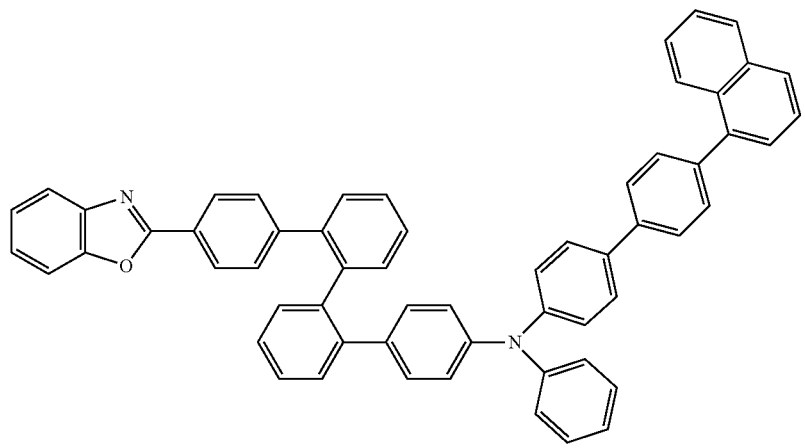
(276)
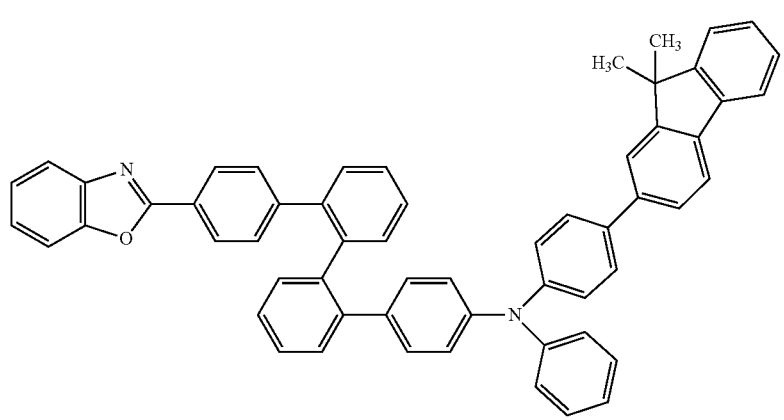

(277)
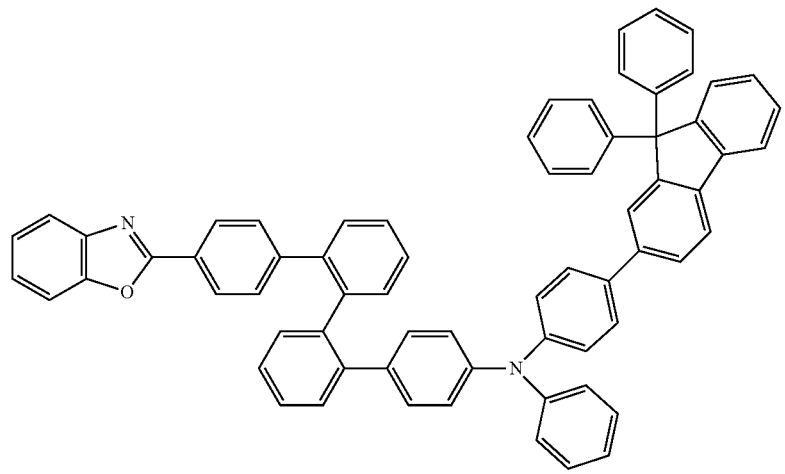
(278)
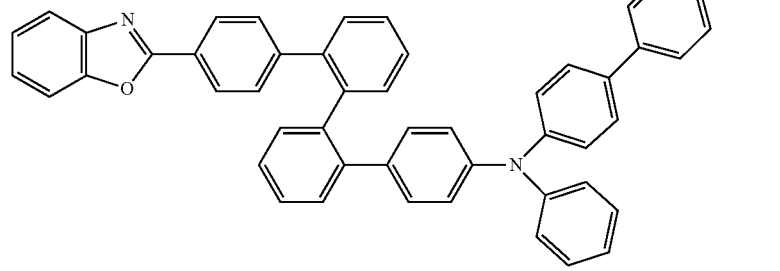
(279)
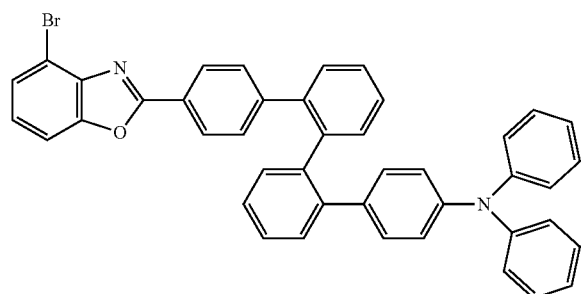
(280)
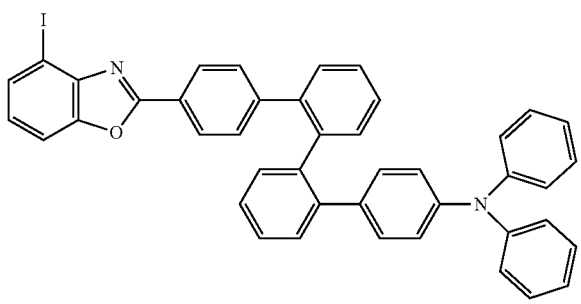
(281)
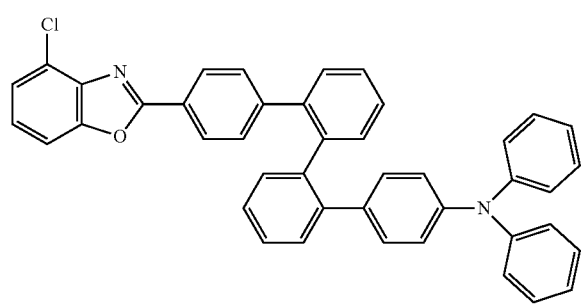
(282)
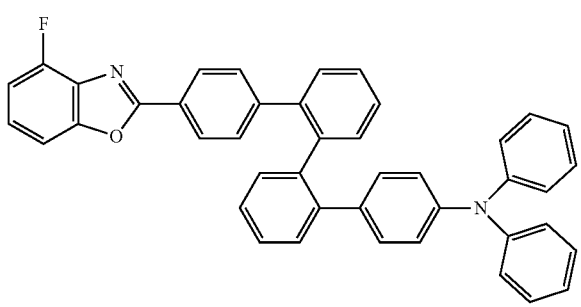

-continued
(283)
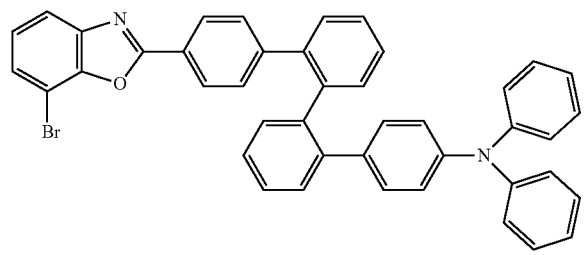
(284)
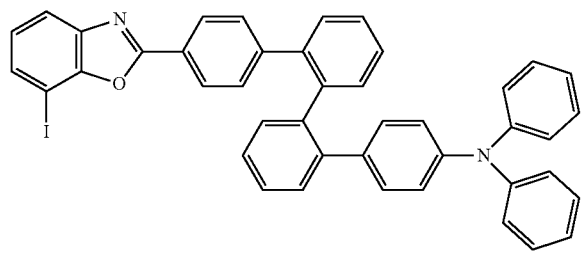
(285)
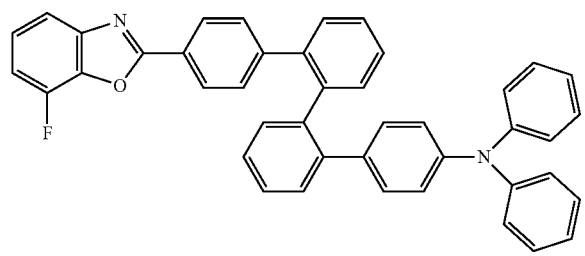
(286)
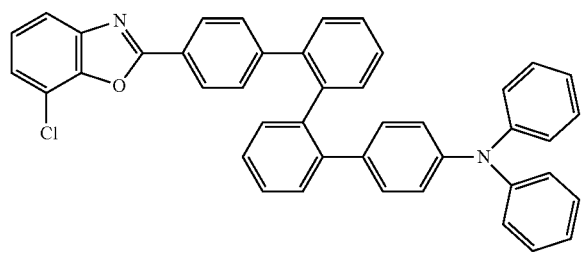
(287)
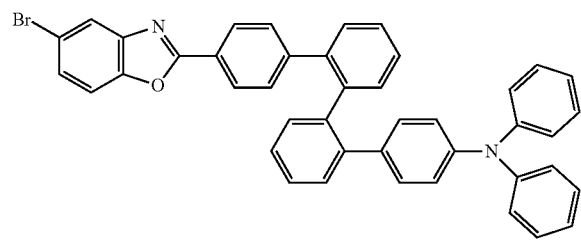
(288)
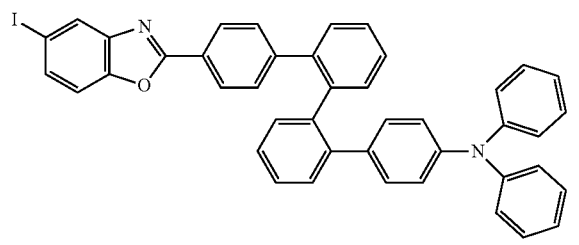
(289)
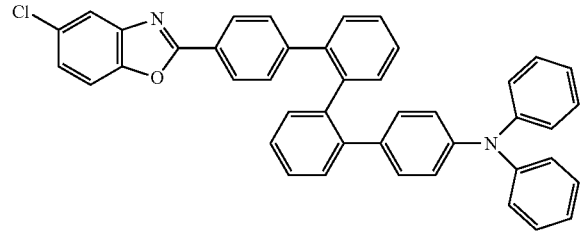
(290)
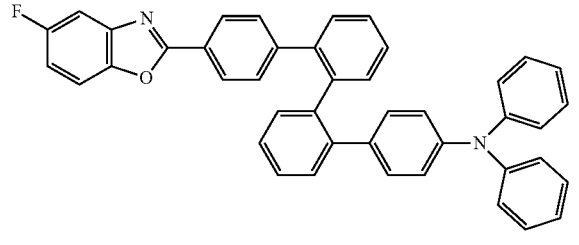
(291)
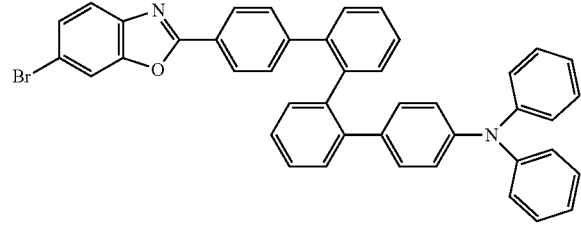
(292)
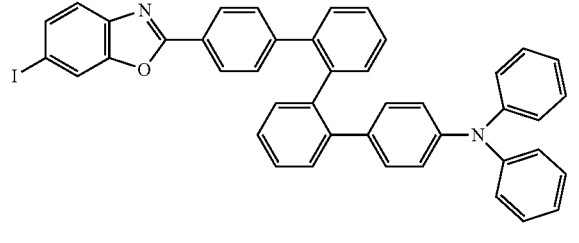
(293)
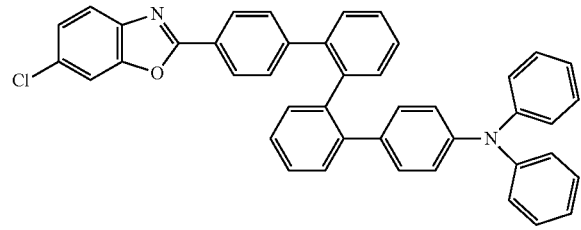
(294)
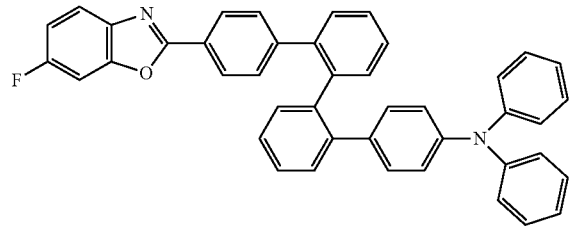

-continued
(301)
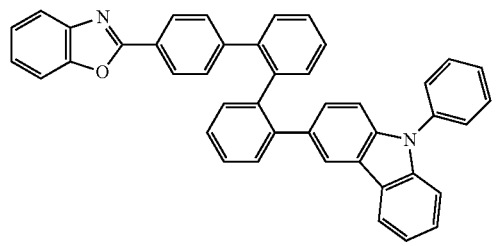
(302)
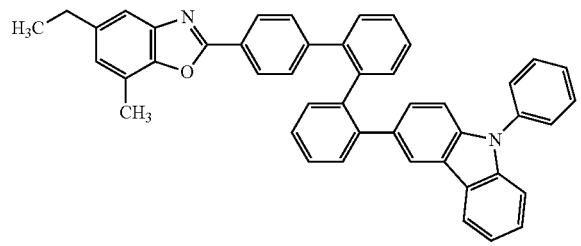
(303)
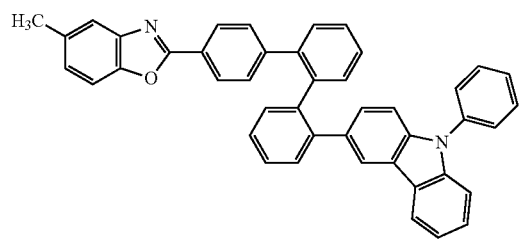
(304)
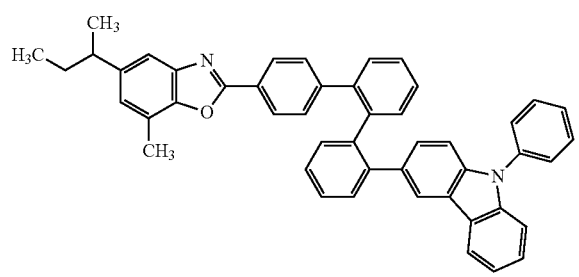
(305)
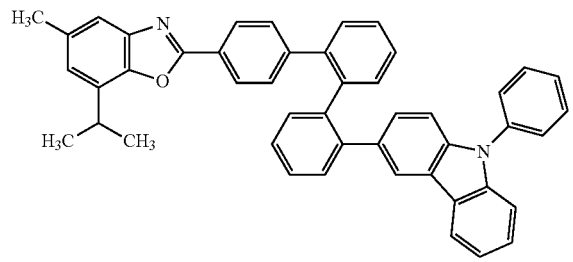
(306)
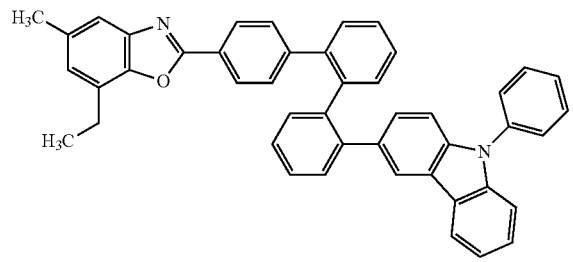
(307)
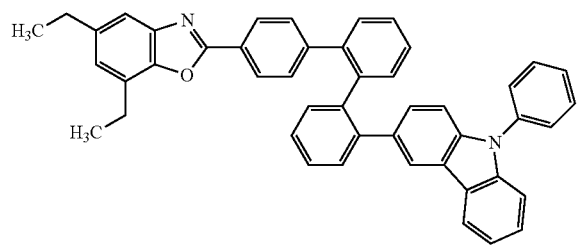
(308)
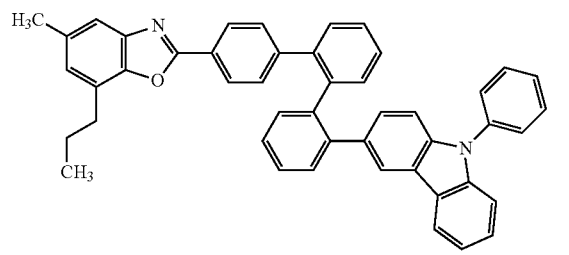
(309)
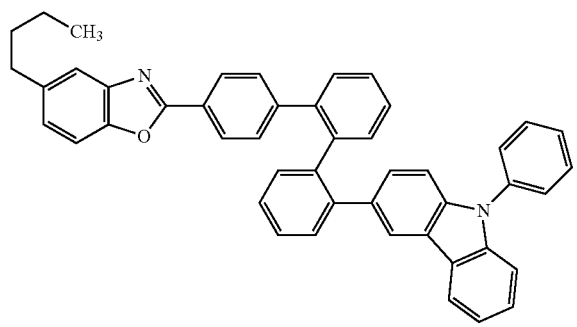
(310)
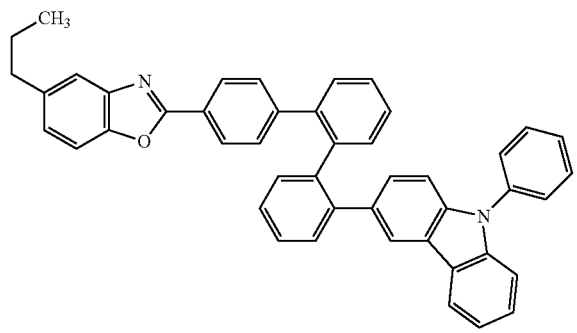

-continued
(311)
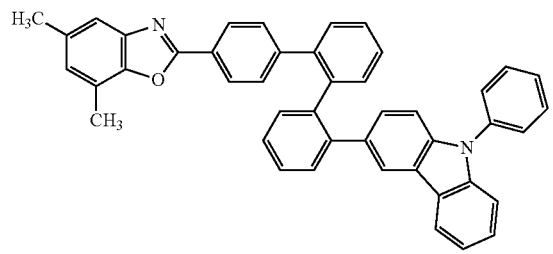
(312)
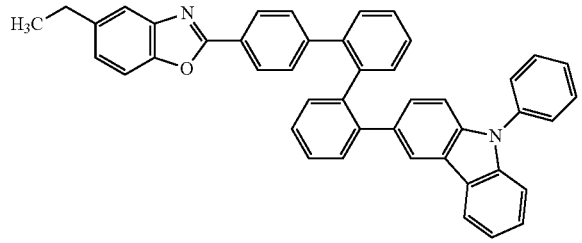
(313)
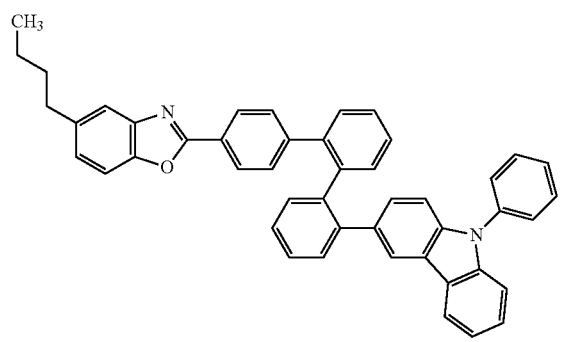
(314)
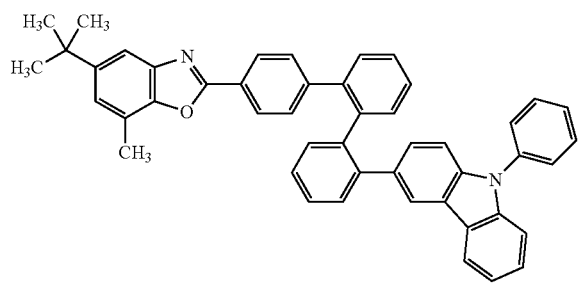
(315)
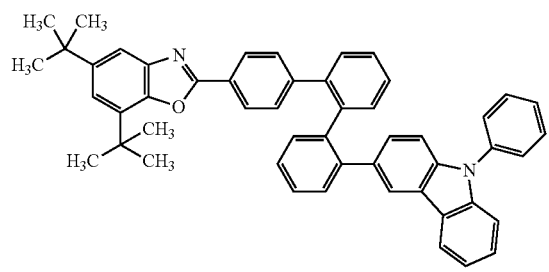
(316)
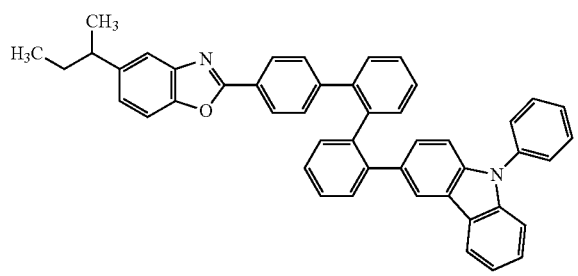
(317)
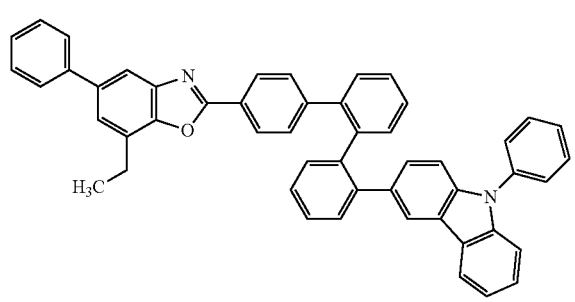
(318)
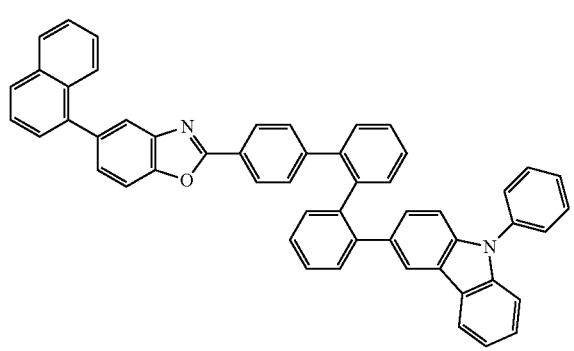
(319)
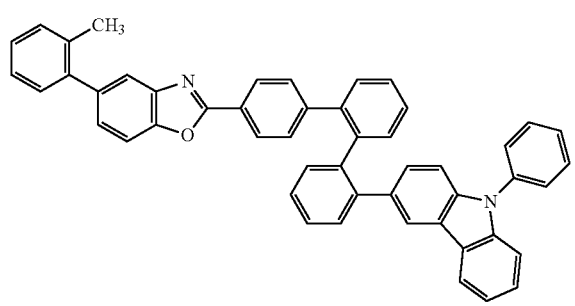
(320)
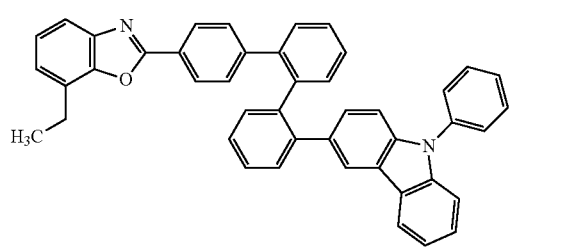

-continued
(321)
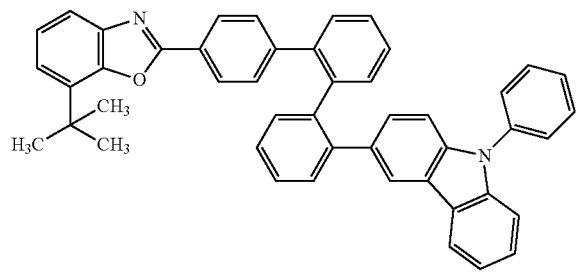
(322)
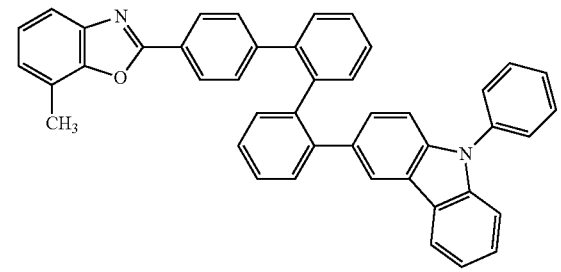
(323)
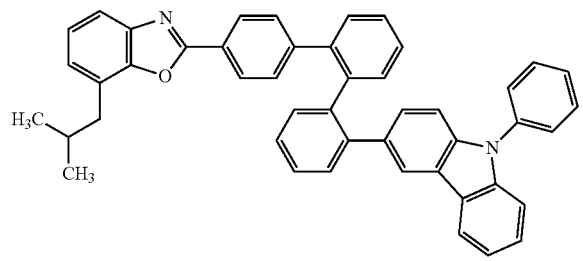
(324)
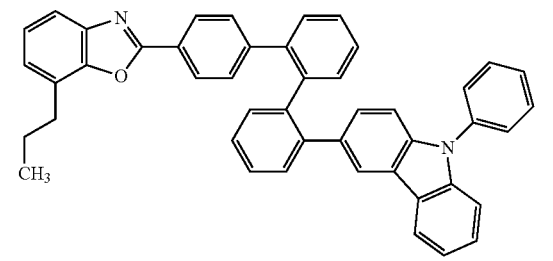
(325)
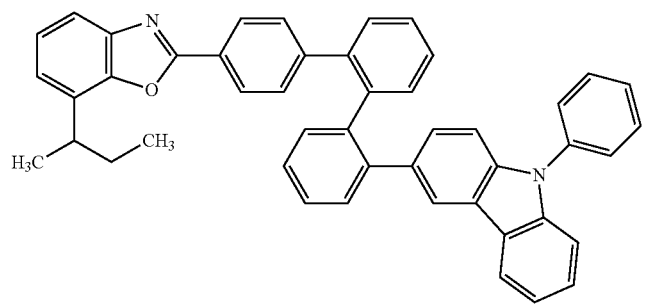
(326)
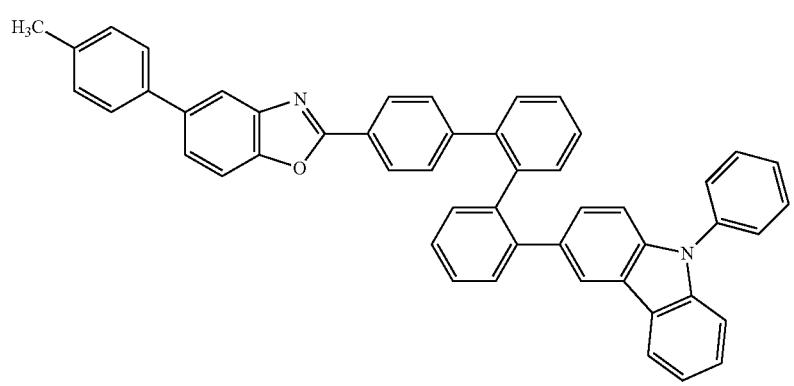
(327)
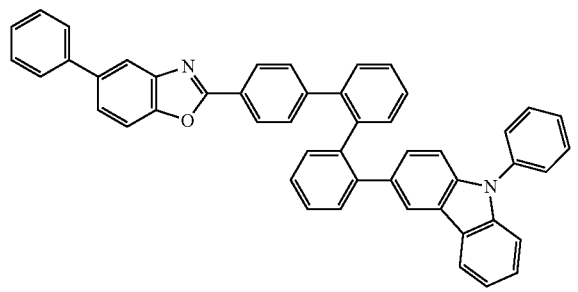
(328)
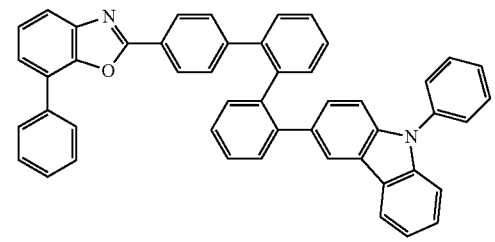

-continued
(329)
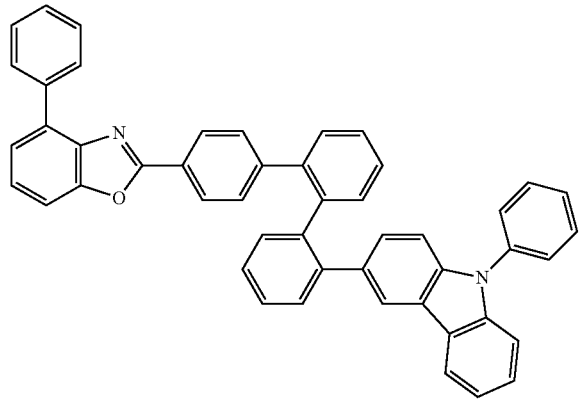
(330)
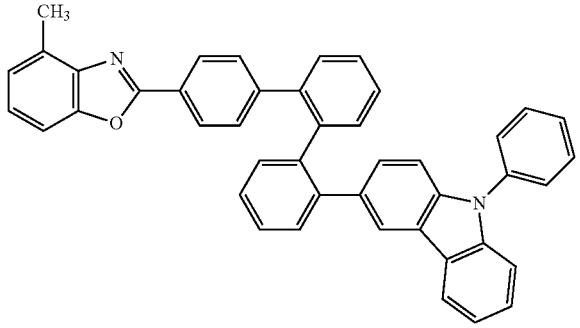
(331)
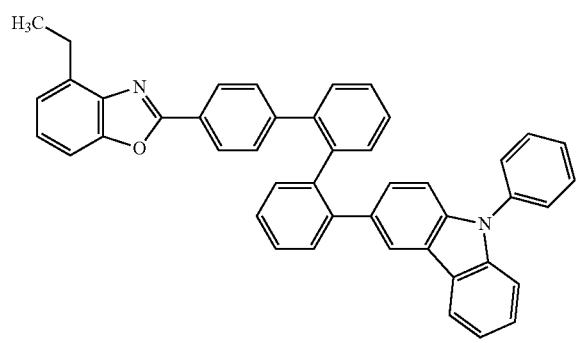
(332)
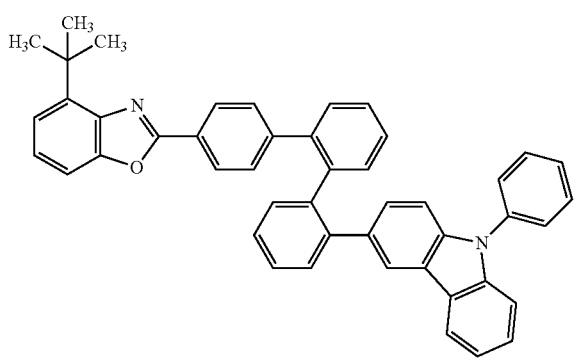
(333)
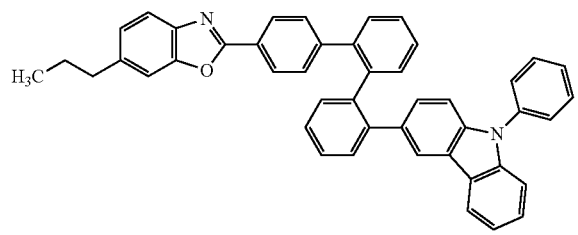
(334)
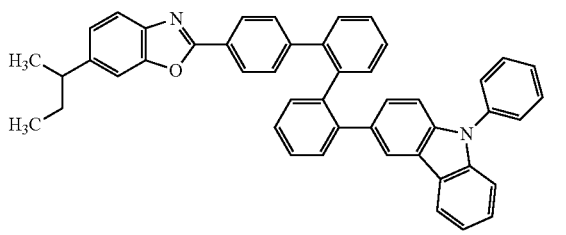
(335)
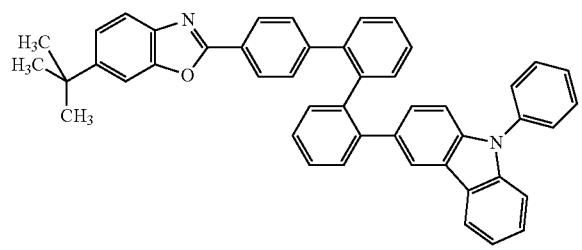
(336)
(337)
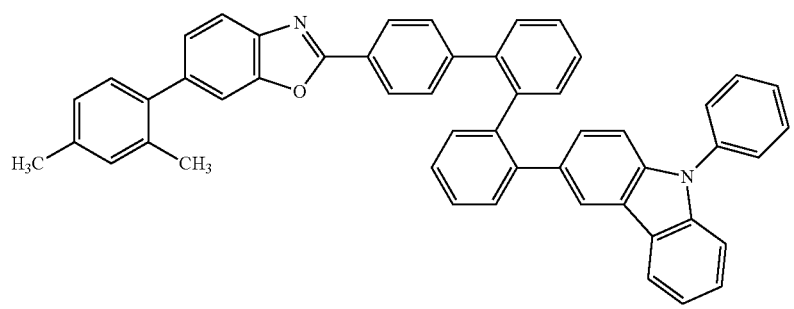

(338)
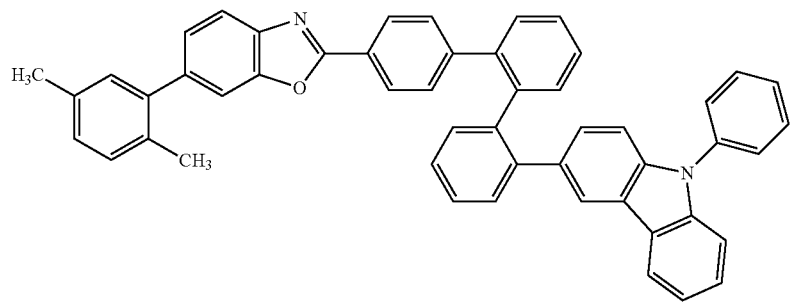
(339)
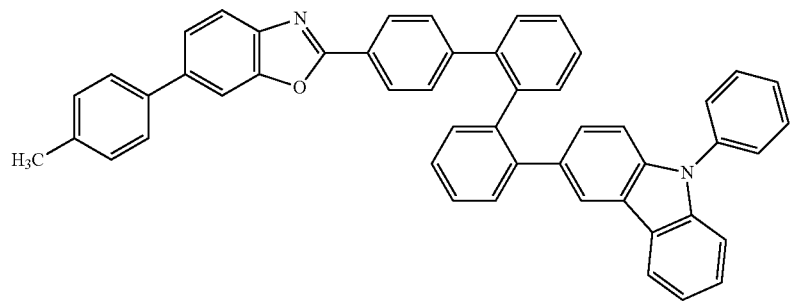
(340)
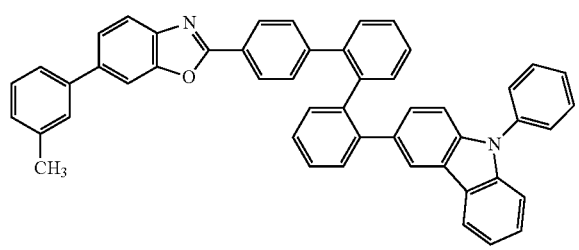
(341)
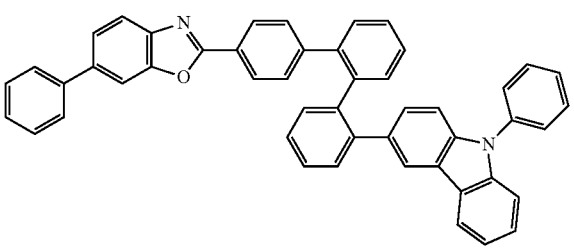
(342)
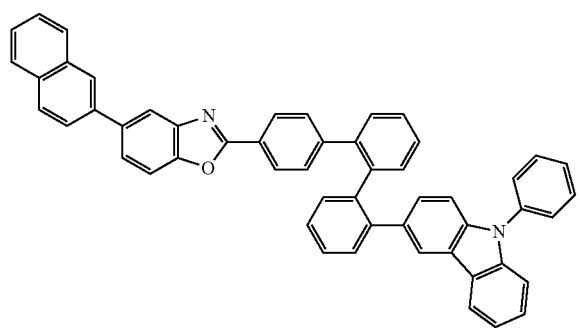
(343)
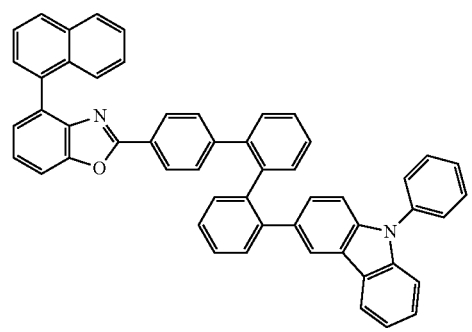
(344)
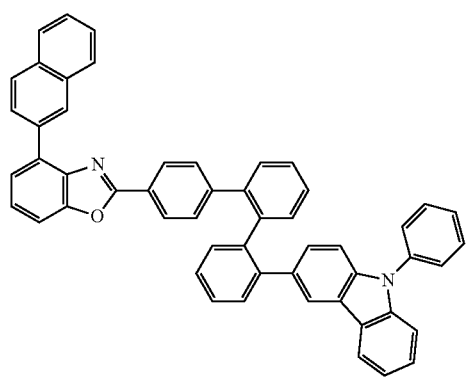
(345)
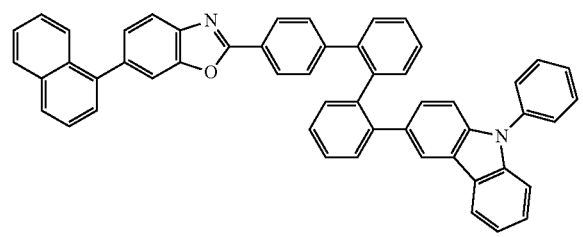

-continued
(346)
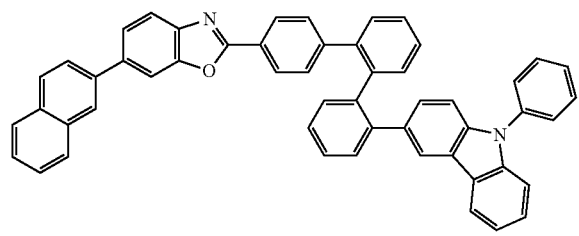
(347)
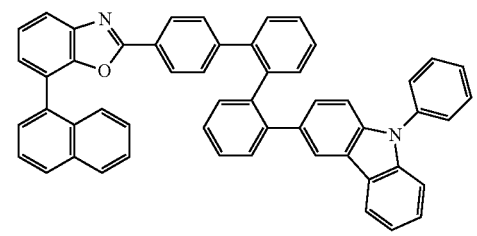
(348)
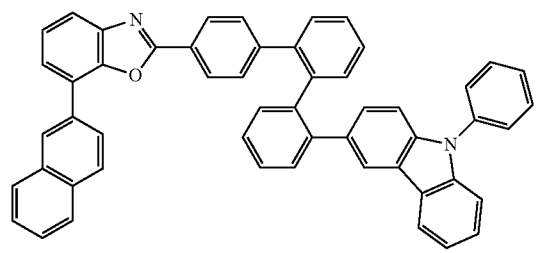
(349)
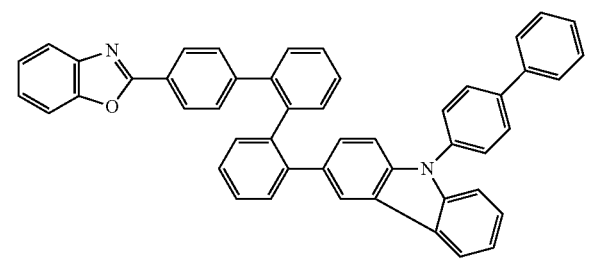
(350)
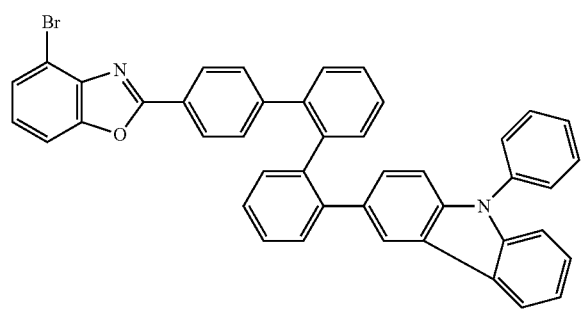
(351)
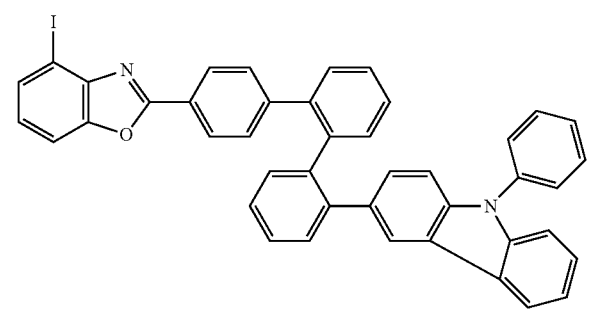
(352)
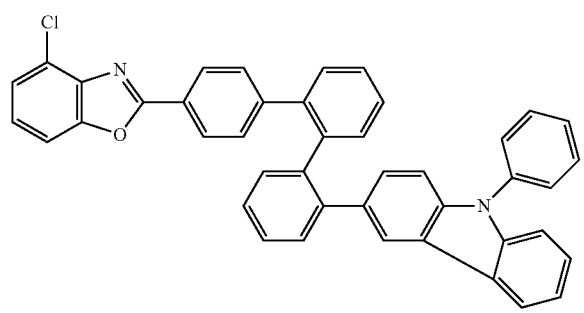
(353)
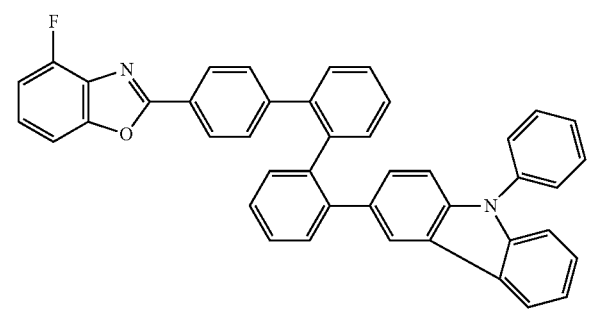
(354)
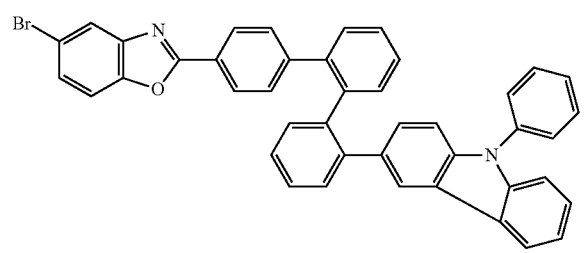
(355)
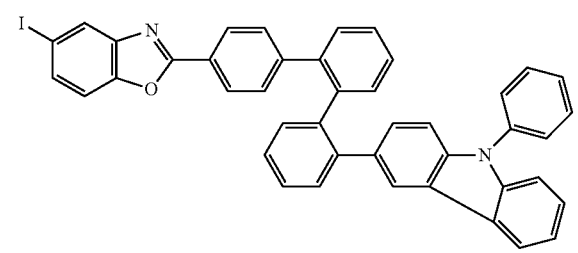

-continued
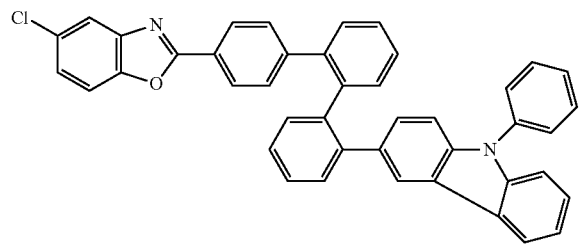
(356)
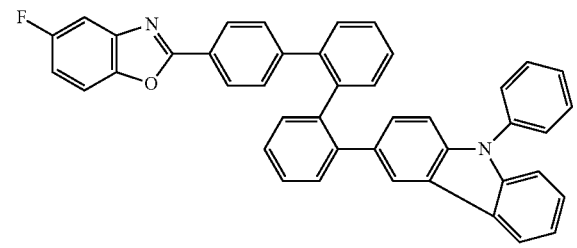
(357)
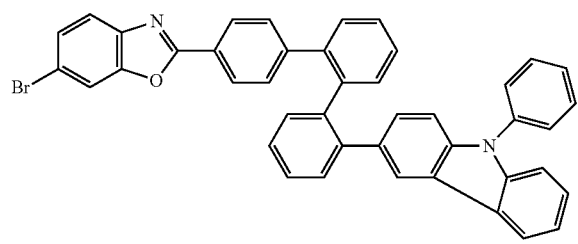
(358)
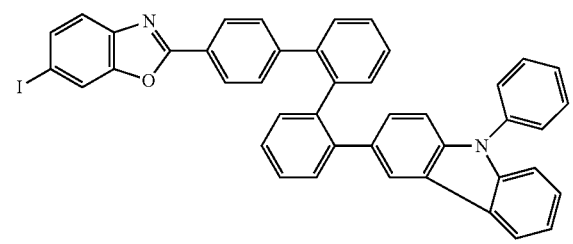
(359)
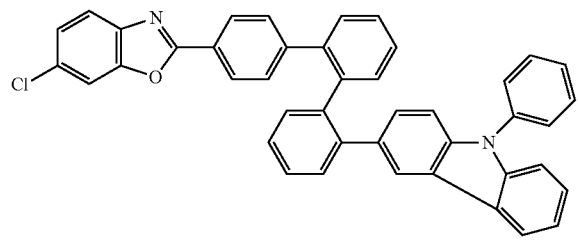
(360)
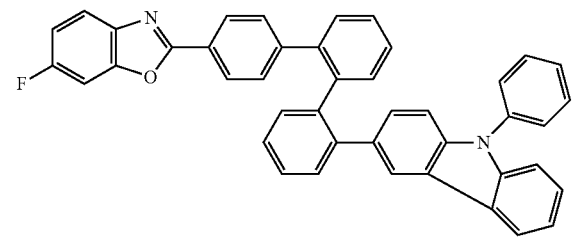
(361)
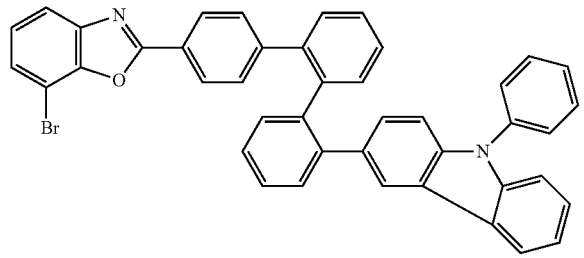
(362)
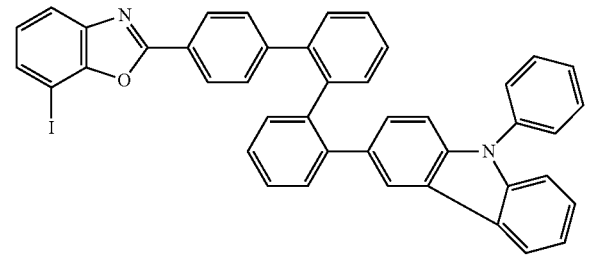
(363)
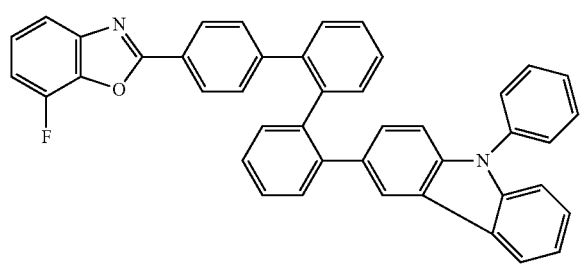
(364)
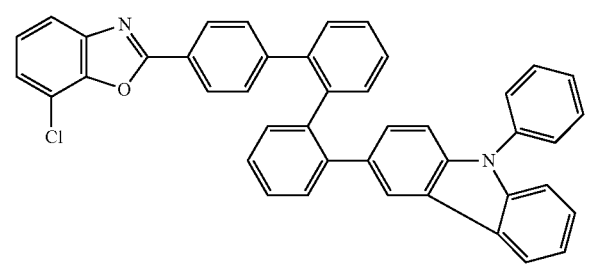
(365)

(366)
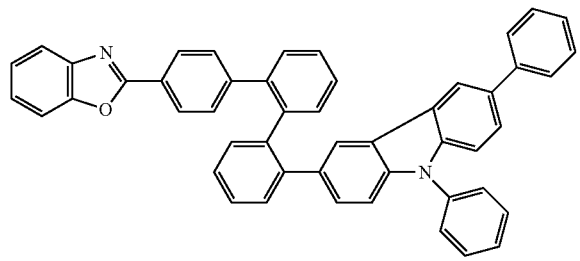
(367)
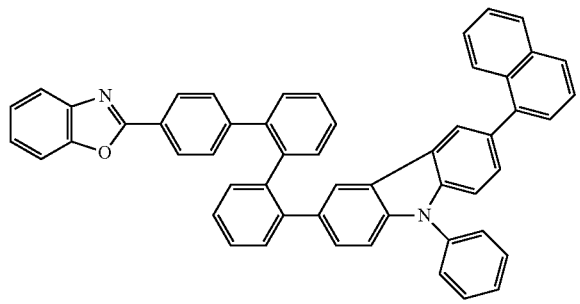
(368)
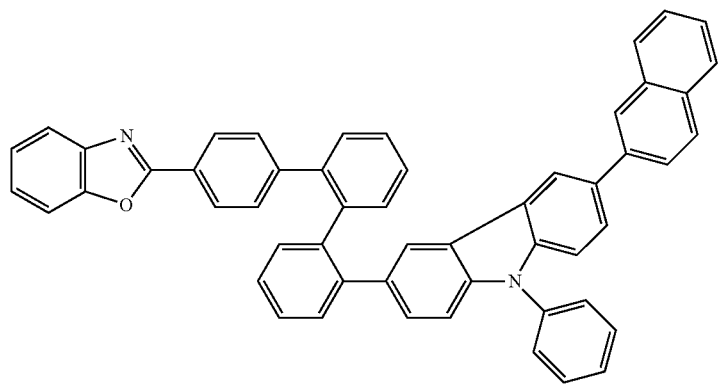
(369)
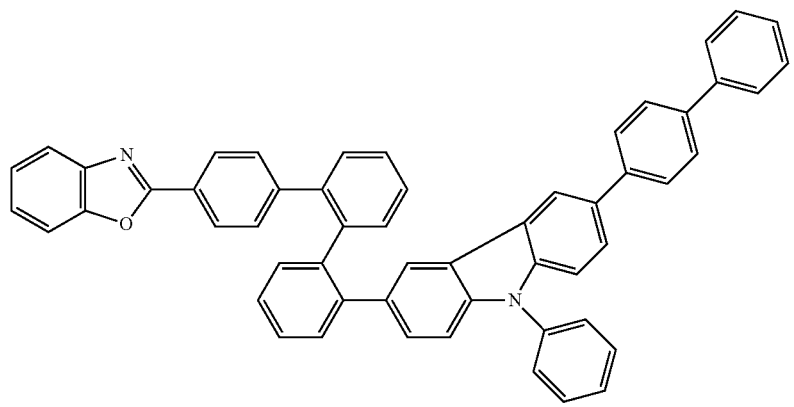
(370)
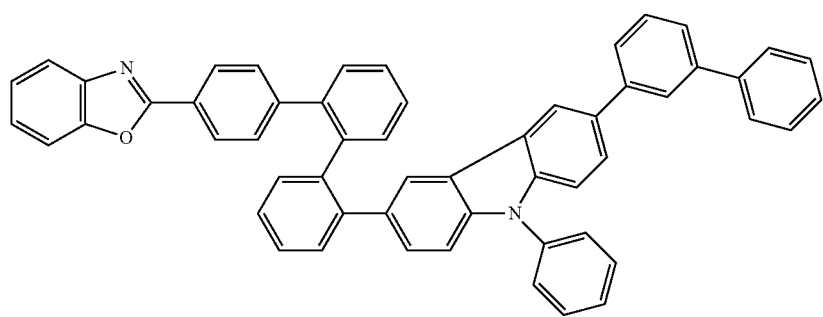

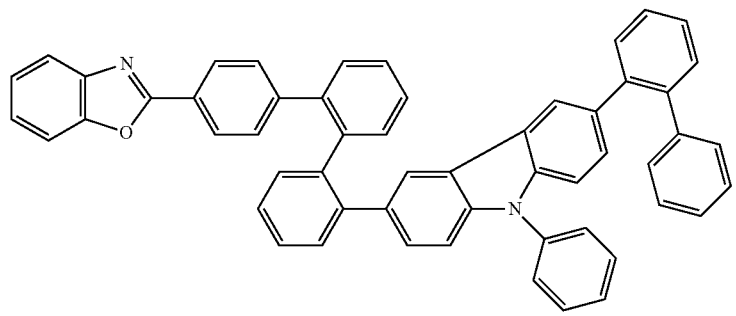
(371)
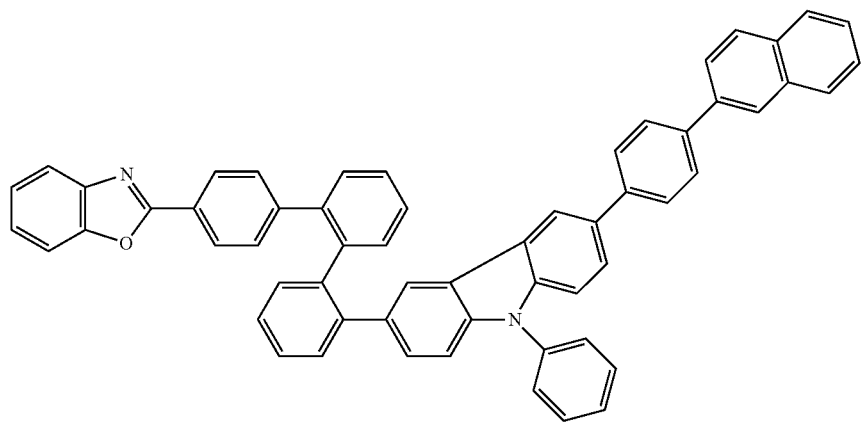
(372)
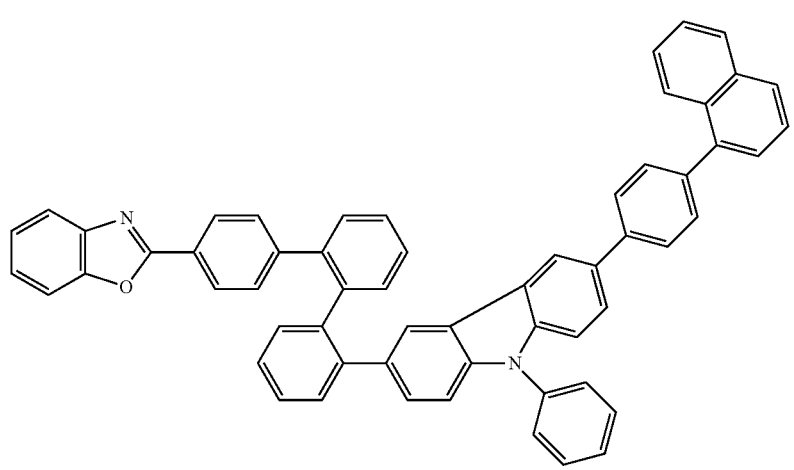
(373)

-continued
(374)
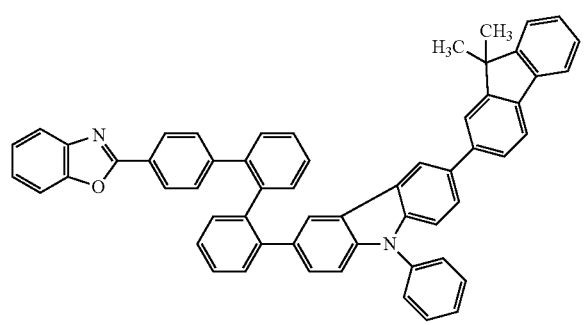
(375)
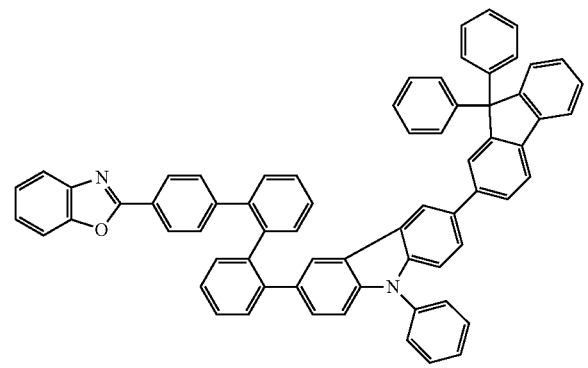
(376)
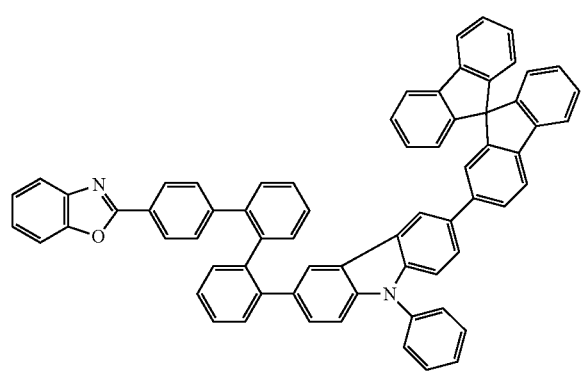
(377)
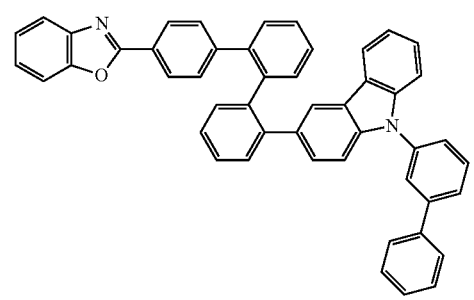
(378)
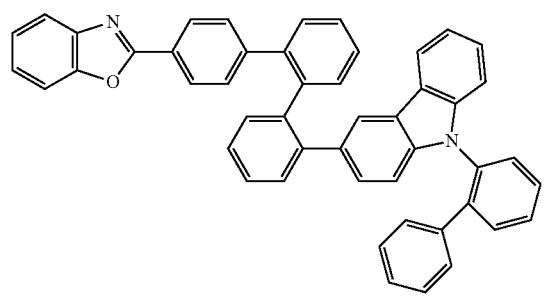
(379)
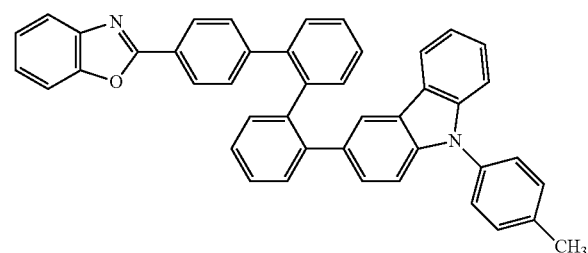
(380)
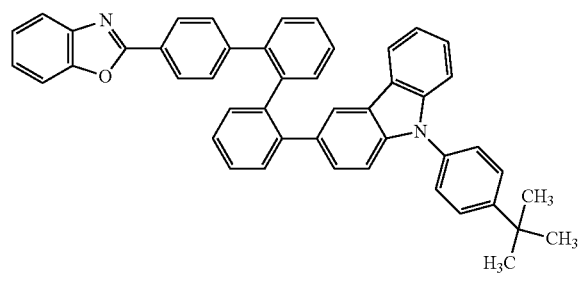
(381)
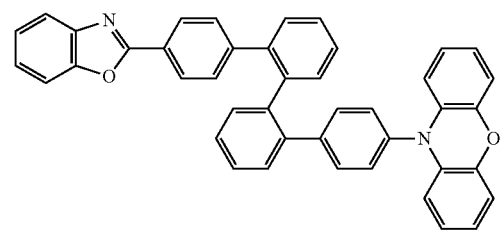
(382)
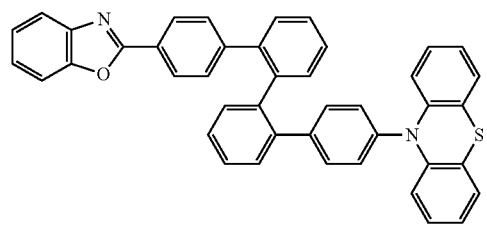
(383)
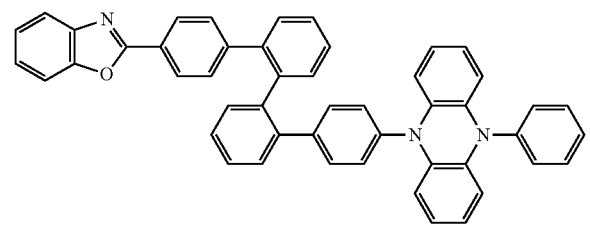

As a synthesis method of the benzoxazole derivatives of Embodiment 2, a variety of reactions can be applied. For example, the benzoxazole derivatives can be synthesized by any of synthesis reactions shown in Synthetic Schemes (1), (1-2), (2), (3), and (4).

Besides Synthesis Scheme (1), a synthesis method such as Synthesis Scheme (1-2) is given as the synthesis method of the halogenated benzoxazole compound (Compound A).

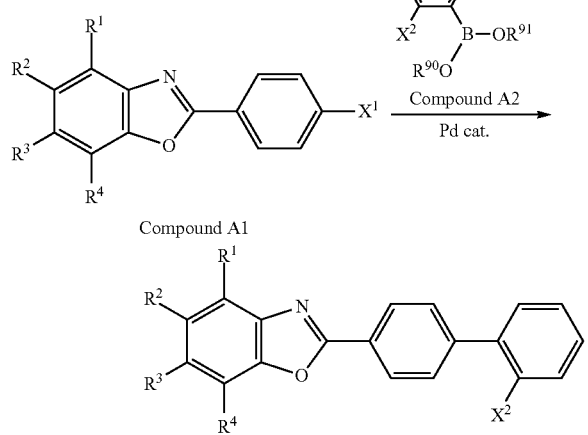

Compound A1

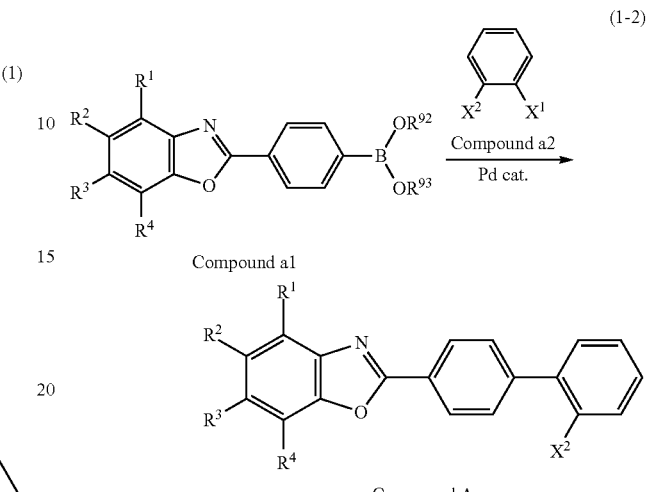

Compound A

<Synthesis of a Halogenated Benzoxazole Compound (Compound A)>

A halogenated benzoxazole compound (Compound A) can be synthesized as in Synthesis Scheme (1). In other words, the halogenated benzoxazole compound (Compound A) can be obtained in such a manner that a halogenated benzoxazole compound (Compound A1) and arylboronic acid or its derivative are coupled by the Suzuki-Miyaura coupling using a palladium catalyst.

In Synthesis Scheme (1), $X^1$ and $X^2$ represent halogen or a triflate group; as the halogen, iodine, bromine, and chlorine are given; and $X^1$ and $X^2$ may represent the same element or different elements. In addition, $R^1$ to $R^4$ represents any of hydrogen, an alkyl group having 1 to 4 carbon atoms, an unsubstituted aryl group having 6 to 10 carbon atoms, or halogen. $R^{90}$ and $R^{91}$ represent a hydrogen atom or an alkyl group having 1 to 6 carbon atoms and may be bonded to each other to form a ring when $R^{90}$ and $R^{91}$ each are an alkyl group. A palladium catalyst that can be used in Synthesis Scheme (1) may be, but not limited to, palladium(II) acetate, tetrakis(triphenylphosphine)palladium(0), or the like. A ligand of the palladium catalyst that can be used in Synthesis Scheme (1) may be, but not limited to, tri(o-tolyl)phosphine, triphenylphosphine, tricyclohexylphosphine, or the like.

Examples of a base that can be used in Synthesis Scheme (1) include, but not limited to, an organic base such as sodium tert-butoxide and an inorganic base such as potassium carbonate. As a solvent that can be used in Synthesis Scheme (1), a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethylene glycol dimethyl ether and water; or the like can be given. A mixed solvent of toluene and water or a mixed solvent of toluene, ethanol, and water is more preferable.

<Synthesis of a Halogenated Benzoxazole Compound (Compound B)>

A halogenated benzoxazole compound (Compound B) can be synthesized as in Synthesis Scheme (1-2). In other words, the halogenated benzoxazole compound (Compound B) can be obtained in such a manner that boronic acid of a halogenated benzoxazole compound or its derivative (Compound a1) and dihalogenated benzene (Compound a2) are coupled by the Suzuki-Miyaura coupling using a palladium catalyst.

In Synthesis Scheme (1-2), $X^1$ and $X^2$ represent halogen or a triflate group; as the halogen, iodine, bromine, and chlorine are given; and $X^1$ and $X^2$ may represent the same element or different elements. In addition, $R^1$ to $R^4$ represents any of hydrogen, an alkyl group having 1 to 4 carbon atoms, an unsubstituted aryl group having 6 to 10 carbon atoms, or halogen. $R^{92}$ and $R^{93}$ represent a hydrogen atom or an alkyl group having 1 to 6 carbon atoms and may be bonded to each other to form a ring when $R^{92}$ and $R^{93}$ each are an alkyl group. A palladium catalyst that can be used in Synthesis Scheme (1-2) may be, but not limited to, palladium(II) acetate, tetrakis(triphenylphosphine)palladium(0), or the like. A ligand of the palladium catalyst that can be used in the synthesis scheme (1-2) may be, but not limited to, tri(o-tolyl)phosphine, triphenylphosphine, tricyclohexylphosphine, or the like.

Examples of a base that can be used in Synthesis Scheme (1-2) include, but not limited to, an organic base such as sodium tert-butoxide and an inorganic base such as potassium carbonate. In Synthesis Scheme (1-2), as a solvent that can be used, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethylene glycol dimethyl ether and water; or the like can be given. A mixed solvent of toluene and water or a mixed solvent of toluene, ethanol, and water is more preferable.

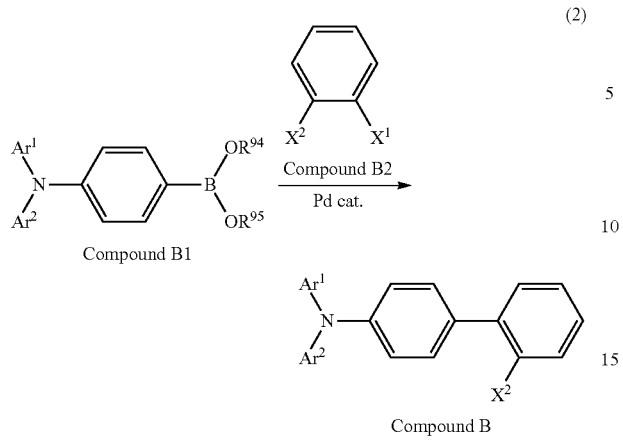

Compound B1

Compound B

<Synthesis of a Halogenated Arylamine Compound (Compound B)>

A halogenated arylamine compound (Compound B) can be synthesized as in Synthesis Scheme (2). In other words, the halogenated arylamine compound (Compound B) can be obtained in such a manner that a compound (Compound B1) in which boronic acid of a tertiary arylamine compound or its derivative and dihalogenated aryl (Compound B2) are coupled by the Suzuki-Miyaura coupling using a palladium catalyst. In Synthesis Scheme (2), $X^1$ and $X^2$ represents halogen or a triflate group; as the halogen, iodine, bromine, and chlorine are given; and $X^1$ and $X^2$ may represent the same element or different elements. In addition, $Ar^1$ and $Ar^2$ each independently represent a substituted or unsubstituted aryl group having 6 to 13 carbon atoms. $R^{94}$ and $R^{95}$ represent a hydrogen atom or an alkyl group having 1 to 6 carbon atoms and may be bonded to each other to form a ring when $R^{94}$ and $R^{95}$ each are an alkyl group.

A palladium catalyst that can be used in Synthesis Scheme (1) may be, but not limited to, palladium(II) acetate, tetrakis(triphenylphosphine)palladium(0), or the like. A ligand of the palladium catalyst that can be used in the synthesis scheme (2) may be, but not limited to, tri(o-tolyl)phosphine, triphenylphosphine, tricyclohexylphosphine, or the like. Examples of a base that can be used in Synthesis Scheme (2) include, but not limited to, an organic base such as sodium tert-butoxide and an inorganic base such as potassium carbonate. In Synthesis Scheme (2), as a solvent that can be used, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethylene glycol dimethyl ether and water; or the like can be given. A mixed solvent of toluene and water or a mixed solvent of toluene, ethanol, and water is more preferable.

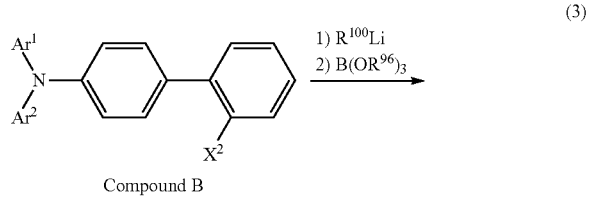

Compound B

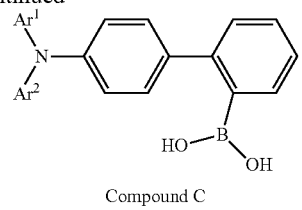

Compound C

<Synthesis of a Tertiary Arylamine Boronic Acid or its Derivative (Compound C)>

A tertiary arylamine boronic acid or its derivative (Compound C) can be synthesized as in Synthesis Scheme (3). In other words, a tertiary amine boronic acid (Compound C) can be obtained in such a manner that a tertiary amine compound (Compound B) is transformed to a boronic acid using an alkyllithium reagent and a boronic ester.

$R^{100}$ represents an alkyl group having 1 to 6 carbon atoms. $R^{96}$ represents an alkyl group having 1 to 6 carbon atoms. As the alkyllithium reagent, n-butyllithium, methyllithium, or the like can be used. As the boronic ester, trimethyl borate, isopropyl borate, or the like can be used. A boronic acid moiety of Compound C may be protected by ethylene glycol or pinacol.

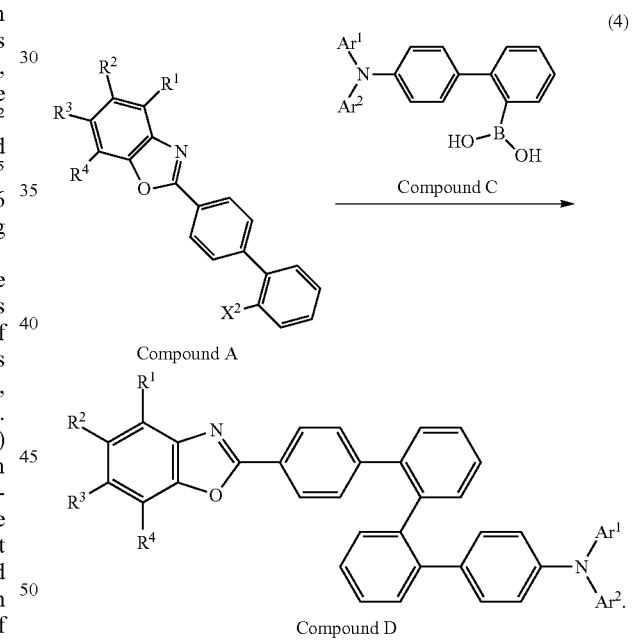

Compound A

Compound D

A benzoxazole compound (Compound D) can be synthesized as in Synthesis Scheme (4). In other words, a tertiary aryl amine compound (Compound D) can be obtained in such a manner that a halogenated benzoxazole compound (Compound A) and the boronic acid of the tertiary amine (Compound C) are coupled by the Suzuki-Miyaura coupling using a palladium catalyst. In Synthesis Scheme (4), $X^2$ represents halogen or a triflate group, and iodine, bromine, and chlorine are given as the halogen. In addition, $Ar^1$ and $Ar^2$ each independently represent any of a substituted or unsubstituted aryl group having 6 to 13 carbon atoms, and $R^1$ to $R^4$ each independently represent any of hydrogen, an alkyl group having 1 to 4 carbon atoms, an unsubstituted aryl group having 6 to 10 carbon atoms, or halogen. In Synthesis Scheme (4), an organoboron compound which is obtained by protecting the boronic acid moiety of Compound by ethylene glycol or pinacol may be used instead of Compound C.

A palladium catalyst that can be used in Synthesis Scheme (4) may be, but not limited to, palladium(II) acetate, tetrakis(triphenylphosphine)palladium(0), or the like. A ligand of the palladium catalyst that can be used in the synthesis scheme (2) may be, but not limited to, tri(o-tolyl) phosphine, triphenylphosphine, tricyclohexylphosphine, or the like. Examples of a base that can be used in Synthesis Scheme (4) include, but not limited to, an organic base such as sodium tert-butoxide and an inorganic base such as potassium carbonate. In Synthesis Scheme (4), as a solvent that can be used, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethylene glycol dimethyl ether and water; or the like can be given. A mixed solvent of toluene and water or a mixed solvent of toluene, ethanol, and water is more preferable.

In the above manner, the benzoxazole derivatives of Embodiment 2 can be synthesized.

Since the benzoxazole derivative of Embodiment 2 has a very large band gap, light emission with favorable color purity can be obtained. In addition, the benzoxazole derivative of Embodiment 2 is a bipolar material having a hole-transporting property and an electron-transporting property and has a large band gap.

Further, as for the benzoxazole derivative of Embodiment 2, a benzoxazole skeleton having an electron-transporting property and a skeleton having a hole-transporting property are bonded with a twisted quaterphenylene skeleton whose conjugation is hardly extended therebetween, whereby the molecular weight can be increased with high triplet excitation energy maintained. Thus, the benzoxazole derivative can have high electrochemical and thermal stabilities. Therefore, use of the benzoxazole derivative of Embodiment 2 makes it possible to improve reliability of a light-emitting element.

The benzoxazole derivative of Embodiment 2 can be used by itself as a host material as well as an emission center material for a light-emitting layer, and a structure is employed in which a dopant material which serves as a light-emitting substance is dispersed in the benzoxazole derivative of Embodiment 2, whereby light emission with good color purity from the dopant material can be efficiently obtained.

Further, the benzoxazole derivative of Embodiment 2 can also be used for a light-emitting substance by being dispersed as a dopant material in a material (a host material) having a larger band gap than the benzoxazole derivative of Embodiment 2, whereby light emission from the benzoxazole derivative of Embodiment 2 can be obtained.

The benzoxazole derivative of Embodiment 2 can be used as a carrier-transporting material for a functional layer of a light-emitting element. For example, the benzoxazole derivative can be used for a hole-transporting layer, a hole-injecting layer, an electron-transporting layer, or an electron-injecting layer. In this specification, a layer formed of a substance with a high carrier-injecting property or a substance with a high carrier-transporting property is also referred to as a functional layer which has functions of injecting and transporting carriers, or the like.

The benzoxazole derivative of Embodiment 2 is used for a light-emitting element, whereby a light-emitting element with high efficiency, high reliability, and a long life can be obtained.

Embodiment 3

In Embodiment 3, an oxadiazole derivative having the structure represented by General Formula (G1) will be described as an example of the organic semiconductor material of an embodiment of the present invention described in Embodiment 1.

An oxadiazole derivative of Embodiment 3 is an oxadiazole derivative represented by General Formula (OXD1).

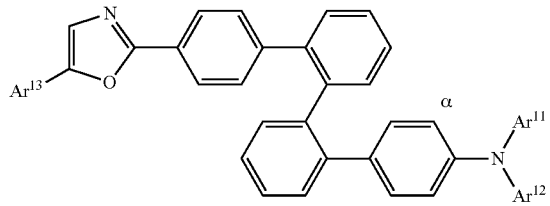

(OXD1)

In the formula, $Ar^{11}$, $Ar^{12}$, and $Ar^{13}$ represent a substituted or unsubstituted aryl group having 6 to 13 carbon atoms. In addition, $Ar^{11}$ and carbon of α, or $Ar^{11}$ and $Ar^{12}$ may be bonded to each other directly or through any of oxygen, sulfur, or nitrogen.

Further, the oxadiazole derivative of Embodiment 3 is preferably an oxadiazole derivative represented by General Formula (OXD2).

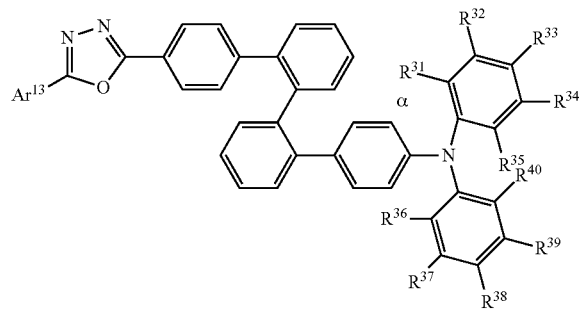

(OXD2)

In the formula, $R^{31}$ to $R^{40}$ each independently represent any of hydrogen, an alkyl group having 1 to 4 carbon atoms, or an unsubstituted aryl group having 6 to 13 carbon atoms, and $Ar^{13}$ represents a substituted or unsubstituted aryl group having 6 to 13 carbon atoms. In addition, a carbon atom of the benzene ring which is bonded to $R^{31}$ and carbon of α, or a carbon atom of the benzene ring which is bonded to $R^{35}$ and a carbon atom of the benzene ring which is bonded to $R^{40}$ may be directly bonded to each other to form a carbazole skeleton.

In General Formula (OXD1) and General Formula (OXD2), as substituents represented by $Ar^{11}$, $Ar^{12}$, and $Ar^{13}$, for example, substituents represented by Structural Formulae (15-1) to (15-16) are given. As a substituent bonded to $Ar^{11}$, $Ar^{12}$, and $Ar^{13}$, an alkyl group having 1 to 4 carbon atoms or an unsubstituted aryl group having 6 to 13 carbon atoms is given. Specifically, a methyl group, an ethyl group, a propyl group, a butyl group, a phenyl group, a naphthyl group, a fluorenyl group, and the like are given. Further, the number of substituents included in the aryl group may be either single or plural. In the case where the aryl group has two substituents, the substituents may be bonded to each other to form a ring. A ring structure may be a spiro ring.

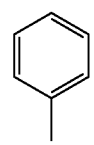
(15-1)

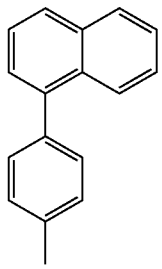
(15-2)

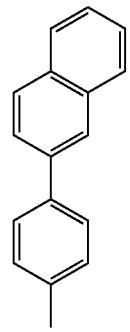
(15-3)

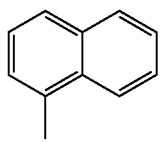
(15-4)

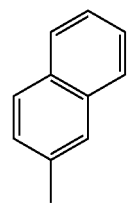
(15-5)

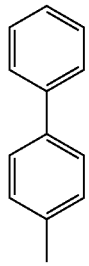
(15-6)

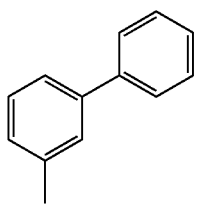
(15-7)

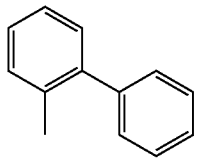
(15-8)

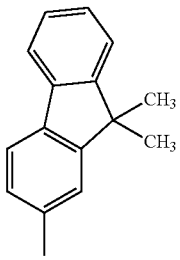
(15-9)

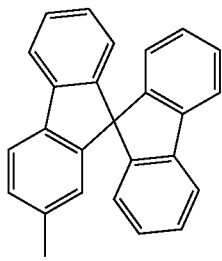
(15-10)

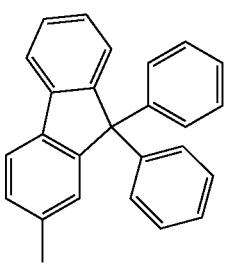
(15-11)

-continued (15-12)
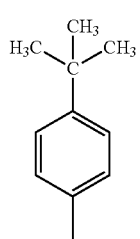

(15-13)
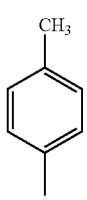

(15-14)
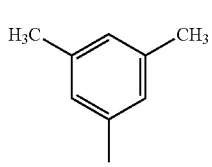

(15-15)
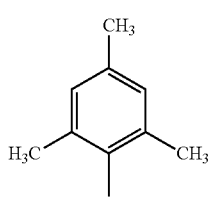

(15-16)
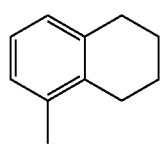

Note that in General Formula (OXD2), $Ar^{13}$ is preferably an aryl group having an alkyl group having 1 to 4 carbon atoms, or an unsubstituted phenyl group or naphthyl group having 6 to 10 carbon atoms as shown in Structural Formulae (15-4) to (15-8) and (15-12) to (15-15), and is more preferably an unsubstituted phenyl group or naphthyl group as shown in Structural Formulae (15-1), (15-4), and (15-5).

Further, in General Formula (OXD2), as substituents represented by $R^{31}$ to $R^{40}$, for example, substituents represented by Structural Formulae (12-1) to (12-25) are given.

(12-1)
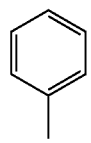

-continued (12-2)
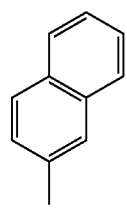

(12-3)
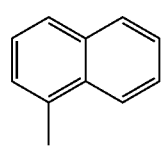

(12-4)
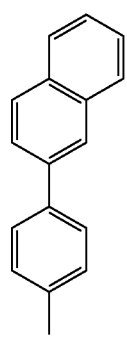

(12-5)
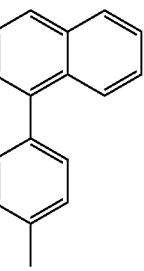

(12-6)
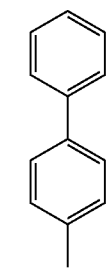

(12-7)
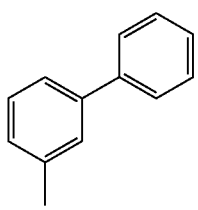

(12-8)
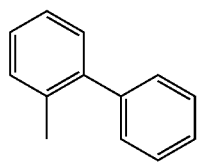
(12-9)
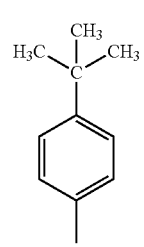
(12-10)
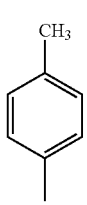
(12-11)
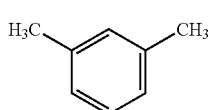
(12-12)
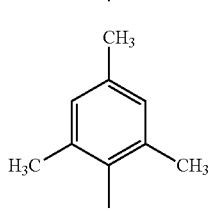
(12-13)
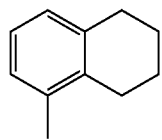
(12-14)
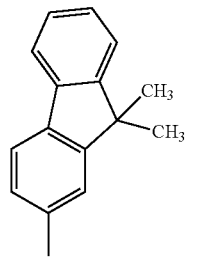
(12-15)
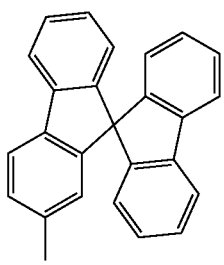
(12-16)
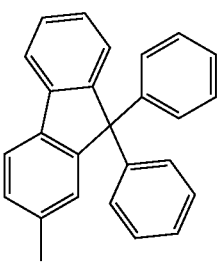
(12-17)
H
(12-18)
CH₃
(12-19)
(12-20)
(12-21)
(12-22)
(12-23)
(12-24)
(12-25)
For example, specific examples of the oxadiazole derivatives of Embodiment 3 include, but not limited to, oxadiazole derivatives represented by Structural Formulae (421) to (533).

| 113 | 114 |
|---|---|
| (421) 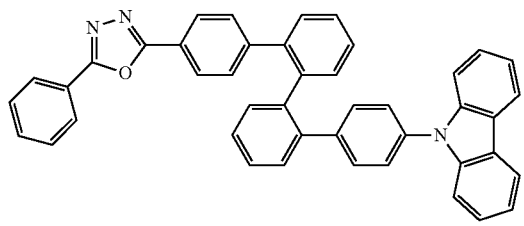 | (422) 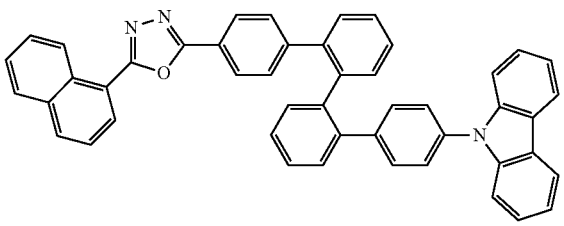 |
| (423) 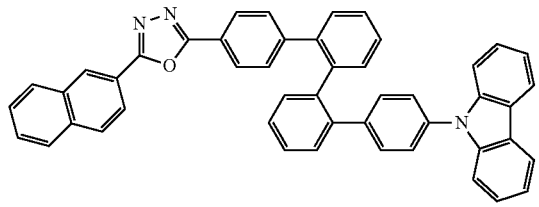 | (424) 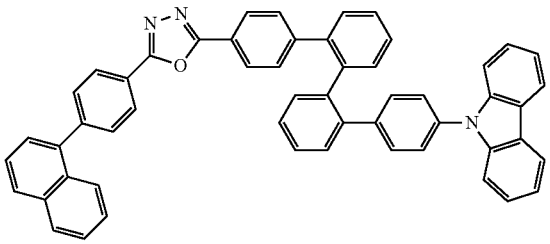 |
| (425) 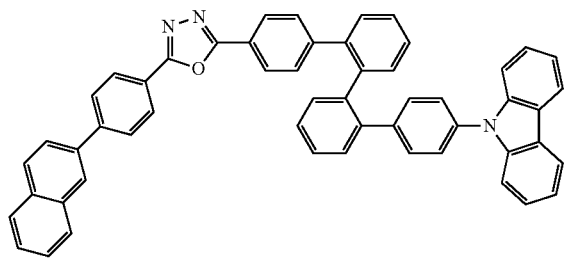 | (426) 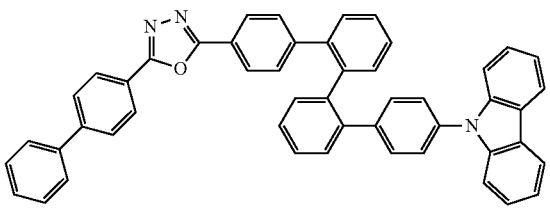 |
| (427) 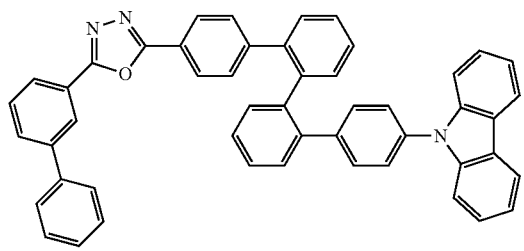 | (428) 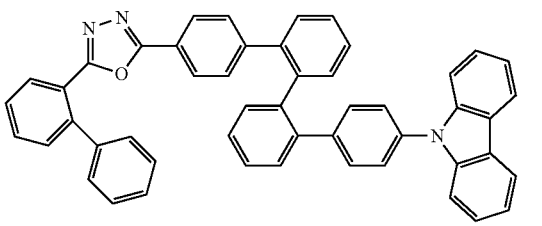 |
| (429) 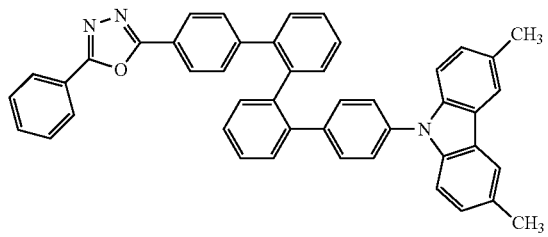 | (430) 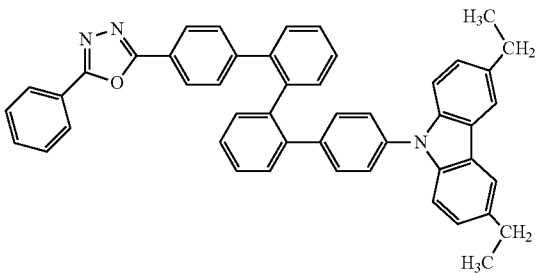 |
| (431) 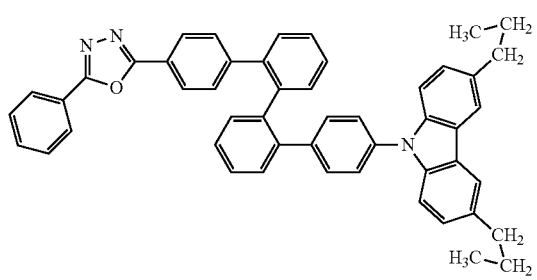 | (432) 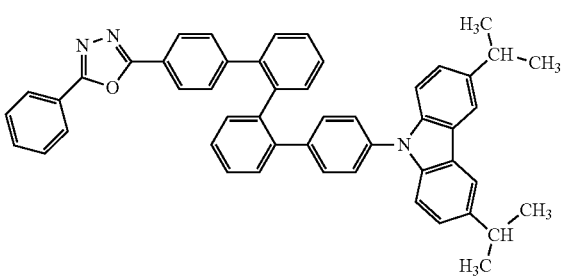 |

-continued
(433)
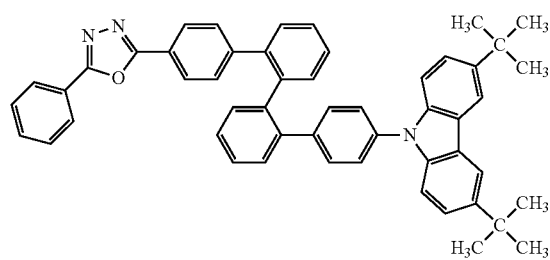
(434)
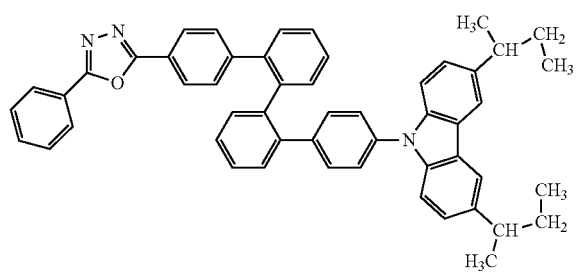
(435)
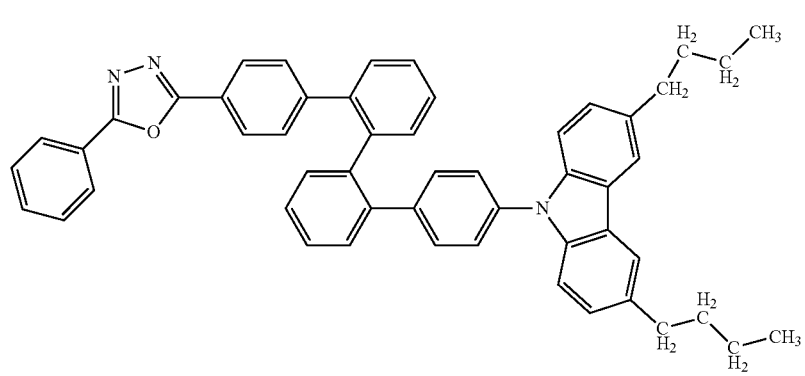
(436)
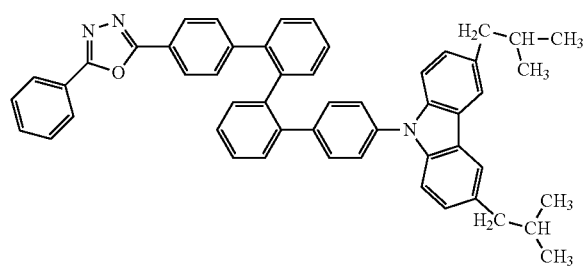
(437)
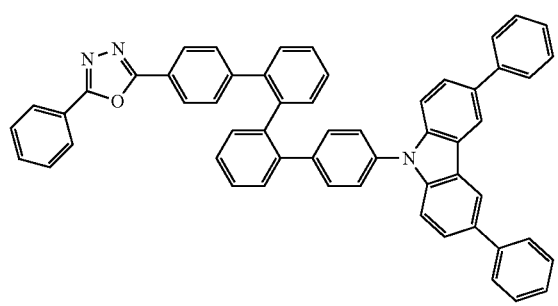
(438)
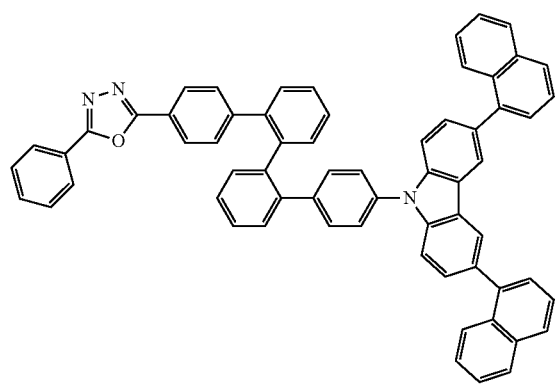
(439)
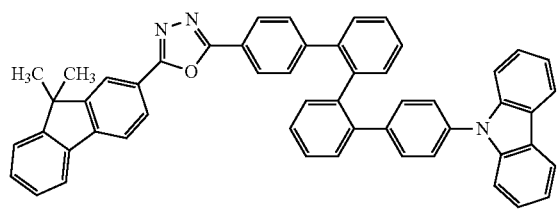

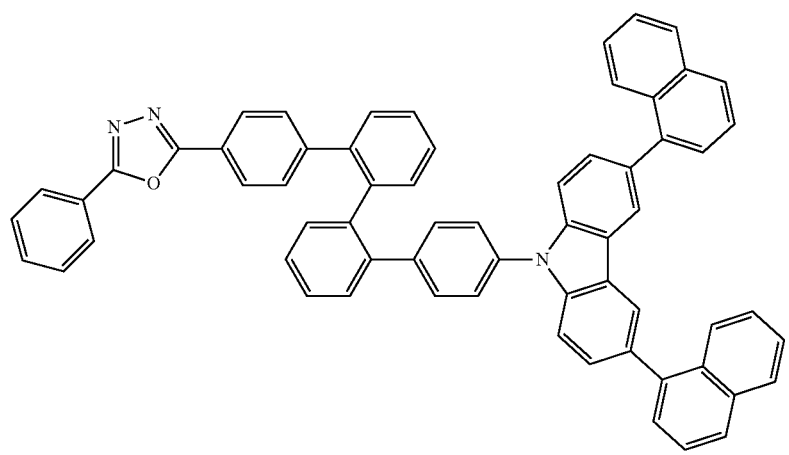
(440)
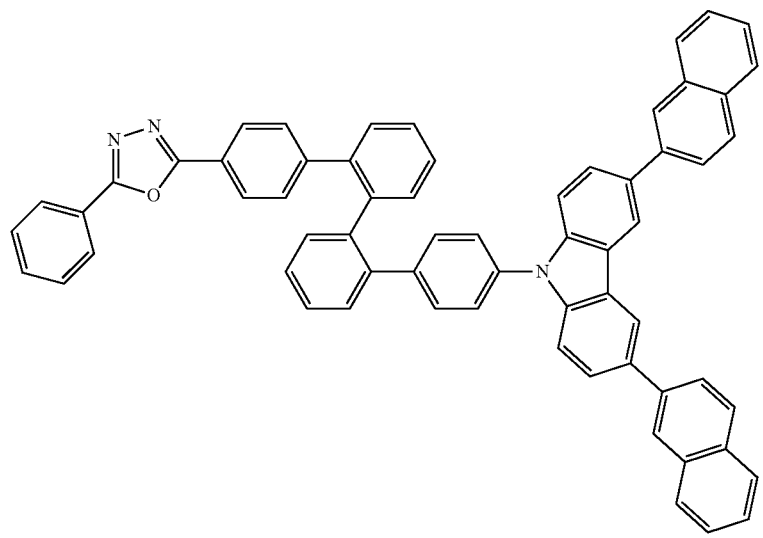
(441)
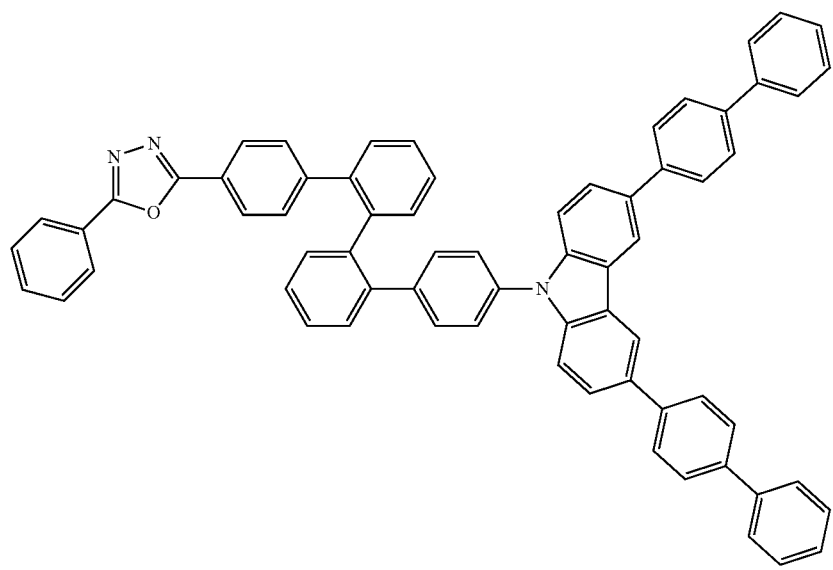
(442)

-continued
(443)
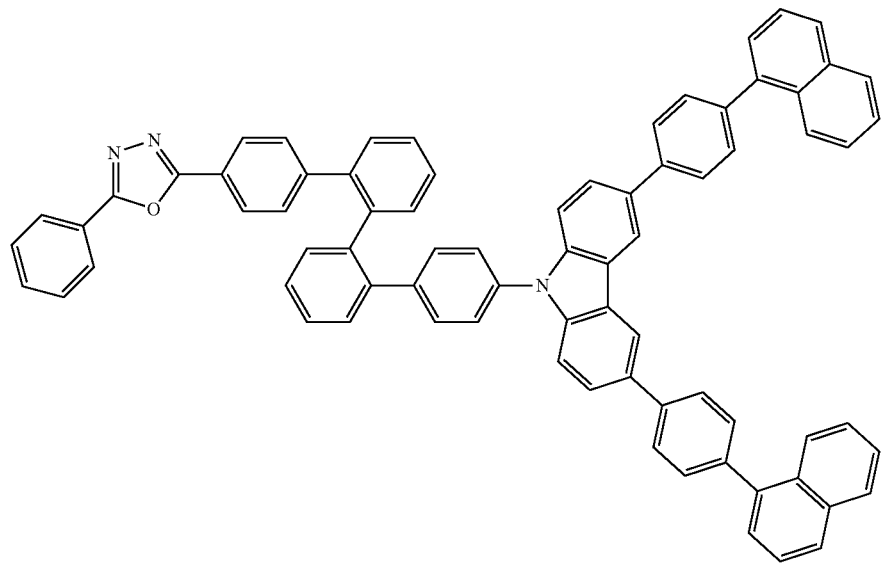
(444)
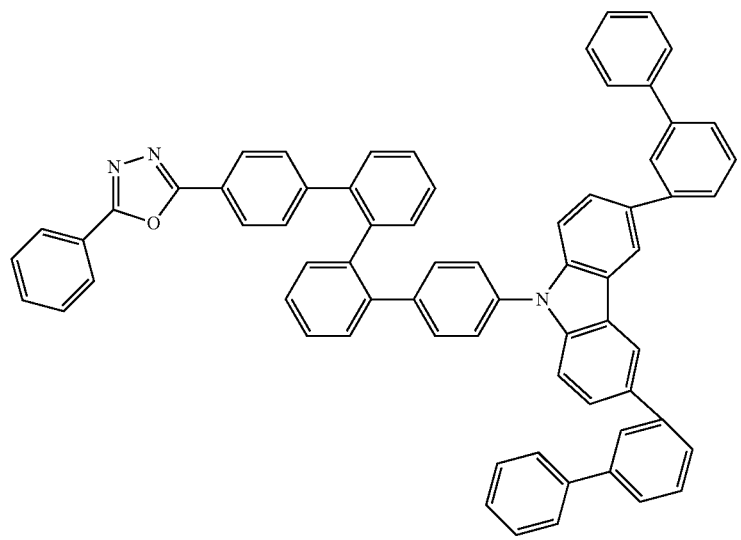
(445)
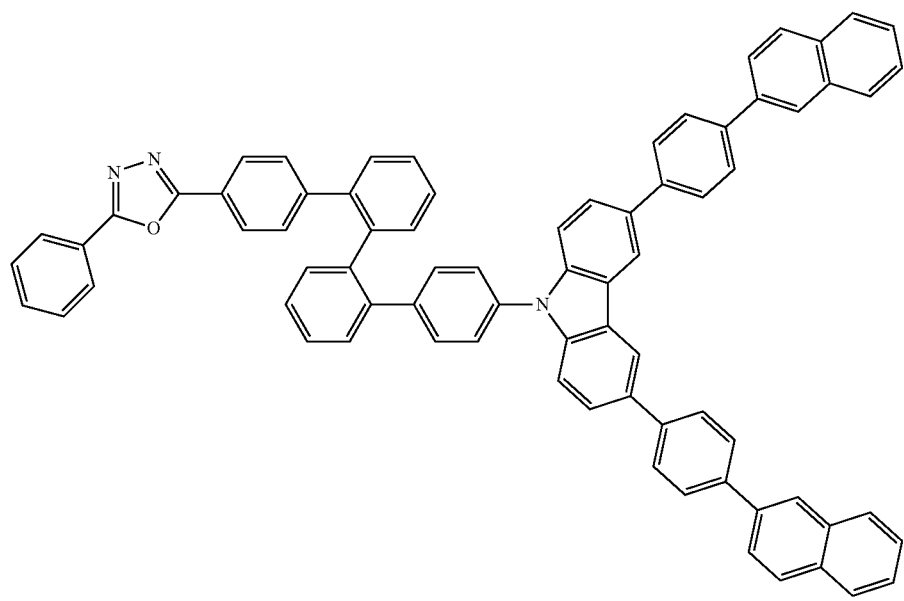

-continued
(446)
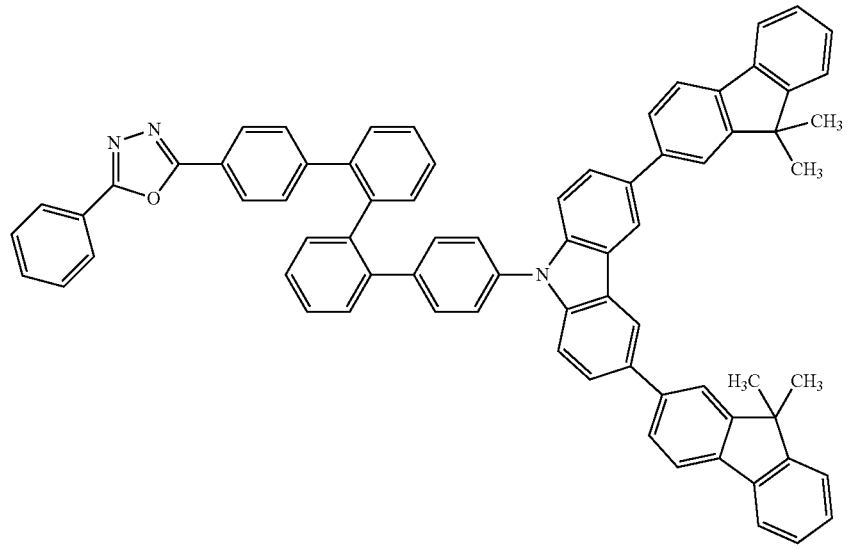
(447)
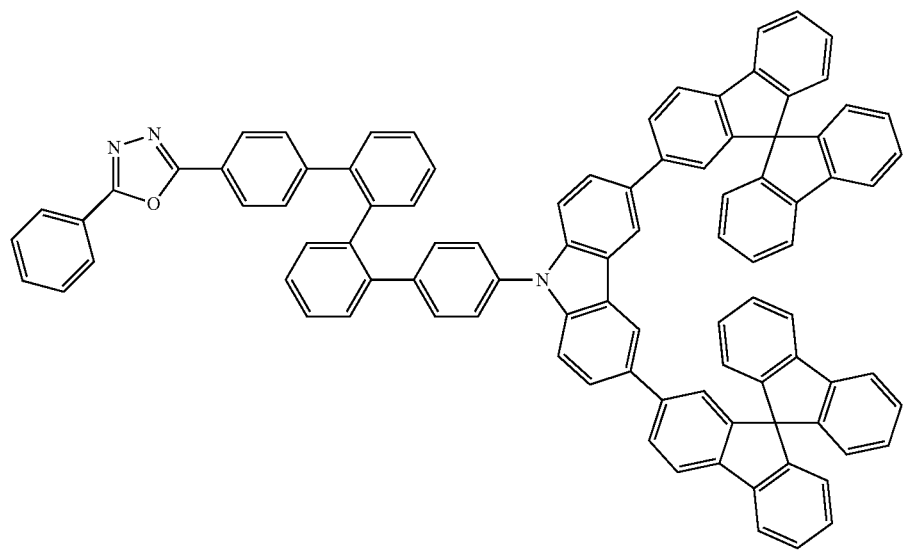
(448)
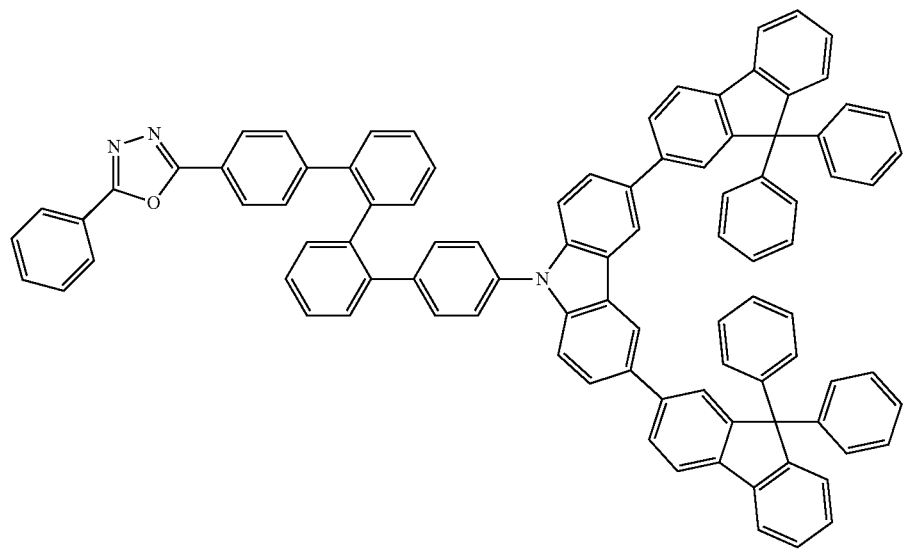

-continued
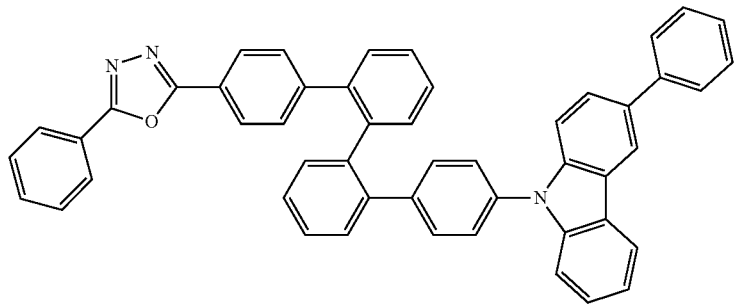
(449)
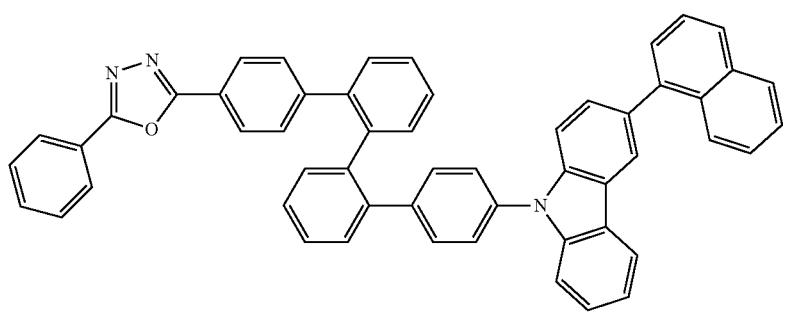
(450)
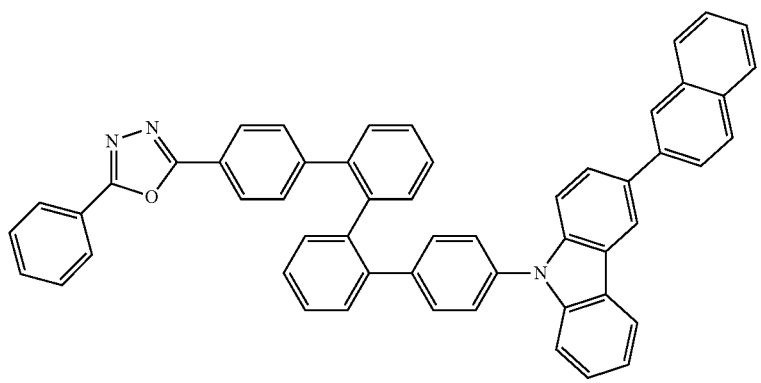
(451)
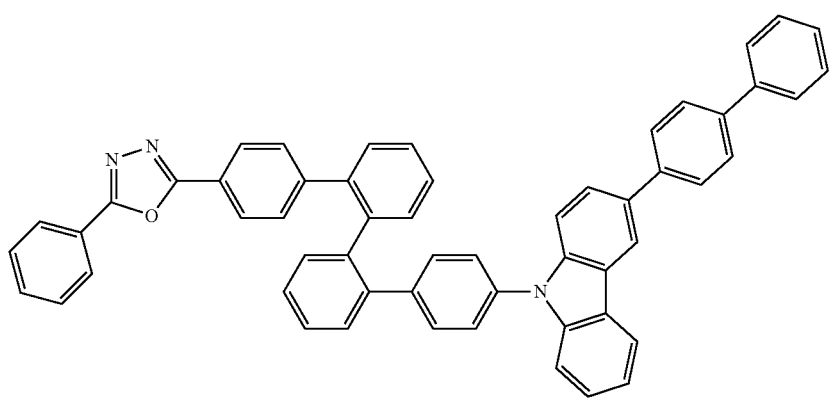
(452)

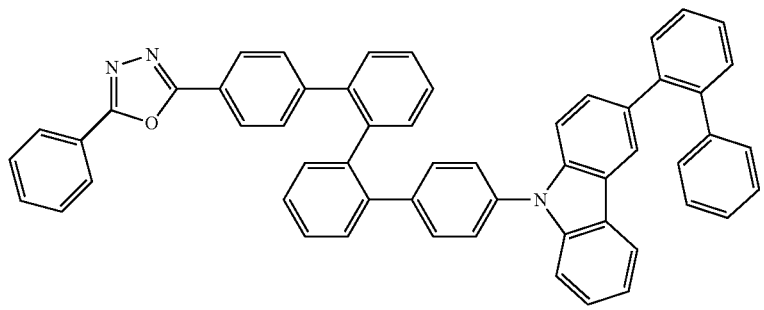
(453)
(454)
(455)
(456)

(457)
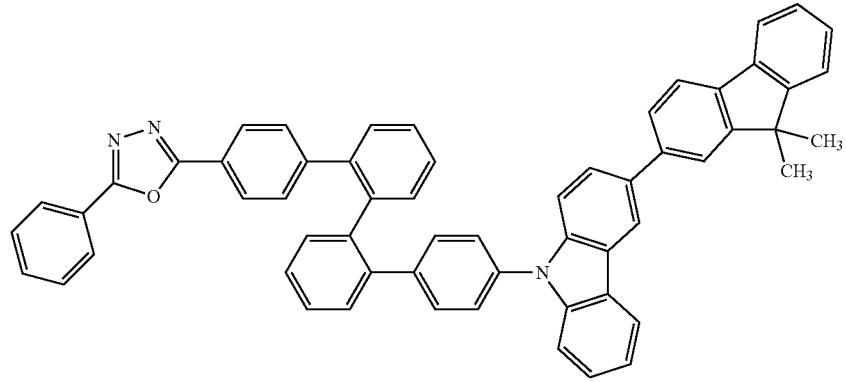
(458)
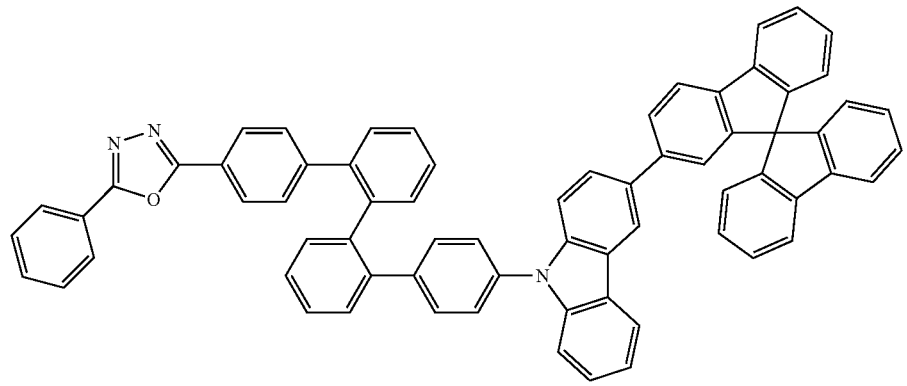
(459)
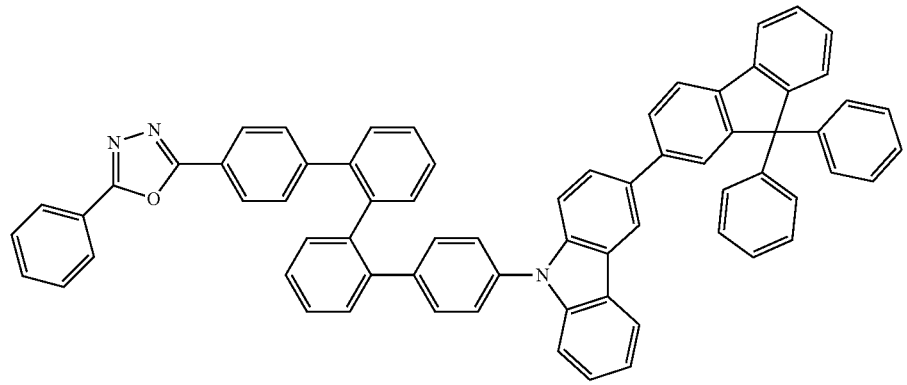
(460)
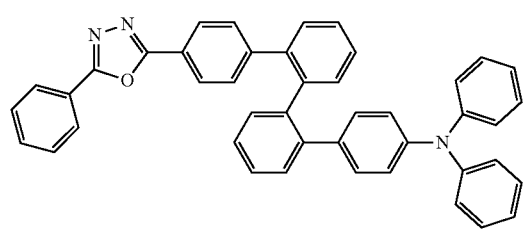
(461)
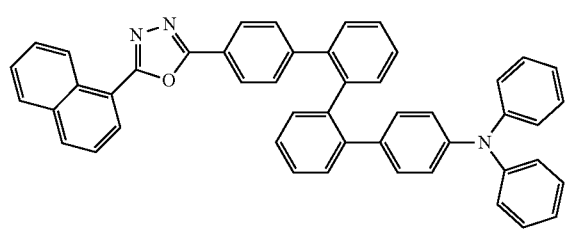

-continued
(462)
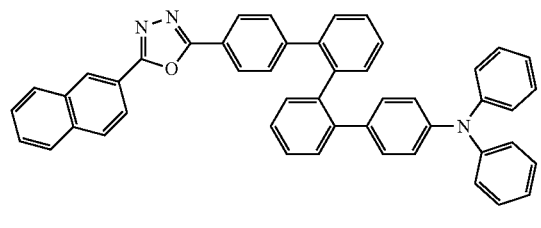
(463)
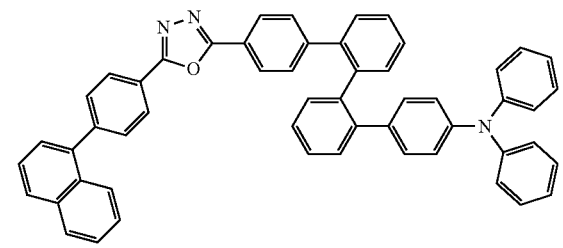
(464)
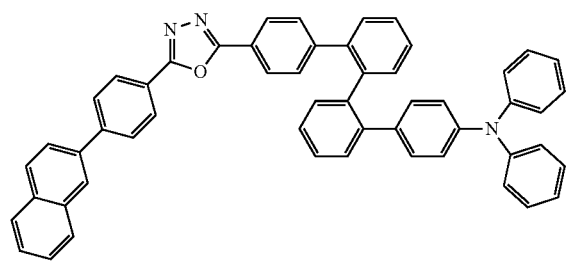
(465)
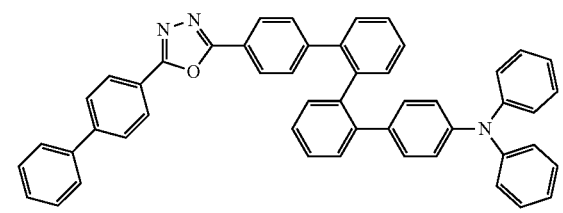
(466)
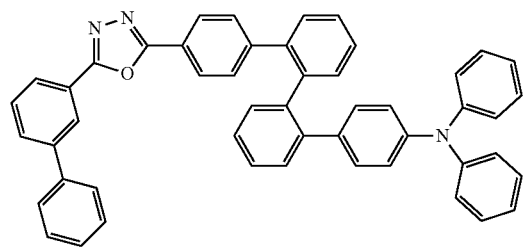
(467)
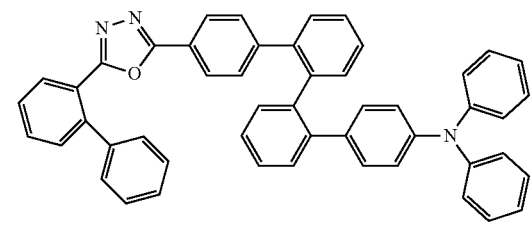
(468)
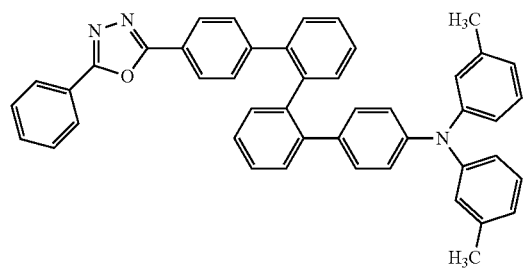
(469)
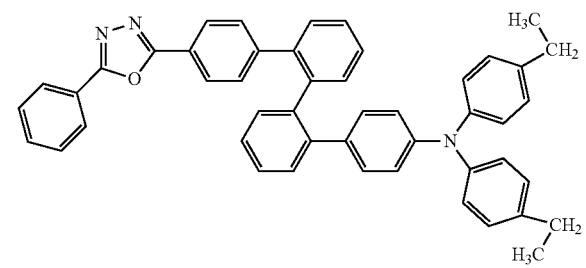
(470)
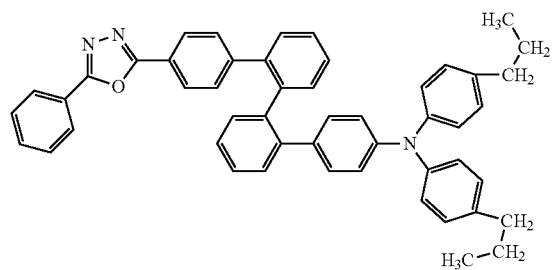
(471)
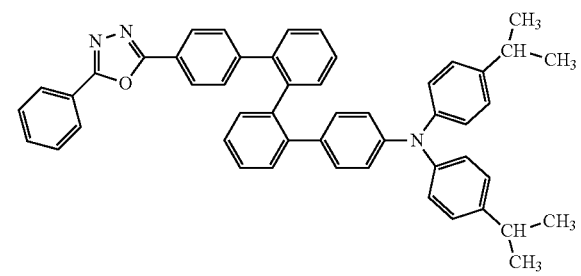

-continued
(472)
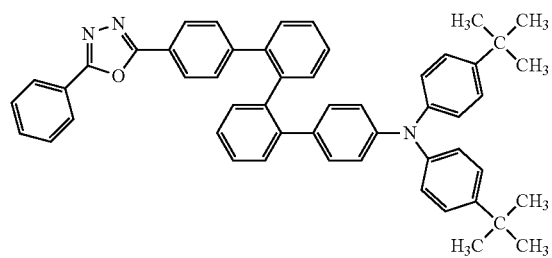
(473)
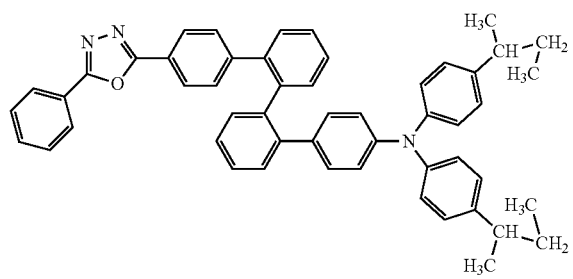
(474)
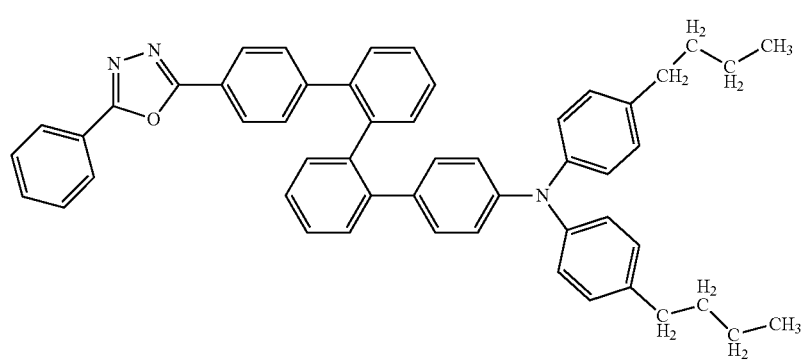
(475)
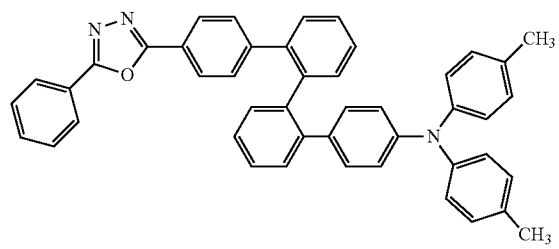
(476)
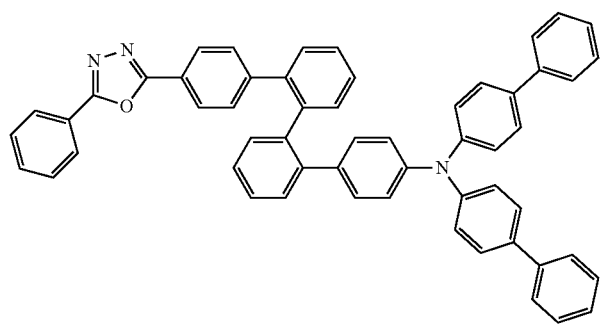
(477)
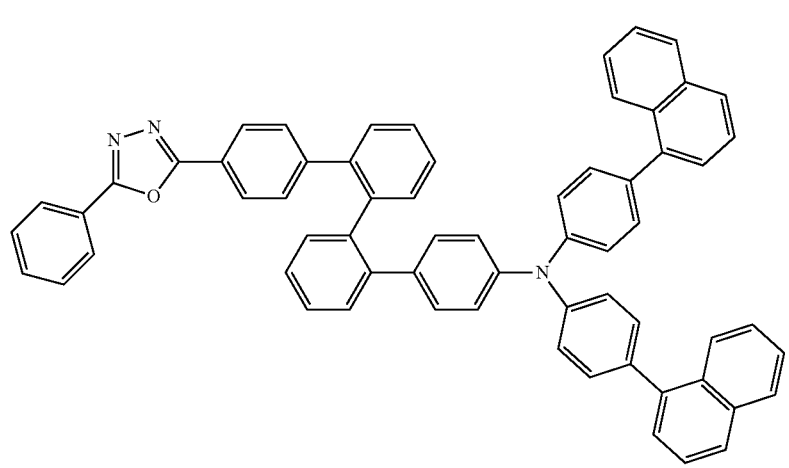

-continued
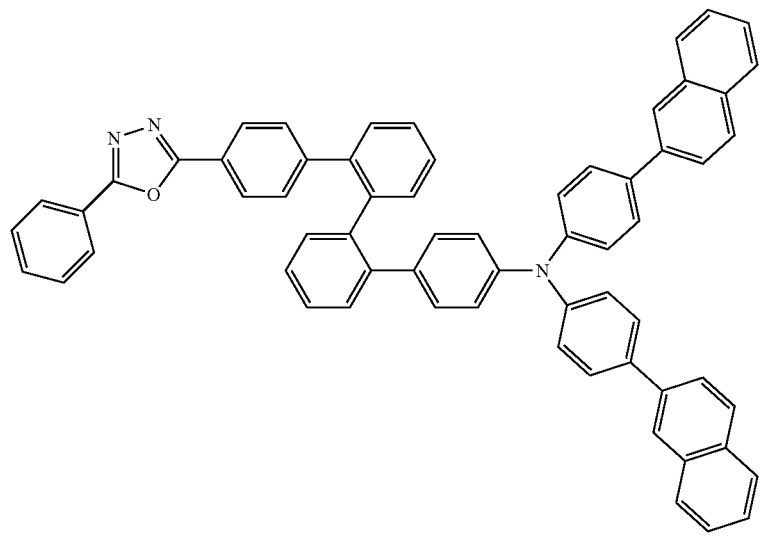
(478)
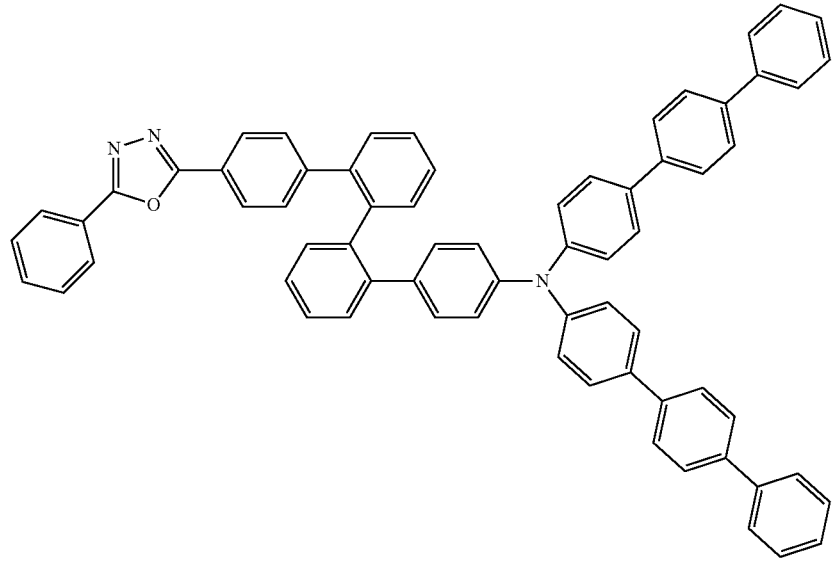
(479)
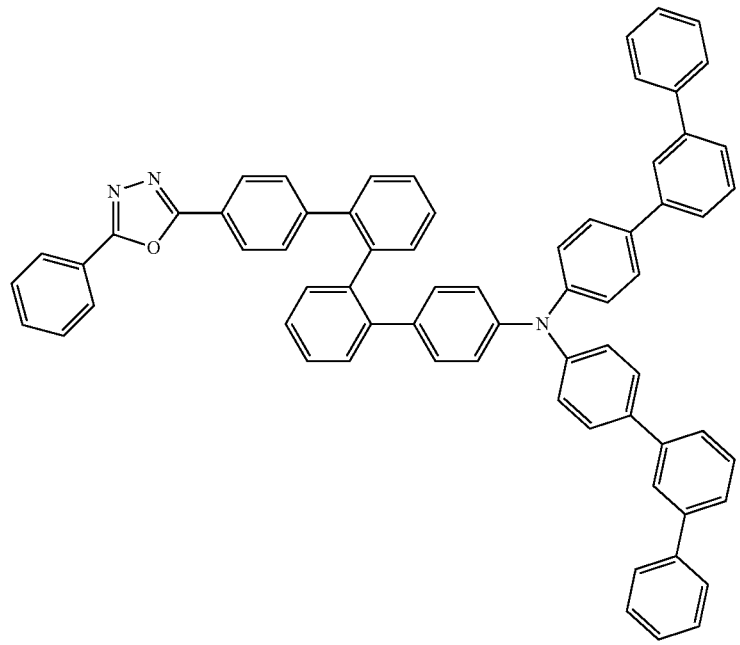
(480)

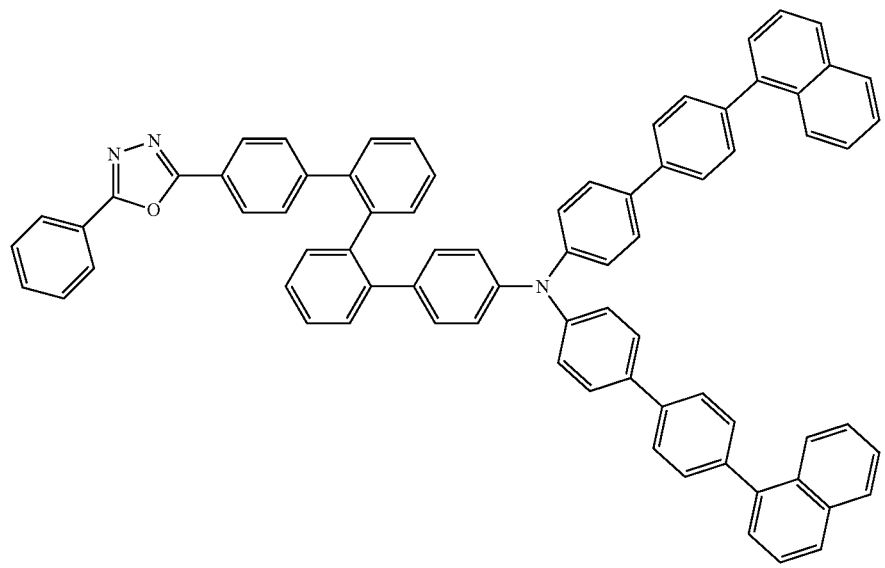
(481)
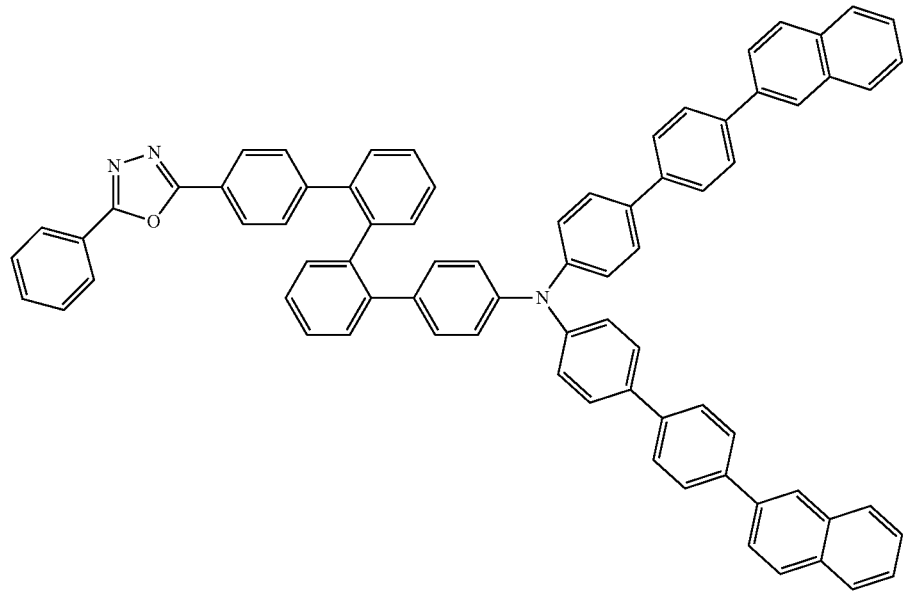
(482)
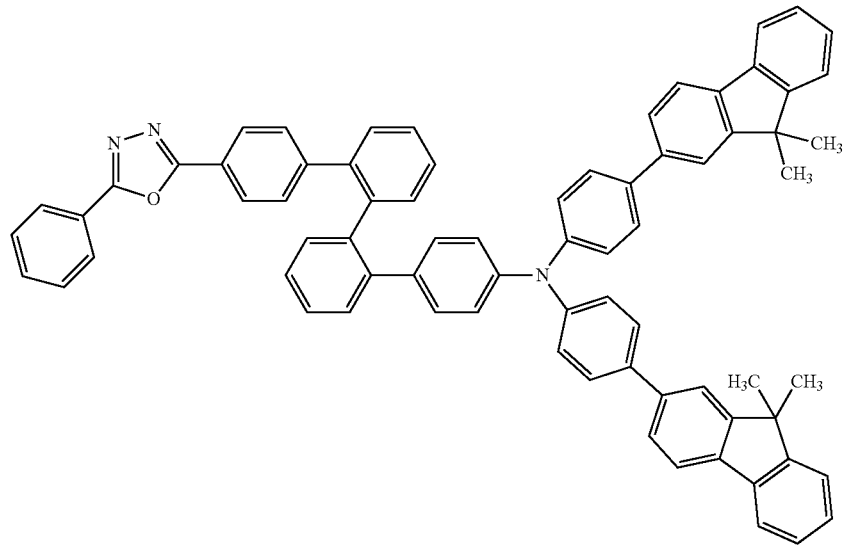
(483)

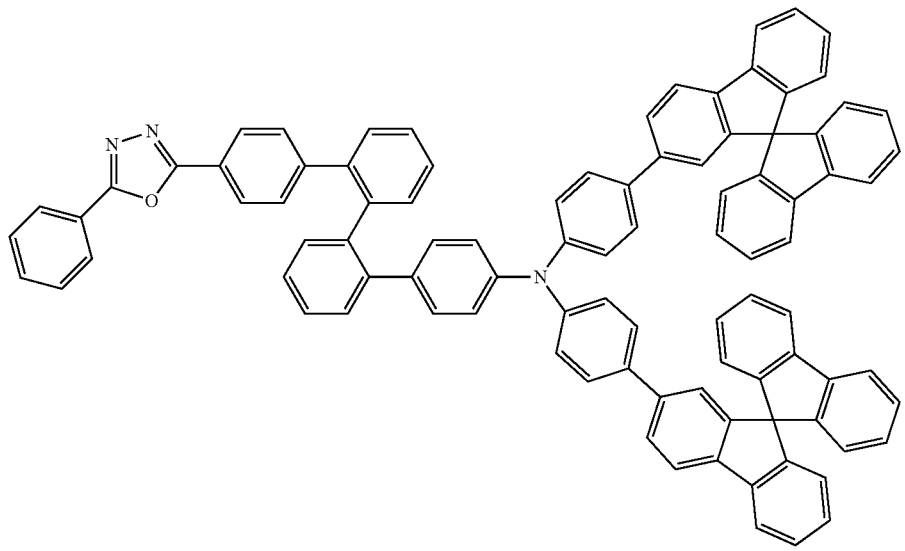
(484)
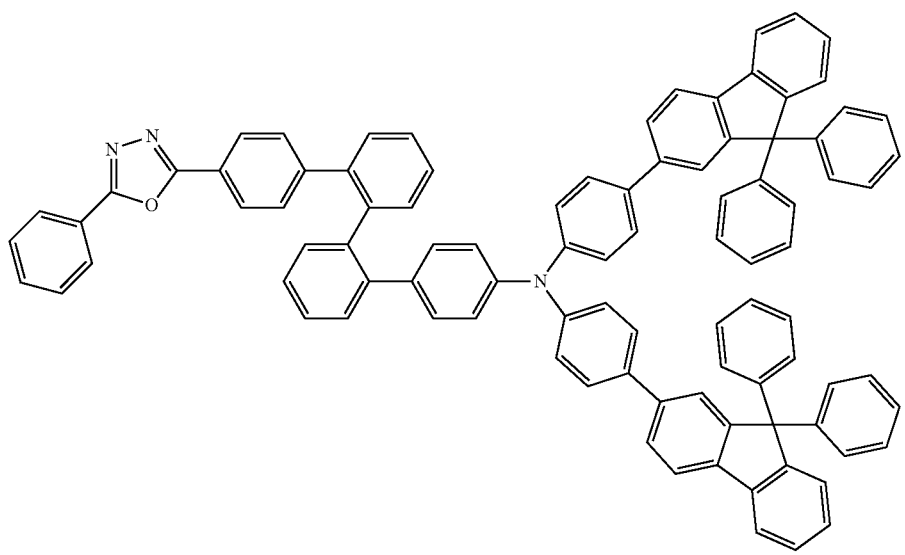
(485)
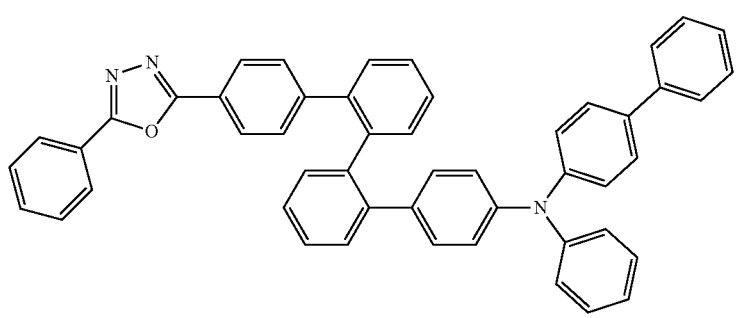
(486)

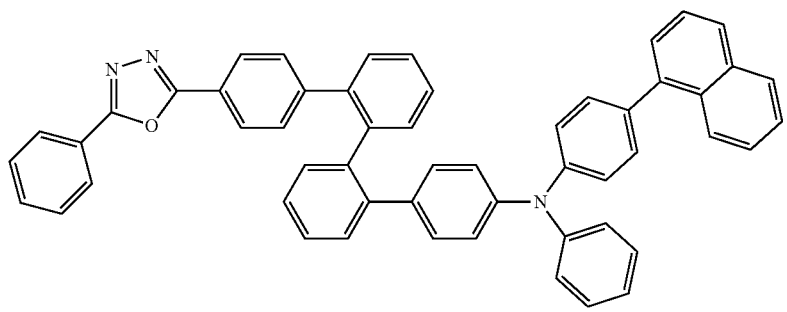
(487)
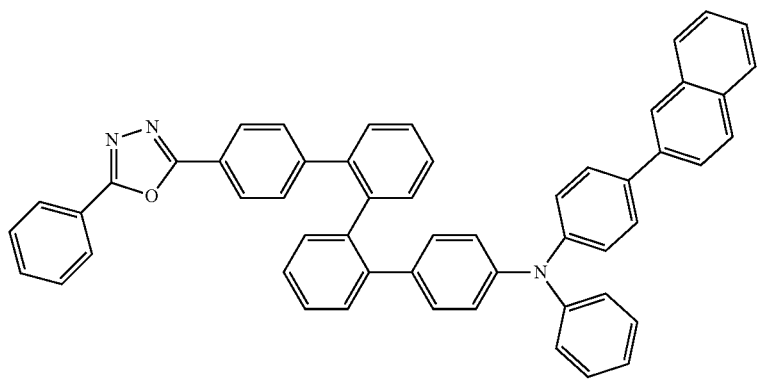
(488)
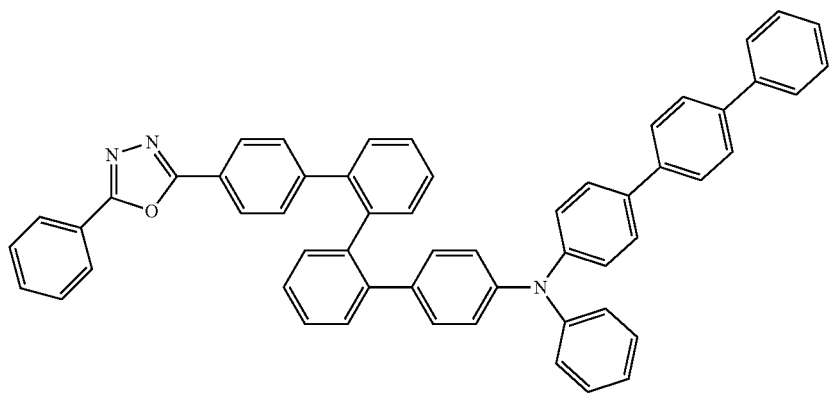
(489)
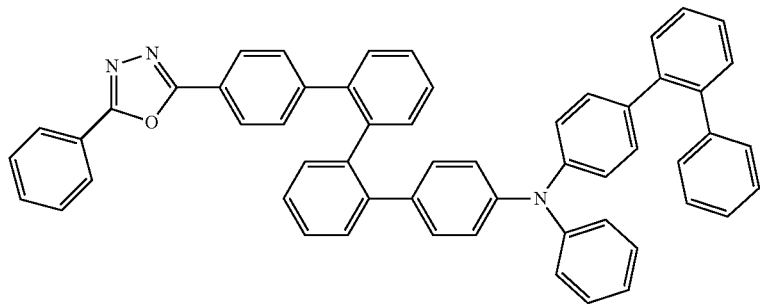
(490)

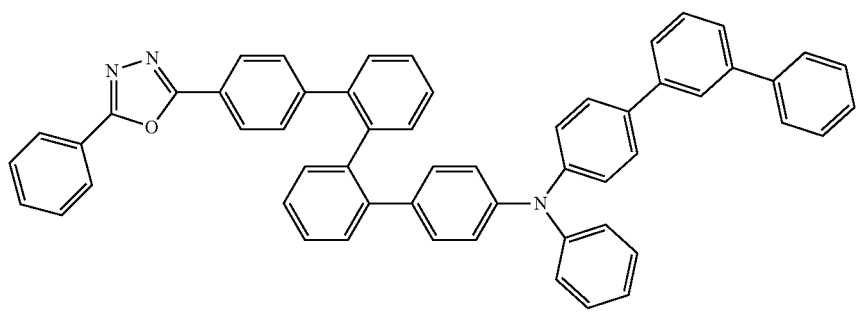
(491)
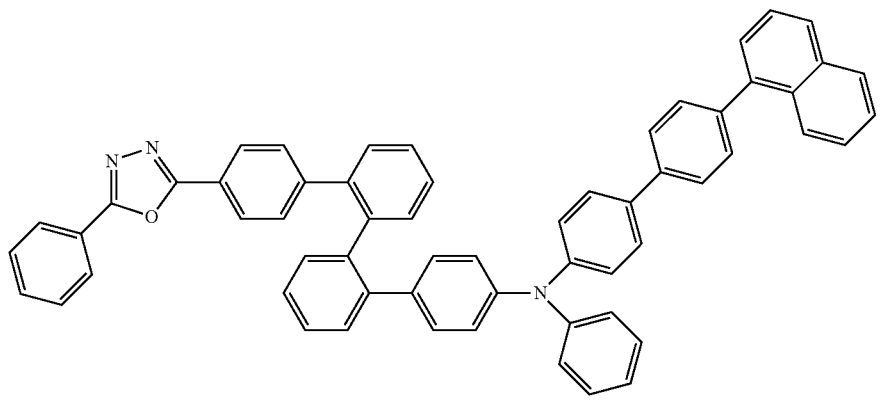
(492)
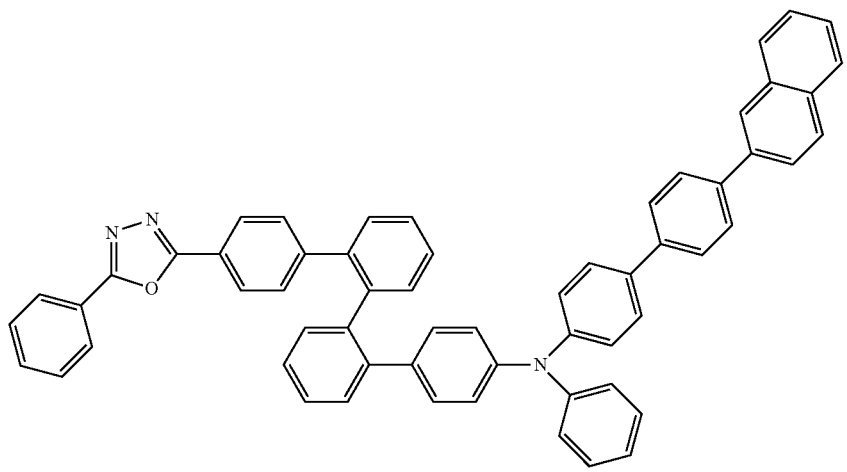
(493)
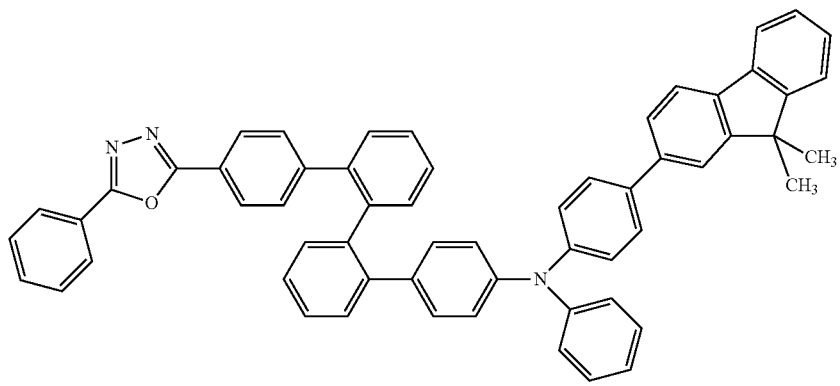
(494)

-continued
(495)
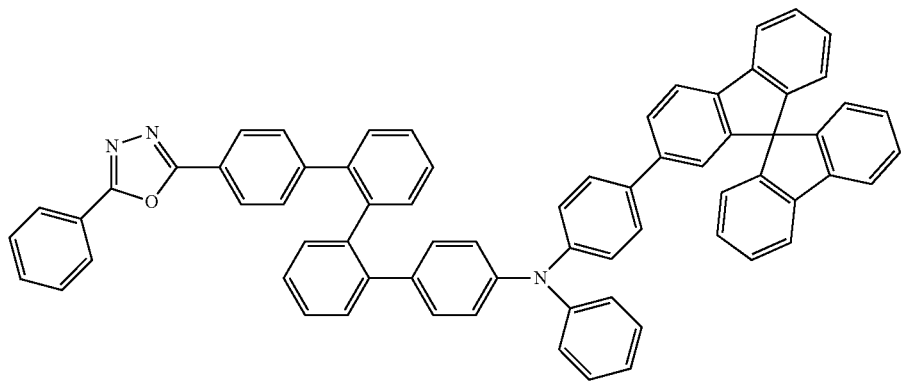
(496)
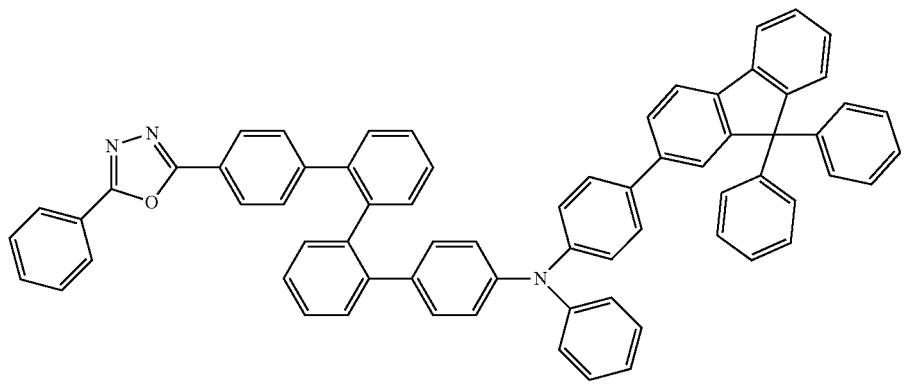
(497)
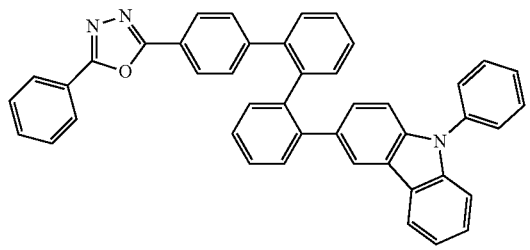
(498)
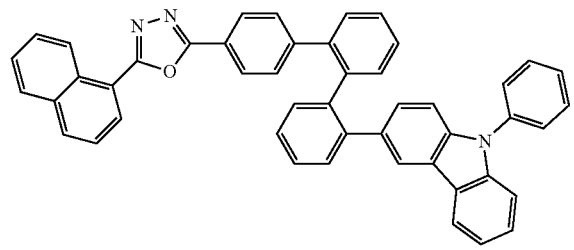
(499)
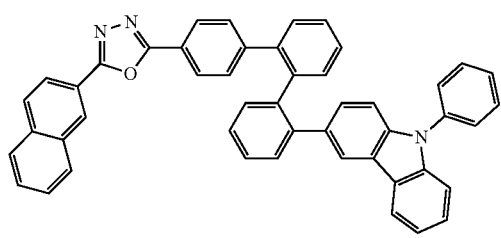
(500)
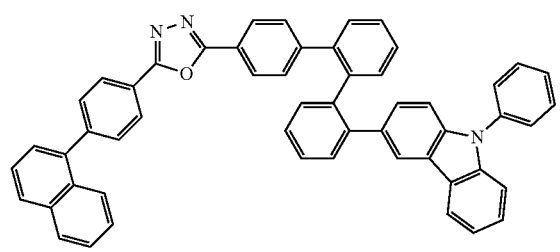
(501)
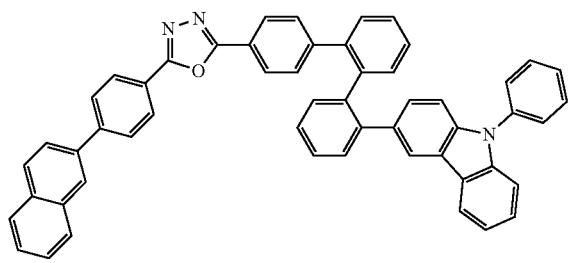
(502)
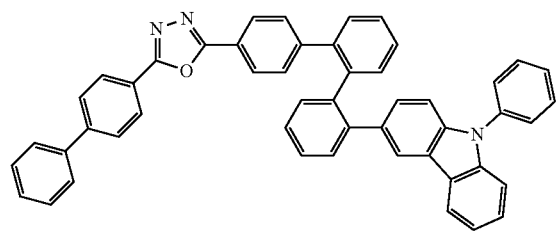

-continued
(503)
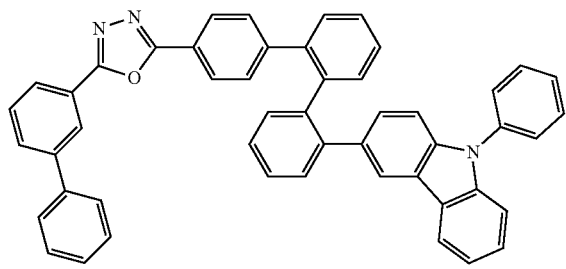
(504)
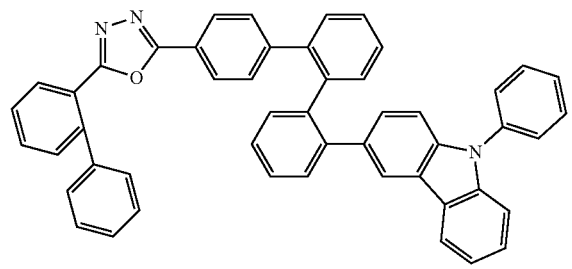
(505)
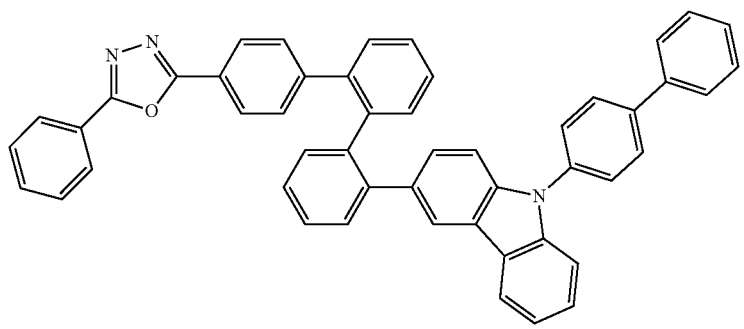
(506)
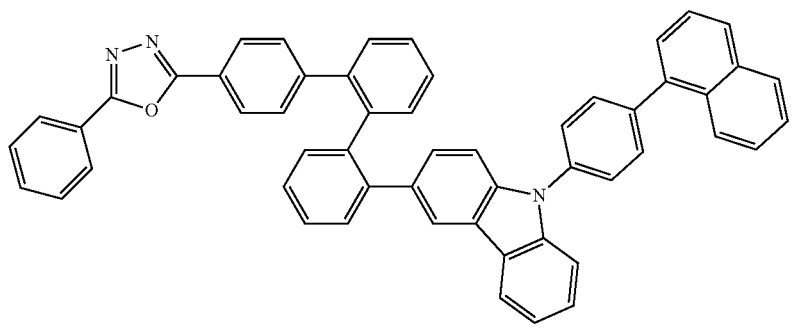
(507)
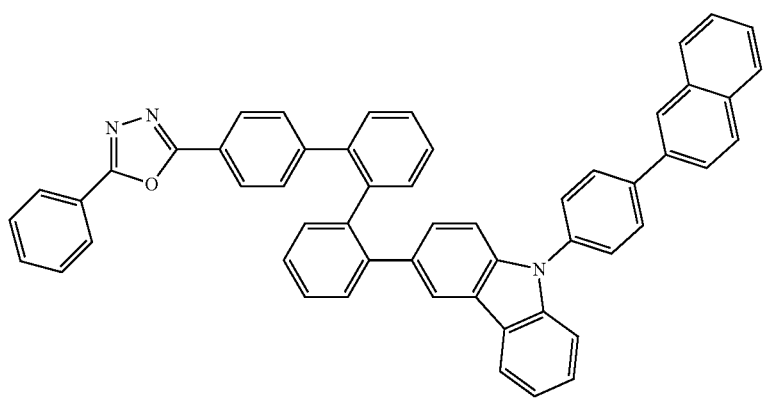
(508)
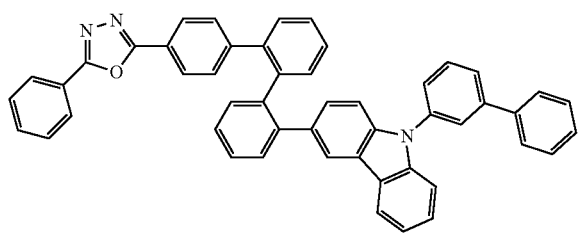
(509)
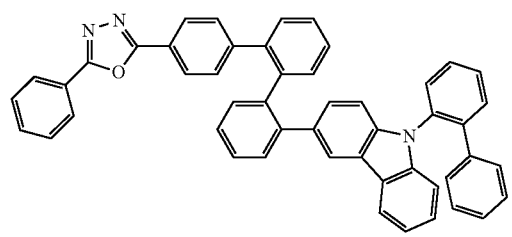

-continued
(510)
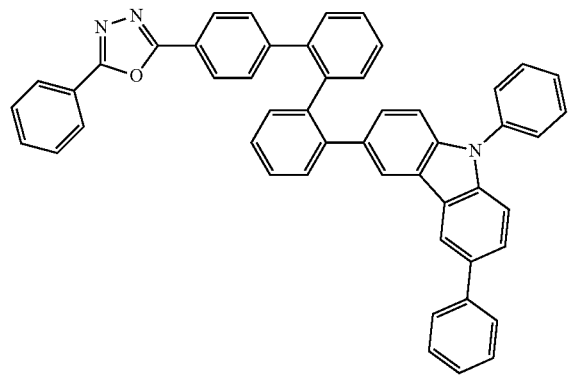
(511)
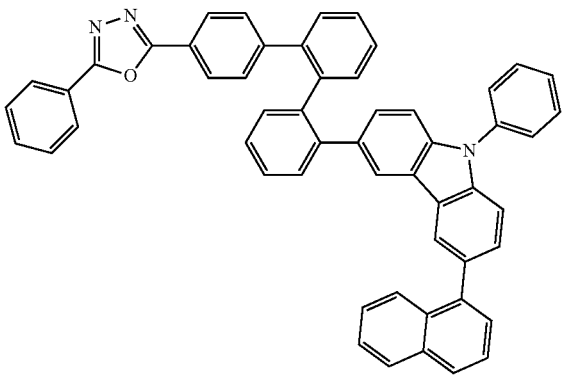
(512)
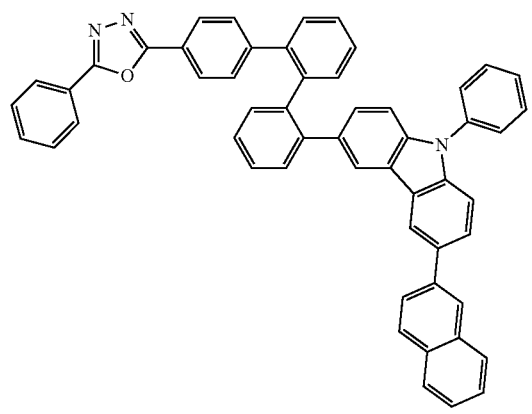
(513)
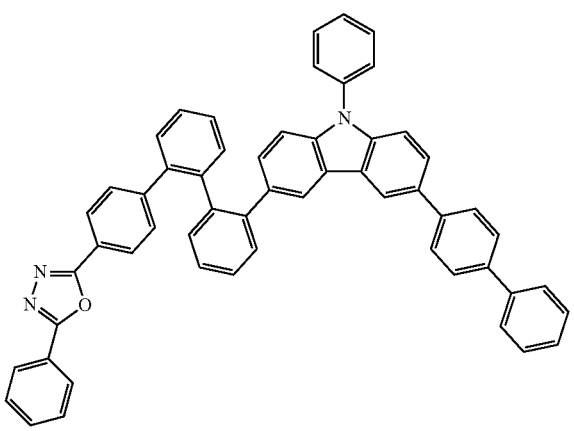
(514)
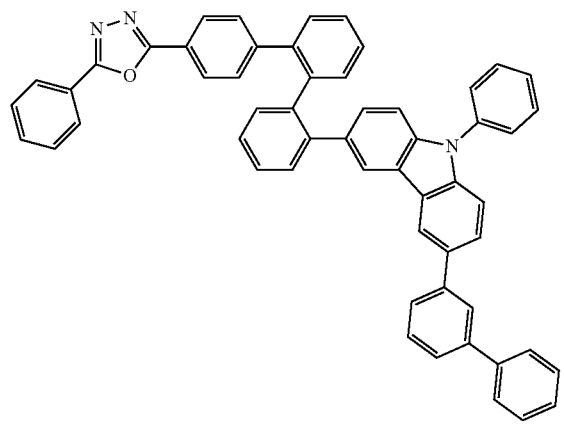
(515)
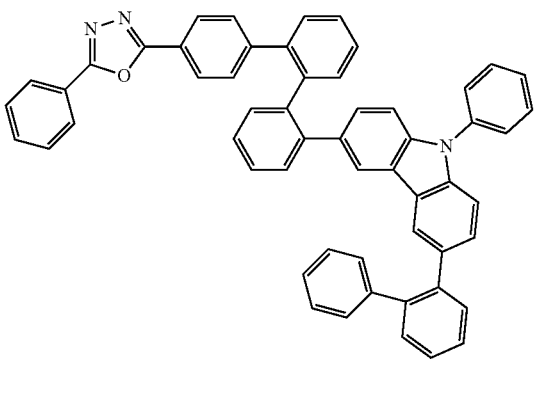

(516)
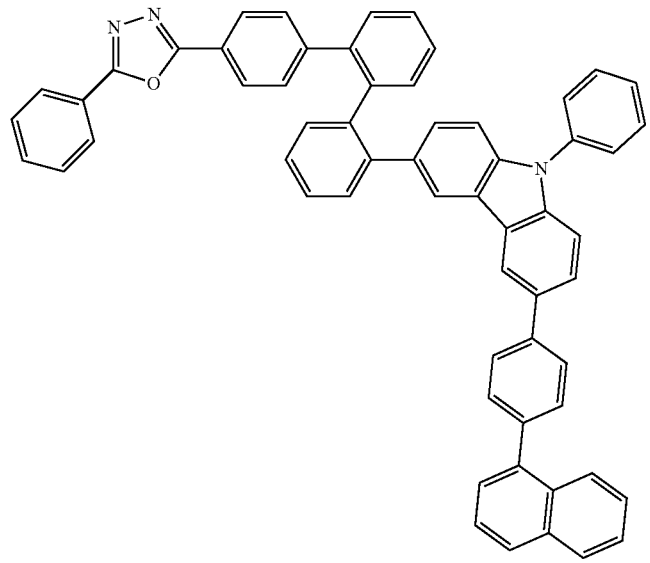
(517)
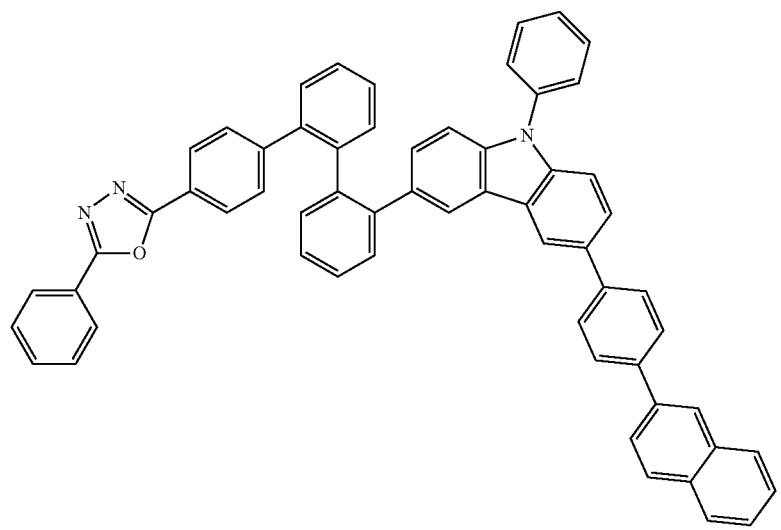
(518)
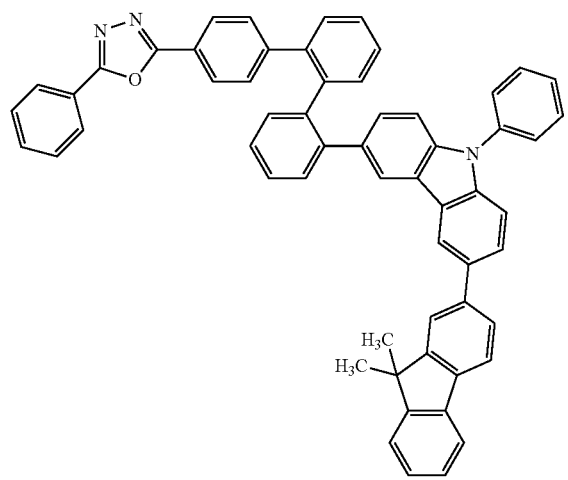
(519)
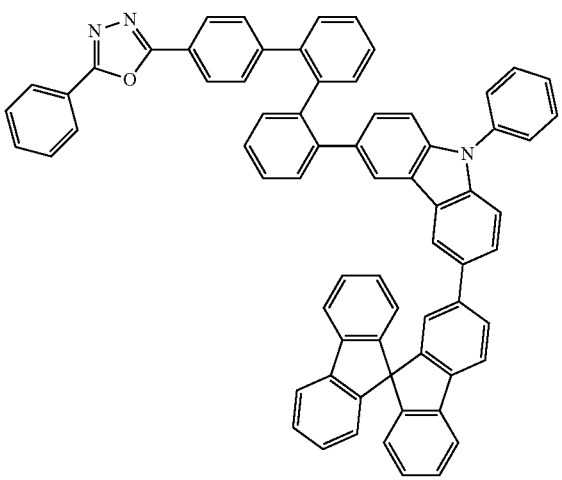

-continued
(520)
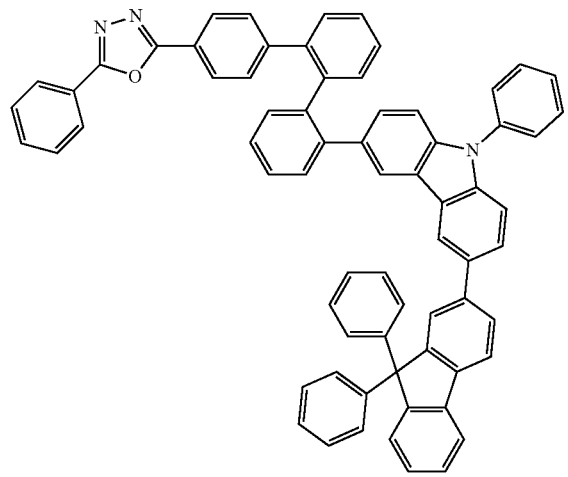
(521)
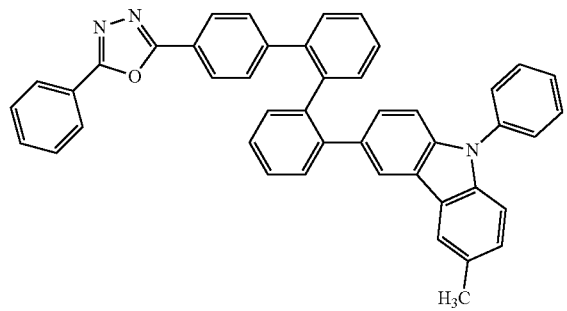
(522)
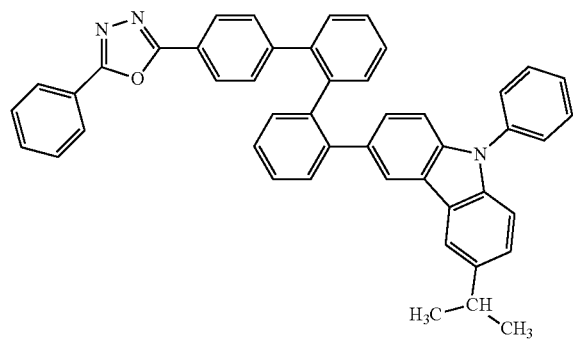
(523)
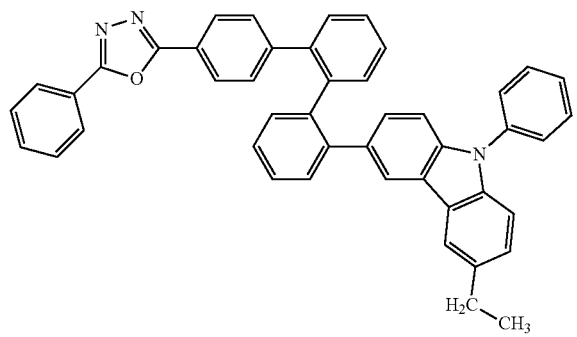
(524)
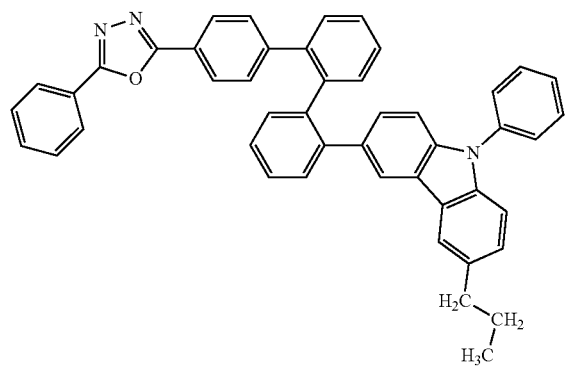
(525)
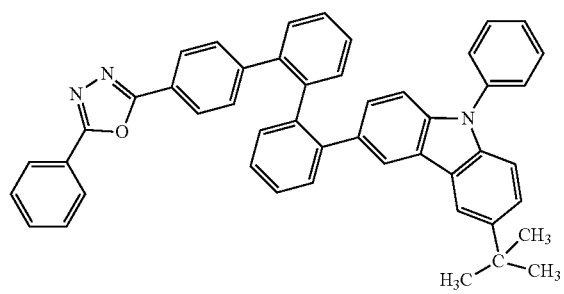
(526)
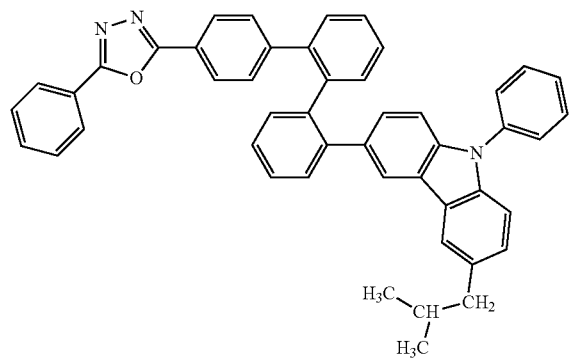
(527)
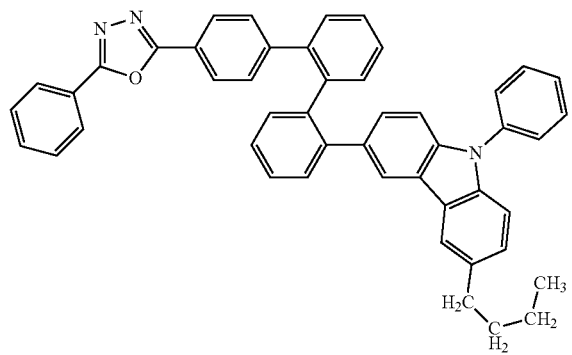

(528)

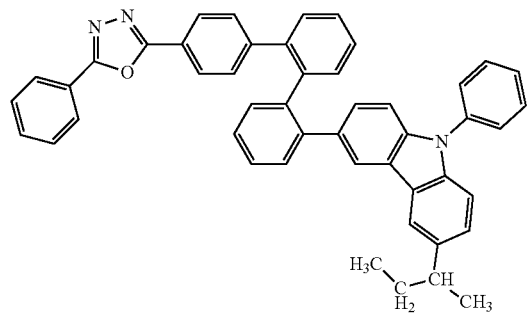

(529)

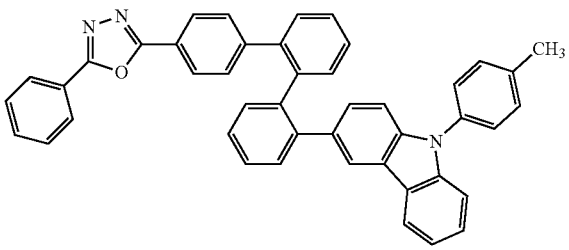

(530)

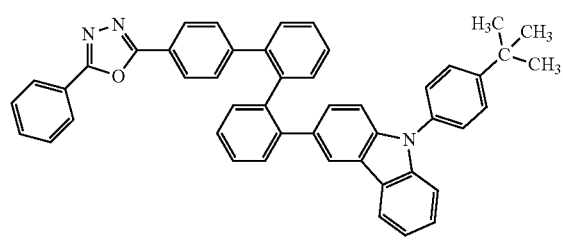

(531)

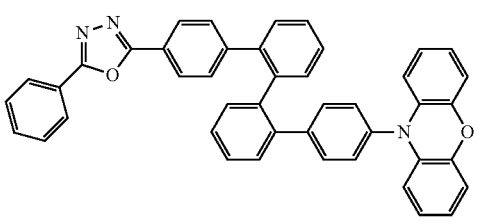

(532)

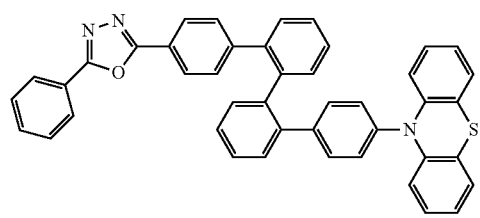

(533)

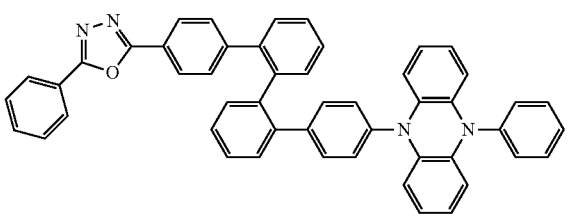

The oxadiazole derivative represented by General Formula (OXD1) can be synthesized by synthesis methods represented by Synthesis Schemes (11) to (14) below. Hereinafter, an example of a synthesis method of the oxadiazole derivative of Embodiment 3 will be described.

First, a halogenated oxadiazole derivative (Compound 5) is synthesized. Synthesis Scheme (11) is shown below.

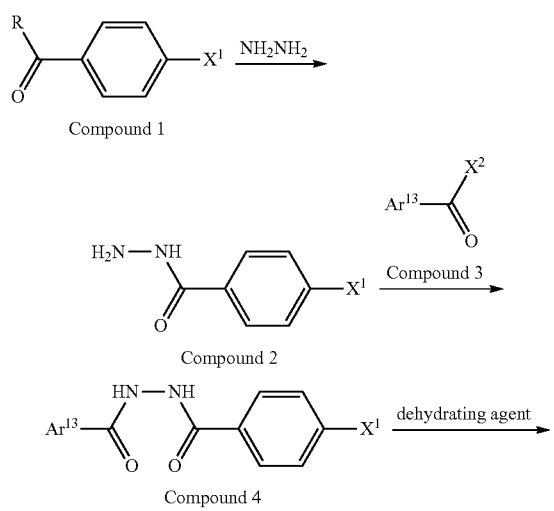

(11)

-continued

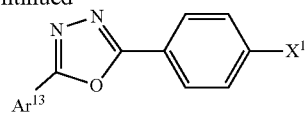

Compound 5

In Synthesis Scheme (11), a halogenated aryl derivative (Compound 1) and hydrazine are reacted to synthesize halogenated aryl hydrazide (Compound 2). Note that in Synthesis Scheme (11), the hydrazine may be a hydrazine hydrate. Next, the halogenated aryl hydrazide (Compound 2) and aryl carboxylic acid halide (Compound 3) are reacted to obtain a diacyl hydrazine derivative (Compound 4). A halogenated oxadiazole derivative (Compound 5) can be obtained by ring closure by dehydration of the diacyl hydrazine derivative (Compound 4) using a dehydrating agent to form a 1,3,4-oxadiazole ring. Note that in Synthesis Scheme (11), R represents an alkoxy group having 1 to 4 carbon atoms or halogen, $Ar^{13}$ represents an aryl group having 6 to 10 carbon atoms, and $X^1$ and $X^2$ represents a halogen group. $X^1$ is preferably a bromo group or an iodine group, and $X^2$ is preferably a chloro group.

Note that phosphoryl chloride, thionyl chloride, or the like can be used as the dehydrating agent.

A method for synthesizing the halogenated oxadiazole derivative (Compound 5) is not limited to above Synthesis Scheme (11), and other known methods can also be used.

Next, an electron-accepting unit in the oxadiazole derivative of Embodiment 3 is synthesized. Specifically, a halogenated oxadiazole compound represented by Compound 7 is synthesized. Synthesis Scheme (12-a) is shown below.

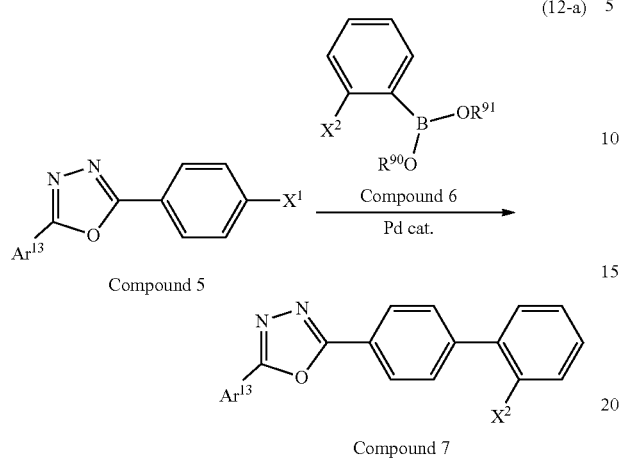

Compound 5

Compound 7

(12-a)

The halogenated oxadiazole compound (Compound 5) and an arylboronic acid or its derivative (Compound 6) are coupled by the Suzuki-Miyaura coupling using a palladium catalyst, whereby a halogenated oxadiazole compound (Compound 7) can be obtained.

In Synthesis Scheme (12-a), $X^1$ and $X^2$ represent halogen or a triflate group, and as the halogen, iodine, bromine, and chlorine are given. In addition, $X^1$ and $X^2$ may represent the same element or different elements. Further, in Synthesis Scheme (12-a), $R^{90}$ represents hydrogen or an alkyl group having 1 to 6 carbon atoms, and $R^{91}$ represents hydrogen or an alkyl group having 1 to 6 carbon atoms. $R^{90}$ and $R^{91}$ may be bonded to each other to form a ring.

A palladium catalyst that can be used in Synthesis Scheme (12-a) may be palladium(II) acetate, tetrakis(triphenylphosphine)palladium(0), or the like. As a ligand of the palladium catalyst that can be used in the synthesis scheme (12-a), tri(o-tolyl)phosphine, triphenylphosphine, tricyclohexylphosphine, and the like are given. As a base that can be used in Synthesis Scheme (1), an organic base such as sodium tert-butoxide and an inorganic base such as potassium carbonate are given.

As a solvent that can be used in Synthesis Scheme (12-a), a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethylene glycol dimethyl ether and water; or the like can be given. Note that a mixed solvent of toluene and water or a mixed solvent of toluene, ethanol, and water is more preferable.

Note that the synthesis method of the halogenated oxadiazole compound represented by Compound 7 is not limited to the synthesis method shown in Synthesis Scheme (12-a). The halogenated oxadiazole compound may be synthesized by, for example, a synthesis method shown in Synthesis Scheme (12-b) below.

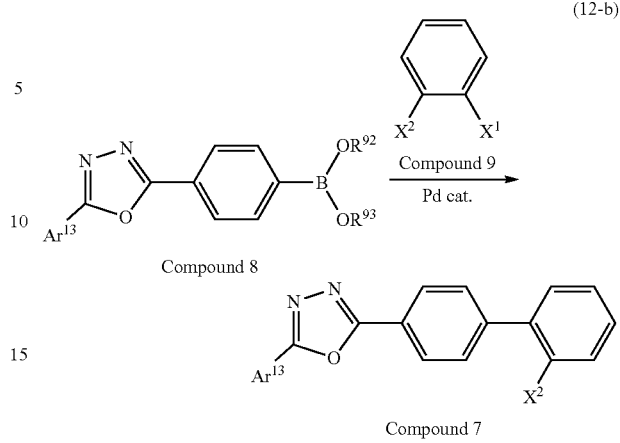

Compound 8

Compound 7

(12-b)

A boronic acid or its derivative (Compound 8) and dihalogenated aryl compound (Compound 9) are coupled by the Suzuki-Miyaura coupling using a palladium catalyst, whereby the halogenated oxadiazole compound (Compound 7) can be obtained.

In Synthesis Scheme (12-b), $X^1$ and $X^2$ represent halogen or a triflate group, and as the halogen, iodine, bromine, or chlorine is given. In addition, $X^1$ and $X^2$ may represent the same element or different elements. Further, in Synthesis Scheme (12-a), $R^{92}$ represents hydrogen or an alkyl group having 1 to 6 carbon atoms, and $R^{93}$ represents hydrogen or an alkyl group having 1 to 6 carbon atoms. $R^{92}$ and $R^{93}$ may be bonded to each other to form a ring.

A palladium catalyst that can be used in Synthesis Scheme (12-b) may be palladium(II) acetate, tetrakis(triphenylphosphine)palladium(0), or the like. As a ligand of the palladium catalyst that can be used in the synthesis scheme (12-b), trio-tolyl)phosphine, triphenylphosphine, tricyclohexylphosphine, and the like are given. Examples of a base that can be used in Synthesis Scheme (12-b) include an organic base such as sodium tert-butoxide and an inorganic base such as potassium carbonate.

As a solvent that can be used in Synthesis Scheme (12-b), a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethylene glycol dimethyl ether and water; or the like can be given. A mixed solvent of toluene and water or a mixed solvent of toluene, ethanol, and water is more preferable.

Next, a hole-accepting unit in the oxadiazole derivative of Embodiment 3 is synthesized. Synthesis Schemes (13-1) and (13-2) are shown below.

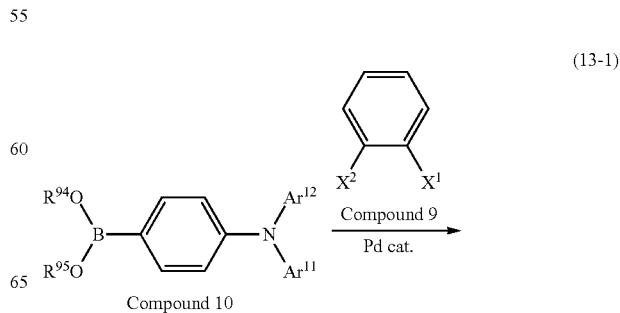

Compound 10

(13-1)

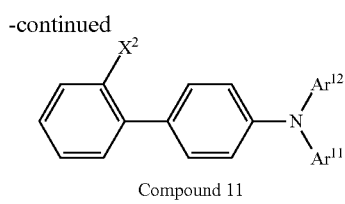

Compound 11

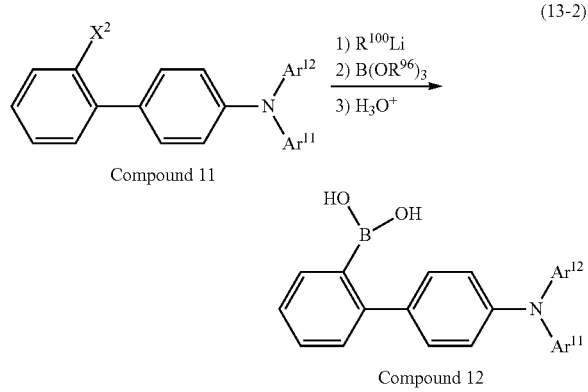

A boronic acid of a tertiary arylamine or its derivative (Compound 10) and dihalogenated aryl compound (Compound 9) are coupled by the Suzuki-Miyaura coupling using a palladium catalyst, whereby a halogenated arylamine compound (Compound 11) is synthesized (Synthesis Scheme (13-1)).

In Synthesis Scheme (13-1), $X^1$ and $X^2$ represent halogen or a triflate group, and as the halogen, iodine, bromine, and chlorine are given. In addition, $X^1$ and $X^2$ may represent the same element or different elements. Further, $Ar^{11}$ and $Ar^{12}$ represent a substituted or unsubstituted aryl group having 6 to 13 carbon atoms. $R^{94}$ and $R^{95}$ each represent an hydrogen atom or an alkyl group having 1 to 6 carbon atoms.

As a palladium catalyst that can be used in Synthesis Scheme (13-1) may be palladium(II) acetate, tetrakis(triphenylphosphine)palladium(0), and the like are given. As a ligand of the palladium catalyst that can be used in the synthesis scheme (13-1), tri(o-tolyl)phosphine, triphenylphosphine, tricyclohexylphosphine, and the like are given.

Examples of a base that can be used in Synthesis Scheme (13-1) include an organic base such as sodium tert-butoxide and an inorganic base such as potassium carbonate. As a solvent that can be used in Synthesis Scheme (13-1), a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethylene glycol dimethyl ether and water; or the like can be given. Note that a mixed solvent of toluene and water or a mixed solvent of toluene, ethanol, and water is more preferable.

Next, a tertiary amine boronic acid (Compound 12) can be obtained in such a manner that a halogenated aryl amine compound (Compound 11) is transformed to a boronic acid using an alkyllithium reagent and a boronic ester (Synthesis Scheme (13-2)).

In Synthesis Scheme (13-2), $R^{100}$ represents an alkyl group having 1 to 6 carbon atoms. $R^{96}$ represents an alkyl group having 1 to 6 carbon atoms. A boronic acid moiety of Compound 12 may be protected by ethylene glycol or pinacol.

In Synthesis Scheme (13-2), n-butyllithium, methyllithium, or the like can be used as the alkyllithium reagent. Trimethyl borate, isopropyl borate, or the like can be used as the boronic ester.

Next, Compound 7 and Compound 12 are coupled to synthesize the oxadiazole derivative of Embodiment 3 represented by General Formula (OXD1). Synthesis Scheme (14) is shown below.

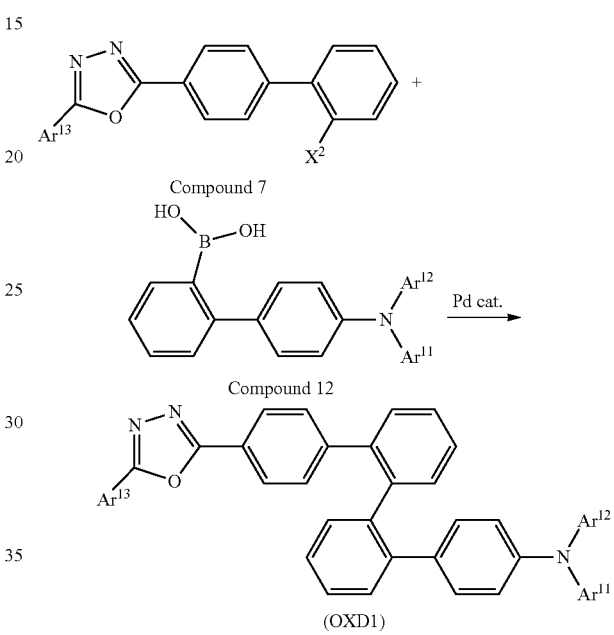

The halogenated oxadiazole derivative (Compound 7) and the boronic acid of the tertiary amine (Compound 12) are coupled by the Suzuki-Miyaura coupling using a palladium catalyst, whereby the oxadiazole derivative of Embodiment 3 represented by General Formula (OXD1) can be obtained.

In Synthesis Scheme (14), $X^2$ represents halogen or a triflate group, and as the halogen, iodine, bromine, and chlorine are given. In addition, $Ar^{11}$, $Ar^{12}$, and $Ar^{13}$ represent a substituted or unsubstituted aryl group having 6 to 13 carbon atoms.

A palladium catalyst that can be used in Synthesis Scheme (14) may be palladium(II) acetate, tetrakis(triphenylphosphine)palladium(0), or the like. As a ligand of the palladium catalyst that can be used in the synthesis scheme (14), tri(o-tolyl)phosphine, triphenylphosphine, tricyclohexylphosphine, and the like are given. Examples of a base that can be used in Synthesis Scheme (14) include an organic base such as sodium tert-butoxide and an inorganic base such as potassium carbonate.

As a solvent that can be used in Synthesis Scheme (14), a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethylene glycol dimethyl ether and water; or the like can be given. A mixed solvent of toluene and water or a mixed solvent of toluene, ethanol, and water is more preferable. Further, instead of Compound 12, a compound obtained by protecting the boronic acid moiety of Compound 12 with an alkyl group may be used.

In the above manner, the oxadiazole derivative of Embodiment 3 can be synthesized.

The oxadiazole derivative of Embodiment 3 has high excitation energy, and an electron-transporting and hole-transporting properties. Therefore, it can be favorably used for a light-emitting element. In particular, the oxadiazole derivative of Embodiment 3 is preferably used for the light-emitting layer because the balance between injected electrons and holes is important for efficient emission of a light-emitting element. Since the oxadiazole derivative of Embodiment 3 has high triplet excitation energy, it can be used for a light-emitting layer together with a substance which emits phosphorescence.

Further, since singlet excitation energy (a difference in energy between a ground state and a singlet excited state) is higher than triplet excitation energy, a substance having high triplet excitation energy also has high singlet excitation energy. Therefore, the oxadiazole derivative of Embodiment 3 having high triplet excitation energy is useful even in the case of being used for a light-emitting layer together with a substance which emits fluorescence.

Further, as for the oxadiazole derivative of Embodiment 3, an oxadiazole skeleton having an electron-transporting property and a skeleton having a hole-transporting property are bonded with a twisted quaterphenylene skeleton whose conjugation is hardly extended therebetween, whereby the molecular weight can be increased with high triplet excitation energy maintained. Thus, the oxadiazole derivative can have high electrochemical and thermal stabilities. Therefore, use of the oxadiazole derivative of Embodiment 3 makes it possible to improve reliability of a light-emitting element.

Further, the oxadiazole derivative of Embodiment 3 can transport carriers, and therefore can be used for a carrier-transporting layer in a light-emitting element. In particular, the oxadiazole derivative of Embodiment 3 has high triplet excitation energy; therefore, energy transfer from a light-emitting layer does not easily occur even in the case where the oxadiazole derivative of Embodiment 3 is used for a layer in contact with the light-emitting layer. Accordingly, high emission efficiency can be achieved.

Embodiment 4

In Embodiment 4, one mode of a light-emitting element in which the organic semiconductor material described in Embodiments 1 to 3 is used will be described with reference to FIG. 1 and FIG. 2.

A light-emitting element of Embodiment 4 has a plurality of layers between a pair of electrodes. The plurality of layers are stacked by combination of layers formed of a substance having a high carrier-injecting property and a substance having a high carrier-transporting property so that a light-emitting region is formed apart from the electrodes, or so that carriers are recombined in a portion apart from the electrodes.

In Embodiment 4, the light-emitting element includes a first electrode 102, a second electrode 104, and an EL layer which is provided between the first electrode 102 and the second electrode 104. Note that in Embodiment 4, description will be made below assuming that the first electrode 102 functions as an anode and the second electrode 104 functions as a cathode. In other words, description will be made below assuming that light emission can be obtained when voltage is applied to the first electrode 102 and the second electrode 104 so that the potential of the first electrode 102 is higher than that of the second electrode 104.

A substrate 101 is used as a support of the light emitting element. The substrate 101 can be made of, for example, glass, plastic, metal, or the like. Note that the substrate 101 may be made of materials other than glass or plastic as long as it can function as a support of the light-emitting element. Note that when light emission from the light-emitting element is extracted outside through the substrate 101, the substrate 101 is preferably a light-transmitting substrate.

The first electrode 102 is preferably formed using any of metals, alloys, or conductive compounds, a mixture thereof, or the like with a high work function (specifically, a work function of greater than or equal to 4.0 eV is preferable). For example, indium tin oxide (ITO), indium tin oxide containing silicon or silicon oxide, indium zinc oxide (IZO), indium oxide containing tungsten oxide and zinc oxide (IWZO), and the like are given. Such a conductive metal oxide film is usually formed by a sputtering method, but may also be formed by an ink-jet method, a spin coating method, or the like by application of a sol-gel method or the like. For example, indium zinc oxide (IZO) can be formed by a sputtering method using indium oxide into which 1 wt % to 20 wt % of zinc oxide is added, as a target. Indium oxide containing tungsten oxide and zinc oxide (IWZO) can be formed by a sputtering method using a target in which 0.5 wt % to 5 wt % of tungsten oxide and 0.1 wt % to 1 wt % of zinc oxide are mixed with indium oxide. Other than those, gold (Au), platinum (Pt), nickel (Ni), tungsten (W), chromium (Cr), molybdenum (Mo), iron (Fe), cobalt (Co), copper (Cu), palladium (Pd), titanium (Ti), nitrides of the metal materials (such as titanium nitride: TiN), and the like are given.

In the case where a layer containing a composite material described below is used as a layer in contact with the first electrode 102, various metals, alloys, electrically conductive compounds, or a mixture thereof can be used for the first electrode 102 regardless of the work function. For example, aluminum (Al), silver (Ag), an aluminum alloy (such as AlSi), or the like can be used. Besides, an element that belongs to Group 1 or 2 of the periodic table which has a low work function, i.e., alkali metals such lithium (Li) and cesium (Cs) and alkaline earth metals such as magnesium (Mg), calcium (Ca), and strontium (Sr); alloys of them (e.g., MgAg and AlLi); rare earth metals such as europium (Eu) and ytterbium (Yb); alloys of them; and the like can also be used. A film of an alkali metal, an alkaline earth metal, or an alloy including these can be formed by a vacuum evaporation method. In addition, an alloy including an alkali metal or an alkaline earth metal can be formed by a sputtering method. Further, a silver paste or the like can be formed by an ink-jet method.

The EL layer 103 described in Embodiment 4 includes a hole-injecting layer 111, a hole-transporting layer 112, a light-emitting layer 113, an electron-transporting layer 114, and an electron-injecting layer 115. The EL layer 103 includes at least a light-emitting layer, and there is no particular limitation on a structure of the other stacked layers. In other words, there is no particular limitation on the stacked structure of layers of the EL layer 103; layers formed of a substance having a high electron-transporting property, a substance having a high hole-transporting property, a substance having a high electron-injecting property, a substance having a high hole-injecting property, a bipolar substance (a substance having high electron-transporting and hole-transporting properties), a substance having a high light-emitting property may be combined with the organic semiconductor material described in Embodiments 1 to 3 as appropriate to form the EL layer 103. For example, the EL layer 103 may be formed by any combination of a hole-injecting layer, a hole-transporting layer, a light-emitting layer, an electron-transporting layer, an electron-injecting layer, and the like, as appropriate. Materials for forming layers will be specifically given below.

The hole-injecting layer 111 is a layer containing a substance having a high hole-injecting property. As a substance having a high hole-injecting property, molybdenum oxide, vanadium oxide, ruthenium oxide, tungsten oxide, manganese oxide, or the like can be used. Besides, as a low molecular organic compound, the following compounds are given: phthalocyanine-based compounds such as phthalocyanine ($H_2Pc$), copper(II) phthalocyanine (CuPc), and vanadyl phthalocyanine (VOPc); aromatic amine compounds such as 4,4',4''-tris(N,N-diphenylamino)triphenylamine (TDATA), 4,4',4''-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazol-3-yl)-N-phenylamino]-9-phenylcarbazole (PCzPCA1), 3,6-bis[N-(9-phenylcarbazol-3-yl)-N-phenylamino]-9-phenylcarbazole (PCzPCA2), and 3-[N-(1-naphthyl)-N-(9-phenylcarbazol-3-yl)amino]-9-phenylcarbazole (PCzPCN1), and the like.

Alternatively, for the hole-injecting layer 111, a composite material in which an acceptor substance is mixed into a substance having a high hole-transporting property can be used. Note that when a material formed by mixing an acceptor substance into a substance with a high hole-transporting property is used, materials for forming the electrode can be selected regardless of the work function. In other words, besides a material with a high work function, a material with a low work function may also be used as the first electrode 102. Such a composite material can be formed by co-deposition of a substance with a high hole-transporting property and an acceptor substance.

Note that, in this specification, "composition" means not only a simple mixture of two materials but also a mixture of a plurality of materials in a condition where an electric charge is given and received among the materials.

As the organic compound used for the composite material, a variety of compounds such as an aromatic amine compound, a carbazole derivative, aromatic hydrocarbon, and a high molecular compound (oligomer, dendrimer, polymer, or the like) can be used. An organic compound used for the composite material is preferably an organic compound having a high hole-transporting property. Specifically, a substance having a hole mobility of higher than or equal to $10^{-6}$ $cm^2/Vs$ is preferably used. However, any substance other than the above substances may also be used as long as it is a substance whose hole-transporting property is higher than the electron-transporting property. Organic compounds that can be used for the composite material is specifically given below.

As the organic compound that can be used for the composite material, the following can be given, for example: aromatic amine compounds such as MTDATA, TDATA, DPAB, DNTPD, DPA3B, PCzPCA1, PCzPCA2, PCzPCN1, 4,4'-bis[N-(1-naphthyl)-N-phenylamino]biphenyl (NPB or α-NPD), and N,N'-bis(3-methylphenyl)-N,N'-diphenyl-[1,1'-biphenyl]-4,4'-diamine (TPD); carbazole derivatives such as 4,4'-di(N-carbazolyl)biphenyl (CBP), 1,3,5-tris[4-(N-carbazolyl)phenyl]benzene (TCPB), 9-[4-(10-phenyl-9-anthryl)phenyl]-9H-carbazole (CzPA), and 1,4-bis[4-(N-carbazolyl)phenyl-2,3,5,6-tetraphenylbenzene; and aromatic hydrocarbon compounds such as 2-tert-butyl-9,10-di(2-naphthyl)anthracene (t-BuDNA), 2-tert-butyl-9,10-di(1-naphthyl)anthracene, 9,10-bis(3,5-diphenylphenyl)anthracene (DPPA), 2-tert-butyl-9,10-bis(4-phenylphenyl)anthracene (t-BuDBA), 9,10-di(2-naphthyl)anthracene (DNA), 9,10-diphenylanthracene (DPAnth), 2-tert-butylanthracene (t-BuAnth), 9,10-bis(4-methyl-1-naphthyl)anthracene (DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (DPVBi), and 9,10-bis[4-(2,2-diphenylvinyl)phenyl]anthracene (DPVPA).

As an acceptor substance, organic compounds such as 7,7,8,8-tetracyano-2,3,5,6-tetrafluoroquinodimethane ($F_4$-TCNQ) and chloranil, and a transition metal oxide can be given. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of a high electron-accepting property. Among those, molybdenum oxide is especially preferable since it is stable in the air, has a low hygroscopic property, and is easily handled.

Further, for the hole-injecting layer 111, a high molecular compound (oligomer, dendrimer, polymer, or the like) can be used. For example, the following high molecular compounds are given: poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). In addition, a high molecular compound doped with acid such as poly(3,4-ethylenedioxythiophene)/poly(styrenesulfonic acid) (PEDOT/PSS) or polyaniline/poly(styrenesulfonic acid) (PAni/PSS) can be used.

Note that the hole-injecting layer 111 can be formed using a composite material of the above high molecular compound, such as PVK, PVTPA, PTPDMA, or Poly-TPD, and the above acceptor substance.

The hole-transporting layer 112 is a layer containing a substance having a high hole-transporting property. As the substance having a high hole-transporting property, the following low molecular organic compound can be used: an aromatic amine compound such as NPB (or α-NPD), TPD, 4,4'-bis[N-(9,9-dimethylfluoren-2-yl)-N-phenylamino]biphenyl (DFLDPBi), or 4,4'-bis[N-(spiro-9,9'-bifluoren-2-yl)-N-phenylamino]-biphenyl (BSPB); 4,4',4''-tris[N-(3-methylphenyl)-N-phenylamino]triphenylamine (m-MTDATA); N-[4-(9H-carbazol-9-yl)phenyl]-N-phenylspiro-9,9'-bifluoren-2-amine (YGASF), N,N'-bis[4-(9H-carbazol-9-yl)phenyl-N,N'-diphenylvinyl-4,4'-diamine (YGABP); 4-(9H-carbazol-9-yl)-2'-phenyltriphenylamine (o-YGA1BP); 4-(9H-carbazol-9-yl)-3'-phenyltriphenylamine (m-YGA1BP); 4-(9H-carbazol-9-yl)-4'-phenyltriphenylamine (p-YGA1BP); 1,3,5-tris(N-carbazolyl)benzene (TCzB); or 4,4',4''-tris(N-carbazolyl)triphenylamine (TCTA). The substances given here are mainly substances each having an electron mobility of higher than or equal to $10^{-6}$ $cm^2/Vs$. However, any substance other than the above substances may also be used as long as it is a substance whose hole-transporting property is higher than the electron-transporting property. The layer containing a substance having a high hole-transporting property is not limited to a single layer, and two or more layers containing the above materials may also be stacked.

Furthermore, for the hole-transporting layer 112, a composite material in which an acceptor substance is contained in the above substance having a high hole-transporting property can be used.

Alternatively, for the hole-transporting layer 112, a high molecular compound such as PVK, PVTPA, PTPDMA, or Poly-TPD can be used.

The light-emitting layer 113 is a layer containing a substance having a high light-emitting property, and a variety of materials can be used for the light-emitting layer 113. As the substance having a high light-emitting property, for example, a fluorescent compound which emits fluorescence or a phosphorescent compound which emits phosphorescence can be used. In addition, plural types of substances having a high light-emitting property may be used without limitation to one type.

Examples of a phosphorescent compound that can be used for the light-emitting layer are given below. As a light-emitting material for blue and blue-tinged light emission, the following are given: bis[2-(4',6'-difluorophenyl)pyridinato-N,$C^{2'}$]iridium(III)tetrakis(1-pyrazolyl)borate (FIr6), bis[2-(4',6'-difluorophenyl)pyridinato-N,$C^{2'}$]iridium(III)picolinate (FIrpic), bis[2-(3',5' bistrifluoromethylphenyl) pyridinato-N,$C^{2'}$]iridium(III)picolinate (Ir($CF_3$ppy)$_2$(pic)), bis[2-(4',6'-difluorophenyl)pyridinato-N,$C^{2'}$]iridium(III) acetylacetonate (FIracac) and the like. As a light-emitting material for green and green-tinged light emission, the following are given: tris(2-phenylpyridinato-N,$C^{2'}$)irridium (III) (Ir(ppy)$_3$), bis(2-phenylpyridinato-N,$C^{2'}$)iridium(III) acetylacetonate (Ir(ppy)$_2$(acac)), bis(1,2-diphenyl-1H-benzimidazolato)iridium(III)acetylacetonate (Ir(pbi)$_2$(acac)), bis(benzo[h]quinolinato)iridium(III)acetylacetonate (Ir(bzq)$_2$(acac)), and the like. As a light-emitting material for yellow and yellow-tinged light emission, the following are given: bis(2,4-diphenyl-1,3-oxazolato-N,$C^{2'}$)iridium(III)acetylacetonate (Ir(dpo)$_2$(acac)), bis[2-(4'-perfluorophenylphenyl) pyridinato]iridium(III)acetylacetonate (Ir(p-PF-ph)$_2$(acac)), bis(2-phenylbenzothiazolato-N,$C^{2'}$)iridium(III)acetylacetonate (Ir(bt)$_2$(acac)), and the like. As a light-emitting material for orange and orange-tinged light emission, the following are given: tris(2-phenylquinolinato-N,$C^{2'}$)iridium(III) (Ir(pq)$_3$), bis(2-phenylquinolinato-N,$C^{2'}$)iridium(III)acetylacetonate (Ir(pq)$_2$(acac)), and the like. As a light-emitting material for red and red-tinged light emission, the following organometallic complex are given: bis[2-(2'-benzo[4,5-α]thienyl)pyridinato-N,$C^{3'}$)iridium(III)acetylacetonate (Ir(btp)$_2$(acac)), bis(1-phenylisoquinolinato-N,$C^{2'}$)iridium(III) acetylacetonate (Ir(piq)$_2$(acac)), (acetylacetonato)bis[2,3-bis(4-fluorophenyl)quinoxalinato]iridium(III) (Ir(Fdpq)$_2$(acac)), 2,3,7,8,12,13,17,18-octaethyl-21H,23H-porphyrinplatinum(II) (PtOEP), and the like are given. In addition, a rare-earth metal complex such as tris(acetylacetonato)(monophenanthroline)terbium(III) (Tb(acac)$_3$(Phen)), tris(1,3-diphenyl-1,3-propanedionato)(monophenanthroline)europiom(III) (Eu(DBM)$_3$(Phen)), or tris[1-(2-thenyl)-3,3,3-trifluoroacetonato](monophenanthroline) europium(III) (Eu(TTA)$_3$(Phen)) performs light emission (electron transition between different multiplicities) from a rare-earth metal ion; therefore, such a rare-earth metal complex can be used as the phosphorescent compound.

Examples of a fluorescent compound that can be used for the light-emitting layer are given below. As a light-emitting material for blue and blue-tinged light emission, the following are given: N,N-bis[4-(9H-carbazol-9-yl)phenyl]-N,N'-diphenylstilbene-4,4'-diamine ((YGA2S), 4-(9H-carbazol-9-yl)-4'-(10-phenyl-9-anthryl)triphenylamine (YGAPA), 4-(9H-carbazol-9-yl)-4'-(9,10-diphenyl-2-anthryl)triphenylamine (2YGAPPA), N,9-diphenyl-N-[4-(10-phenyl-9-anthryl)phenyl]-9H-carbazol-3-amine (PCAPA), perylene, 2,5,8,11-tetra-tert-butylperylene (TBP), 4-(10-phenyl-9-anthryl)-4'-(9-phenyl-9H-carbazol-3-yl)triphenylamine (PCBAPA), and the like. As a light-emitting material for green and green-tinged light emission, the following are given: N-(9,10-diphenyl-2-anthryl)-N,9-diphenyl-9H-carbazol-3-amine (2PCAPA), N-[9,10-bis(1,1'-biphenyl-2-yl)-2-anthryl]-N,9-diphenyl-9H-carbazol-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazol-9-yl)phenyl]-N-phenylanthracen-2-amine (2YGABPhA), N,N,9-triphenylanthracen-9-amine (DPhAPhA), and the like. As a light-emitting material for yellow and yellow-tinged light emission, rubrene, 5,12-bis(1,1'-biphenyl-4-yl)-6,11-diphenyltetracene (BPT), and the like are given. As a light-emitting material for red and red-tinged light emission, the following are given: N,N,N',N'-tetrakis(4-methylphenyl)tetracene-5,11-diamine (p-mPhTD), 7,13-diphenyl-N,N,N',N'-tetrakis(4-methylphenyl)acenaphtho[1,2-a]fluoranthene-3,10-diamine (p-mPhAFD), and the like.

Note that the light-emitting layer may have a structure in which any of the above substances having a high light-emitting property (guest material) is dispersed into another substance (host material). A variety of types of substances can be used for a material for dispersing the light-emitting substance (host material), and it is preferable to use a substance whose lowest unoccupied molecular orbital (LUMO) level is higher than that of a substance having a high light-emitting property (guest material) and whose highest occupied molecular orbital (HOMO) level is lower than that of the substance having a high light-emitting property (guest material). Note that in this specification, "the HOMO level or the LUMO level is high" means that the energy level is high, while "the HOMO level or the LUMO level is low" means that the energy level is low. For example, Substance A having a HOMO level of −5.5 eV has the HOMO level which is lower by 0.3 eV than Substance B having a HOMO level of −5.2 eV and higher by 0.2 eV than Substance C having a HOMO level of −5.7 eV.

The organic semiconductor material described in Embodiments 1 to 3 has a large band gap and a bipolar property, and thus is suitable as a host material. The organic semiconductor material described in Embodiments 1 to 3 has a large band gap; thus, light emission from a guest material can be efficiently obtained even in the case where a guest material which exhibits light emission of a short wavelength is used. In addition, the driving voltage of the light-emitting element can be reduced.

Further, the organic semiconductor material described in Embodiments 1 to 3 has high triplet excitation energy; thus, light emission from a guest material can be efficiently obtained even in the case where a phosphorescent compound is used as a guest material. Especially in the case where a phosphorescent compound which exhibits light emission of a short wavelength is used, a prominent effect can be obtained.

Plural types of materials can be used as the host material. For example, in order to suppress crystallization, a substance which suppresses crystallization, such as rubrene, may be further added. In addition, NPB, Alq, or the like may be further added so that energy is transferred more efficiently to the substance with a light-emitting property.

The structure in which a substance having a high light-emitting property (guest material) is dispersed in another substance (host material) is used for the light-emitting layer, whereby crystallization of the light-emitting layer 113 can be suppressed. In addition, concentration quenching due to the increase in concentration of the substance having a high light-emitting property (guest material) can also be suppressed.

The electron-transporting layer 114 is a layer containing a substance having a high electron-transporting property. As a low molecular organic compound, for example, a metal complex such as tris(8-quinolinolato)aluminum(III) (Alq), tris(4-methyl-8-quinolinolato)aluminum(III) (Almq$_3$), bis(10-hydroxybenzo[h]quinolinato)beryllium(II) (BeBq$_2$), bis(2-methyl-8-quinolinolato)(4-phenylphenolato)aluminum (III) (BAlq), bis(8-quinolinolato)zinc(II) (Znq), bis[2-(2-benzoxazolyl)phenolato]zinc(II) (ZnPBO), or bis[2-(2-benzothiazolyl)phenolato]zinc(II) (ZnBTZ) can be used. Further, besides the above metal complex, a heterocyclic compound such as 2-(4-biphenylyl)-5-(4-tert-butylphenyl)-1,3,4-oxadiazole (PBD), 1,3-bis[5-(p-tert-butylphenyl)-1,3,4-oxadiazol-2-yl]benzene (OXD-7), 3-(4-biphenylyl)-4-phenyl-5-(4-tert-butylphenyl)-1,2,4-triazole (TAZ01), 2,2',2"-(1,3,5-benzenetriyl)-tris(1-phenyl-1H-benzimidazole) TPBI), bathophenanthroline (BPhen), or bathocuproine (BCP) can be used. The substances described here are mainly materials having an electron mobility of higher than or equal to $10^{-6}$ cm$^2$/Vs. Note that the electron-transporting layer 114 may be formed of substances other than those described above as long as the substances have higher electron-transporting properties than hole-transporting properties. Further, the electron-transporting layer 114 may be formed as not only a single-layer structure but also a layered structure in which two or more layers formed of the above substances are stacked.

For the electron-transporting layer 114, a high molecular compound can be used. For example, poly[(9,9-dihexylfluorene-2,7-diyl)-co-(pyridine-3,5-diyl)] (PF-Py), poly[(9,9-dioctylfluorene-2,7-diyl)-co-(2,2'-bipyridine-6,6'-diyl)] (PF-BPy), or the like can be used.

The electron-injecting layer 115 is a layer containing a substance having a high electron-injecting property. As the substance having a high electron-injecting property, an alkali metal or an alkaline earth metal such as lithium (Li) or magnesium (Mg), or a compound thereof such as lithium fluoride (LiF), cesium fluoride (CsF), or calcium fluoride (CaF$_2$) can be used. For example, a layer formed of a material having an electron-transporting property containing an alkali metal, an alkaline earth metal, or a compound thereof, such as a layer formed of Alq which contains magnesium (Mg), may be used. It is preferable to use a layer of a substance having an electron-transporting property containing an alkali metal or an alkaline earth metal as the electron-injecting layer because electron injection from the second electrode 104 is efficiently performed.

As a substance for forming the second electrode 104, a metal, an alloy, an electrically conductive compound, a mixture thereof, or the like with a low work function (specifically, a work function of lower than or equal to 3.8 eV is preferable) can be used. As a specific example of such a cathode material, an element that belongs to Group 1 or 2 in the periodic table, that is, an alkali metal such as lithium (Li) or cesium (Cs); an alkaline earth metal such as magnesium (Mg), calcium (Ca), or strontium (Sr); an alloy containing the element that belongs to Group 1 or 2 (such as MgAg, AlLi); a rare-earth metal such as europium (Eu) or ytterbium (Yb); an alloy thereof; or the like can be used. A film of an alkali metal, an alkaline earth metal, or an alloy including these can be formed by a vacuum evaporation method. In addition, an alloy including an alkali metal or an alkaline earth metal can be formed by a sputtering method. Further, the second electrode 104 can be formed by applying a silver paste or the like by an ink-jet method.

In the case where the electron-injecting layer 115 has a function of promoting electron injection is provided between the second electrode 104 and the electron-transporting layer 114, the second electrode 104 can be formed using a variety of conductive materials such as Al, Ag, ITO, and indium tin oxide containing silicon or silicon oxide, regardless of their work functions. These conductive materials can be formed by a sputtering method, an ink-jet method, a spin coating method, or the like.

Note that since the organic semiconductor material described in Embodiment 1 exhibits blue light emission, it can be used for the light-emitting layer as a substance having a high light-emitting property. For example, the oxadiazole derivative described in Embodiment 3 exhibits light emission ranging from purple to blue, and thus can be favorably used for the light-emitting element as a substance having a high light-emitting property. In addition, the organic semiconductor material described in Embodiments 1 to 3 has a bipolar property, and thus can also be used for layers other than the light-emitting layer (e.g., the hole-transporting layer and the electron-transporting layer). Moreover, the organic semiconductor material described in Embodiments 1 to 3 has a large band gap, and thus can also be used for an electron-blocking layer or a hole-blocking layer. Furthermore, the organic semiconductor material described in Embodiments 1 to 3 has high triplet excitation energy, and thus can also be used for an exciton-blocking layer.

As a formation method of the EL layer, a variety of methods can be used regardless of a dry process or a wet process. For example, a vacuum evaporation method, an ink-jet method, a spin coating method, or the like may be used. In addition, the electrodes or the layers may be formed by different deposition methods.

For example, the EL layer may be formed using a high molecular compound by a wet process. Alternatively, the EL layer can be formed using a low molecular organic compound by a wet process. Further alternatively, the EL layer may be formed using a low molecular organic compound by a dry process such as a vacuum evaporation method.

The electrode may be formed using a sol-gel method by a wet method, or using a paste of a metal material by a wet method. Alternatively, the electrode may be formed by a dry process such as a sputtering method or a vacuum evaporation method.

For example, in the case where the light-emitting element of Embodiment 4 is applied to a display device and the display device is manufactured using a large substrate, the light-emitting layer is preferably formed by a wet process. When the light-emitting layer is formed by an inkjet method, selective deposition of the light-emitting layer for each color can be easily performed even when a large substrate is used.

In the light-emitting element of Embodiment 4 having the above structure, current flows by provision of a potential difference between the first electrode 102 and the second electrode 104 and holes and electrons are recombined in the EL layer 103, whereby light is emitted.

The emitted light is extracted through one or both of the first electrode 102 and the second electrode 104. Accordingly, one or both of the first electrode 102 and the second electrode 104 is/are an electrode having a light-transmitting property. For example, when only the first electrode 102 has a light-transmitting property, the emitted light is extracted from the substrate side through the first electrode 102. In the case where only the second electrode 104 is a light-transmitting electrode, light is extracted from the side opposite to the substrate through the second electrode 104. In the case where both the first electrode 102 and the second electrode 104 are light-transmitting electrodes, emitted light is extracted from both the substrate side and the side opposite to the substrate through the first electrode 102 and the second electrode 104.

The structure of the layers provided between the first electrode 102 and the second electrode 104 is not limited to the above structure. Any structure other than the above structure can be employed as long as a light-emitting region for recombination of holes and electrons is positioned away from the first electrode 102 and the second electrode 104 so as to prevent quenching caused by proximity of the light-emitting region to metal, and the organic semiconductor material described in Embodiment 1 is provided.

In other words, there is no particular limitation on the stacked structure of the layers; layers formed of a substance having a high electron-transporting property, a substance having a high hole-transporting property, a substance having a high electron-injecting property, a substance having a high hole-injecting property, a bipolar substance (a substance having high electron-transporting and hole-transporting properties), and the like may be combined with the organic semiconductor material described in Embodiments 1 to 3 as appropriate to form the stacked structure.

Figure 2:
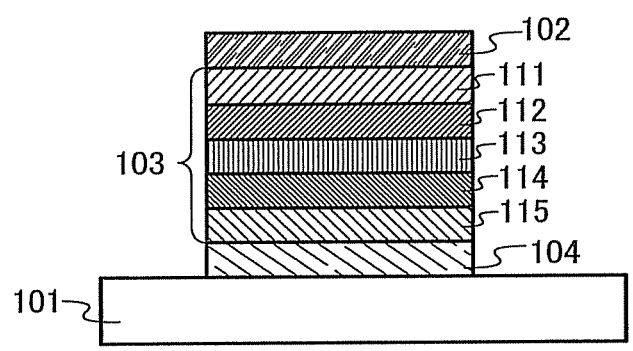
FIG. 2 illustrates a light-emitting element of an embodiment of the present invention.

For example, as illustrated in FIG. 2, a structure may be employed in which the second electrode 104 functioning as a cathode, the EL layer 103, and the first electrode 102 functioning as an anode are stacked in this order over the substrate 101. In FIG. 2, a structure in which the electron-injecting layer 115, the electron-transporting layer 114, the light-emitting layer 113, the hole-transporting layer 112, and the hole-injecting layer 111 are stacked in this order over the second electrode 104 is employed.

Note that in Embodiment 4, the light-emitting element is formed over a substrate made of glass, plastic, or the like. Formation of a plurality of such light-emitting elements over one substrate enables formation of a passive matrix light-emitting device. Alternatively, for example, a thin film transistor (TFT) may be formed over a substrate made of glass, plastic, or the like, and a light-emitting element may be manufactured over an electrode that is electrically connected to the TFT. Thus, an active matrix light-emitting device which controls driving of a light-emitting element by a TFT can be manufactured. There is no particular limitation on the structure of the TFT. The TFT may be either of staggered type or of inverted staggered type. In addition, a driving circuit formed over a TFT substrate may be formed using an N-type TFT and a P-type TFT, or may be formed using any one of an N-type TFT and a P-type TFT. In addition, there is also no particular limitation on the crystallinity of a semiconductor film used for the TFT. Either an amorphous semiconductor film or a crystalline semiconductor film may be used for the TFT. Alternatively, a single crystalline semiconductor film may be used. The single crystalline semiconductor film can be formed by Smart Cut (registered trademark) or the like.

Note that Embodiment 4 can be combined with any of the other embodiments as appropriate.

Embodiment 5

In this embodiment, a mode of a light-emitting element in which a plurality of light-emitting units according to an embodiment of the present invention are stacked (hereinafter, such a light-emitting element is also referred to as a stacked type element) will be described with reference to FIG. 3. This light-emitting element is a stacked type light-emitting element that has a plurality of light-emitting units between a first electrode and a second electrode. The structure of each of the light-emitting units can be similar to that described in Embodiment 4. In other words, the light-emitting element described in Embodiment 4 is a light-emitting element having one light-emitting unit. In this embodiment, a light-emitting element having a plurality of light-emitting units will be described.

Figure 3:
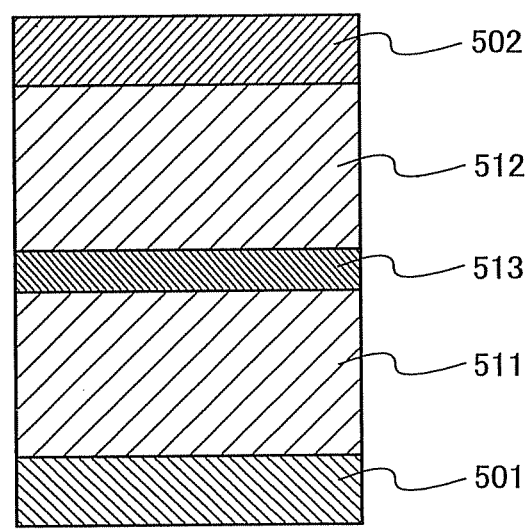
FIG. 3 illustrates a light-emitting element of an embodiment of the present invention.

In FIG. 3, a first light-emitting unit 511 and a second light-emitting unit 512 are stacked between a first electrode 501 and a second electrode 502. A charge generating layer 513 is provided between the first light-emitting unit 511 and the second light-emitting unit 512. As the first electrode 501 and the second electrode 502, electrodes similar to those in Embodiment 4 can be applied. In addition, the first light-emitting unit 511 and the second light-emitting unit 512 may have the same structure or different structures. Structures of the first light-emitting unit 511 and the second light-emitting unit 512 can be similar to the structure described in Embodiment 4.

The charge generating layer 513 is a layer that injects electrons into one of the light-emitting units and injects holes into the other of the light-emitting units when a voltage is applied to the first electrode 501 and the second electrode 502. The charge generating layer 513 may have a single-layer structure or a stacked-layer structure. As a stacked structure of plural layers, a structure in which a hole-injecting layer and an electron-injecting layer are stacked is preferable.

As the hole-injecting layer, a semiconductor or an insulator, such as molybdenum oxide, vanadium oxide, rhenium oxide, or ruthenium oxide, can be used. Alternatively, the hole-injecting layer may have a structure in which an acceptor substance is added into a substance having a high hole-transporting property. The layer including a substance having a high hole-transporting property and an acceptor substance is formed using the composite material described in Embodiment 4 and includes, as an acceptor substance, 7,7,8,8-tetracyano-2,3,5,6-tetrafluoroquinodimethane ($F_4$-TCNQ) or metal oxide such as vanadium oxide, molybdenum oxide, or tungsten oxide. As the substance having a high hole-transporting property, any of various compounds such as aromatic amine compounds, carbazole derivatives, aromatic hydrocarbons, and high molecular compounds (such as oligomers, dendrimers, and polymers) can be used. Note that a substance having a hole mobility of $10^{-6}$ cm$^2$/Vs or higher is preferably used as the substance having a high hole-transporting property. However, any substance other than the above substances may also be used as long as it is a substance in which the hole-transporting property is higher than the electron-transporting property. Since the composite material which includes the substance having a high hole-transporting property and the acceptor substance is superior in carrier-injecting property and carrier-transporting property, low-voltage driving and low-current driving can be realized.

As the electron-injecting layer, an insulator or a semiconductor, such as lithium oxide, lithium fluoride, or cesium carbonate, can be used. Alternatively, the electron-injecting layer may have a structure in which a donor substance is added into a substance having a high electron-transporting property. As the donor substance, an alkali metal, an alkaline earth metal, a rare earth metal, a metal that belongs to Group 13 of the periodic table, or an oxide or carbonate of them can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used for the donor substance. As the substance having a high electron-transporting property, the materials described in Embodiment 4 can be used. Note that a substance having an electron mobility of $10^{-6}$ cm$^2$/Vs or higher is preferably used as the substance having a high electron-transporting property. Note that any substance that has a higher electron-transporting property than a hole-transporting property may be used other than the above substances. Since the composite material of the substance having a high electron-transporting property and the donor substance has excellent carrier-injecting and carrier-transporting properties, low-voltage driving and low-current driving can be realized.

Further, the electrode materials described in Embodiment 4 can be used for the charge generating layer 513. For example, the charge generating layer 513 may be formed with a combination of a layer including a substance having a high hole-transporting property and metal oxide with a transparent conductive film. Note that a layer having a high light-transmitting property is preferably used as the charge generating layer in terms of light extraction efficiency.

In any case, the charge generating layer 513, which is interposed between the first light-emitting unit 511 and the second light-emitting unit 512, is acceptable as long as electrons are injected to one of the light-emitting units and holes are injected to the other of the light-emitting units when a voltage is applied to the first electrode 501 and the second electrode 502. For example, in a case of applying a voltage so that a potential of the first electrode is higher than a potential of the second electrode, any structure is acceptable for the charge generating layer 513 as long as the charge generating layer 513 injects electrons and holes into the first light-emitting unit 511 and the second light-emitting unit 512, respectively.

Although the light-emitting element having two light-emitting units is described in this embodiment, a light-emitting element in which three or more light-emitting units are stacked can be applied in a similar way. By arranging a plurality of light-emitting units between a pair of electrodes so as to be partitioned by a charge generating layer as in the light-emitting element of this embodiment, the element can perform light emission in a high luminance region while keeping a current density low; whereby the element can have long life. Moreover, a light-emitting device with low power consumption, which can be driven at low voltage, can be achieved.

The light-emitting units emit light of different colors from each other, thereby obtaining light emission of a desired color as the whole light-emitting element. For example, in a light-emitting element having two light-emitting units, the emission colors of the first light-emitting unit and the second light-emitting unit are made complementary, so that the light-emitting element which emits white light as the whole element can be obtained. Note that "complementary color" means a relation between colors which becomes an achromatic color when they are mixed. That is, white light emission can be obtained by mixture of lights obtained from substances emitting the lights of complementary colors. The same can be applied to a light-emitting element having three light-emitting units. For example, when the first light-emitting unit emits red light, the second light-emitting unit emits green light and the third light-emitting unit emits blue light, white light can be emitted from the whole light-emitting element.

Note that this embodiment can be combined with another embodiment as appropriate.

Embodiment 6

In this embodiment, a light-emitting device having a light-emitting element of an embodiment of the present invention which is described in the above embodiment will be described.

In this embodiment, a light-emitting device having a light-emitting element of an embodiment of the present invention in a pixel portion will be described with reference to FIGS. 4A and 4B. Note that FIG. 4A is a top view of the light-emitting device and FIG. 4B is a cross-sectional view taken along line A-A' and line B-B' in FIG. 4A. This light-emitting device includes a driver circuit portion (source side driver circuit) 601 and a driver circuit portion (gate side driver circuit) 603 which are indicated by dotted lines in order to control the light emission of the light-emitting element provided in a pixel portion 602. Further, a reference numeral 604 represents a sealing substrate, a reference numeral 605 represents a sealant, and the inside surrounded by the sealant 605 is a space 607.

Note that a leading wiring 608 is a wiring for transmitting signals input in the source side driver circuit 601 and the gate side driver circuit 603. The leading wiring 608 receives video signals, clock signals, start signals, reset signals, and the like from an FPC (flexible printed circuit) 609 that serves as an external input terminal. Although only the FPC is illustrated here, this FPC may be provided with a printed wiring board (PWB). The light-emitting device in this specification includes in its category not only a light-emitting device itself but also a light-emitting device with an FPC or a PWB attached thereto.

Next, a sectional structure of the light-emitting device will be described with reference to FIG. 4B. The driver circuit portion and the pixel portion are formed over an element substrate 610. In this case, one pixel in the pixel portion 602 and the source side driver circuit 601 which is the driver circuit portion are illustrated.

Note that as the source side driving circuit 601, a CMOS circuit in which an n-channel TFT 623 and a p-channel TFT 624 are combined is formed. The driver circuit may be formed by various CMOS circuits, PMOS circuits, or NMOS circuits. In this embodiment, a driver-integrated type in which a driver circuit is formed over the substrate provided with the pixel portion is described; however, the present invention is not limited to this type, and the driver circuit can be formed outside the substrate.

The pixel portion 602 includes a plurality of pixels each having a switching TFT 611, a current controlling TFT 612, and a first electrode 613 that is electrically connected to a drain of the current controlling TFT 612. Note that an insulator 614 is formed to cover an end portion of the first electrode 613. Here, the insulator 614 is formed using a positive photosensitive acrylic resin.

In order to improve the coverage, the insulator 614 is provided such that either an upper edge portion or a lower edge portion of the insulator 614 has a curved surface with a curvature. For example, when positive photosensitive acrylic is used as a material for the insulator 614, it is preferable that only the upper edge portion of the insulator 614 have a curved surface with a radius of curvature (0.2 μm to 3 μm). Further, the insulator 614 can be formed using either negative photosensitive acrylic that becomes insoluble in an etchant due to light irradiation, or positive photosensitive acrylic that becomes soluble in an etchant due to light irradiation.

An EL layer 616 and a second electrode 617 are formed over the first electrode 613. Here, various metals, alloys, electrically conductive compounds, or mixtures thereof can be used for a material of the first electrode 613. If the first electrode 613 is used as an anode, it is preferable that the first electrode be formed using a metal, an alloy, an electrically conductive compound, or a mixture thereof with a high work function (preferably, a work function of 4.0 eV or higher) among such materials. For example, the first electrode 613 can be Mimed using a single-layer film of an indium tin oxide film containing silicon, an indium zinc oxide film, a titanium nitride film, a chromium film, a tungsten film, a Zn film, a Pt film, or the like; or a stacked film, such as a stack of a titanium nitride film and a film containing aluminum as its main component or a three-layer structure of a titanium nitride film, a film containing aluminum as its main component, and a titanium nitride film. Note that when a stacked structure is employed, the first electrode 613 has low resistance as a wiring, forms a favorable ohmic contact, and can serve as an anode.

The EL layer 616 is formed by various methods such as an evaporation method using an evaporation mask, an inkjet method, a spin coating method, or the like. The EL layer 616 includes the organic semiconductor material described in Embodiments 1 to 3. Any of low molecular compounds, high molecular compounds, oligomers and dendrimers may be employed as the material used for the EL layer 616. As the material for the EL layer, not only an organic compound but also an inorganic compound may be used.

As the material for the second electrode 617, various types of metals, alloys, electrically conductive compounds, and mixtures of these can be used. If the second electrode is used as a cathode, it is preferable that the second electrode be formed using a metal, an alloy, an electrically conductive compound, a mixture thereof, or the like with a low work function (preferably, a work function of 3.8 eV or lower) among such materials. As an example, an element belonging to Group 1 or Group 2 in the periodic table; i.e., an alkali metal such as lithium (Li) or cesium (Cs), an alkaline earth metal such as magnesium (Mg), calcium (Ca), or strontium (Sr), or an alloy containing any of these (such as MgAg or AlLi); and the like can be given. If light generated in the EL layer 616 is transmitted through the second electrode 617, the second electrode 617 can be formed using a stack of a metal thin film and a transparent conductive film (indium tin oxide (ITO), indium tin oxide containing silicon or silicon oxide, indium zinc oxide (IZO), indium oxide containing tungsten oxide and zinc oxide (IWZO), or the like).

By attaching the sealing substrate 604 to the element substrate 610 with the sealant 605, a light-emitting element 618 is provided in the space 607 which is surrounded by the element substrate 610, the sealing substrate 604, and the sealant 605. Note that the space 607 is filled with a filler such as an inert gas (e.g., nitrogen, argon, or the like) or the sealant 605.

As the sealant 605, an epoxy resin is preferably used. In addition, it is desirable to use a material that allows permeation of moisture or oxygen as little as possible. As the sealing substrate 604, a plastic substrate formed using FRP (Fiberglass-Reinforced Plastics), PVF (polyvinyl fluoride), polyester, acrylic, or the like can be used besides a glass substrate or a quartz substrate.

As described above, a light-emitting device having the light-emitting element in Embodiment 4 or 5 can be obtained.

The light-emitting device described in this embodiment includes the light-emitting element described in Embodiment 4 or 5. The light-emitting element described in Embodiment 4 or 5 has high emission efficiency and the driving voltage is low. Therefore, a light-emitting device which can emit light with high luminance can be obtained. Further, a light-emitting device with low power consumption can be obtained.

Figure 5A:
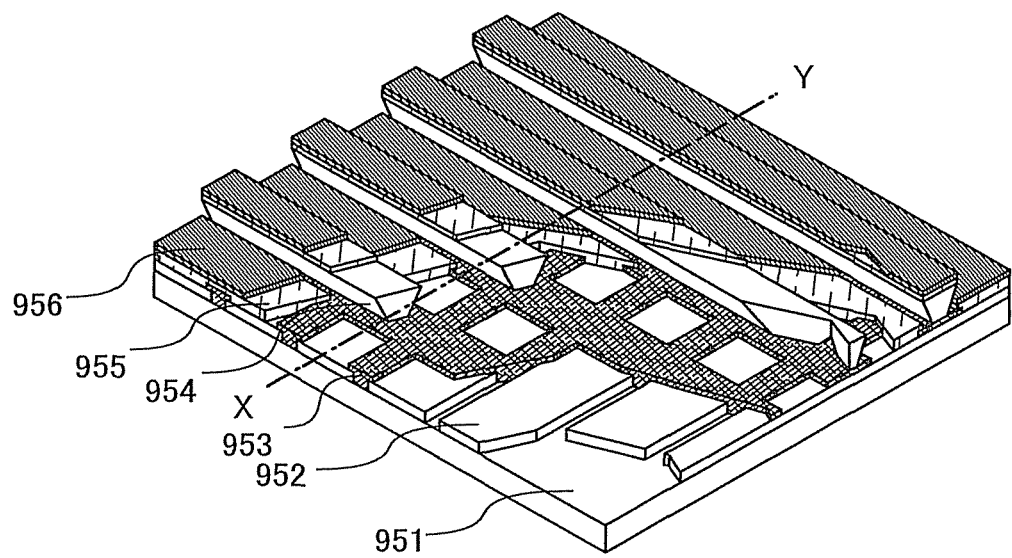
FIGS. 5A and 5B illustrate a light-emitting device of an embodiment of the present invention.
Figure 5B:
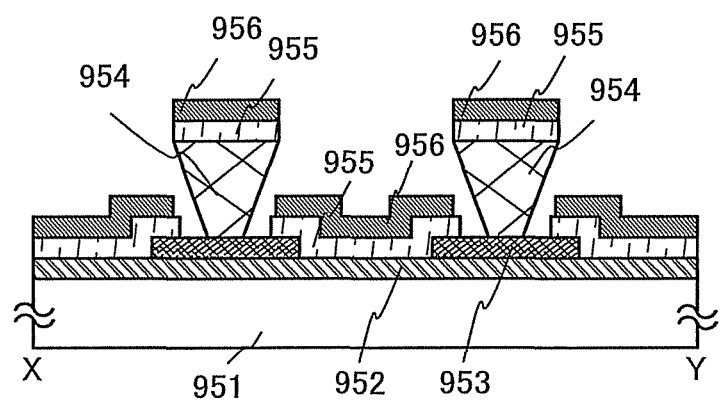

As described above, an active-matrix light-emitting device which controls driving of a light-emitting element with a transistor is described in this embodiment; however, passive-matrix light-emitting device may be used. FIGS. 5A and 5B illustrate a passive matrix light-emitting device manufactured by applying an embodiment of the present invention. FIG. 5A is a perspective view of the light-emitting device, and FIG. 5B is a cross-sectional view taken along line X-Y in FIG. 5A. In FIGS. 5A and 5B, an EL layer 955 is provided between an electrode 952 and an electrode 956 over a substrate 951. The edge of the electrode 952 is covered with an insulating layer 953. A partition wall layer 954 is provided on the insulating layer 953. The sidewalls of the partition wall layer 954 are aslope so that a distance between both sidewalls is gradually narrowed toward the surface of the substrate. In other words, a cross section taken along the direction of the short side of the partition wall layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). A cathode can be patterned by providing the partition wall layer 954 in this manner. In addition, in a passive matrix light-emitting device, a light-emitting device with low power consumption can be obtained by including a light-emitting element with high emission efficiency and low driving voltage according to an embodiment of the present invention.

Note that this embodiment can be combined with another embodiment as appropriate.

Embodiment 7

In this embodiment, an electronic device according to an embodiment of the present invention including the light-emitting device described in Embodiment 6 as a part will be described. The electronic device according to an embodiment of the present invention has the light-emitting element described in Embodiment 4 or 5, and thus has a display portion with low power consumption.

As examples of an electronic device manufactured using a light-emitting device according to an embodiment of the present invention, there are a camera such as a video camera or a digital camera, a goggle type display, a navigation system, an audio reproducing device (a car audio component, an audio component, or the like), a computer, a game machine, a portable information terminal (mobile computer, mobile phone, mobile game machine, an electronic book, or the like), an image reproducing device having a recording medium (specifically, a device for reproducing a recording medium such as a digital versatile disc (DVD) and having a display device for displaying the reproduced image), and the like. FIGS. 6A to 6E illustrate specific examples of these electronic devices.

Figure 6A:
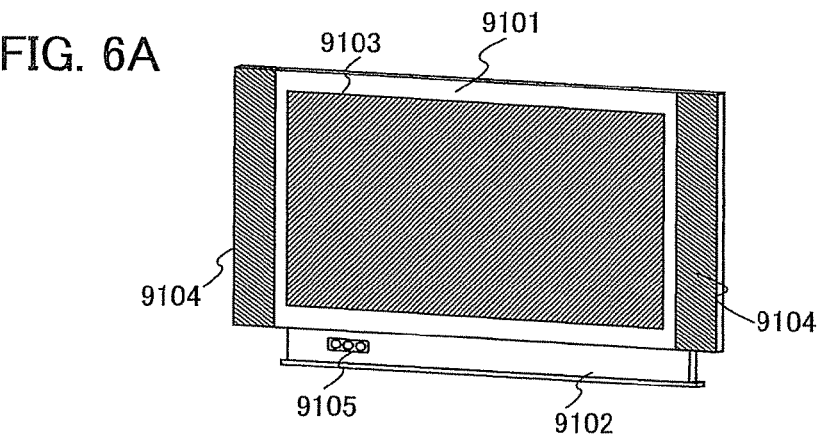
FIGS. 6A to 6E each illustrate an electronic device of an embodiment of the present invention.

FIG. 6A illustrates a television device of this embodiment, which includes a housing 9101, a supporting base 9102, a display portion 9103, speaker portions 9104, a video input terminal 9105, and the like. In the display portion 9103 of this television device, light-emitting elements similar to those described in the above embodiments are arranged in matrix. The light-emitting element has a feature that light emission efficiency is high and power consumption is low. In addition, the light-emitting element also has a feature that driving voltage thereof is low. The display portion 9103 which includes the light-emitting element has similar features. Therefore, in this television device, low power consumption is achieved. With such features, a power supply circuit can be significantly reduced or downsized in the television device; therefore, reduction in size and weight of the housing 9101 and the supporting base 9102 can be achieved. As for the television device of this embodiment, less power consumption and reduction in size and weight are achieved; therefore, the television can be provided as a product which is suitable for living environment.

Figure 6B:
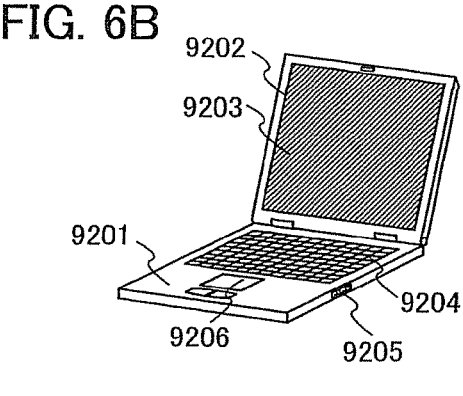

FIG. 6B illustrates a computer of this embodiment, which includes a main body 9201, a housing 9202, a display portion 9203, a keyboard 9204, an external connection port 9205, a pointing device 9206, and the like. In the display portion 9203 of this computer, light-emitting elements similar to those described in the above embodiments are arranged in matrix. The light-emitting element has a feature that light emission efficiency is high and power consumption is low. In addition, the light-emitting element also has a feature that driving voltage thereof is low. The display portion 9103 which includes the light-emitting element has similar features. Therefore, in this computer, low power consumption is achieved. With such features, a power supply circuit can be significantly reduced or downsized in the computer; therefore, reduction in size and weight of the main body 9201 and the housing 9202 can be achieved. As for the computer of this embodiment, low power consumption and reduction in size and weight are achieved; therefore, the computer can be provided as a product which is suitable for environment.

Figure 6C:
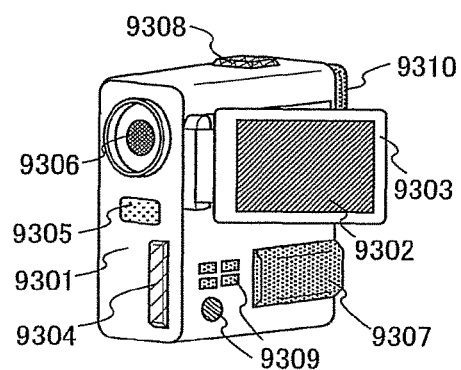

FIG. 6C illustrates a camera of this embodiment, which includes a main body 9301, a display portion 9302, a housing 9303, an external connection port 9304, a remote control receiving portion 9305, an image receiving portion 9306, a battery 9307, an audio input portion 9308, operation keys 9309, an eyepiece portion 9310, and the like. In the display portion 9302 of this camera, light-emitting elements similar to those described in the above embodiments are arranged in matrix. The light-emitting element has a feature that light emission efficiency is high and power consumption is low. In addition, the light-emitting element also has a feature that driving voltage thereof is low. The display portion 9302 which includes the light-emitting element has similar features. Therefore, in the camera, low power consumption is achieved. With such features, a power supply circuit can be significantly reduced or downsized in the camera; therefore, reduction in size and weight of the main body 9301 can be achieved. As for the camera of this embodiment, low power consumption and reduction in size and weight are achieved; therefore, the camera can be provided as a product which is suitable for being carried.

Figure 6D:
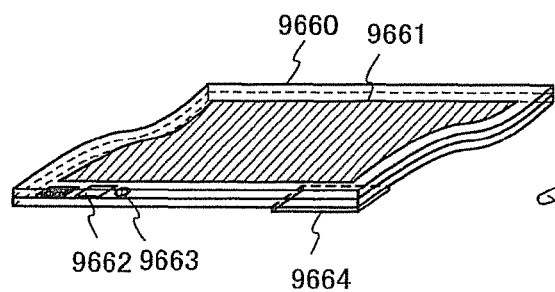

FIG. 6D illustrates electronic paper according to the present invention which is flexible and includes a main body 9660, a display portion 9661 which displays images, a driver IC 9662, a receiver 9663, a film battery 9664, and the like. The driver IC, the receiver, or the like may be mounted using a semiconductor component. In the electronic paper of the present invention, the main body 9660 is formed using a flexible material such as plastic or a film. In the electronic paper, the display portion 9661 has light-emitting elements similar to those described in Embodiments 1 to 3, which are arranged in matrix. The light-emitting elements have features of a long lifetime and low power consumption. Since the display portion 9661 including the light-emitting elements also has similar features, the electronic paper has high reliability and low power consumption thereof is achieved.

Figure 6E:
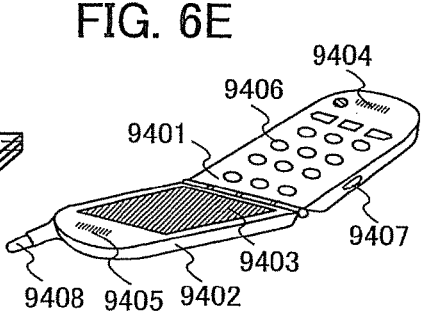

FIG. 6E illustrates a cellular phone of this embodiment which includes a main body 9401, a housing 9402, a display portion 9403, an audio input portion 9404, an audio output portion 9405, operation keys 9406, an external connection port 9407, an antenna 9408, and the like. In the display portion 9403 of this cellular phone, light-emitting elements similar to that described in Embodiment 2 are arranged in matrix. The light-emitting element has a feature that light emission efficiency is high and power consumption is low. In addition, the light-emitting element also has a feature that driving voltage thereof is low. The display portion 9403 which includes the light-emitting element has similar features. Therefore, in the cellular phone, low power consumption is achieved. With such features, a power supply circuit can be significantly reduced or downsized in the cellular phone; therefore, reduction in size and weight of the main body 9401 and the housing 9402 can be achieved. As for the cellular phone of this embodiment, low power consumption and reduction in size and weight are achieved; therefore, the cellular phone can be provided as a product which is suitable for being carried.

Figure 12A:
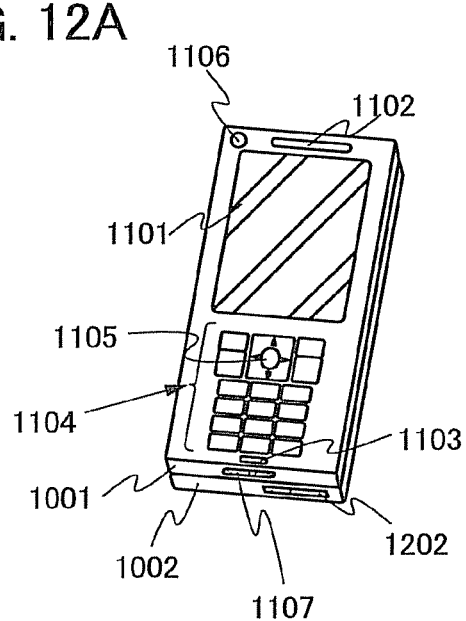
FIGS. 12A to 12C illustrate an electronic device of an embodiment of the present invention.
Figure 12B:
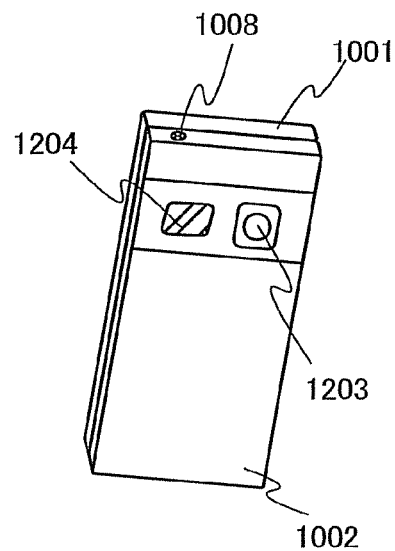
Figure 12C:
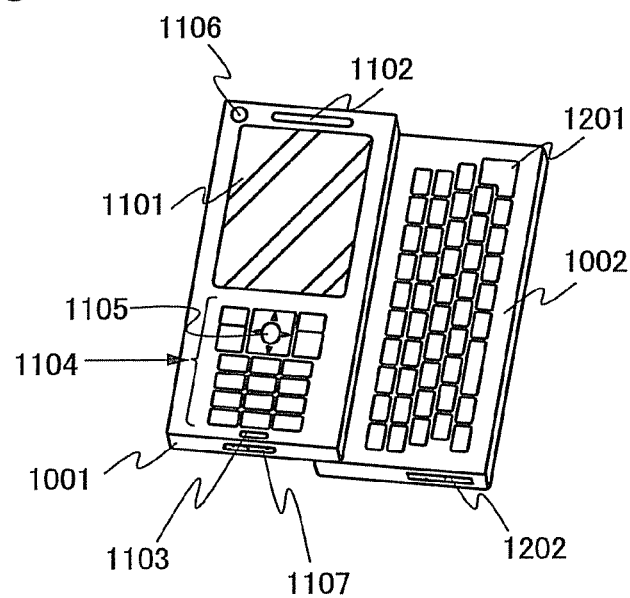

FIGS. 12A to 12C illustrate an example of a structure of a cellular phone, which is different from a structure of the cellular phone of FIG. 6E. FIG. 12A is a front view, FIG. 12B is a rear view, and FIG. 12C is a development view. The cellular phone in FIGS. 12A to 12C is a so-called smartphone which has both functions of a phone and a portable information terminal, and incorporates a computer to conduct a variety of data processing in addition to voice calls.

The cellular phone illustrated in FIGS. 12A to 12C has two housings 1001 and 1002. The housing 1001 includes a display portion 1101, a speaker 1102, a microphone 1103, operation keys 1104, a pointing device 1105, a camera lens 1106, an external connection terminal 1107, an earphone terminal 1008, and the like, while the housing 1002 includes a keyboard 1201, an external memory slot 1202, a camera lens 1203, a light 1204, and the like. In addition, an antenna is incorporated in the housing 1001.

Further, in addition to the above structure, the cellular phone may incorporate a non-contact IC chip, a small-sized memory device, or the like.

In the display portion 1101, the light-emitting device described in the above embodiment can be incorporated, and a display direction can be appropriately changed depending on the usage mode. The cellular phone is provided with the camera lens 1106 on the same surface as the display portion 1101; therefore, the cellular phone can be used as a videophone. Further, a still image and a moving image can be taken with the camera lens 1203 and the light 1204 using the display portion 1101 as a viewfinder. The speaker 1102 and the microphone 1103 can be used for video calls, recording, reproducing, and the like without being limited to voice calls. With the use of the operation keys 1104, making and receiving calls, inputting simple information such as e-mail or the like, scrolling the screen, moving the cursor, and the like are possible. Furthermore, the housing 1001 and the housing 1002 (FIG. 12A), which are overlapped with each other, are developed by sliding as illustrated in FIG. 12C, and can be used as a portable information terminal. In this case, smooth operation can be conducted using the keyboard 1201 and the pointing device 1105. The external connection terminal 1107 can be connected to an AC adaptor and various types of cables such as a USB cable, and charging, data communication with a computer, and the like are possible. Furthermore, a large amount of data can be stored and transferred by inserting a recording medium into the external memory slot 1202.

Further, in addition to the above functions, the cellular phone may include an infrared communication function, a television receiving function, or the like.

Figure 7:
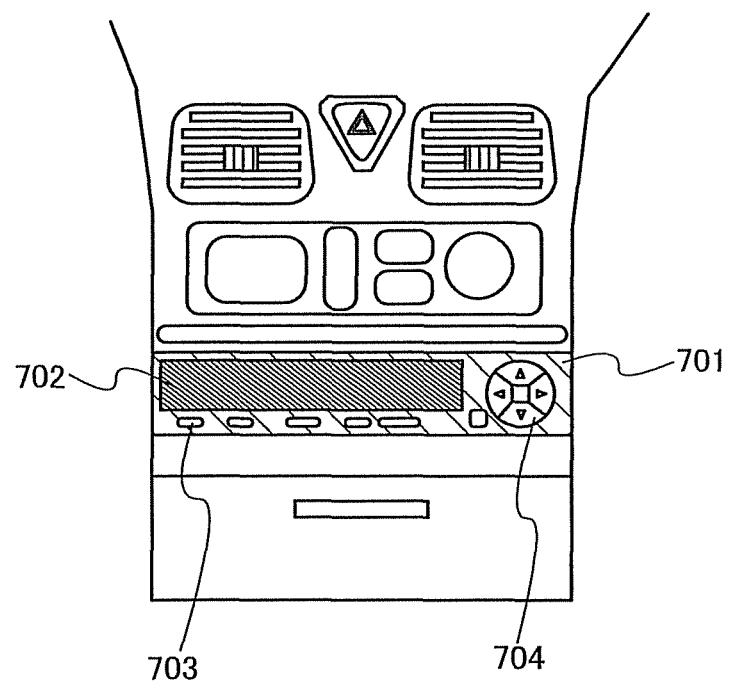
FIG. 7 illustrates an electronic device of an embodiment of the present invention.

FIG. 7 illustrates an audio reproducing device, specifically, a car audio system, which includes a main body 701, a display portion 702, and operation switches 703 and 704. The display portion 702 can be realized with the light-emitting device (passive matrix type or active matrix type) described in the above embodiment. Further, the display portion 702 may be formed using a segment type light-emitting device. In any case, the use of a light-emitting element according to an embodiment of the present invention makes it possible to form a bright display portion while achieving less power consumption, with the use of a vehicle power source (12 to 42 V). Further, although this embodiment describes an in-car audio system, a light-emitting device according to an embodiment of the present invention may also be used in portable audio systems or audio systems for home use.

Figure 8:
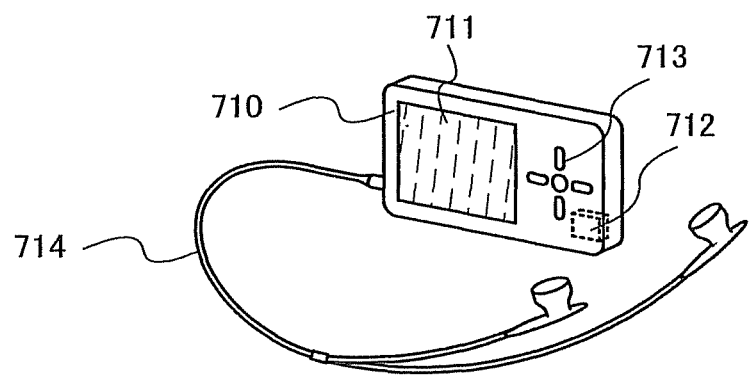
FIG. 8 illustrates an electronic device of an embodiment of the present invention.

FIG. 8 illustrates a digital player as an example of an audio reproducing device. The digital player illustrated in FIG. 8 includes a main body 710, a display portion 711, a memory portion 712, an operation portion 713, earphones 714, and the like. Note that headphones or wireless earphones can be used instead of the earphones 714. The display portion 711 can be realized with the light-emitting device (passive matrix type or active matrix type) described in the above embodiment. Further, the display portion 711 may be formed using a segment type light-emitting device. In any case, the use of the light-emitting element according to an embodiment of the present invention makes it possible to form a bright display portion which can display images even when using a secondary battery (a nickel-hydrogen battery or the like) while achieving less power consumption. As the memory portion 712, a hard disk or a nonvolatile memory is used. For example, by using a NAND-type nonvolatile memory with a recording capacity of 20 to 200 gigabytes (GB), and operating the operation portion 713, an image or a sound (music) can be recorded and reproduced. Note that in the display portion 702 and the display portion 711, white characters are displayed against a black background, and thus, power consumption can be reduced. This is particularly effective for portable audio systems.

As described above, the applicable range of the light-emitting device manufactured by applying an embodiment of the present invention is so wide that the light-emitting device is applicable to electronic devices in various fields. By applying an embodiment of the present invention, an electronic device which has a display portion consuming low power can be manufactured.

A light-emitting device to which an embodiment of the present invention is applied has a light-emitting element with high light emission efficiency, and can also be used as a lighting device. A light-emitting device to which an embodiment of the present invention is applied can emit light with high luminance and is preferably used as a lighting device. One mode of using a light-emitting element to which an embodiment of the present invention is applied for a lighting device will be described with reference to FIG. 9.

Figure 9:
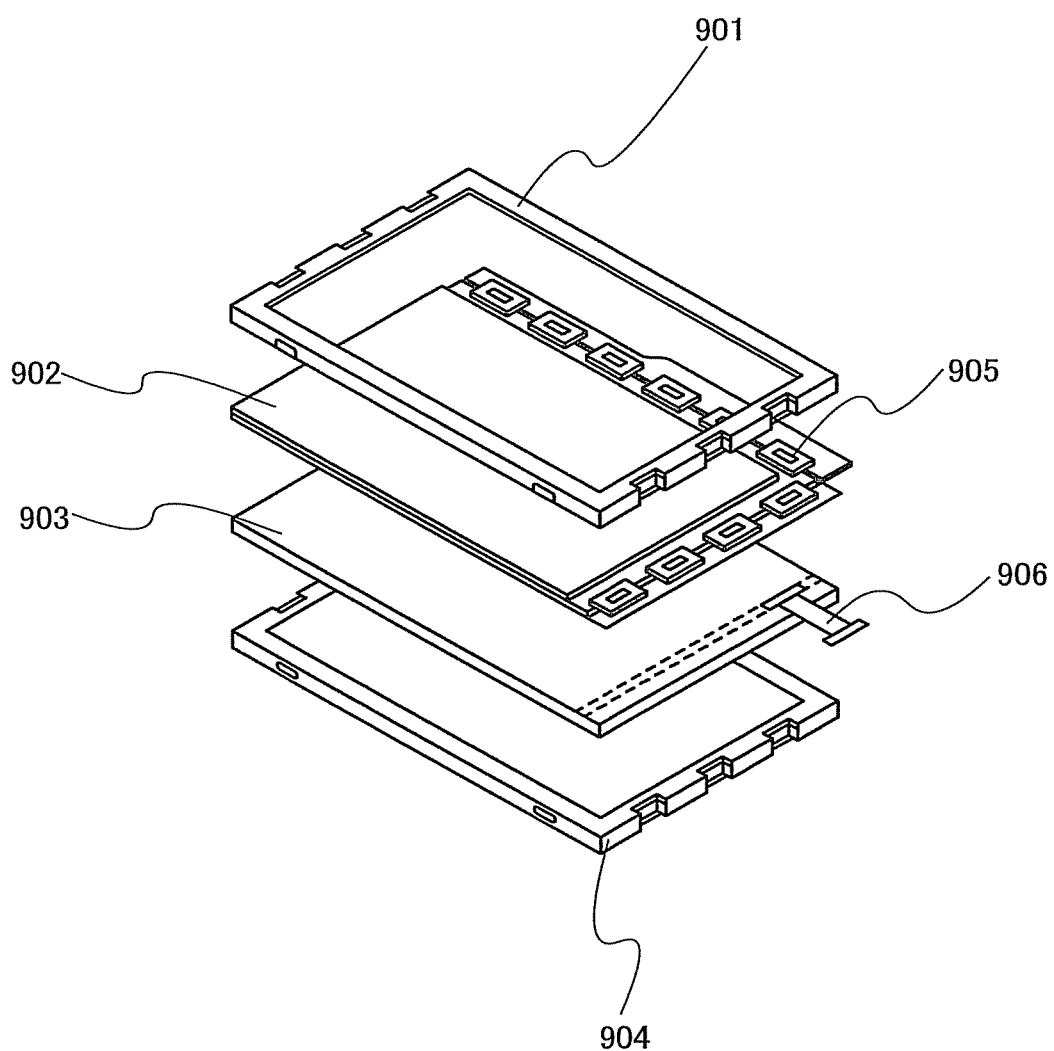
FIG. 9 illustrates an electronic device of an embodiment of the present invention.

FIG. 9 illustrates a liquid crystal display device using the light-emitting device to which an embodiment of the present invention is applied for a backlight, as an example of the electronic device using a light-emitting device according to an embodiment of the present invention for a lighting device. The liquid crystal display device illustrated in FIG. 9 includes a housing 901, a liquid crystal layer 902, a backlight 903, and a housing 904, and the liquid crystal layer 902 is connected to a driver IC 905. The light-emitting device to which an embodiment of the present invention is applied is used for the backlight 903, and current is supplied through a terminal 906.

Since the light-emitting device according to an embodiment of the present invention is thin and consumes less power, reduction in thickness and power consumption of a liquid crystal display device is possible by using a light-emitting device according to an embodiment of the present invention as a backlight of the liquid crystal display device. Moreover, a light-emitting device according to an embodiment of the present invention is a plane emission type lighting device, and can have a large area. Therefore, the backlight can have a large area, and a liquid crystal display device having a large area can be obtained.

Figure 10:
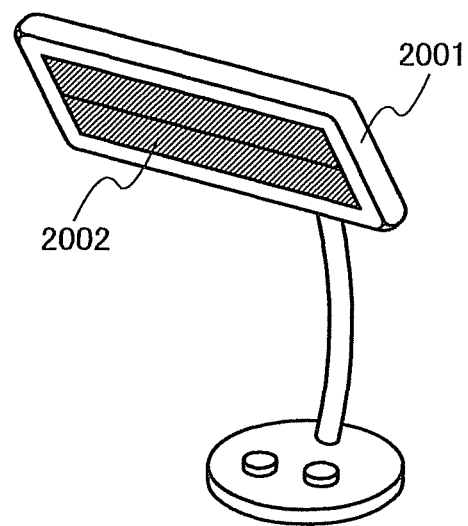
FIG. 10 illustrates a lighting device of an embodiment of the present invention.

FIG. 10 illustrates an example in which a light-emitting device according to an embodiment of the present invention is used as a desk lamp, which is one of lighting devices. The desk lamp illustrated in FIG. 10 includes a housing 2001 and a light source 2002, and a light-emitting device according to an embodiment of the present invention is used as the light source 2002. Since a light-emitting device according to an embodiment of the present invention consumes less power, the desk lamp also consumes less power.

Figure 11:
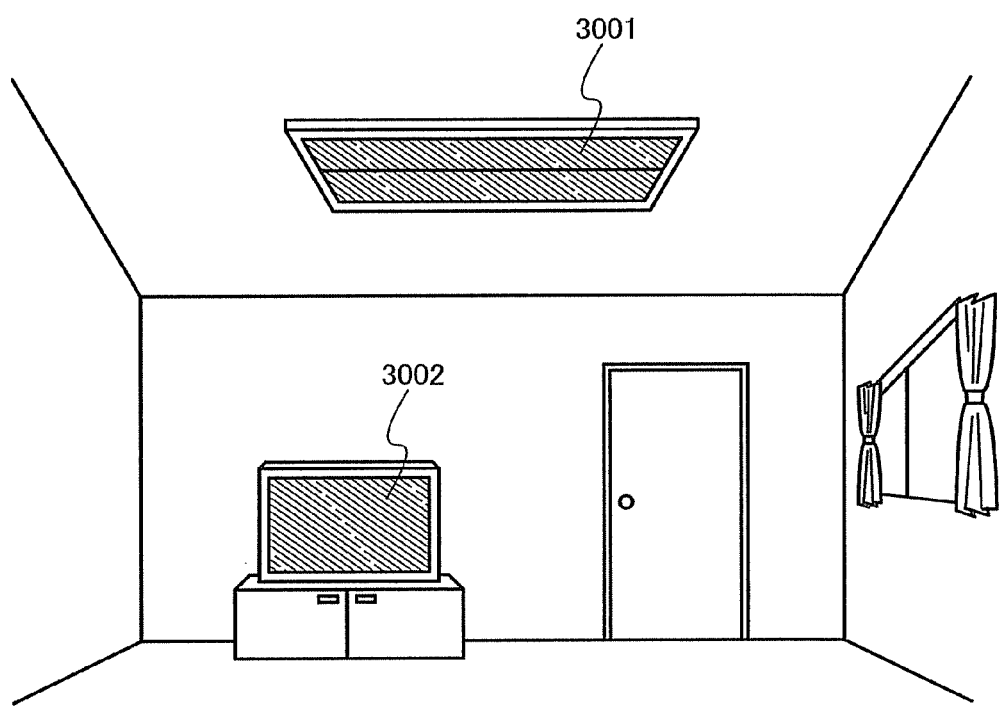
FIG. 11 illustrates a lighting device of an embodiment of the present invention.

FIG. 11 illustrates an example in which a light-emitting device to which an embodiment of the present invention is applied is used as an interior lighting device 3001. Since a light-emitting device according to an embodiment of the present invention can have a large area, a light-emitting device according to an embodiment of the present invention can be used as a lighting device having a large area. Moreover, since a light-emitting device according to an embodiment of the present invention consumes less power, a light-emitting device according to an embodiment of the present invention can be used as a lighting device which consumes less power. Thus, a television device 3002 according to an embodiment of the present invention such as that illustrated in FIG. 6A may be placed in a room where a light-emitting device to which an embodiment of the present invention is applied is used as the interior lighting device 3001, and public broadcasting or movies can be watched there. In such a case, since both devices consume low power, environmental load can be reduced.

Note that this embodiment can be combined with another embodiment as appropriate.

Example 1

In this example, an example of an electron-accepting unit and a hole-accepting unit in an organic semiconductor material according to an embodiment of the present invention will be described.

As described in Embodiment 1, it is difficult to evaluate the electron affinity and the ionization potential of an electron-accepting unit and a hole-accepting unit of an organic semiconductor material according to an embodiment of the present invention. Therefore, the electron affinity and the ionization potential of each unit were evaluated using a compound represented by General Formula (G2A) which corresponds to a partial structure a of an organic semiconductor material represented by General Formula (G1). Further, the hole-accepting unit was evaluated using a compound represented by General Formula (G2B) which corresponds to a partial structure b of an organic semiconductor material represented by General Formula (G1).

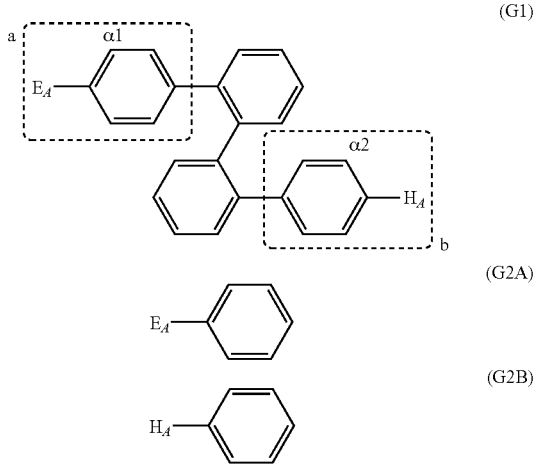

In this example, the electron affinity and the ionization potential were estimated by cyclic voltammetry (CV) measurement by using 2,5-diphenyl-1,3,4-oxadiazole and 2-phenylbenzoxazole which correspond to the partial structure a represented by General Formula (G2A). Structural formulae of 2,5-diphenyl-1,3,4-oxadiazole and 2-phenylbenzoxazole which were measured in this example are shown below.

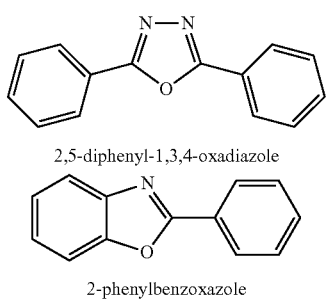

In this example, the electron affinity and the ionization potential were calculated by cyclic voltammetry (CV) measurement by using 9-phenyl-9H-carbazole and triphenylamine which correspond to the partial structure b represented by General Formula (G2B). Structural formulae of 9-phenyl-9H-carbazole and triphenylamine which were measured in this example are shown below.

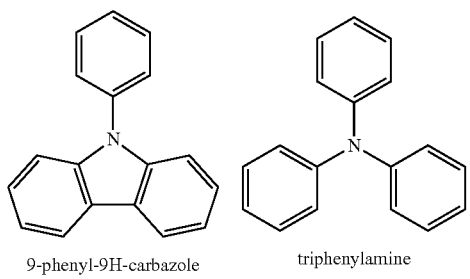

9-phenyl-9H-carbazole          triphenylamine

An electrochemical analyzer (ALS model 600A or 600C, manufactured by BAS Inc.) was used for the CV measurement. As a solution used for the CV measurement, dehydrated dimethylformamide (DMF, product of Sigma-Aldrich Inc., 99.8%, Catalog No. 22705-6) was used as a solvent, and tetra-n-butylammonium perchlorate (n-Bu$_4$NClO$_4$, product of Tokyo Chemical Industry Co., Ltd., Catalog No. T0836), which was a supporting electrolyte, was dissolved in the solvent such that the concentration of tetra-n-butylammonium perchlorate was 100 mmol/L. Further, the measurement object was also dissolved such that the concentration thereof was 2 mmol/L. Further, as a working electrode, a platinum electrode (a PTE platinum electrode, manufactured by BAS Inc.) was used. As an auxiliary electrode, a platinum electrode (a VC-3 Pt counter electrode (5 cm), manufactured by BAS Inc.) was used. As a reference electrode, an Ag/Ag$^+$ electrode (an RE7 nonaqueous solvent reference electrode, manufactured by BAS Inc.) was used. Note that the measurement was conducted at a room temperature (20° C. to 25° C.). In addition, the scan speed at the CV measurement was 0.1 V/sec in all the measurements.

[Calculation of the Potential Energy of the Reference Electrode with Respect to the Vacuum Level]

First, potential energy (eV) of the reference electrode (Ag/Ag$^+$ electrode) used in this example with respect to the vacuum level was calculated. That is, the Fermi level of the Ag/Ag$^+$ electrode was calculated. It is known that the oxidation-reduction potential of ferrocene in methanol is +0.610 [V vs. SHE] with respect to a standard hydrogen electrode (Reference: Christian R. Goldsmith et al., J. Am. Chem. Soc., Vol. 124, No. 1, pp. 83-96, 2002). On the other hand, by using the reference electrode used in this example, the oxidation-reduction potential of ferrocene in methanol was calculated to be +0.11 [V vs. Ag/Ag$^+$]. Therefore, it was found that the potential energy of the reference electrode used in this example was lower than that of the standard hydrogen electrode by 0.50 [eV].

Here, it is known that the potential energy of the standard hydrogen electrode with respect to the vacuum level is −4.44 eV (Reference: Toshihiro Ohnishi and Tamami Koyama, *High Molecular EL Material*, Kyoritsu Shuppan, pp. 64-67). Accordingly, the potential energy of the reference electrode used in this example with respect to the vacuum level could be calculated to be −4.44−0.50=−4.94 [eV].

Measurement Example 1

2,5-diphenyl-1,3,4-oxadiazole

First, in this measurement example, calculation of the ionization potential and the electron affinity by the CV measurement will be described in detail.

Figure 13:
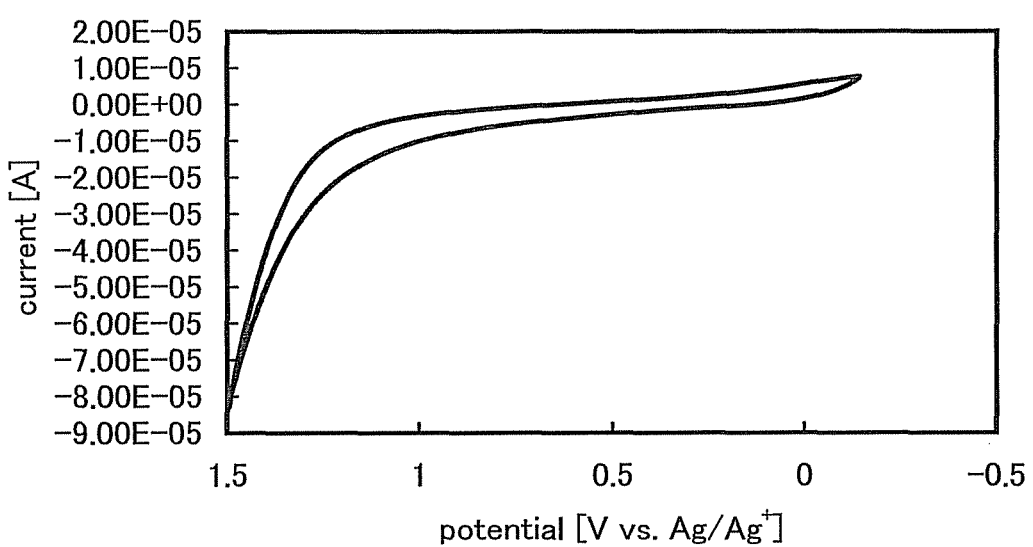
FIG. 13 shows CV measurement results of 2,5-diphenyl-1,3,4-oxadiazole.

Further, FIG. 13 shows CV measurement results of the oxidation characteristics of 2,5-diphenyl-1,3,4-oxadiazole. The measurement of the oxidation characteristics was performed by scanning the potential of the working electrode with respect to the reference electrode from −0.14 V to 1.50 V, and then from 1.50 V to −0.14 V.

As shown in FIG. 13, in the measurement of the oxidation characteristics, a peak which indicates oxidation does not appear until about at least 1.20 V. Further, even if there was a peak which indicates oxidation at a voltage greater than or equal to 1.20 V, the peak could not be observed due to the influence of flow of a large amount of current. That is, from this data, it is found that the oxidation potential of 2,5-diphenyl-1,3,4-oxadiazole is greater than or equal to at least 1.20 V. Here, the potential energy of the reference electrode used in this example with respect to the vacuum level is −4.94 [eV] as described above. Therefore, the oxidation potential of 1.20 V in the CV measurement is converted into the HOMO level to give −(−4.94−1.20)=−6.14 eV. Accordingly, it was found that the ionization potential of 2,5-diphenyl-1,3,4-oxadiazole is greater than or equal to at least 6.14 eV.

Figure 14:
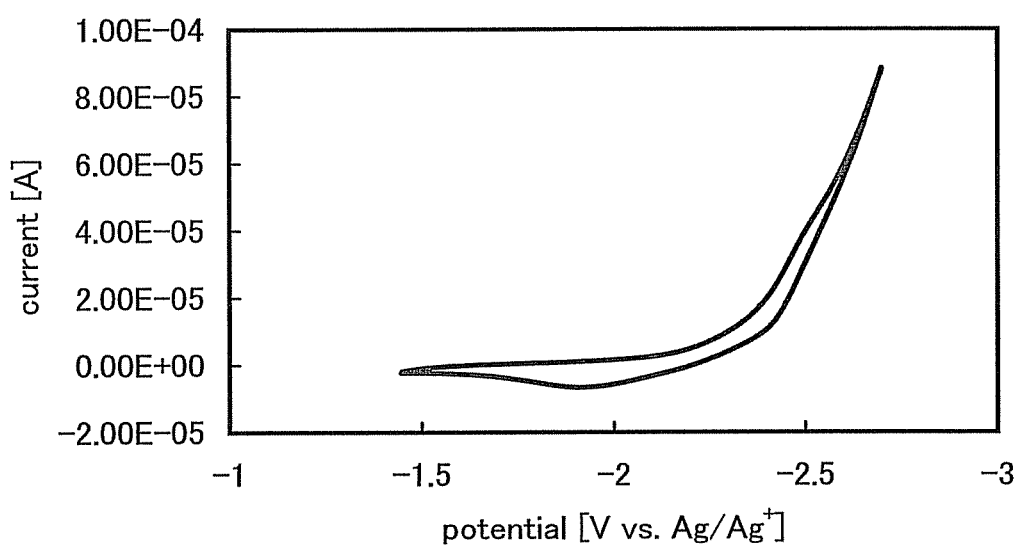
FIG. 14 shows CV measurement results of 2,5-diphenyl-1,3,4-oxadiazole.

FIG. 14 shows CV measurement results of the reduction characteristics of 2,5-diphenyl-1,3,4-oxadiazole. Note that the measurement of the reduction characteristics was conducted by scanning the potential of the working electrode with respect to the reference electrode from −1.45 V to −2.70 V, and then from −2.70 V to −1.45 V.

As shown in FIG. 14, in the measurement of the reduction characteristics, the reduction peak potential $E_{pc}$ was −2.51V. Further, the oxidation peak potential $E_{pa}$ was −2.39V. Therefore, the half-wave potential (an intermediate potential between $E_{pc}$ and $E_{pa}$) can be calculated to be −2.45 V. This shows that 2,5-diphenyl-1,3,4-oxadiazole is reduced by an electric energy of −2.45 [V vs. Ag/Ag$^+$], and this energy corresponds to the LUMO level. Here, the potential energy of the reference electrode used in this example with respect to the vacuum level is −4.94 [eV] as described above. Therefore, the LUMO level of 2,5-diphenyl-1,3,4-oxadiazole was found to be −4.94−(−2.45)=−2.49 [eV]. Accordingly, the electron affinity of 2,5-diphenyl-1,3,4-oxadiazole was calculated to be 2.49 eV.

Measurement Example 2

2-phenylbenzoxazole

Figure 15:
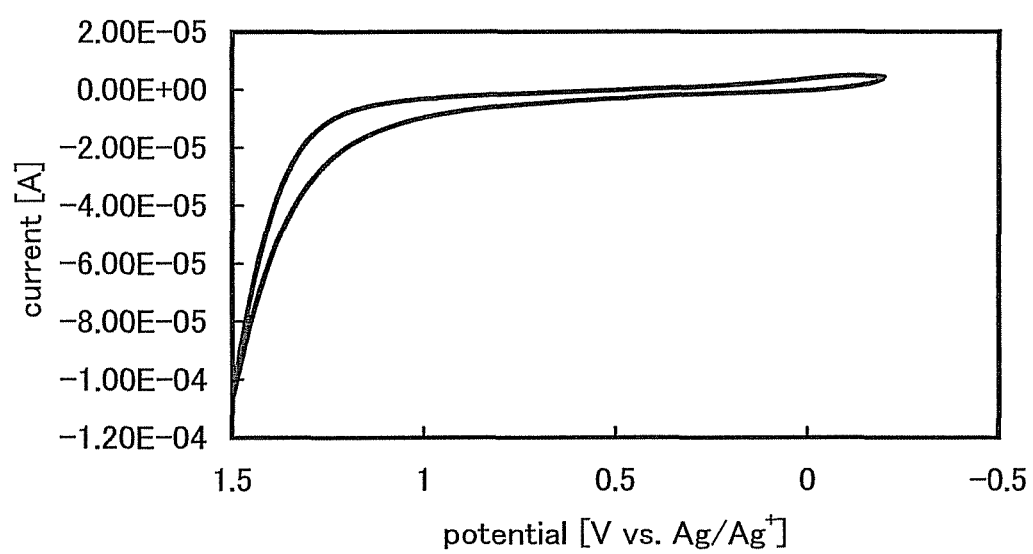
FIG. 15 shows CV measurement results of 2-phenylbenzoxazole.

Further, FIG. 15 shows CV measurement results of the oxidation characteristics of 2-phenylbenzoxazole. The measurement of the oxidation characteristics was performed by scanning the potential of the working electrode with respect to the reference electrode from −0.18 V to 1.50 V, and then from 1.50 V to −0.18 V.

As shown in FIG. 15, in the measurement of the oxidation characteristics, a peak which indicates oxidation does not appear until about at least 1.20 V. Further, even if there were a peak which indicates oxidation at a voltage greater than or equal to 1.20 V, the peak could not be observed due to the influence of flow of a large amount of current. That is, from this data, it is found that the oxidation potential of 2-phenylbenzoxazole is greater than or equal to at least 1.20 V. Here, the potential energy of the reference electrode used in this example with respect to the vacuum level is −4.94 [eV] as described above. Therefore, the oxidation potential of 1.20 V in the CV measurement is converted into the HOMO level to give −(−4.94−1.20)=−6.14 eV. Accordingly, it was found that the ionization potential of 2-phenylbenzoxazole is greater than or equal to at least 6.14 eV.

Figure 16:
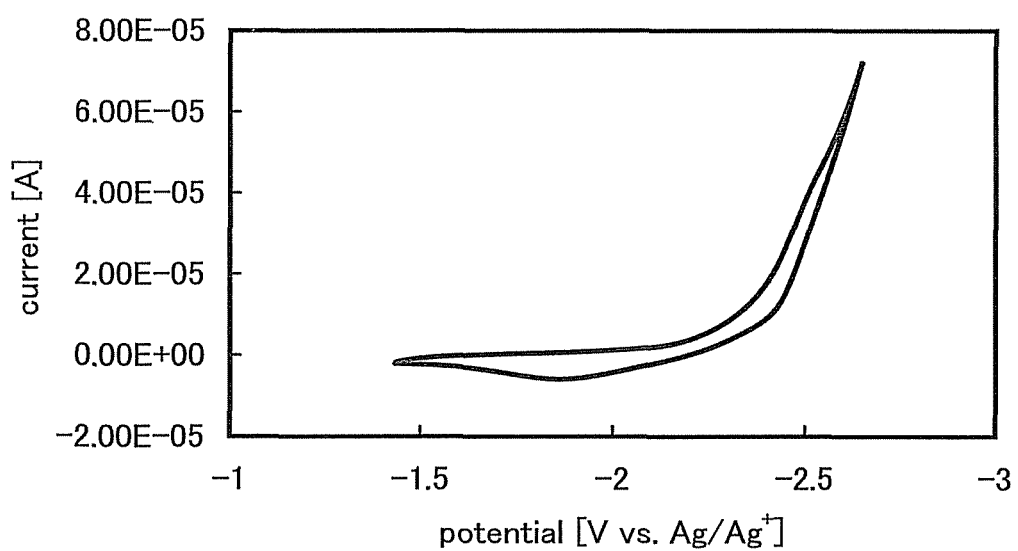
FIG. 16 shows CV measurement results of 2-phenylbenzoxazole.

FIG. 16 shows CV measurement results of the reduction characteristics of 2-phenylbenzoxazole. Note that the measurement of the reduction characteristics was conducted by scanning the potential of the working electrode with respect to the reference electrode from −1.43 V to −2.64 V, and then from −2.64 V to −1.43 V.

As shown in FIG. 16, in the measurement of the reduction characteristics, the reduction peak potential $E_{pc}$ was −2.51V. Further, the oxidation peak potential $E_{pa}$ was −2.42V. Therefore, the half-wave potential (an intermediate potential between $E_{pc}$ and $E_{pa}$) can be calculated to be −2.47 V. This shows that 2-phenylbenzoxazole is reduced by an electric energy of −2.47 [V vs. Ag/Ag$^+$], and this energy corresponds to the LUMO level. Here, the potential energy of the reference electrode used in this example with respect to the vacuum level is −4.94 [eV] as described above. Therefore, the LUMO level of 2-phenylbenzoxazole was found to be −4.94−(−2.47)=−2.47 [eV]. Accordingly, the electron affinity of 2-phenylbenzoxazole was calculated to be 2.47 eV.

Measurement Example 3

Phenylcarbazole

Figure 17:
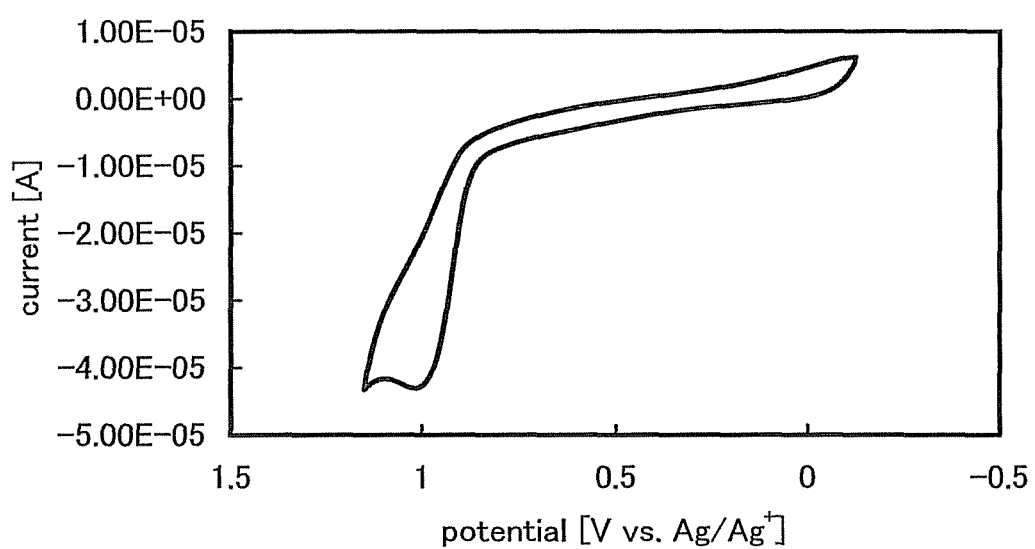
FIG. 17 shows CV measurement results of 9-phenyl-9H-carbazole.

Further, FIG. 17 shows CV measurement results of the oxidation characteristics of phenylcarbazole. The measurement of the oxidation characteristics was performed by scanning the potential of the working electrode with respect to the reference electrode from −0.13 V to 1.15 V, and then 1.15 V to −0.13 V.

As shown in FIG. 17, in the measurement of the reduction characteristics, the oxidation peak potential $E_{pa}$ was 1.02V. Further, the reduction peak potential $E_{pc}$ was 0.86V. Therefore, the half-wave potential (an intermediate potential between $E_{pa}$ and $E_{pc}$) can be calculated to be 0.94V. This shows that phenylcarbazole is oxidized by an electric energy of 0.44 [V vs. Ag/Ag$^+$], and this energy corresponds to the HOMO level. Here, the potential energy of the reference electrode used in this example with respect to the vacuum level is −4.94 [eV] as described above. Therefore, the HOMO level of phenylcarbazole was found to be −4.94−0.94=−5.88 [eV]. Accordingly, the ionization potential of phenylcarbazole was calculated to be 5.88 [eV].

Figure 18:
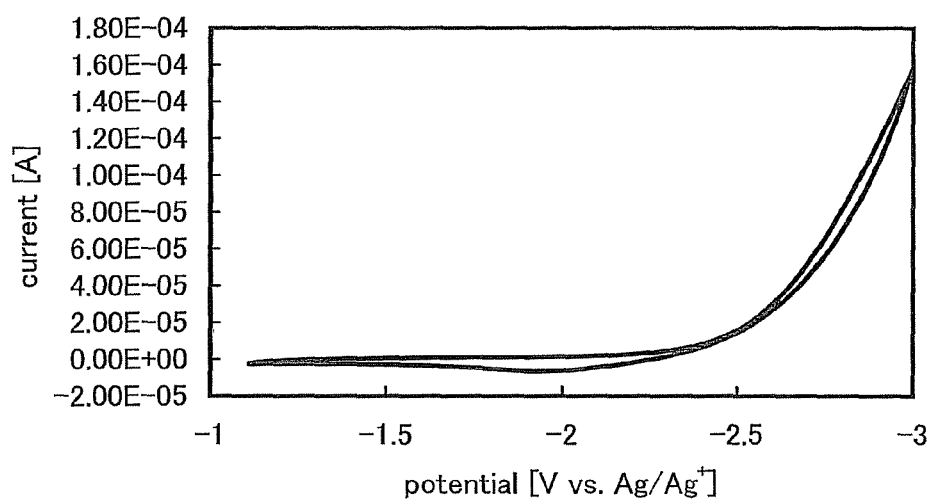
FIG. 18 shows CV measurement results of 9-phenyl-9H-carbazole.

FIG. 18 shows CV measurement results of the reduction characteristics of phenylcarbazole. Note that the measurement of the reduction characteristics was conducted by scanning the potential of the working electrode with respect to the reference electrode from −1.10 V to −3.00 V, and then from −3.00 V to −1.10 V.

As shown in FIG. 18, in the measurement of the reduction characteristics, a peak which indicates reduction does not appear until about at least −2.70 V. Further, even if there were a peak which indicates reduction at a voltage less than or equal to −2.70 V, the peak could not be observed due to the influence of flow of a large amount of current. That is, from this data, it is found that the reduction potential of phenylcarbazole is less than or equal to at least −2.70 V. Here, the potential energy of the reference electrode used in this example with respect to the vacuum level is −4.94 [eV] as described above. Therefore, the reduction potential of −2.70 V in the CV measurement is converted into the LUMO level to give −4.94−(−2.70)=−2.24 eV. Accordingly, it was found that the electron affinity of phenylcarbazole was less than or equal to at least 2.24 eV.

Measurement Example 4

Triphenylamine

Figure 19:
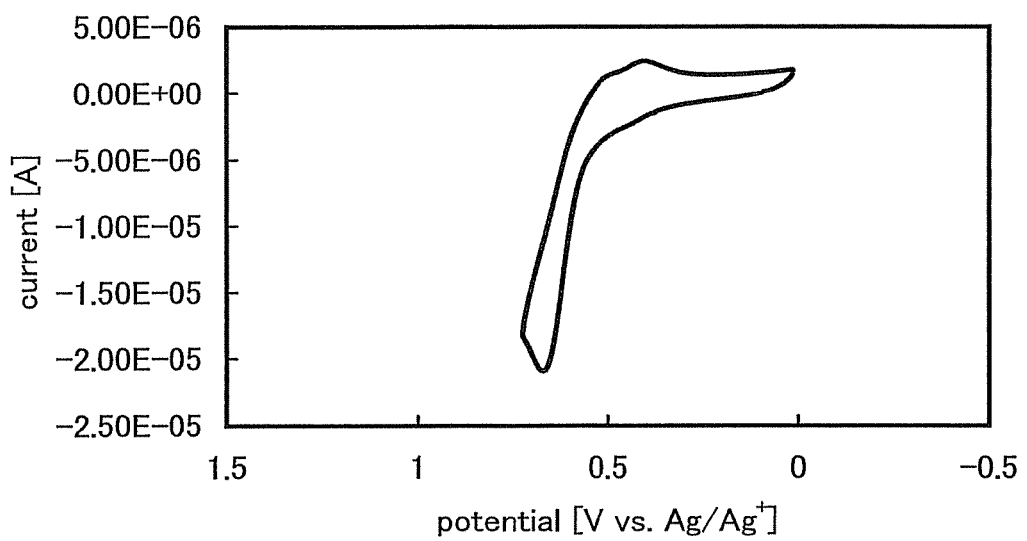
FIG. 19 shows CV measurement results of triphenylamine.

FIG. 19 shows CV measurement results of the oxidation characteristics of triphenylamine. The measurement of the oxidation characteristics was performed by scanning the potential of the working electrode with respect to the reference electrode from 0.01 V to 0.73 V, and then 0.73 V to 0.01 V.

As shown in FIG. 19, in the measurement of the oxidation characteristics, the oxidation peak potential $E_{pa}$ was 0.67 V. Further, the reduction peak potential $E_{pc}$ was 0.50 V. Therefore, the half-wave potential (an intermediate potential between $E_{pa}$ and $E_{pc}$) can be calculated to be 0.59V. This shows that triphenylamine is oxidized by an electric energy of 0.44 [V vs. Ag/Ag$^+$], and this energy corresponds to the HOMO level. Here, the potential energy of the reference electrode used in this example with respect to the vacuum level is −4.94 [eV] as described above. Therefore, the HOMO level of triphenylamine was found to be −4.94−0.59=−5.53 [eV]. Accordingly, the ionization potential of triphenylamine was calculated to be 5.53 [eV].

Figure 20:
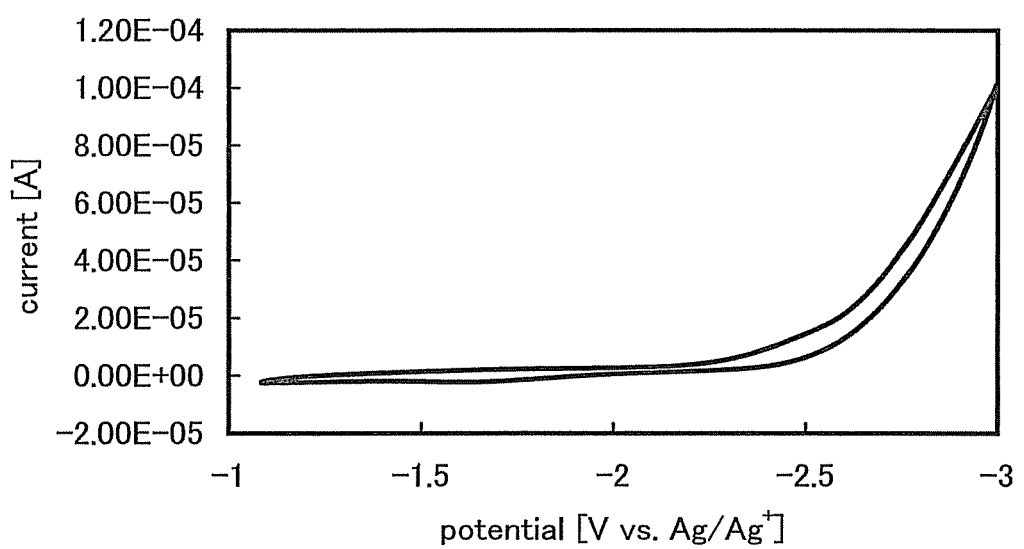
FIG. 20 shows CV measurement results of triphenylamine.

FIG. 20 shows CV measurement results of the reduction characteristics of triphenylamine. Note that the measurement of the reduction characteristics was conducted by scanning the potential of the working electrode with respect to the reference electrode from −1.08 V to −3.00 V, and then from −3.00 V to −1.08 V.

As shown in FIG. 20, in the measurement of the reduction characteristics, a peak which indicates reduction does not appear until about at least −2.70 V. Further, even if there were a peak which indicates reduction at a voltage less than or equal to −2.70 V, the peak could not be observed due to the influence of flow of a large amount of current. That is, from this data, it is found that the reduction potential of triphenylamine is less than or equal to at least −2.70 V. Here, the potential energy of the reference electrode used in this example with respect to the vacuum level is −4.94 [eV] as described above. Therefore, the reduction potential of −2.70 V in the CV measurement is converted into the LUMO level to give −4.94−(−2.70)=−2.24 eV. Accordingly, it was found that the electron affinity of triphenylamine was less than or equal to at least 2.24 eV.

The electron affinity and the ionization potential of 2,5-diphenyl-1,3,4-oxadiazole, 2-phenylbenzoxazole, 9-phenyl-9H-carbazole, and triphenylamine, which were calculated in the above measurements, are shown in Table 1.

TABLE 1

|  | Name | Electron affinity [eV] | Ionization potential [eV] |
|---|---|---|---|
| General formula (G2A) | 2,5-diphenyl-1,3,4-oxadiazole | 2.49 | ≥6.14 |
|  | 2-phenylbenzoxazole | 2.48 | ≥6.14 |
| General formula (G2B) | 9-phenyl-9H-carbazole | ≤2.24 | 5.88 |
|  | triphenylamine | ≤2.24 | 5.53 |

As apparent from Table 1, 2,5-diphenyl-1,3,4-oxadiazole and 2-phenylbenzoxazole have higher electron affinity and higher ionization potential than 9-phenyl-9H-carbazole and triphenylamine.

Further, the electron affinity of 2,5-diphenyl-1,3,4-oxadiazole and 2-phenylbenzoxazole is greater than or equal to 2.4 eV and less than or equal to 3.5 eV, and the ionization potential of 9-phenyl-9H-carbazole and triphenylamine is greater than or equal to 5.0 eV and less than or equal to 6.0 eV.

Accordingly, as the partial structure a of the organic semiconductor material according to an embodiment of the present invention, a 4-(5-phenyl-1,3,4-oxadiazol-2-yl)phenyl group which is a 2,5-diphenyl-1,3,4-oxadiazole skeleton, or a 4-(benzoxazol-2-yl) group which is a 2-phenylbenzoxazole skeleton can be preferably used. As the partial structure b, a 4-(9H-carbazol-9-yl) group which has a 9-phenyl-9H-carbazole skeleton, or a 4-(diphenylamino)phenyl group which is a triphenylamine skeleton can be preferably used.

Example 2

In this example, an organic semiconductor material having the electron-accepting unit and the hole-accepting unit which are described in Example 1 will be described.

By combining the partial structure a and the partial structure b of the compound described in Example 1, four kinds of organic semiconductor materials were synthesized. Structural formulae of the synthesized organic semiconductor materials are shown below.

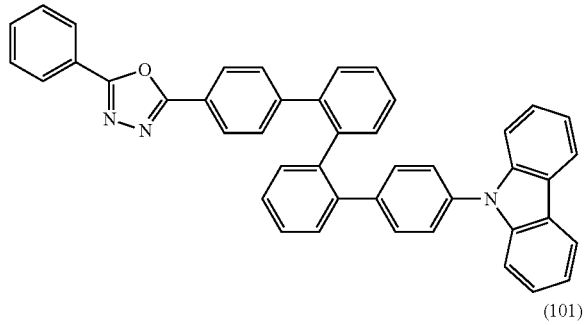

(421)

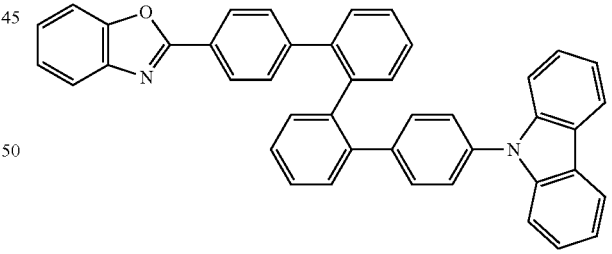

(101)

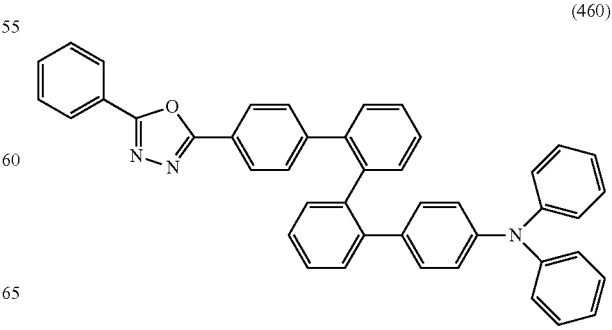

(460)

-continued (201)

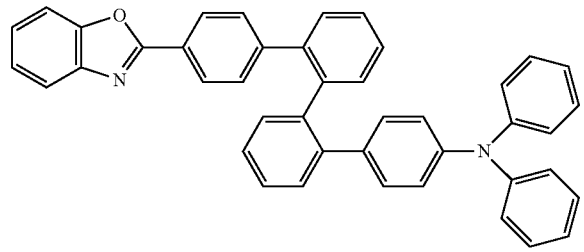

9-[4'''-(5-phenyl-1,3,4-oxadiazol-2-yl)-[1,1':2',1'':2'',1''']
quaterphenyl-4-yl)]-9H-carbazole (Z-CzPO11) which is represented by Structural Formula (421) has a 4-(5-phenyl-1,3,4-oxadiazol-2-yl)phenyl group which has a 2,5-diphenyl-1,3,4-oxadiazole skeleton as the partial structure a, and has a 4-(9H-carbazol-9-yl) group which has a 9-phenyl-9H-carbazole skeleton as the partial structure b.

4-[4''-(5-phenyl-1,3,4-oxadiazol-2-yl)-[1,1':2',1'']terphenyl-2-yl]triphenylamine (Z-DPhAO11) which is represented by Structural Formula (460) has a 4-(5-phenyl-1,3,4-oxadiazol-2-yl)phenyl group which has a 2,5-diphenyl-1,3,4-oxadiazole skeleton as the partial structure a, and has a 4-(diphenylamino)phenyl group which has a triphenylamine skeleton as the partial structure b.

9-[4'''-(benzoxazol-2-yl)-[1,1':2',1'':2'',1''']quaterphenyl-4-yl)]-9H-carbazole (Z-CzPBOx) which is represented by Structural Formula (101) has a 4-(benzoxazol-2-yl)group which has a 2-phenylbenzoxazole skeleton as the partial structure a, and has a 4-(9H-carbazol-9-yl) group which has a 9-phenyl-9H-carbazole skeleton as the partial structure b.

4-[4''-(benzoxazol-2-yl)-[1,1':2',1'']quaterphenyl-2-yl]triphenylamine (Z-DPhABOx) which is represented by Structural Formula (201) has a 4-(benzoxazol-2-yl) group which has a 2-phenylbenzoxazole skeleton as the partial structure a, and has a 4-(diphenylamino)phenyl group which has a triphenylamine skeleton as the partial structure b.

Physical properties of these organic semiconductor materials were measured. Specifically, CV measurement and measurement of an absorption spectrum and an emission spectrum were performed.

The CV measurement was performed under the same conditions as that of Example 1. An electrochemical analyzer (ALS model 600A or 600C, manufactured by BAS Inc.) was used for the measurement. As a solution used for the CV measurement, dehydrated dimethylformamide (DMF, product of Sigma-Aldrich Inc., 99.8%, Catalog No. 22705-6) was used as a solvent, and tetra-n-butylammonium perchlorate (n-Bu$_4$NClO$_4$, product of Tokyo Chemical Industry Co., Ltd., Catalog No. T0836), which was a supporting electrolyte, was dissolved in the solvent such that the concentration of tetra-n-butylammonium perchlorate was 100 mmol/L. Further, the measurement object was also dissolved such that the concentration thereof was 2 mmol/L. Further, as a working electrode, a platinum electrode (a PTE platinum electrode, manufactured by BAS Inc.) was used. As an auxiliary electrode, a platinum electrode (a VC-3 Pt counter electrode (5 cm), manufactured by BAS Inc.) was used. As a reference electrode, an Ag/Ag$^+$ electrode (an RE7 nonaqueous solvent reference electrode, manufactured by BAS Inc.) was used. Note that the measurement was conducted at a room temperature (20° C. to 25° C.). In addition, the scan speed at the CV measurement was 0.1 V/sec in all the measurements.

The measurement of the absorption spectrum and the emission spectrum was performed using an ultraviolet-visible spectrophotometer (V-550, manufactured by JASCO Corporation). The solution was put into a quartz cell, and the absorption spectrum from which the absorption spectrum measured when only toluene was put into the quartz cell was subtracted is shown. Thin film samples were each formed by evaporation on a quartz substrate, and the absorption spectrum from which the absorption spectrum of the quartz substrate was subtracted is shown.

<Z-CzPO11>

The oxidation characteristics of Z-CzPO11 were examined as follows. The potential of the working electrode with respect to the reference electrode was changed from −0.35 V to 1.01 V, and then changed from 1.01 V to −0.35 V. This change in potential was regarded as one cycle, and measurement was performed for 100 cycles. Further, the reduction characteristics of Z-CzPO11 were examined as follows. The potential of the working electrode with respect to the reference electrode was changed from −1.51 V to −2.50 V, and then changed from −2.50 V to −1.51 V. This change in potential was regarded as one cycle, and measurement was performed for 100 cycles.

Figure 21:
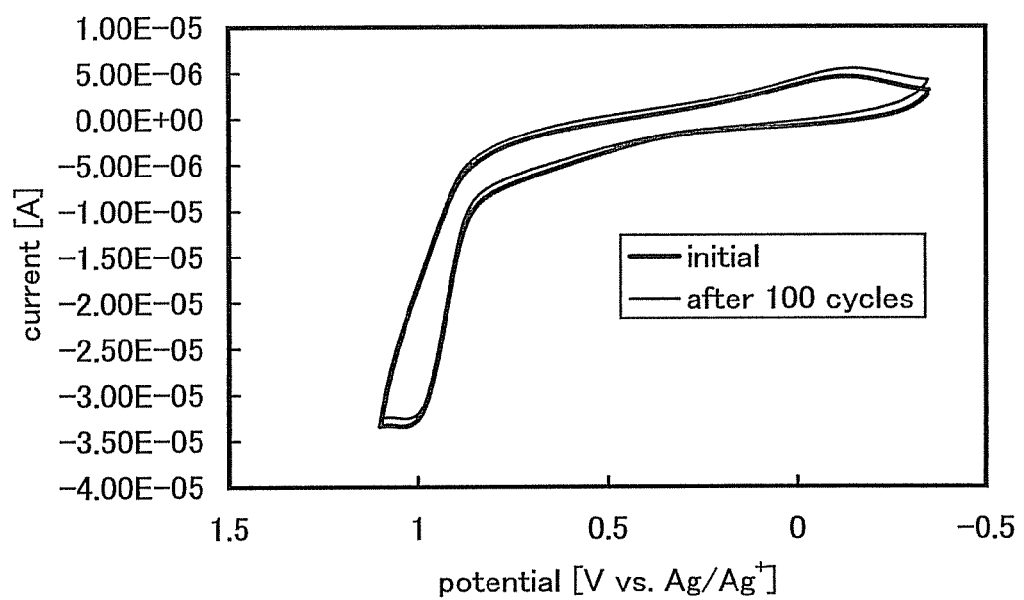
FIG. 21 shows CV measurement results of Z-CzPO11.
Figure 22:
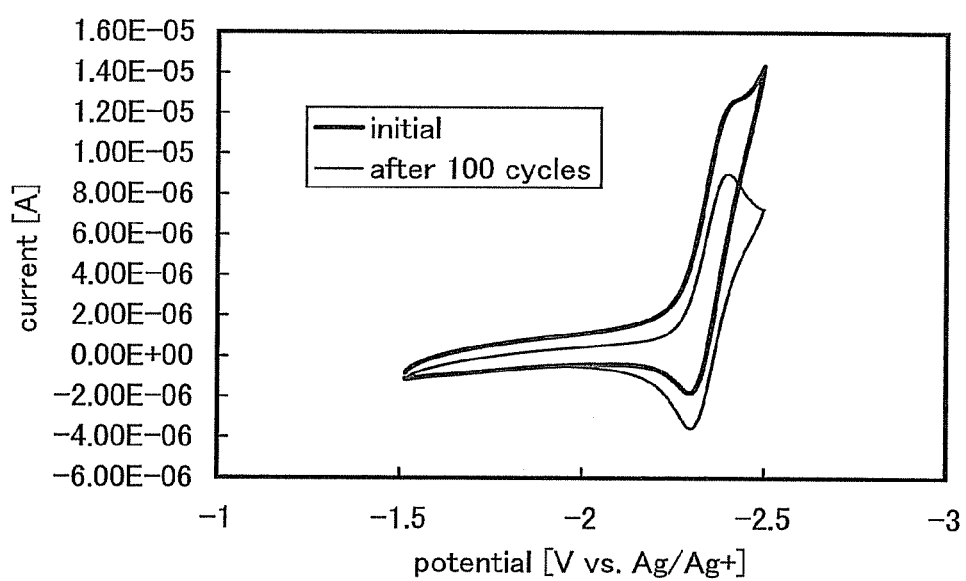
FIG. 22 shows CV measurement results of Z-CzPO11.

FIG. 21 shows the CV measurement result of Z-CzPO11 on the oxidation side, and FIG. 22 shows the CV measurement result of Z-CzPO11 on the reduction side. In each of FIGS. 21 and 22, the horizontal axis indicates a potential (V) of the working electrode with respect to the reference electrode, and the vertical axis indicates a current value (A) flowing between the working electrode and the auxiliary electrode. In FIG. 21, a current indicating oxidation was observed at 1.04 V (vs. Ag/Ag$^+$ electrode). In FIG. 22, a current indicating reduction was observed at −2.40 V (vs. the Ag/Ag$^+$ electrode). Since both oxidation and reduction occurred, it was found that Z-CzPO11 was a material into which both electrons and holes can be injected, that is, a bipolar material.

In spite of the fact that 100 cycles of scanning were conducted repeatedly, a peak position and a peak intensity at the CV curve scarcely changed in the oxidation and the reduction. From the result, it was found that Z-CzPO11 which is an organic semiconductor material of the present invention is extremely stable against repetition of the oxidation and reduction. That is, it was found that Z-CzPO11 is electrochemically stable.

The ionization potential and the electron affinity of Z-CzPO11 were calculated from the CV measurement result.

As shown in FIG. 21, in the measurement of the oxidation characteristics, the oxidation peak potential $E_{pa}$ was 1.04 V. Further, the reduction peak potential $E_{pc}$ was 0.85 V. Therefore, the half-wave potential (an intermediate potential between $E_{pa}$ and $E_{pc}$) can be calculated to be 0.95V. Since the same reference electrode as that in Example 1 is used in this example, the potential energy of the reference electrode with respect to the vacuum level is −4.94 [eV]. Therefore, the HOMO level of Z-CzPO11 was found to be −4.94−0.95=−5.89 [eV]. Accordingly, the ionization potential of Z-CzPO11 was calculated to be 5.89 [eV].

As shown in FIG. 22, in the measurement of the reduction characteristics, the reduction peak potential $E_{pc}$ was −2.40 V. Further, the oxidation peak potential $E_{pa}$ was −2.30 V. Therefore, the half-wave potential (an intermediate potential between $E_{pc}$ and $E_{pa}$) can be calculated to be −2.35V. Since the same reference electrode as that in Example 1 is used in this example, the potential energy of the reference electrode with respect to the vacuum level is −4.94 [eV]. Therefore, the LUMO level of Z-CzPO11 was found to be −4.94−(−2.35)=−2.49 [eV]. Accordingly, the electron affinity of Z-CzPO11 was calculated to be 2.59 [eV].

Figure 23A:
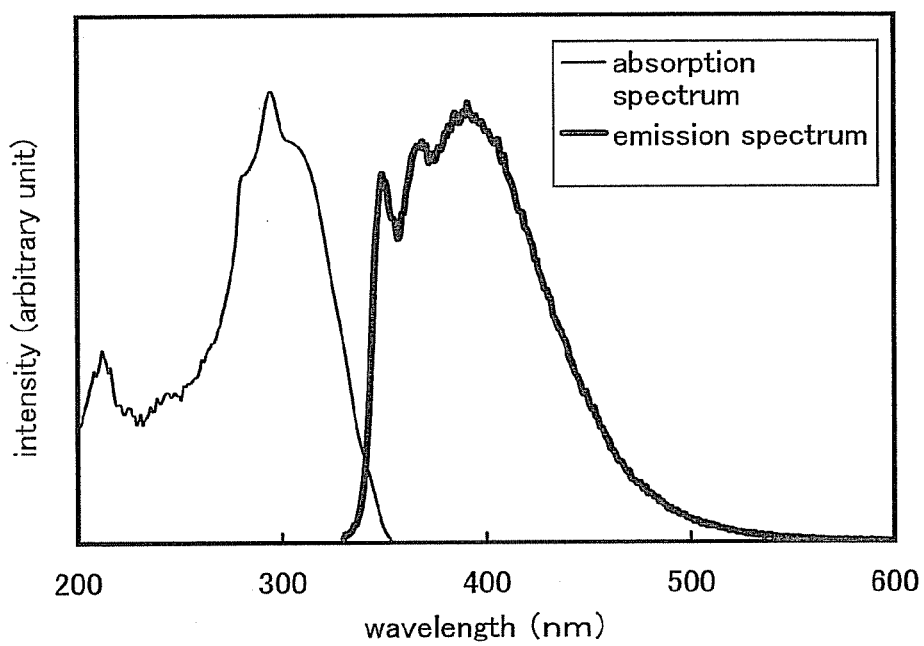
FIGS. 23A and 23B each show an absorption spectrum and an emission spectrum of Z-CzPO11.
Figure 23B:
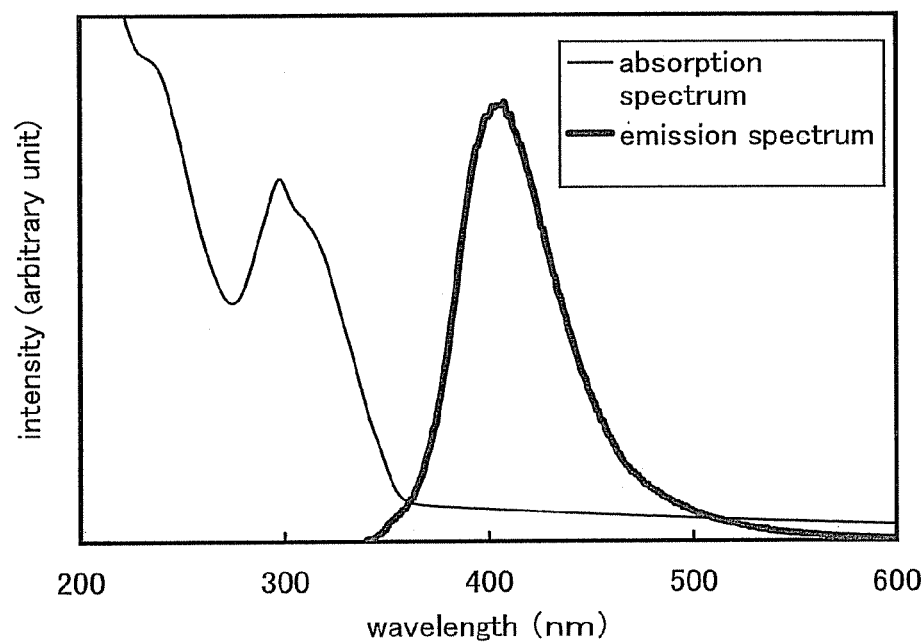

FIG. 23A shows an absorption spectrum and an emission spectrum of Z-CzPO11 included in a toluene solution and FIG. 23B shows an absorption spectrum and an emission spectrum of a thin film of Z-CzPO11. In FIGS. 23A and 23B, the horizontal axis indicates a wavelength (am) and the vertical axis indicates intensity (arbitrary unit). In the case of the toluene solution, absorption was observed at around 302 nm. In the case of the toluene solution, the maximum emission wavelength was 392 nm (excitation wavelength: 320 nm). In the case of the thin film, absorption was observed at around 236 nm and 298 nm. In the case of the thin film, the maximum emission wavelength was 407 nm (an excitation wavelength: 321 nm).

An absorption edge was obtained from a Tauc plot assuming direct transition with the use of the absorption spectrum data of the thin film of Z-CzPO11, and the absorption edge was regarded as an optical energy gap. Then, the energy gap was estimated to be 3.64 eV. Accordingly, it was found that Z-CzPO11 has a large optical energy gap.

<Z-DPhAO11>

The oxidation characteristic of Z-DPhAO11 was examined as follows. The potential of the working electrode with respect to the reference electrode was changed from −0.31 V to 0.75 V, and then changed from 0.75 V to −0.31 V. This change in potential was regarded as one cycle, and measurement was performed for 100 cycles. Further, the reduction characteristics of Z-DPhAO11 were examined as follows. The potential of the working electrode with respect to the reference electrode was changed from −1.36 V to −2.50 V, and then changed from −2.50 V to −1.36 V. This change in potential was regarded as one cycle, and measurement was performed for 100 cycles.

Figure 24:
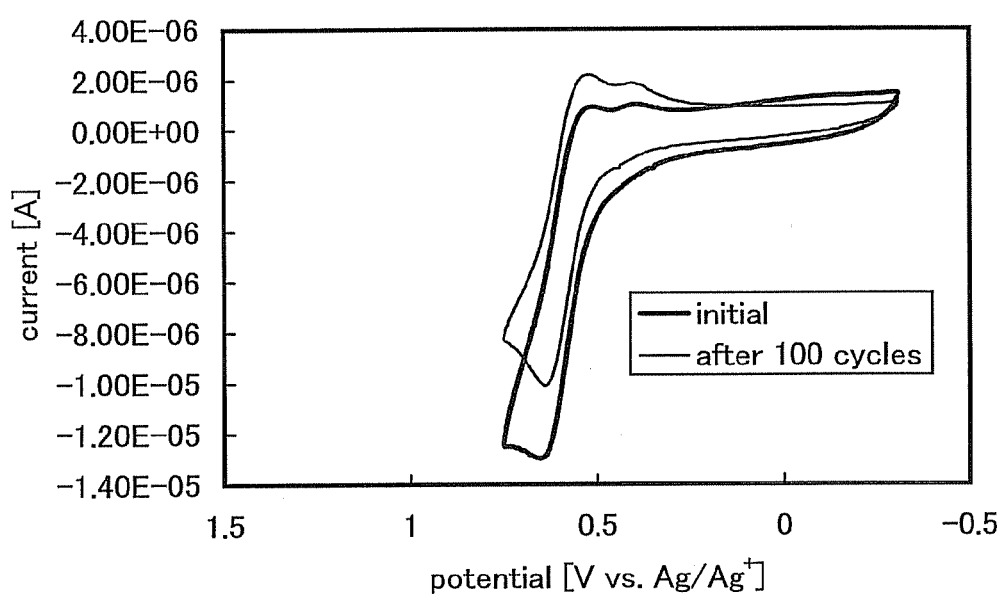
FIG. 24 shows CV measurement results of Z-DPhAO11.
Figure 25:
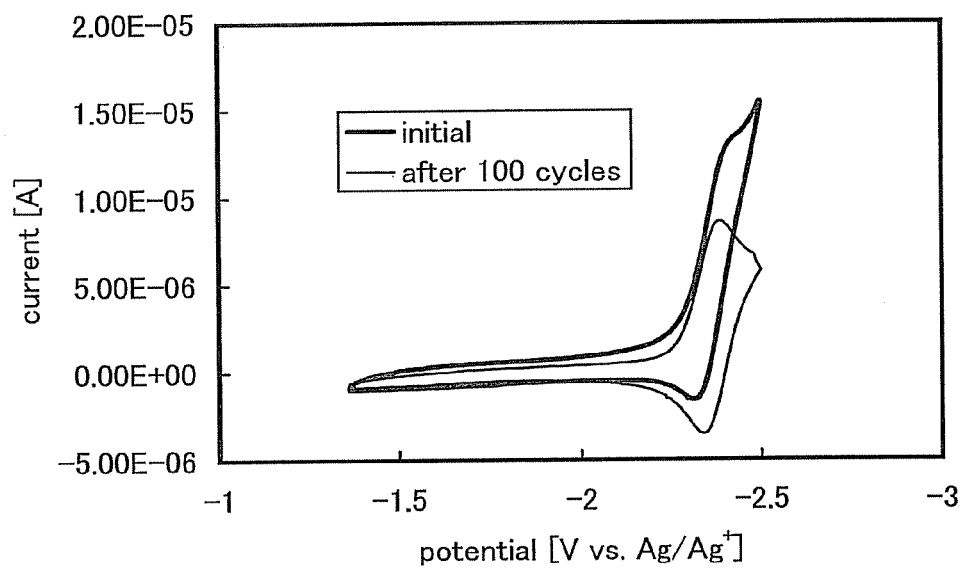
FIG. 25 shows CV measurement results of Z-DPhAO11.

FIG. 24 shows the CV measurement result of Z-DPhAO11 on the oxidation side, and FIG. 25 shows the CV measurement result of Z-DPhAO11 on the reduction side. In each of FIGS. 24 and 25, the horizontal axis indicates a potential (V) of the working electrode with respect to the reference electrode, and the vertical axis indicates a current value (A) flowing between the working electrode and the auxiliary electrode. In FIG. 24, a current indicating reduction was observed at around 0.65 V (vs. Ag/Ag$^+$ electrode). In FIG. 25, a current indicating reduction was observed at around −2.43 V (vs. the Ag/Ag$^+$ electrode). Since oxidation and reduction occurred, it was found that Z-DPhAO11 was a material into which electrons and holes can be injected, that is, a bipolar material.

In spite of the fact that 100 cycles of scanning were conducted repeatedly, a peak position at the CV curve scarcely changed in the oxidation and the reduction. From the result, it was found that Z-DPhAO11 which is an organic semiconductor material of the present invention is extremely stable against repetition of the oxidation and the reduction. That is, it was found that Z-DPhAO11 is electrochemically stable.

The ionization potential and the electron affinity of Z-DPhAO11 were calculated from the CV measurement result.

As shown in FIG. 24, in the measurement of the oxidation characteristics, the oxidation peak potential $E_{pa}$ was 0.65 V. Further, the reduction peak potential $E_{pc}$ was 0.51 V. Therefore, the half-wave potential (an intermediate potential between $E_{pa}$ and $E_{pc}$) can be calculated to be 0.58V. Since the same reference electrode as that in Example 1 is used in this example, the potential energy of the reference electrode with respect to the vacuum level is −4.94 [eV]. Therefore, the HOMO level of Z-DPhAO11 was found to be −4.94−0.58=−5.52 [eV]. Accordingly, the ionization potential of Z-DPhAO11 was calculated to be 5.52 eV.

As shown in FIG. 25, in the measurement of the reduction characteristics, the reduction peak potential $E_{pc}$ was −2.43 V. Further, the oxidation peak potential $E_{pa}$ was −2.31 V. Therefore, the half-wave potential (an intermediate potential between $E_{pc}$ and $E_{pa}$) can be calculated to be −2.37V. Since the same reference electrode as that in Example 1 is used in this example, the potential energy of the reference electrode with respect to the vacuum level is −4.94 [eV]. Therefore, the LUMO level of Z-DPhAO11 was found to be −4.94−(−237)=−2.57 [eV]. Accordingly, the electron affinity of Z-DPhAO11 was calculated to be 2.57 [eV].

Figure 26A:
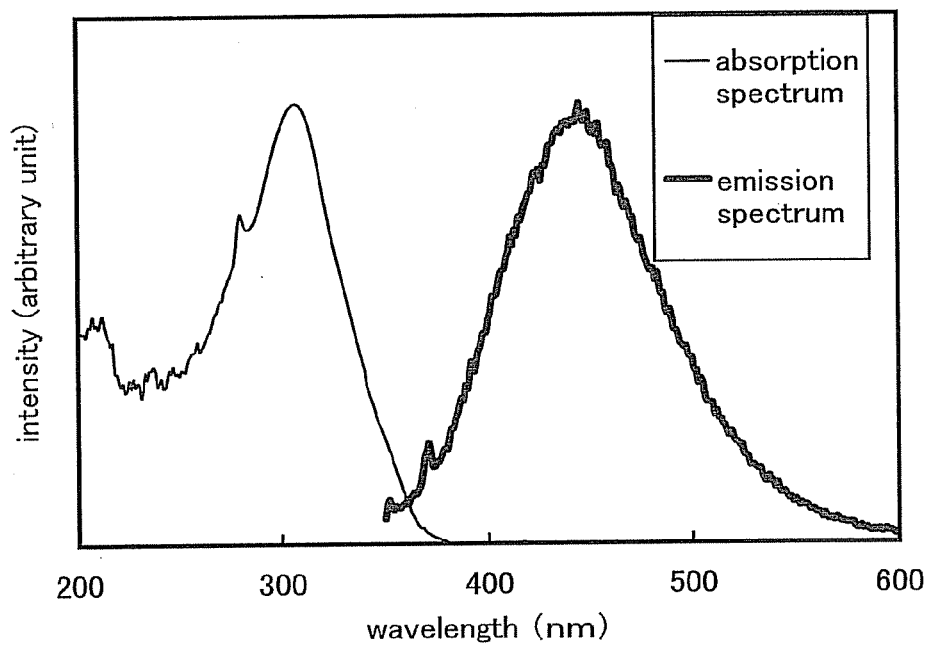
FIGS. 26A and 26B each show an absorption spectrum and an emission spectrum of Z-DPhAO11.
Figure 26B:
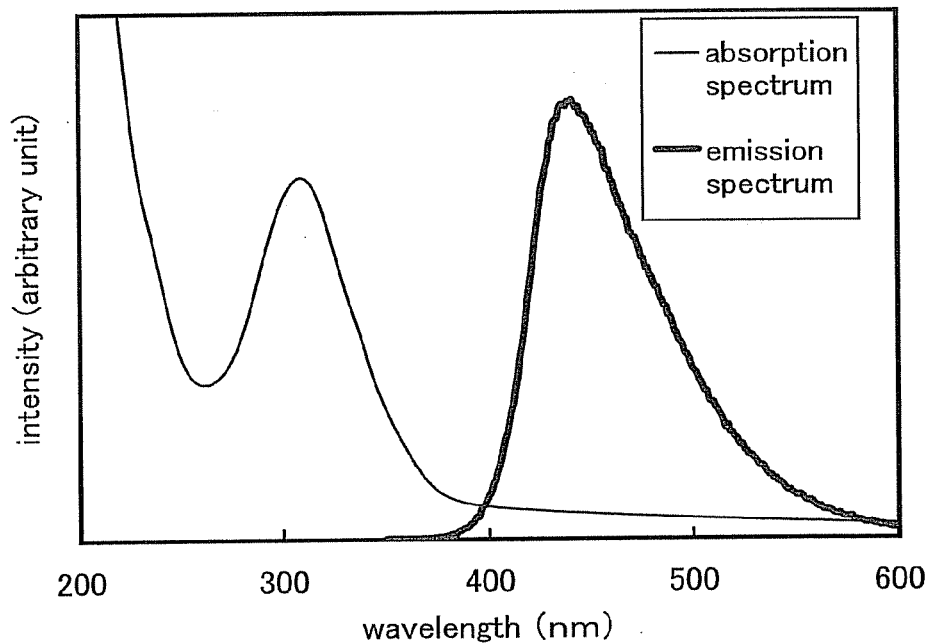

FIG. 26A shows an absorption spectrum and an emission spectrum of Z-DPhAO11 included in a toluene solution and FIG. 26B shows an absorption spectrum and an emission spectrum of a thin film of Z-DPhAO11. In FIGS. 26A and 26B, the horizontal axis indicates a wavelength (nm) and the vertical axis indicates intensity (arbitrary unit). In the case of the toluene solution, absorption was observed at around 305 nm. In the case of the toluene solution, the maximum emission wavelength was 446 nm (excitation wavelength: 334 nm). In the case of the thin film, absorption was observed at around 309 nm. In the case of the thin film, the maximum emission wavelength was 440 nm (excitation wavelength: 322 nm).

An absorption edge was obtained from a Tauc plot assuming direct transition with the use of the absorption spectrum data of the thin film of Z-DPhAO11, and the absorption edge was regarded as an optical energy gap. Then, the energy gap was estimated to be 3.62 eV. Accordingly, it was found that Z-DPhAO11 has a large optical energy gap.

<Z-CzPBOx>

The oxidation characteristics of Z-CzPBOx were examined as follows. The potential of the working electrode with respect to the reference electrode was changed from −0.16 V to 1.10 V, and then changed from −1.10 V to −0.16 V. This change in potential was regarded as one cycle, and measurement was performed for 100 cycles. Further, the reduction characteristics of Z-CzPBOx were examined as follows. The potential of the working electrode with respect to the reference electrode was changed from −1.24 V to −2.55 V, and then changed from −2.55 V to −1.24 V. This change in potential was regarded as one cycle, and measurement was performed for 100 cycles.

Figure 27:
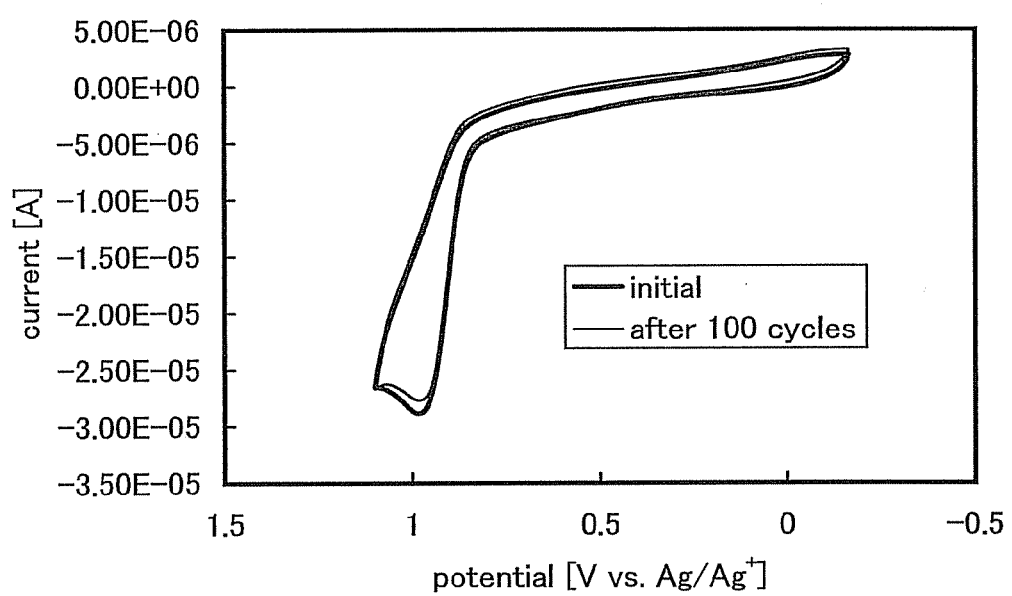
FIG. 27 shows CV measurement results of Z-CzPBOx.
Figure 28:
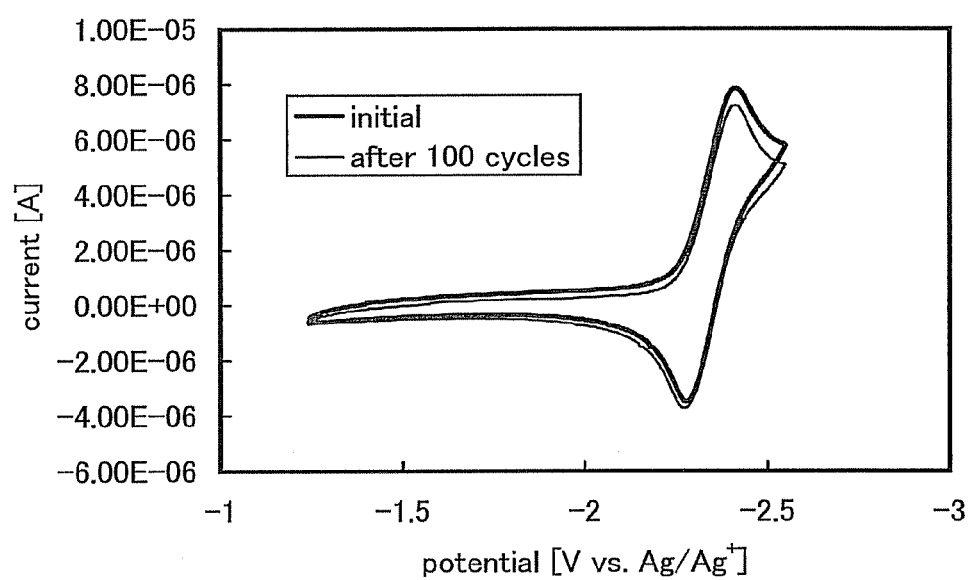
FIG. 28 shows CV measurement results of Z-CzPBOx.

FIG. 27 shows the CV measurement result of Z-CzPBOx on the oxidation side, and FIG. 28 shows the CV measurement result of Z-CzPBOx on the reduction side. In each of FIGS. 27 and 28, the horizontal axis indicates a potential (V) of the working electrode with respect to the reference electrode, and the vertical axis indicates a current value (A) flowing between the working electrode and the auxiliary electrode. In FIG. 27, a current indicating reduction was observed at around 0.98 V (vs. Ag/Ag$^+$ electrode). In FIG. 28, a current indicating reduction was observed at around −2.41 V (vs. the Ag/Ag$^+$ electrode). Since both oxidation and reduction occurred, it was found that Z-CzPBOx was a material into which both electrons and holes can be injected, that is, a bipolar material.

In spite of the fact that 100 cycles of scanning were conducted repeatedly, a peak position and a peak intensity at the CV curve scarcely changed in the oxidation and the reduction. From the result, it was found that Z-CzPBOx which is an organic semiconductor material of the present invention is extremely stable against repetition of the oxidation and the reduction. That is, it was found that Z-CzPBOx is electrochemically stable.

The ionization potential and the electron affinity of Z-CzPBOx were calculated from the CV measurement result.

As shown in FIG. 27, in the measurement of the oxidation characteristics, the oxidation peak potential $E_{pa}$ was 0.98 V. Further, the reduction peak potential $E_{pc}$ was 0.85 V. Therefore, the half-wave potential (an intermediate potential between $E_{pa}$ and $E_{pc}$) can be calculated to be 0.92V. Since the same reference electrode as that in Example 1 is used in this example, the potential energy of the reference electrode with respect to the vacuum level is −4.94 [eV]. Therefore, the HOMO level of Z-CzPBOx was found to be −4.94−0.92=−5.86 [eV]. Accordingly, the ionization potential of Z-CzPBOx was calculated to be 5.86 [eV].

As shown in FIG. 28, in the measurement of the reduction characteristics, the reduction peak potential $E_{pc}$ was −2.41 V. Further, the oxidation peak potential $E_{pa}$ was −2.28 V. Therefore, the half-wave potential (an intermediate potential between $E_{pc}$ and $E_{pa}$) can be calculated to be −2.35V. Since the same reference electrode as that in Example 1 is used in this example, the potential energy of the reference electrode with respect to the vacuum level is −4.94 [eV]. Therefore, the LUMO level of Z-CzPBOx was found to be −4.94−(−2.35)=−2.60 [eV]. Accordingly, the electron affinity of Z-CzPBOx was calculated to be 2.60 [eV].

Figure 29A:
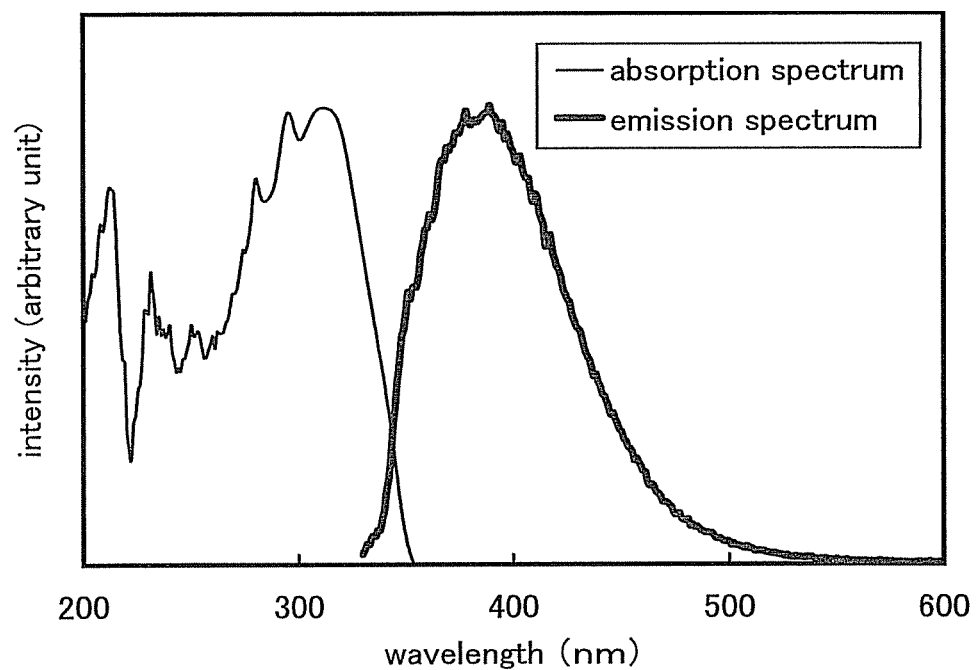
FIGS. 29A and 29B each illustrate an absorption spectrum and an emission spectrum of Z-CzPBOx.
Figure 29B:
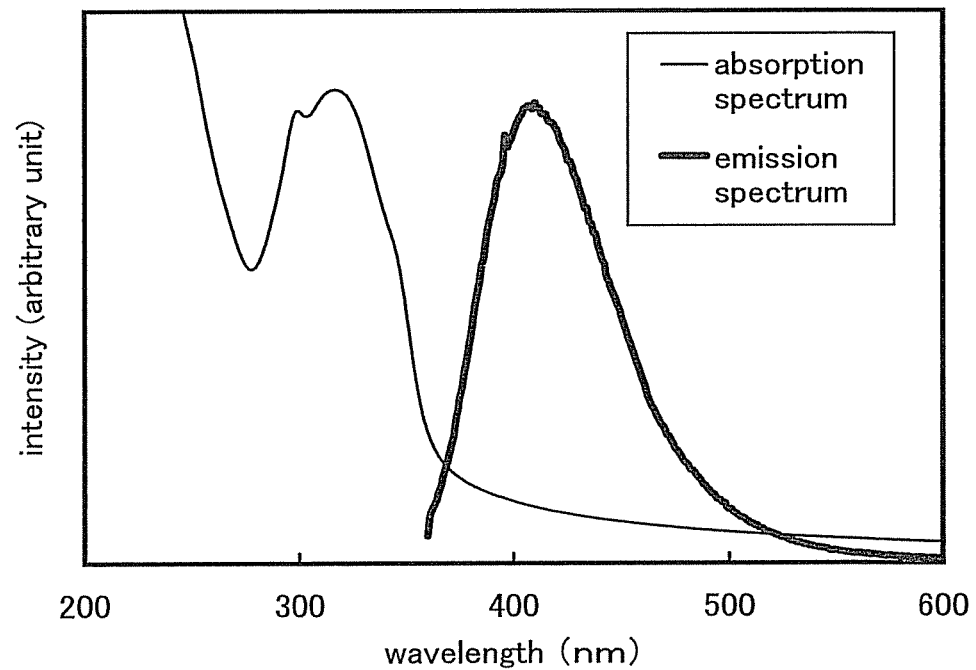

FIG. 29A shows an absorption spectrum and an emission spectrum of Z-CzPBOx included in a toluene solution and FIG. 29B shows an absorption spectrum and an emission spectrum of a thin film of Z-CzPBOx. In FIGS. 29A and 29B, the horizontal axis indicates a wavelength (nm) and the vertical axis indicates intensity (arbitrary unit). In the case of the toluene solution, absorption was observed at around 312 nm. In the case of the toluene solution, the maximum emission wavelength was 390 nm (excitation wavelength: 324 nm). In the case of the thin film, absorption was observed at around 236 nm, 299 nm, and 317 nm. In the case of the thin film, the maximum emission wavelength was 410 nm (excitation wavelength: 345 nm).

An absorption edge was obtained from a Tauc plot assuming direct transition with the use of the absorption spectrum data of the thin film of Z-CzPBOx, and the absorption edge was regarded as an optical energy gap. Then, the energy gap was estimated to be 3.46 eV. Accordingly, it was found that Z-CzPBOx has a large optical energy gap.

<Z-DPhABOx>

The oxidation characteristics of Z-DPhABOx were examined as follows. The potential of the working electrode with respect to the reference electrode was changed from 0.02 V to 0.80 V, and then changed from 0.80 V to 0.02 V. This change in potential was regarded as one cycle, and measurement was performed for 100 cycles. Further, the reduction characteristics of Z-DPhABOx were examined as follows. The potential of the working electrode with respect to the reference electrode was changed from −1.32 V to −2.55 V, and then changed from −2.55 V to −1.32 V. This change in potential was regarded as one cycle, and measurement was performed for 100 cycles.

Figure 30:
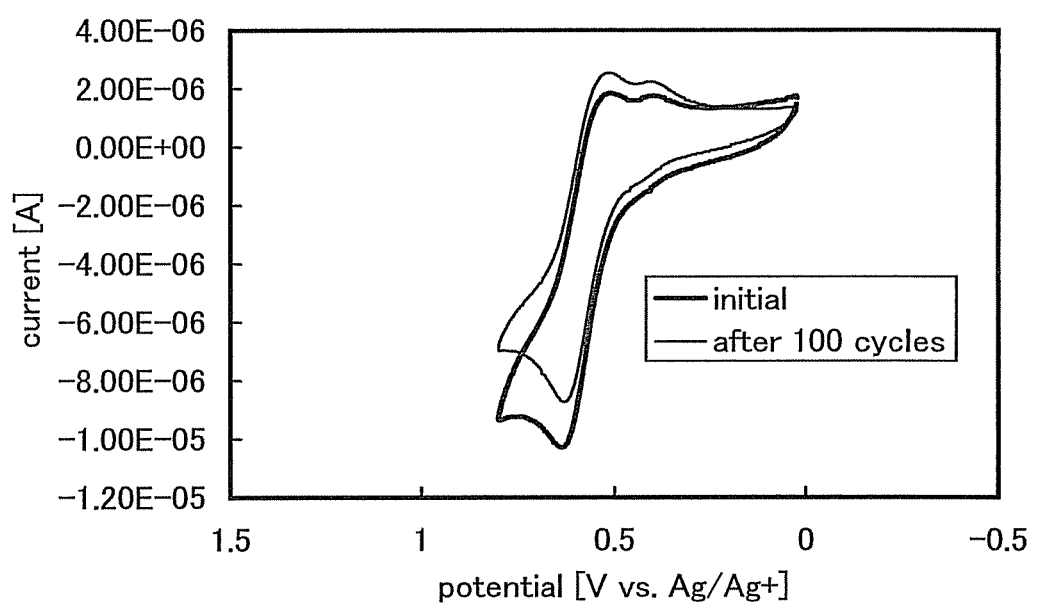
FIG. 30 shows CV measurement results of Z-DPhABOx.
Figure 31:
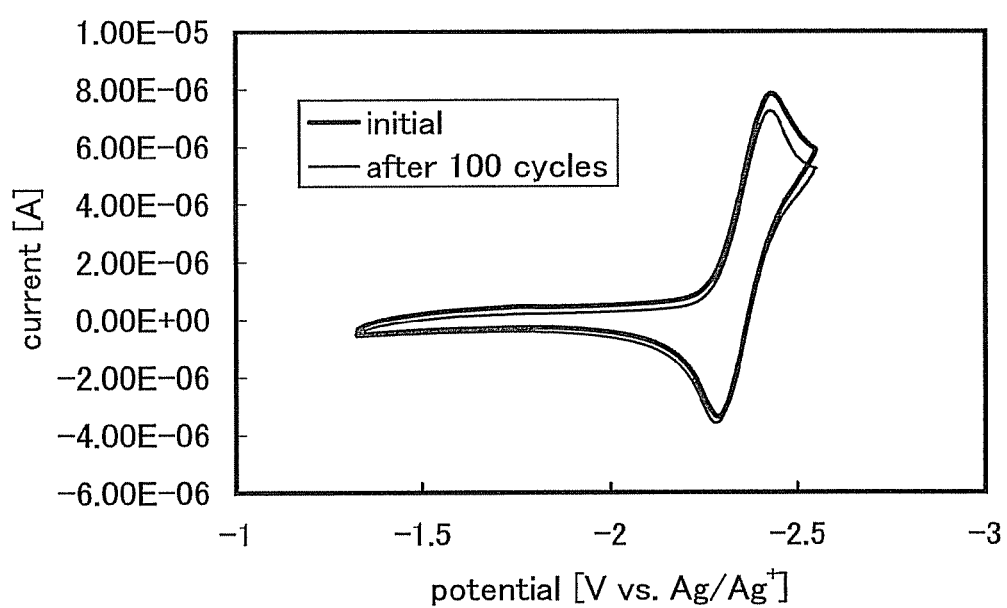
FIG. 31 shows CV measurement results of Z-DPhABOx.

FIG. 30 shows the CV measurement result of Z-DPhABOx on the oxidation side, and FIG. 31 shows the CV measurement result of Z-DPhABOx on the reduction side. In each of FIGS. 30 and 31, the horizontal axis indicates a potential (V) of the working electrode with respect to the reference electrode, and the vertical axis indicates a current value (A) flowing between the working electrode and the auxiliary electrode. In FIG. 30, a current indicating reduction was observed at around 0.63 V (vs. Ag/Ag$^+$ electrode). In FIG. 31, a current indicating reduction was observed at around −2.18 V (vs. the Ag/Ag$^+$ electrode). Since oxidation and reduction occurred, it was found that Z-DPhABOx was a material into which electrons and holes can be injected, that is, a bipolar material.

In spite of the fact that 100 cycles of scanning were conducted repeatedly, a peak position and a peak intensity at the CV curve scarcely changed in the oxidation and the reduction. From the result, it was found that Z-DPhABOx which is an organic semiconductor material of the present invention is extremely stable against repetition of the oxidation and the reduction. That is, it was found that Z-DPhABOx is electrochemically stable.

The ionization potential and the electron affinity of Z-DPhABOx were calculated from the CV measurement result.

As shown in FIG. 30, in the measurement of the oxidation characteristics, the oxidation peak potential $E_{pa}$ was 0.63 V. Further, the reduction peak potential $E_{pc}$ was 0.51 V. Therefore, the half-wave potential (an intermediate potential between $E_{pa}$ and $E_{pc}$) can be calculated to be 0.57V. Since the same reference electrode as that in Example 1 is used in this example, the potential energy of the reference electrode with respect to the vacuum level is −4.94 [eV]. Therefore, the HOMO level of Z-DPhABOx was found to be −4.94−0.57=−5.51 [eV]. Accordingly, the ionization potential of Z-DPhABOx was calculated to be 5.51 [eV].

As shown in FIG. 31, in the measurement of the reduction characteristics, the reduction peak potential $E_{pc}$ was −2.42 V. Further, the oxidation peak potential $E_{pa}$ was −2.29 V. Therefore, the half-wave potential (an intermediate potential between $E_{pc}$ and $E_{pa}$) can be calculated to be −2.36V. Since the same reference electrode as that in Example 1 is used in this example, the potential energy of the reference electrode with respect to the vacuum level is −4.94 [eV]. Therefore, the LUMO level of Z-DPhABOx was found to be −4.94−(−2.36)=−2.59 [eV]. Accordingly, the electron affinity of Z-DPhABOx was calculated to be 2.59 eV.

Figure 32A:
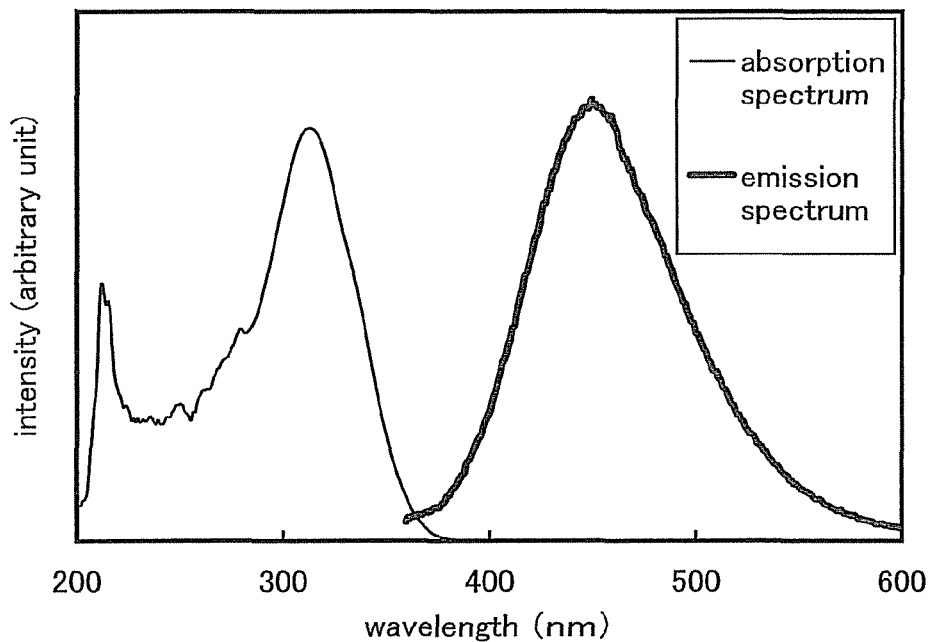
FIGS. 32A and 32B each show an absorption spectrum and an emission spectrum of Z-DPhABOx.
Figure 32B:
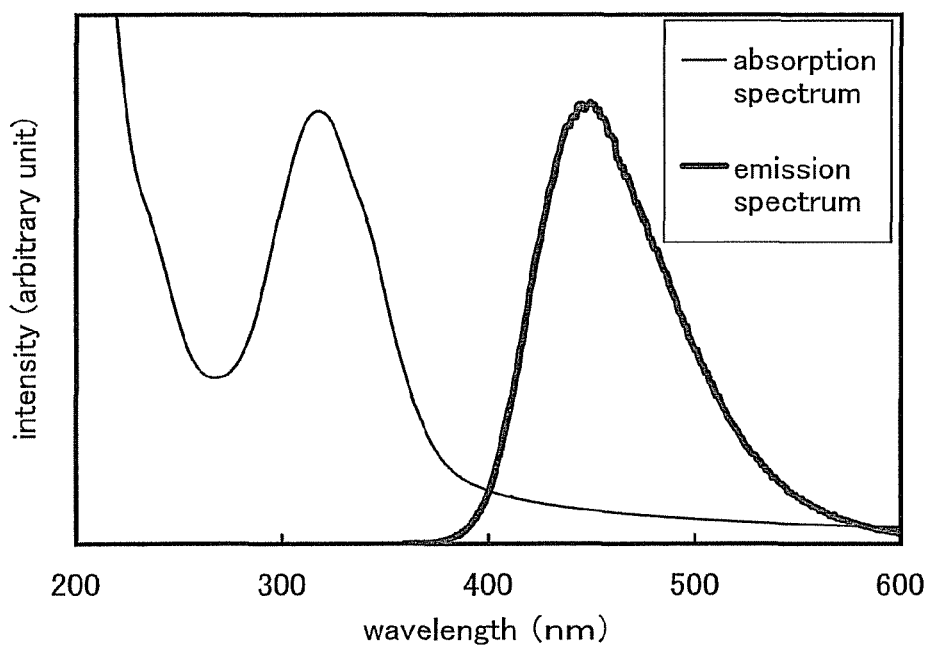

FIG. 32A shows an absorption spectrum and an emission spectrum of Z-DPhABOx included in a toluene solution and FIG. 32B shows an absorption spectrum and an emission spectrum of a thin film of Z-DPhABOx. In FIGS. 32A and 32B, the horizontal axis indicates a wavelength (nm) and the vertical axis indicates intensity (arbitrary unit). In the case of the toluene solution, absorption was observed at around 310 nm. In the case of the toluene solution, the maximum emission wavelength was 450 nm (excitation wavelength: 319 nm). In the case of the thin film, absorption was observed at around 318 nm. In the case of the thin film, the maximum emission wavelength was 450 nm (excitation wavelength: 344 nm).

An absorption edge was obtained from a Tauc plot assuming direct transition with the use of the absorption spectrum data of the thin film of Z-DPhABOx, and the absorption edge was regarded as an optical energy gap. Then, the energy gap was estimated to be 3.42 eV. Accordingly, it was found that Z-DPhABOx has a large optical energy gap.

The electron affinity and the ionization potential of Z-CzPO11, Z-DPhAO11, Z-CzPBOx, Z-DPhABOx, which were calculated in the above measurement results, are shown in Table 2.

TABLE 2

| Structural formula | Abbreviated name | Electron affinity [eV] | Ionization potential [eV] |
|---|---|---|---|
| (421) | Z-CzPO11 | 2.59 | 5.89 |
| (460) | Z-DPhPA11 | 2.57 | 5.52 |
| (101) | Z-CzPBOx | 2.60 | 5.86 |
| (201) | Z-DPhABOx | 2.59 | 5.53 |

As apparent from Table 2, the ionization potentials of Z-CzPO11 and Z-CzPBOx which have the same partial structure b are substantially the same and substantially the same as the ionization potential of 9-phenyl-9H-carbazole shown in Table 1. Similarly, the ionization potentials of Z-DPhAO11 and Z-DPhABOx which have the same partial structure b are substantially the same and substantially the same as the ionization potential of triphenylamine shown in Table 1. In other words, the ionization potential of the hole-accepting unit is substantially the same as that of the organic semiconductor material.

On the other hand, as to the electron-accepting unit, the electron affinities of Z-CzPO11, Z-DPhAO11, Z-CzPBOx, and Z-DPhABOx are substantially the same and substantially the same as those of 2,5-diphenyl-1,3,4-oxadiazole and 2-phenylbenzoxazole shown in Table 1.

From the results, it can be said that in an organic semiconductor material according to the present invention, extension of conjugation is suppressed by a quaterphenylene group and interaction between an electron-accepting unit and a hole-accepting unit in a molecule are suppressed. Accordingly, it was found that the organic semiconductor material according to the present invention maintained part of properties of an electron-accepting unit and a hole-accepting unit and was a bipolar material which can transport both electrons and holes. Further, it is considered that even when an electron-accepting unit with large electron affinity and a hole-accepting unit with a small ionization potential are used in a molecule at the same time, an organic semiconductor material with a large band gap can be obtained.

Example 3

Figure 33:
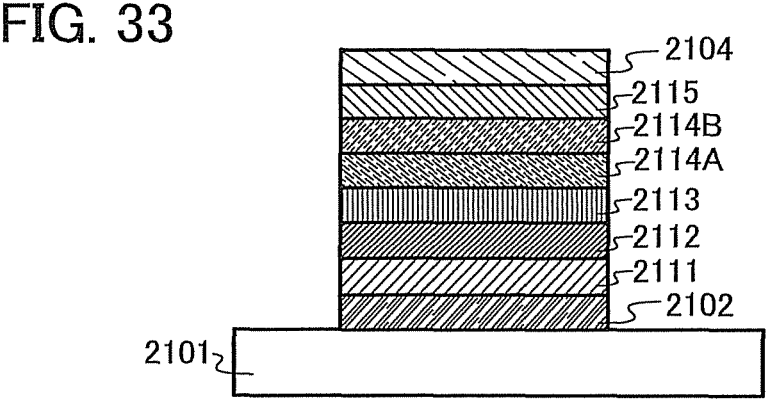
FIG. 33 illustrates a light-emitting element in Examples.

In this example, an example of a light-emitting element to which the organic semiconductor material described in Example 2 is applied will be described with reference to FIG. 33. Structural formulae of materials used in this example are shown below. The material of which structural formula has already been shown is omitted.

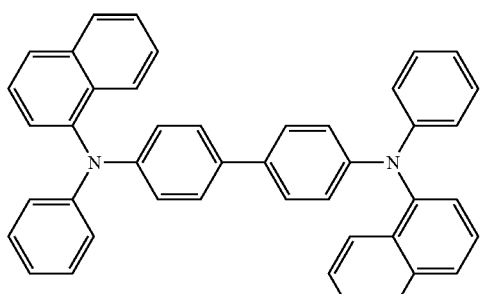

NPB

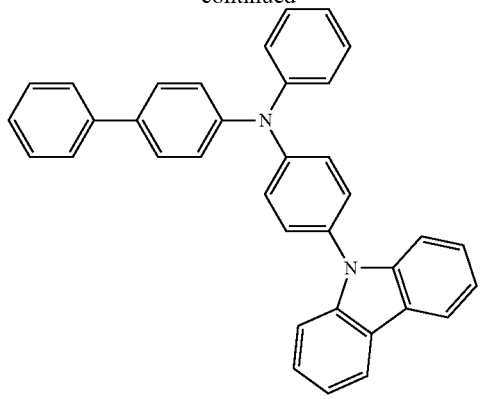

p-YGA1BP

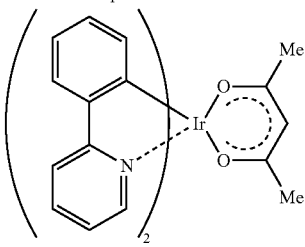

Ir(ppy)2(acac)

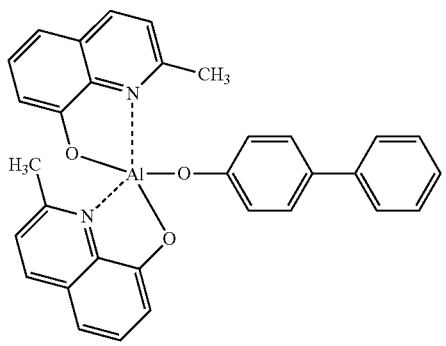

BAlq

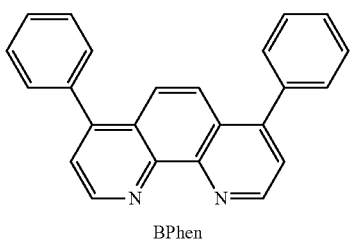

BPhen

A method for manufacturing a light-emitting element of this example will be described below.

(Light-Emitting Element 1)

First, a film of indium tin oxide containing silicon oxide (ITSO) was formed by a sputtering method over a glass substrate 2101 to form a first electrode 2102. Note that the thickness was 110 nm and the electrode area was 2 mm×2 mm.

Next, the substrate provided with the first electrode 2102 was fixed to a substrate holder provided in a vacuum evaporation apparatus such that the side on which the first electrode 2102 was formed faced downward. After the pressure in a film formation chamber was lowered to approximately $10^{-4}$ Pa, a layer 2111 containing a composite material of an organic compound and an inorganic compound was formed on the first electrode 2102 by co-evaporation of 4,4'-bis[N-(1-naphthyl)-N-phenylamino] biphenyl (NPB) and molybdenum(VI) oxide. The thickness of the layer 2111 was set to be 40 nm and the weight ratio of NPB to molybdenum(VI) oxide was controlled to 4:1 (=NPB:molybdenum oxide). Note that a co-evaporation method refers to an evaporation method by which evaporation is concurrently conducted from a plurality of evaporation sources in one treatment chamber.

Next, 4-(9H-carbazol-9-yl)-4'-phenyltriphenylamine (YGA1BP) is deposited to have a thickness of 20 nm by an evaporation method using resistance heating to form a hole-transporting layer 2112 on the layer 2111 containing a composite material.

Z-CzPO11 which is represented by Structural Formula (421) and bis(2-phenylpyridinato-N,$C^{2'}$)iridium(III)acetylacetonate (Ir(ppy)$_2$(acac)) were co-evaporated, whereby a light-emitting layer 2113 was faulted to a thickness of 40 nm on the hole-transporting layer 2112. Here, the weight ratio of Z-CzPO11 to Ir(ppy)$_2$(acac) was adjusted so as to be 1:0.06 (=Z-CzPO11:Ir(ppy)$_2$(acac)).

Subsequently, by an evaporation method using resistance heating, bis(2-methyl-8-quinolinolato)(4-phenylphenolato) aluminum(III) (BAlq) was deposited to a thickness of 10 nm on the light-emitting layer 2113, whereby a first electron-transporting layer 2114A was formed. Moreover, bathophenanthroline (BPhen) was deposited on the first electron-transporting layer 2114A so as to have a thickness of 20 nm by an evaporation method using resistance heating, whereby a second electron-transporting layer 2114B was formed.

Furthermore, a lithium fluoride film was deposited to a thickness of 1 nm on the second electron-transporting layer 2114B, whereby an electron-injecting layer 2115 was formed.

Lastly, an aluminum film was formed to a thickness of 200 nm on the electron-injecting layer 2115 by an evaporation method using resistance heating to form a second electrode 2104. Thus, a light-emitting element 1 was manufactured.

(Light-Emitting Element 2)

In a manner similar to that of the light-emitting element 1, with the use of the same substrate as the light-emitting element 1, a light-emitting element 2 was manufactured using Z-DPhAO11 which is represented by Structural Formula (460) instead of Z-CzPO11. That is, Z-DPhAO11 and Ir(ppy)$_2$(acac) were co-evaporated, whereby the light-emitting layer 2113 was formed to a thickness of 40 nm over the hole-transporting layer 2112. Here, the weight ratio of Z-DPhAO11 to Ir(ppy)$_2$(acac) was adjusted so as to be 1:0.06 (=Z-DPhAO11:Ir(ppy)$_2$(acac)). The layers other than the light-emitting layer 2113 were formed in a manner similar to that of the light-emitting element 1.

The thus obtained light-emitting elements 1 and 2 were sealed in a glove box under a nitrogen atmosphere without being exposed to atmospheric air. Then, the operating characteristics of these light-emitting elements were measured. The measurement was carried out at a room temperature (in the atmosphere kept at 25° C.).

Figure 34:
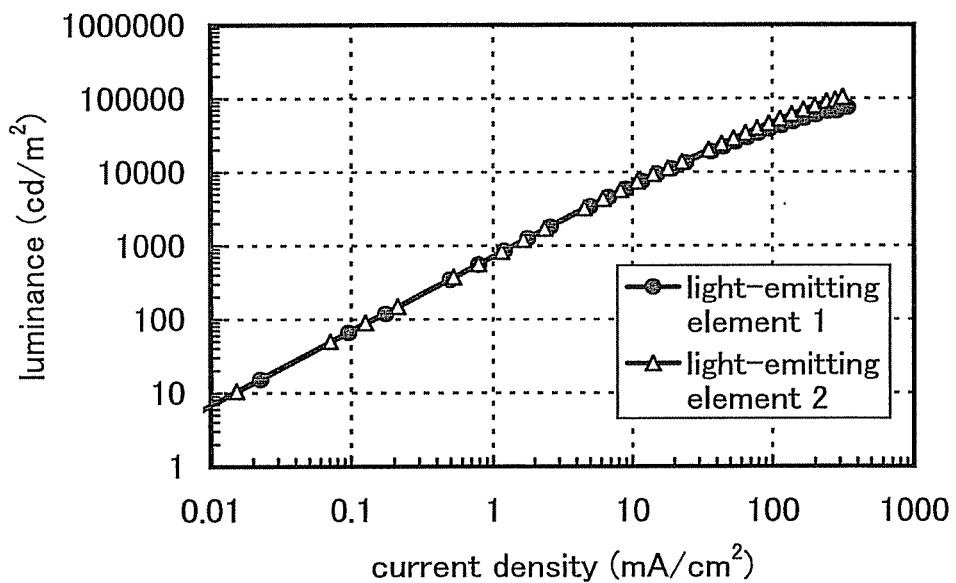
FIG. 34 shows current density-luminance characteristics of light-emitting elements manufactured in Example 3.
Figure 35:
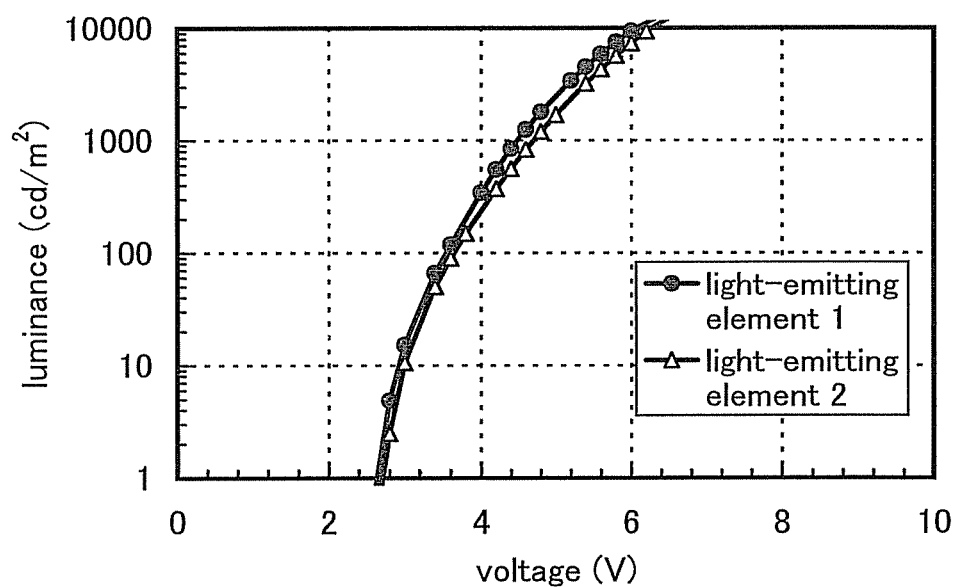
FIG. 35 shows voltage-luminance characteristics of light-emitting elements manufactured in Example 3.
Figure 36:
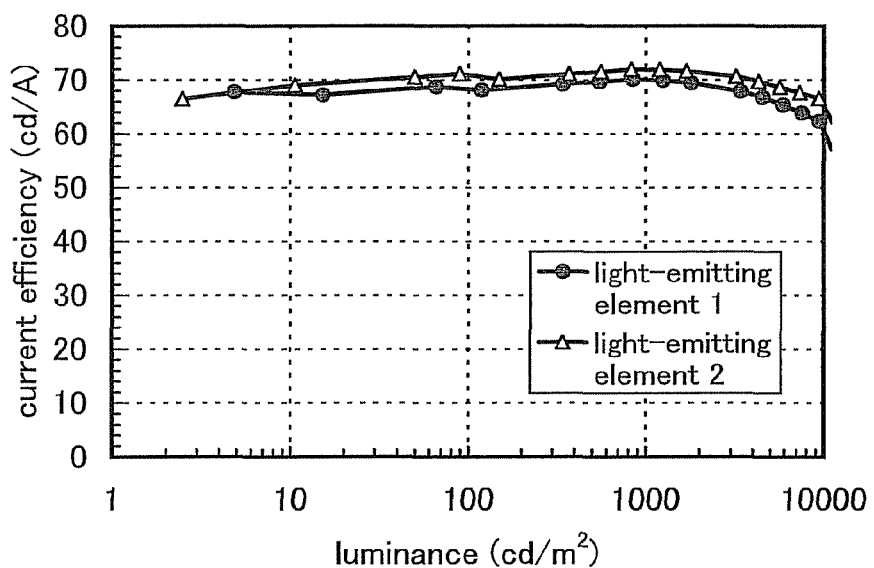
FIG. 36 shows luminance-current efficiency characteristics of the light-emitting elements manufactured in Example 3.

FIG. 34 shows the current density-luminance characteristics of the light-emitting element 1 and the light-emitting element 2. FIG. 35 shows the voltage-luminance characteristics. FIG. 36 shows the luminance-current efficiency characteristics. FIG. 34 and FIG. 35 show measurement data. Based on the data, the luminance-current efficiency characteristics (FIG. 36) were calculated.

Figure 37:
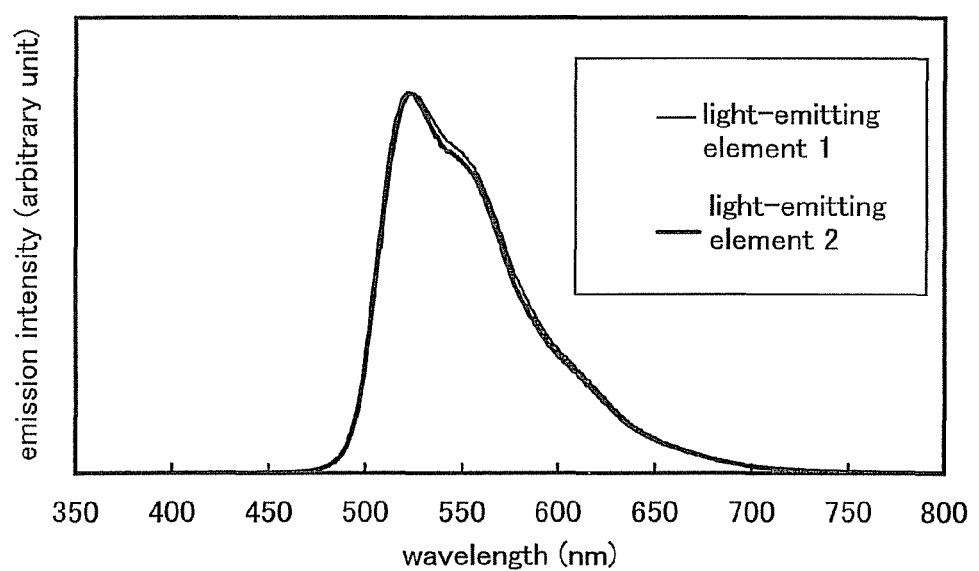
FIG. 37 shows emission spectra of the light-emitting elements manufactured in Example 3.

In addition, a light emission spectrum at current of 1 mA is shown in FIG. 37. From the result shown in FIG. 37, it can be seen that light emission of the light-emitting elements 1 and 2 is light emission derived from Ir(ppy)$_2$(acac). It can be seen that since an organic semiconductor material of the present invention has high triplet excitation energy, by using it as a host material of the light-emitting layer, light emission from a phosphorescent compound which exhibits green light was obtained efficiently.

The CIE chromaticity coordinates of the light-emitting element 1 at a luminance of 850 cd/m$^2$ were x=0.35 and y=0.62, and green light emission was exhibited. In addition, the current efficiency and external quantum efficiency of the light-emitting element 1 at a luminance of 850 cd/m$^2$ were 70 cd/A and 19.5%, respectively; thus, the light-emitting element 1 had extremely high emission efficiency. The voltage and the current density at a luminance of 850 cd/m$^2$ were 4.4 V and 1.21 mA/cm$^2$, respectively. The power efficiency of the light-emitting element 1 was 501 m/W, and the light-emitting element 1 had extremely high power efficiency. Further, energy conversion efficiency was calculated to be 9.9% which was high. Furthermore, it can be seen that from FIG. 36, the light-emitting element 1 has extremely high current efficiency of 70 cd/A at maximum.

The CIE chromaticity coordinates of the light-emitting element 2 at a luminance of 830 cd/m$^2$ were x=0.35 and y=0.62, and green light emission was exhibited. In addition, the current efficiency and external quantum efficiency of the light-emitting element 2 at a luminance of 830 cd/m$^2$ were 72 cd/A and 20.1%, respectively; thus, the light-emitting element 2 had extremely high emission efficiency. The voltage and the current density at a luminance of 830 cd/m$^2$ were 4.6 V and 1.15 mA/cm$^2$, respectively. The power efficiency of the light-emitting element 2 was 491 m/W, and the light-emitting element 2 had extremely high power efficiency. Further, energy conversion efficiency was calculated to be 9.8% which was high. Furthermore, it can be seen that from FIG. 36, the light-emitting element 2 has extremely high current efficiency of 72 cd/A at maximum.

As seen from the above, by applying an embodiment of the present invention, a light-emitting element having extremely high emission efficiency can be obtained. Further, a light-emitting element with low driving voltage can be obtained. The emission efficiency is extremely high and the driving voltage is reduced; therefore, power consumption can be reduced.

Example 4

In this example, an example of a light-emitting element to which an organic semiconductor material described in Example 2 is applied will be described with reference to FIG. 33. Structural formulae of materials used in this example are shown below. The material of which structural formula has already been shown is omitted.

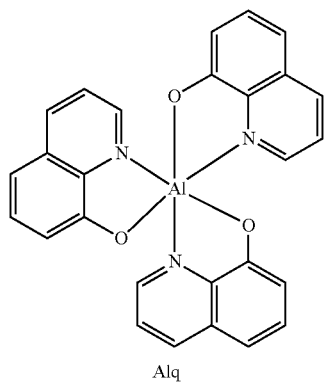

Alq

A method for manufacturing a light-emitting element of this example will be described below.
(Light-Emitting Element 3)

A light-emitting element 3 was manufactured using tris(8-quinolinolato)aluminum(III) (Alq) instead of BAlq of the light-emitting element 1 which was used in Example 3. That is, an Alq film was deposited to a thickness of 10 nm to form a first electron-transporting layer 2114A. Except for the first electron-transporting layer 2114A, the light-emitting element 3 was formed in a manner similar to that of the light-emitting element 1.

The light-emitting element 3 thus obtained was sealed in a glove box under a nitrogen atmosphere without being exposed to atmospheric air. Then, the operating characteristics of the light-emitting element were measured. The measurement was carried out at a room temperature (in the atmosphere kept at 25° C.).

Figure 38:
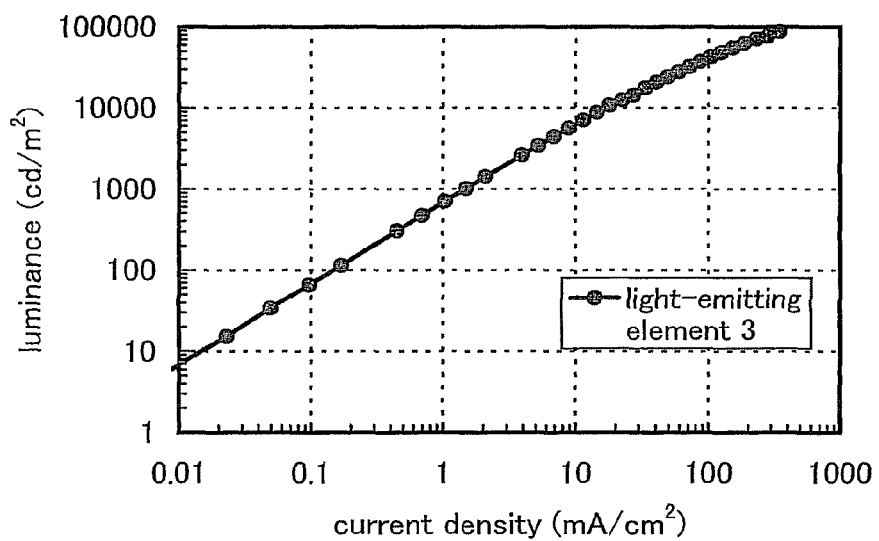
FIG. 38 shows current density-luminance characteristics of a light-emitting element manufactured in Example 4.
Figure 39:
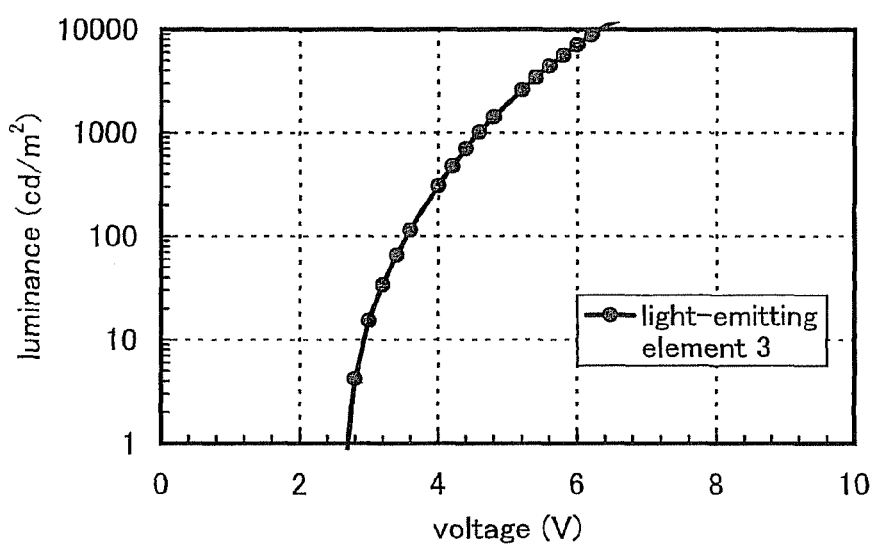
FIG. 39 shows voltage-luminance characteristics of the light-emitting element manufactured in Example 4.
Figure 40:
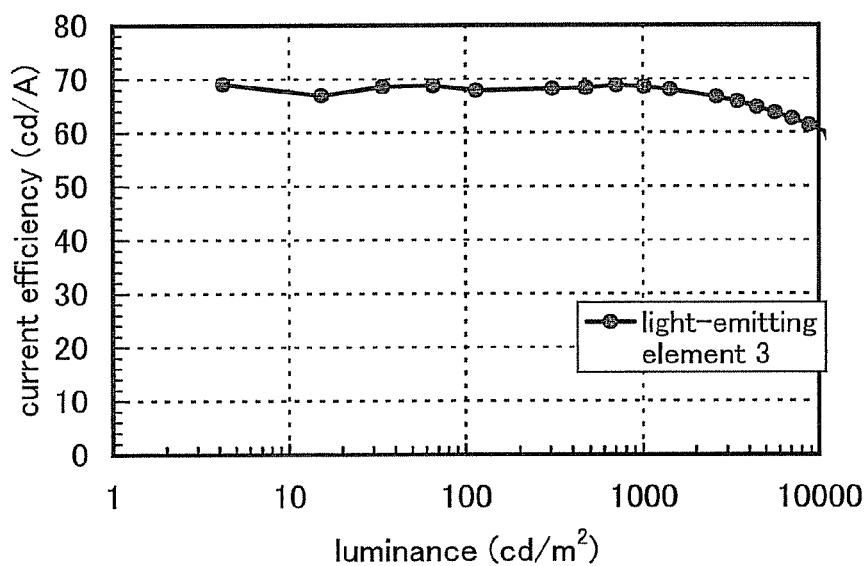
FIG. 40 shows luminance-current efficiency characteristics of the light-emitting element manufactured in Example 4.

FIG. 38 shows the current density-luminance characteristics of the light-emitting element 3. FIG. 39 shows the voltage-luminance characteristics. FIG. 40 shows the luminance-current efficiency characteristics. FIG. 38 and FIG. 39 show measurement data. Based on the data, the luminance-current efficiency characteristics (FIG. 40) were calculated.

Figure 41:
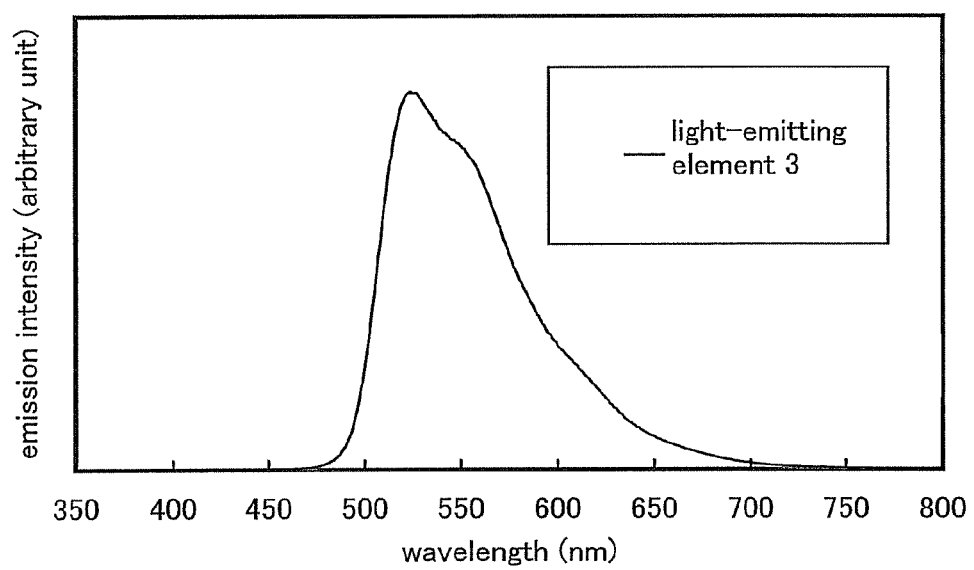
FIG. 41 shows an emission spectrum of the light-emitting element manufactured in Example 4.

In addition, a light emission spectrum at current of 1 mA is shown in FIG. 41. From the result shown in FIG. 41, it can be seen that light emission of the light-emitting element 3 is light emission derived from $Ir(ppy)_2(acac)$. It can be seen that since an organic semiconductor material of the present invention has high triplet excitation energy, by using it as a host material of the light-emitting layer, light emission from a phosphorescent compound which exhibits green light was obtained efficiently.

The CIE chromaticity coordinates of the light-emitting element 3 at a luminance of 1020 $cd/m^2$ were x=0.35 and y=0.62, and green light emission was exhibited. In addition, the current efficiency and external quantum efficiency of the light-emitting element 3 at a luminance of 1020 $cd/m^2$ were 69 cd/A and 18.9%, respectively; thus, the light-emitting element 3 had extremely high emission efficiency. The voltage and the current density at a luminance of 1020 $cd/m^2$ were 4.6 V and 1.48 $mA/cm^2$, respectively. The power efficiency of the light-emitting element 3 was 471 m/W, and the light-emitting element 3 had extremely high power efficiency. Further, energy conversion efficiency was calculated to be 9.2% which was high. Furthermore, it can be seen that from FIG. 40, the light-emitting element 3 has extremely high current efficiency of 69 cd/A at maximum.

As seen from the above, by applying an embodiment of the present invention, a light-emitting element having extremely high emission efficiency can be obtained. Further, a light-emitting element with low driving voltage can be obtained. The emission efficiency is extremely high and the driving voltage is reduced; therefore, power consumption can be reduced.

Example 5

In this example, an example of a light-emitting element to which the organic semiconductor material described in Example 2 is applied will be described with reference to FIG. 33.

A method for manufacturing a light-emitting element of this example will be described below.
(Light-Emitting Element 4)

A light-emitting element 4 was manufactured in a manner similar to that of the light-emitting element 1 except that Z-CzPBOx which is represented by Structural Formula (101) was used instead of Z-CzPO11 of the light-emitting element 1 which was used in Example 3. That is, Z-CzPBOx and $Ir(ppy)_2(acac)$ were co-evaporated, whereby the light-emitting layer 2113 was formed to a thickness of 40 nm on the hole-transporting layer 2112. Here, the weight ratio of Z-CzPBOx to $Ir(ppy)_2(acac)$ was adjusted so as to be 1:0.06 (=Z-CzPBOx:$Ir(ppy)_2(acac)$). The layers other than the light-emitting layer 2113 were formed in a manner similar to that of the light-emitting element 1.
(Light-Emitting Element 5)

With the use of the same substrate as the light-emitting element 4, a light-emitting element 5 was manufactured in a manner similar to that of the light-emitting element 4 except that Z-DPhABOx which is represented by Structural Formula (201) was used instead of Z-CzPBOx. That is, Z-DPhABOx and $Ir(ppy)_2(acac)$ were co-evaporated, whereby the light-emitting layer 2113 was formed to a thickness of 40 nm on the hole-transporting layer 2112. Here, the weight ratio of Z-DPhABOx to $Ir(ppy)_2(acac)$ was adjusted so as to be 1:0.06 (=Z-DPhABOx:$Ir(ppy)_2(acac)$). The layers other than the light-emitting layer 2113 were formed in a manner similar to those of the light-emitting element 4.

The thus obtained light-emitting elements 4 and 5 were sealed in a glove box under a nitrogen atmosphere without being exposed to atmospheric air. Then, the operating characteristics of these light-emitting elements were measured. The measurements were carried out at a room temperature (in the atmosphere kept at 25° C.).

Figure 42:
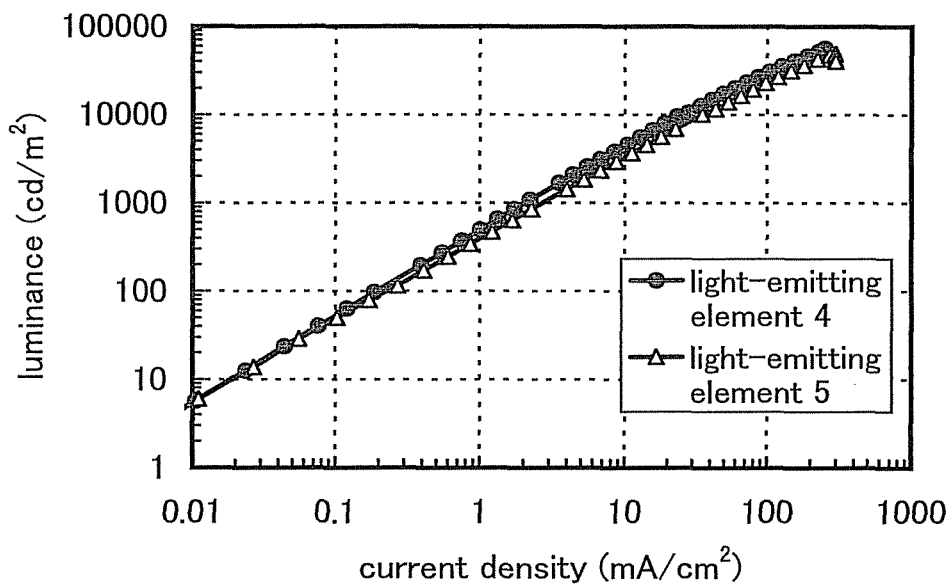
FIG. 42 shows current density-luminance characteristics of light-emitting elements manufactured in Example 5.
Figure 43:
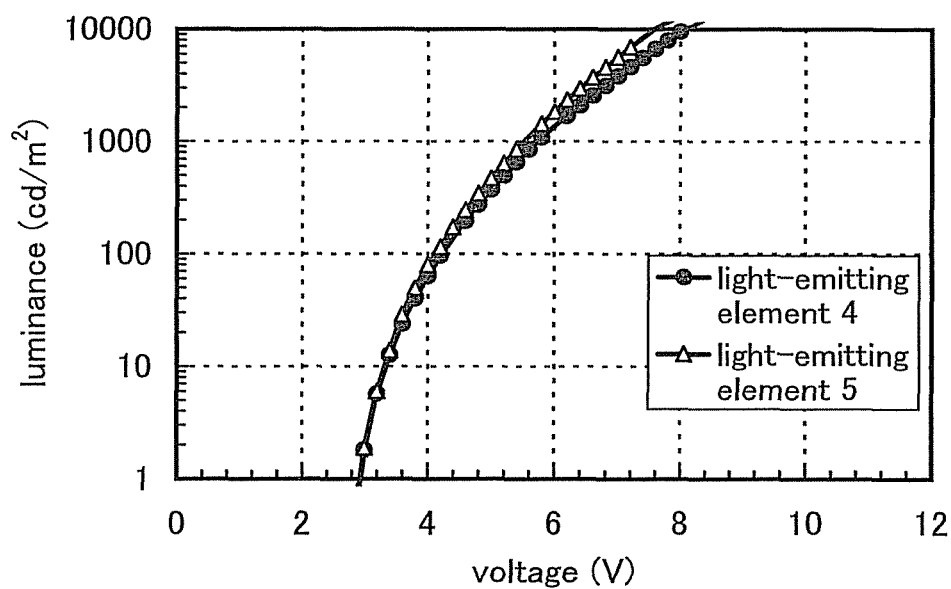
FIG. 43 shows voltage-luminance characteristics of the light-emitting elements manufactured in Example 5.
Figure 44:
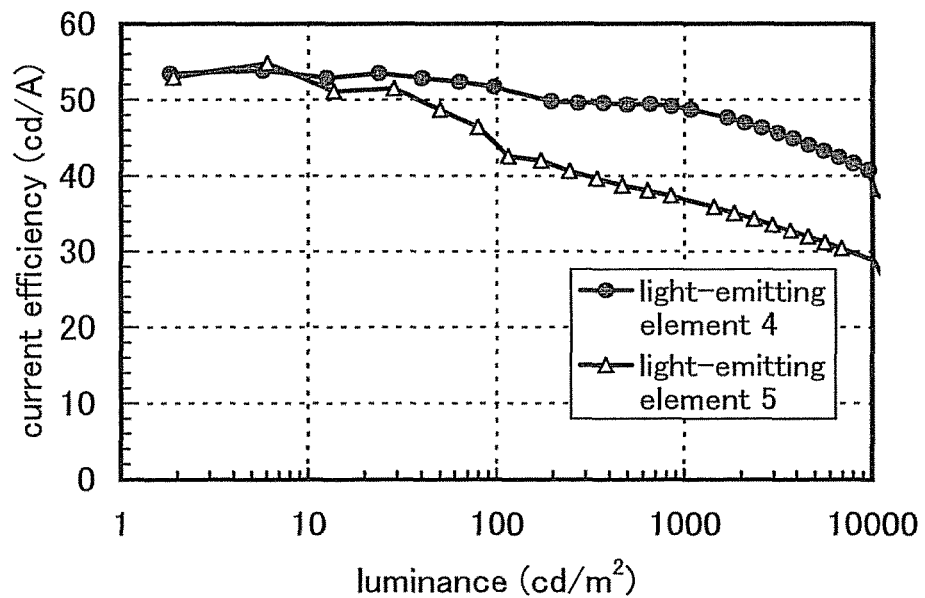
FIG. 44 shows luminance-current efficiency characteristics of the light-emitting elements manufactured in Example 5.

FIG. 42 shows the current density-luminance characteristics of the light-emitting element 4 and the light-emitting element 5. FIG. 43 shows the voltage-luminance characteristics. FIG. 44 shows the luminance-current efficiency characteristics. FIG. 42 and FIG. 43 show measurement data. Based on the data, the luminance-current efficiency characteristics (FIG. 44) were calculated.

Figure 45:
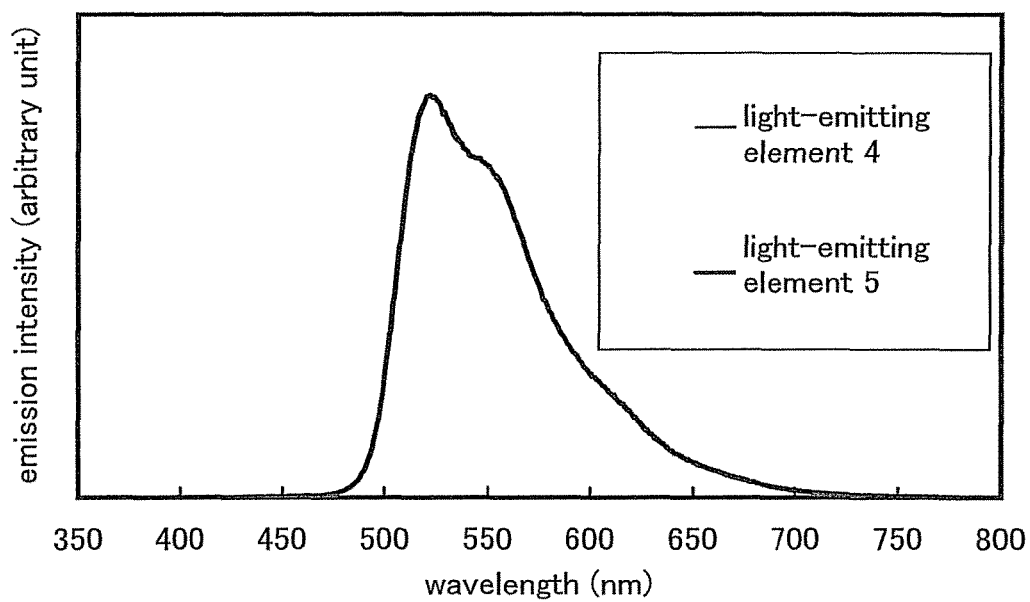
FIG. 45 shows emission spectra of the light-emitting elements manufactured in Example 5.

In addition, a light emission spectrum at current of 1 mA is shown in FIG. 45. From the result shown in FIG. 45, it can be seen that light emission of the light-emitting elements 4 and 5 is light emission derived from $Ir(ppy)_2(acac)$. It can be seen that since a benzoxazole derivative described in Embodiment 2 has high triplet excitation energy, by using it as a host material of the light-emitting layer, light emission from a phosphorescent compound which exhibits green light was obtained efficiently.

The CIE chromaticity coordinates of the light-emitting element 4 at a luminance of 1080 $cd/m^2$ were x=0.35 and y=0.62, and green light emission was exhibited. In addition, the current efficiency and external quantum efficiency of the light-emitting element 4 at a luminance of 1080 $cd/m^2$ were 49 cd/A and 13.6%, respectively; thus, the light-emitting element 4 had high emission efficiency. The voltage and the current density at a luminance of 1080 cd/m² were 5.8 V and 2.22 mA/cm², respectively. The power efficiency of the light-emitting element 4 was 261 m/W, and the light-emitting element 4 had high power efficiency. Further, energy conversion efficiency was calculated to be 5.3% which was high. Furthermore, it can be seen that from FIG. 44, the light-emitting element 4 has high current efficiency of 54 cd/A at maximum.

The CIE chromaticity coordinates of the light-emitting element 5 at a luminance of 850 cd/m² were x=0.35 and y=0.62, and green light emission was exhibited. In addition, the current efficiency and external quantum efficiency of the light-emitting element 5 at a luminance of 850 cd/m² were 37 cd/A and 10.4%, respectively; thus, the light-emitting element 5 had high emission efficiency. The voltage and the current density at a luminance of 850 cd/m² were 5.4 V and 2.27 mA/cm², respectively. The power efficiency of the light-emitting element 5 was 221 m/W, and the light-emitting element 5 had high power efficiency. Further, energy conversion efficiency was calculated to be 4.3% which was high. Furthermore, it can be seen that from FIG. 44, the light-emitting element 5 has high current efficiency of 55 cd/A at maximum.

As seen from the above, by applying an embodiment of the present invention, a light-emitting element having extremely high emission efficiency can be obtained. Further, a light-emitting element with low driving voltage can be obtained. The emission efficiency is extremely high and the driving voltage is reduced; therefore, power consumption can be reduced.

Example 6

In this example, an example of a light-emitting element to which an organic semiconductor material described in Example 2 is applied will be described with reference to FIG. 33.

A method for manufacturing a light-emitting element of this example will be described below.

(Light-Emitting Element 6)

A light-emitting element 6 was manufactured using tris (8-quinolinolato)aluminum(III) (Alq) instead of BAlq of the light-emitting element 4 in Example 5. That is, an Alq film was deposited to a thickness of 10 nm to form a first electron-transporting layer 2114A. Except for the first electron-transporting layer 2114A, the light-emitting element 6 was formed in a manner similar to that of the light-emitting element 4.

The light-emitting element 6 thus obtained was sealed in a glove box under a nitrogen atmosphere without being exposed to atmospheric air. Then, the operating characteristics of the light-emitting element were measured. The measurement was carried out at a room temperature (in the atmosphere kept at 25° C.).

Figure 46:
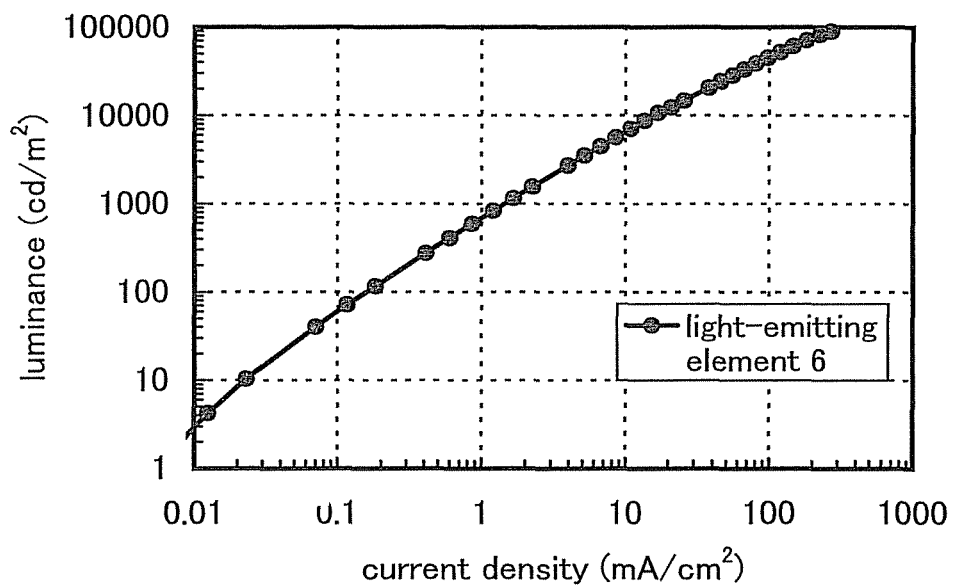
FIG. 46 shows current density-luminance characteristics of a light-emitting element manufactured in Example 6.
Figure 47:
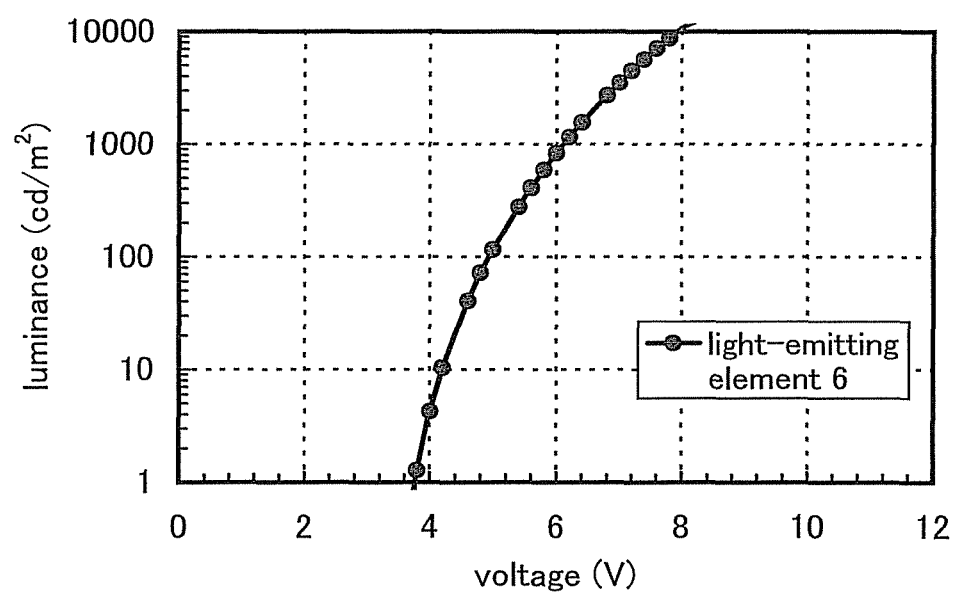
FIG. 47 shows voltage-luminance characteristics of the light-emitting element manufactured in Example 6.
Figure 48:
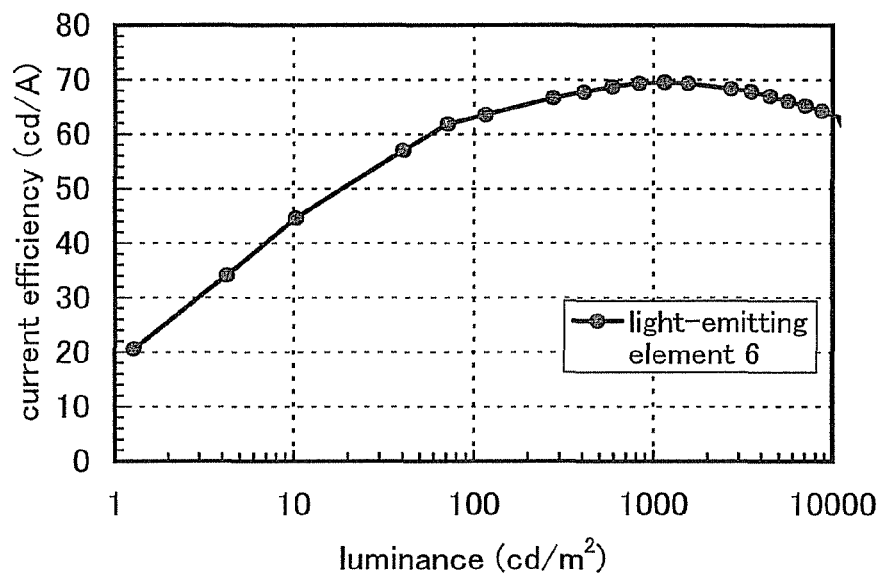
FIG. 48 shows luminance-current efficiency characteristics of the light-emitting element manufactured in Example 6.

FIG. 46 shows the current density-luminance characteristics of the light-emitting element 6. FIG. 47 shows the voltage-luminance characteristics. FIG. 48 shows the luminance-current efficiency characteristics. FIG. 46 and FIG. 47 show measurement data. Based on the data, the luminance-current efficiency characteristics (FIG. 48) were calculated.

Figure 49:
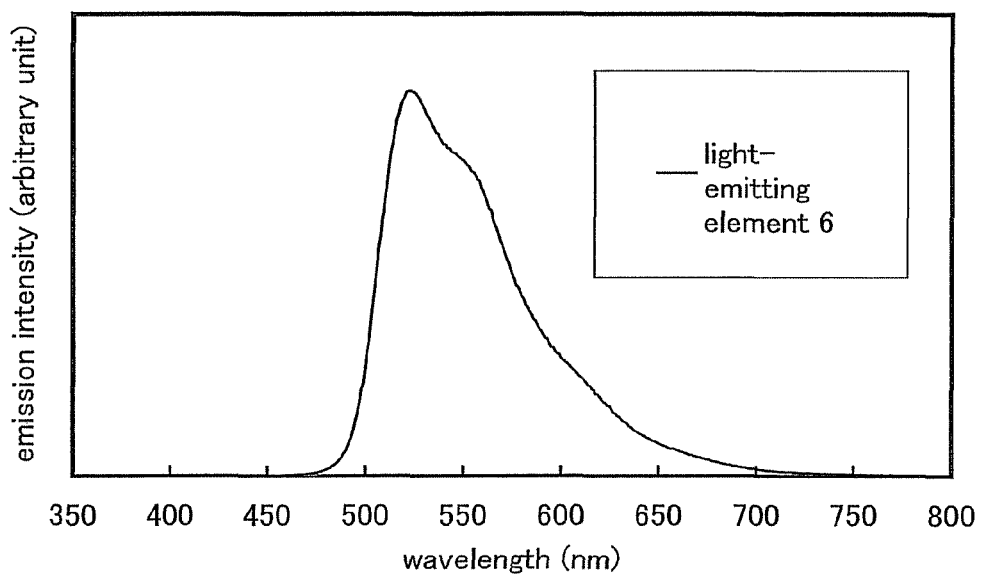
FIG. 49 shows an emission spectrum of the light-emitting element manufactured in Example 6.

In addition, a light emission spectrum at current of 1 mA is shown in FIG. 49. From the result shown in FIG. 49, it can be seen that light emission of the light-emitting element 6 is light emission derived from Ir(ppy)₂(acac). It can be seen that since an organic semiconductor material of the present invention has high triplet excitation energy, by using it as a host material of the light-emitting layer, light emission from a phosphorescent compound which exhibits green light was obtained efficiently.

The CIE chromaticity coordinates of the light-emitting element 6 at a luminance of 1150 cd/m² were x=0.35 and y=0.62, and green light emission was exhibited. In addition, the current efficiency and external quantum efficiency of the light-emitting element 6 at a luminance of 1150 cd/m² were 70 cd/A and 19.3%, respectively; thus, the light-emitting element 6 had extremely high emission efficiency. The voltage and the current density at a luminance of 1150 cd/m² were 6.2 V and 1.66 mA/cm², respectively. The power efficiency of the light-emitting element 6 was 351 m/W, and the light-emitting element 6 had high power efficiency. Further, energy conversion efficiency was calculated to be 7.0% which was high. Furthermore, it can be seen that from FIG. 48, the light-emitting element 6 has high current efficiency of 70 cd/A at maximum.

As seen from the above, by applying an embodiment of the present invention, a light-emitting element having extremely high emission efficiency can be obtained. Further, a light-emitting element with low driving voltage can be obtained. The emission efficiency is extremely high and the driving voltage is reduced; therefore, power consumption can be reduced.

Example 7

In this example, a synthesis method of the organic semiconductor material according to an embodiment of the present invention which is described in Example 2 will be described in detail.

Synthesis Example 1

Z-CzPO11

A synthesis method of 9-[4'''-(5-phenyl-1,3,4-oxadiazol-2-yl)-[1,1':2',1'':2''',1''']quaterphenyl-4-yl)]-9H-carbazole (Z-CzPO11) which is represented by following Structural Formula (421) and which is one of the oxadiazole derivatives described in Embodiment 3 will be described.

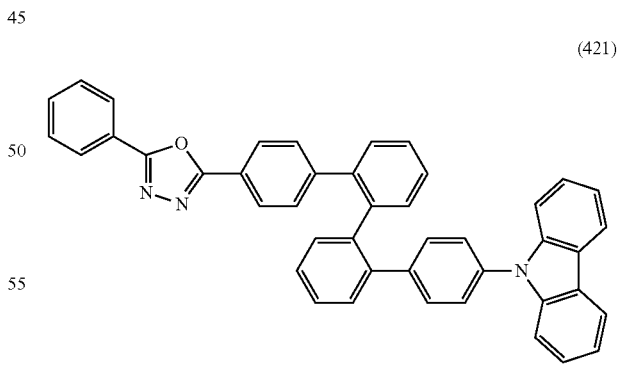

(421)

Step 1: Synthesis of 2-(2'-bromobiphenyl-4-yl)-5-phenyl-1,3,4-oxadiazole (i) Synthesis of 4-iodobenzoylhydrazine A synthetic scheme of 4-iodobenzoylhydrazine is shown in (A-1).

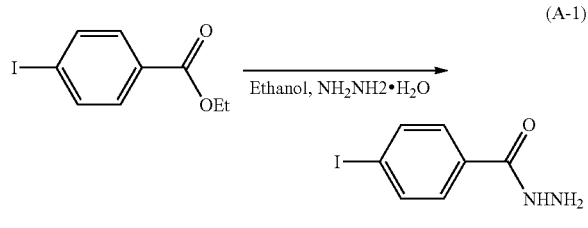

Into a 200 mL three-neck flask was put 25 g (90 mmol) of ethyl-4-iodobenzoate, 80 mL of ethanol was added thereto, and the mixture was stirred for 10 minutes at a room temperature. After the stirring, 20 mL of hydrazine monohydrate was added into the solution, and the mixture was stirred at 80° C. for 5 hours. After the stirring, about 500 mL of water was added into the mixture and the mixture was washed. After the washing, the mixture was subjected to suction filtration, and the solid was collected to give 23 g of a white needle-like solid in a yield of 98%.

(ii) Synthesis of 1-benzoyl-2-(4-iodobenzoyl)hydrazine

A synthetic scheme of 1-benzoyl-2-(4-iodobenzoyl)hydrazine is shown in (A-2).

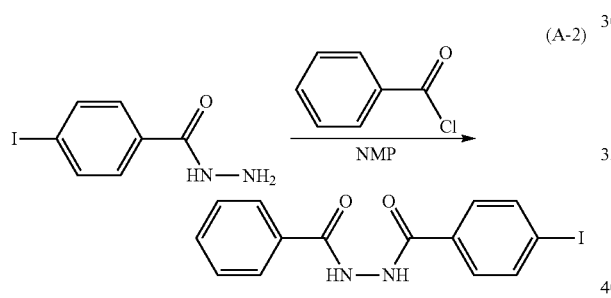

Into a 300 mL three-neck flask was put 15 g (57 mmol) of 4-iodobenzoylhydrazine, 15 mL of N-methyl-2-pyrrolidone (NMP) was added thereto, and the mixture was stirred for 10 minutes at a room temperature. After the stirring, 50 mL of a mixed solution of 5 mL of N-methyl-2-pyrrolidone and 7.9 mL (69 mmol) of benzoyl chloride was dripped into the solution through a dropping funnel, and the solution was stirred at a room temperature for 18 hours. After the stirring, water was added into the solution, and a solid was precipitated. The precipitated solid was collected by suction filtration. The collected solid was added into about 500 mL of a saturated aqueous solution of sodium hydrogen carbonate, stirred, and washed. After the washing, the mixture was subjected to suction filtration to obtain a solid. The obtained solid was added into about 500 mL of water, stirred, and washed. After the washing, the mixture was subjected to suction filtration to obtain a solid. The obtained solid was washed with methanol to give 20 g of a powdery white solid in a yield of 97%.

(iii) Synthesis of 2-(4-iodophenyl)-5-phenyl-1,3,4-oxadiazole

A synthetic scheme of 2-(4-iodophenyl)-5-phenyl-1,3,4-oxadiazoe is shown in (A-3).

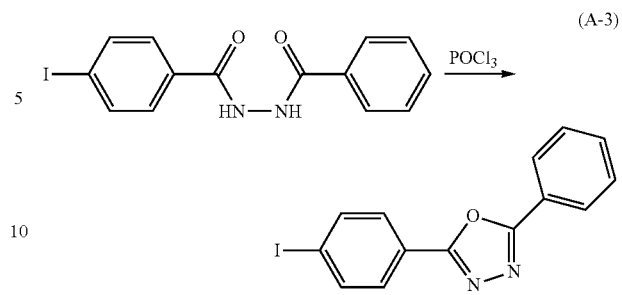

Into a 300 mL three-neck flask was put 15 g (41 mmol) of 1-benzoyl-2-(4-iodobenzoyl)hydrazine, 100 mL of phosphoryl chloride was added thereto. The mixture was stirred at 100° C. for 5 hours under a nitrogen stream. After the stirring, phosphoryl chloride in the solution was distilled off to give a solid. The obtained solid was washed with water, and then washed with a saturated aqueous solution of sodium hydrogen carbonate. The obtained solid was washed with methanol to give 9.0 g of a powdery white solid in a yield of 63%.

(vi) Synthesis of 2-(2'-bromophenyl-4-yl)-5-phenyl-1,3,4-oxadiazole

A synthetic scheme of 2-(2'-bromophenyl-4-yl)-5-phenyl-1,3,4-oxadiazole is shown in (A-4).

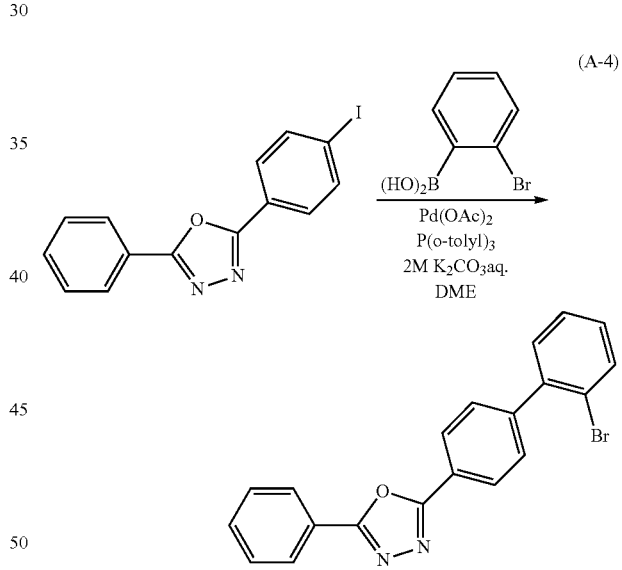

Into a 100 mL three-neck flask were put 5.0 g (14 mmol) of 2-(4-iodophenyl)-5-phenyl-1,3,4-oxadiazole, 2.9 g (14 mmol) of 2-bromophenyl boronic acid, 0.032 g (0.14 mmol) of palladium(II) acetate, and 0.30 g (1.0 mmol) of tri(o-tolyl)phosphine. 40 mL of 1,2-dimethoxyethane (DME) and 15 mL of a 2M aqueous solution of potassium carbonate were added into the mixture. After this mixture was degassed under low pressure, the atmosphere in the flask was substituted by nitrogen. This mixture was stirred at 90° C. for 5 hours. After the reaction, toluene was added into the mixture, the mixture was separated into an aqueous layer and an organic layer, and the organic layer was washed with a saturated aqueous solution of sodium carbonate and brine in this order. After the washing, magnesium sulfate was added into the organic layer to dry the organic layer.

After the drying, this mixture was subjected to suction filtration to give a filtrate. The obtained filtrate was subjected to suction filtration through Celite (manufactured by Wako. Pure Chemical Industries, Ltd., Catalog No. 531-16855) to give a filtrate. The compound obtained by concentrating the obtained filtrate was purified by silica gel column chromatography. The column chromatography was performed first using toluene as a developing solvent and then using a mixed solvent of toluene and ethyl acetate (toluene:ethyl acetate=10:1) as a developing solvent. The obtained fraction was concentrated, methanol was added thereto, and irradiation with ultrasonic waves was performed, so that a solid was precipitated. The precipitated solid was collected by suction filtration. The collected solid was recrystallized with a mixed solvent of ethanol and hexane to give 3.1 g of a powdery white solid in a yield of 58%.

Step 2: Synthesis of 4'-(9H-carbazol-9-yl)biphenyl-2-boronic acid (i) Synthesis of 9-(2'-bromophenyl-4-yl)-9H-carbazole A synthetic scheme of 9-(2'-bromophenyl-4-yl)-9H-carbazole is shown in (B-1).

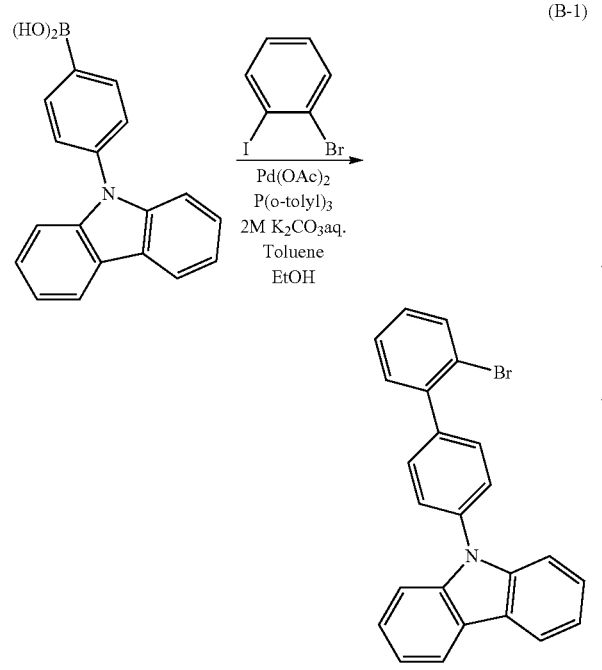

Into a 200 mL three-neck flask were put 5.0 g (17 mmol) of 4-(9H-carbazol-9-yl)phenylboronic acid, 9.9 g (35 mmol) of 2-bromoiodobenzene, 0.039 g (0.17 mmol) of palladium (II) acetate, and 0.37 g (1.2 mmol) of tri(o-tolyl)phosphine. After 30 mL of toluene, 5 mL of ethanol, 15 mL of a 2M aqueous solution of potassium carbonate were added into the mixture and this mixture was degassed under low pressure, the atmosphere in the flask was substituted by nitrogen. This mixture was stirred at 90° C. for 5 hours. After the stirring, toluene was added into the mixture and the organic layer was washed with a saturated aqueous solution of sodium carbonate and brine in this order. After the washing, magnesium sulfate was added into the organic layer to dry the organic layer. After the drying, this mixture was subjected to suction filtration to give a filtrate. The obtained filtrate was concentrated, and was purified by silica gel column chromatography. The column chromatography was performed first using hexane as a developing solvent and then using a mixed solvent of hexane and ethyl acetate (hexane:ethyl acetate=20:1) as a developing solvent. The obtained fraction was concentrated and dried to give 6.0 g of colorless oily substance in a yield of 86%.

(ii) Synthesis of 4'-(9H-carbazol-9-yl)biphenyl-2-boronic acid

A synthesis scheme of 4'-(9H-carbazol-9-yl)biphenyl-2-boronic acid is shown in (B-2).

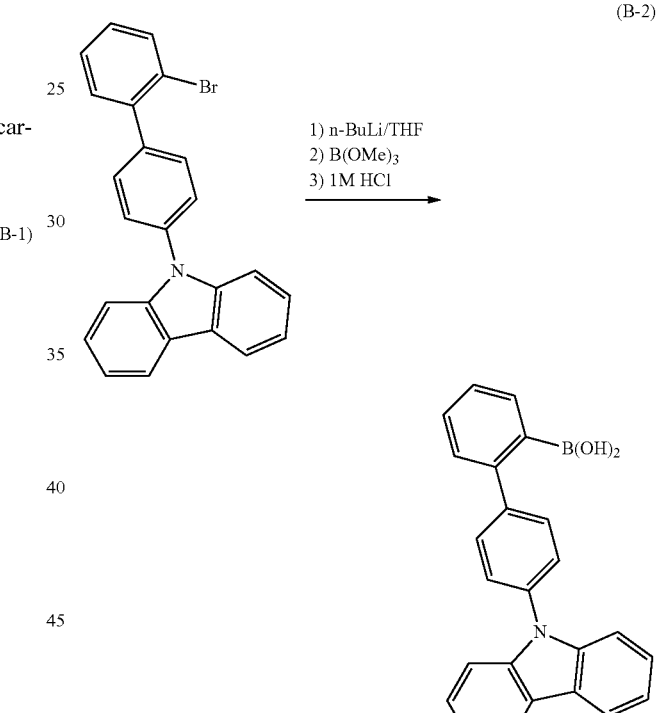

Into 300 mL three-neck flask were put a mixed solution of 6.2 g (16 mmol) of 9-(2'-bromophenyl)-9H-carbazole and 100 mL of tetrahydrofuran (THF). After the solution was degassed under low pressure, the atmosphere in the flask was substituted by nitrogen. The solution was stirred at −78° C. for 20 minutes. After the stirring, 12 mL (19 mmol) of hexane solution of 1.55 mol/L of n-butyllithium was dripped with a syringe, and the solution was stirred at −78° C. for 2 hours. After the stirring, 4.0 mL of trimethyl borate was added and the mixture was stirred −78° C. for 1 hour, and then was stirred for about 24 hours while the temperature of the mixture was being gradually brought back to room temperature. After the stirring, to this solution was added 50 mL of 1M dilute hydrochloric acid, and the solution was stirred for 30 minutes at a room temperature. After the stirring, to this mixture was added ethyl acetate, and extraction with ethyl acetate was performed. After the extraction, the extracted solution was combined with the organic layer and washed with brine. After the washing, magnesium sulfate was added into the organic layer to dry the organic layer. After the drying, the mixture was subjected to suction filtration to give a filtrate. The obtained filtrate was concentrated and recrystallized with a mixture solvent of chloroform and hexane to give 3.2 g of a powdery white solid in a yield of 55%.

Step 3: Synthesis of Z-CzPO11

A synthetic scheme of Z-CzPO11 is shown in (E-1).

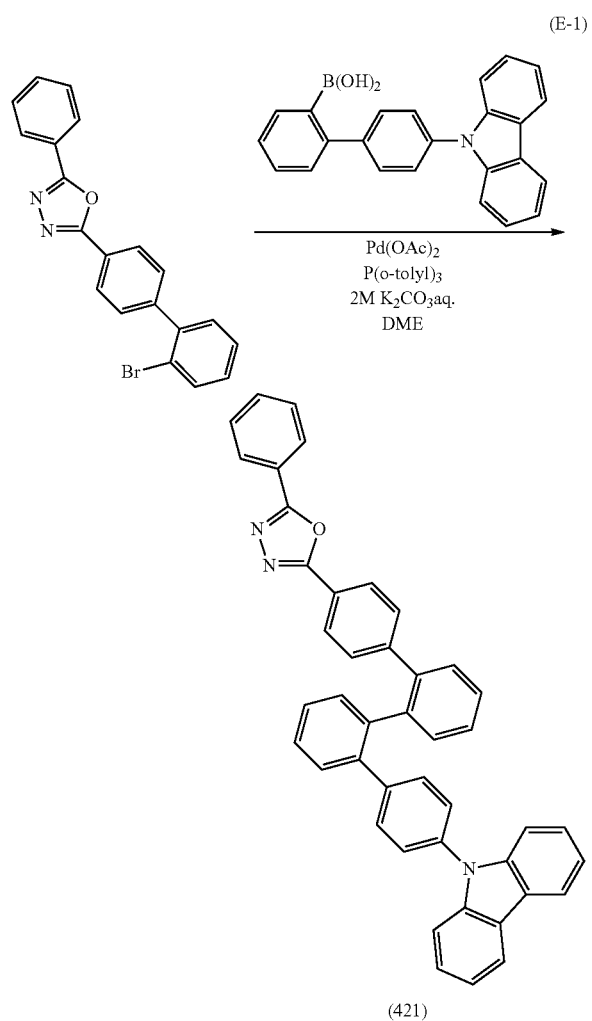

(421)

Into a 100 mL three-neck flask were put 1.0 g (2.7 mmol) of 2-(2'-bromobiphenyl-4-yl)-5-phenyl-1,3,4-oxadiazole which was synthesized in Step 1 of Synthesis Example 1, 1.0 g (2.7 mmol) of 4'-(9H-carbazol-9-yl)biphenyl-2-boronic acid, 0.010 g (0.045 mmol) of palladium(II) acetate, and 0.10 g (0.33 mmol) of tri(o-tolyl)phosphine which were synthesized in Step 2 of Synthesis Example 1. Into the solution were added 15 mL of 1,2-dimethoxyethane (DME) and 10 mL of a 2M aqueous solution of potassium carbonate.

After the mixture was degassed under low pressure, the atmosphere in the flask was substituted by nitrogen. This mixture was stirred at 90° C. for 10 hours. After the stirring, chloroform was added into the mixture, the mixture was separated into an aqueous layer and an organic layer, and the organic layer was washed with a saturated aqueous solution of sodium carbonate and brine in this order. After the washing, magnesium sulfate was added into the organic layer to dry the organic layer. After the drying, this mixture was subjected to suction filtration to give a filtrate. The obtained filtrate was subjected to suction filtration through Celite (manufactured by Wako Pure Chemical Industries, Ltd., Catalog No. 531-16855) to give a filtrate. The compound obtained by concentrating the obtained filtrate was purified by silica gel column chromatography. The column chromatography was performed first using toluene as a developing solvent and then using a mixed solvent of toluene and ethyl acetate (toluene:ethyl acetate=10:1) as a developing solvent. A solid which was obtained by concentrating the obtained fraction was dissolved in chloroform and purified by high performance liquid chromatography (HPLC). The chromatography was performed using chloroform as a developing solvent. The solid which was obtained by concentrating the obtained fraction was recrystallized with a mixed solvent of chloroform and methanol to give 0.30 g of a powdery white solid in a yield of 18%.

The obtained compound was analyzed by nuclear magnetic resonance (NMR) measurement, whereby it was confirmed that the compound was 9-[4'''-(5-phenyl-1,3,4-oxadiazol-2-yl)-[1,1':2',1'':2'',1''']quaterphenyl-4-yl)]-9H-carbazole (Z-CzPO11).

Hereinafter, the $^1$H NMR data is shown.

$^1$H NMR (CDCl$_3$, 300 MHz): δ=6.79 (d, J=8.3 Hz, 2H), 6.88 (d, J=8.3 Hz, 2H), 7.22 (d, J=8.3 Hz, 2H), 7.25-7.33 (m, 4H), 7.39-7.62 (m, 13H), 7.84 (d, J=8.3 Hz, 2H), 8.09-8.18 (m, 4H)

Figure 50A:
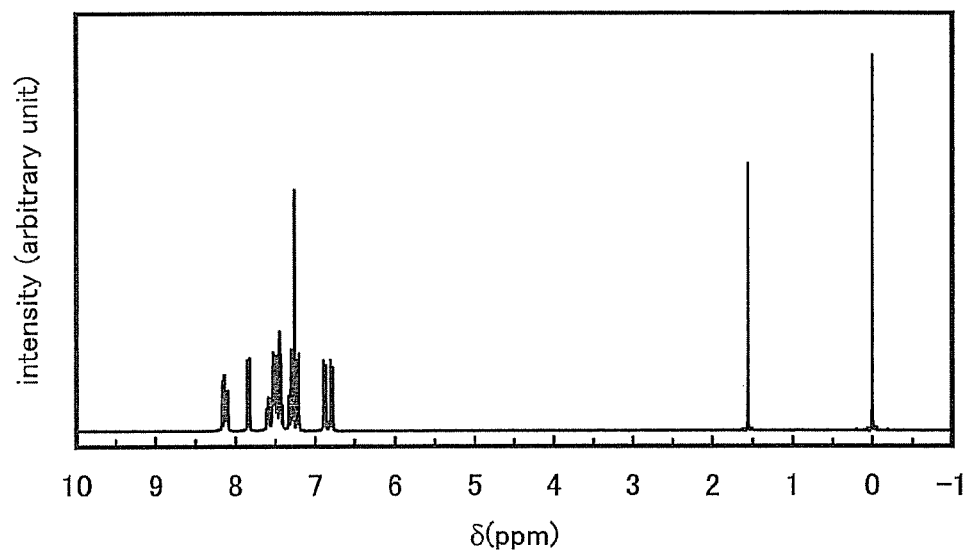
FIGS. 50A and 50B show $^1$H NMR charts of Z-CzPO11.
Figure 50B:
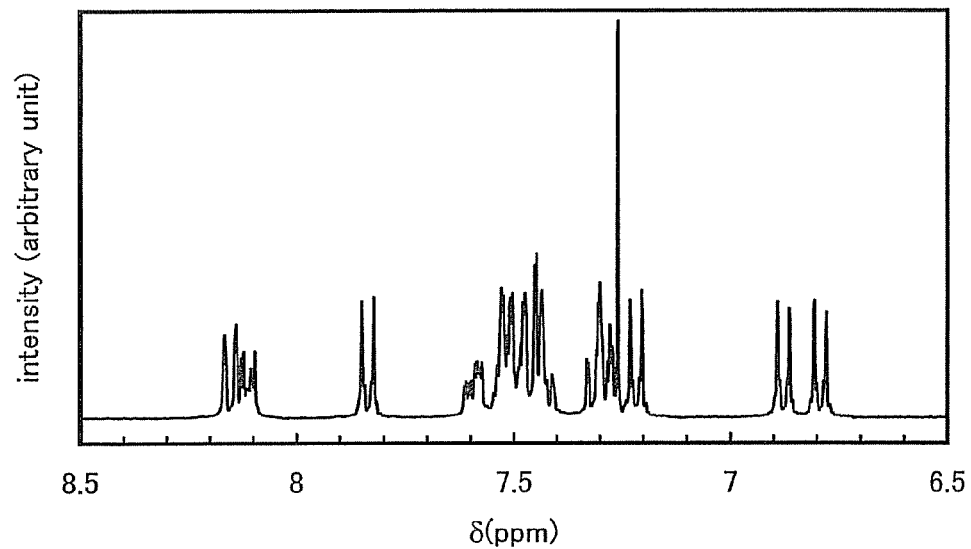

Further, $^1$H NMR charts are shown in FIGS. 50A and 50B. Note that FIG. 50B shows an enlarged chart showing the range of 6.5 ppm to 8.5 ppm in FIG. 50A.

Thermogravimetry-differential thermal analysis (TG-DTA) was performed on the obtained Z-CzPO11. A thermogravimetric-differential thermal analyzer (TG/DTA-320, manufactured by Seiko Instruments Inc.) was used for the measurement, and it was found that the temperature at which the weight is 95% with respect to the weight at the onset of measurement under atmospheric pressure (hereinafter, this temperature is referred to as "5% weight loss temperature") was 387° C. The glass transition temperature of Z-CzPO11, which was measured using a differential scanning calorimetry (Pyris 1 DSC, manufactured by Perkin Elmer Co., Ltd.), was 119° C. From these results, it was found that Z-CzPO11 was a material having favorable heat resistance.

Synthesis Example 2

Z-DPhAO11

A synthesis method of 4-[4''-(5-phenyl-1,3,4,-oxadiazol-2-yl)-[1,1':2',1'']terphenyl-2-yl]triphenylamine (Z-DPhAO11) represented by Structural Formula (460) which is one of the oxadiazole derivatives described in Embodiment 3 will be described.

(460)

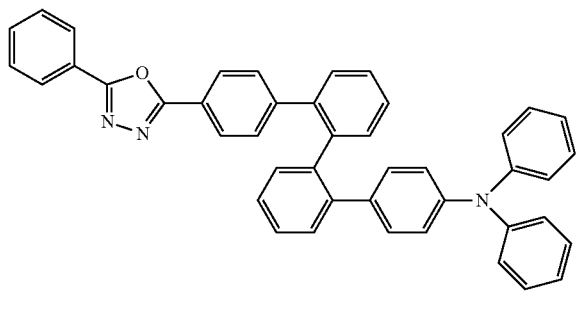

Step 1: Synthesis of 4'-(N,N-diphenylamino)biphenyl-2-boronic acid (i) Synthesis of 4-(diphenylamino)phenylboronic acid A synthetic scheme of 4-(diphenylamino)phenylboronic acid is shown in (C-1).

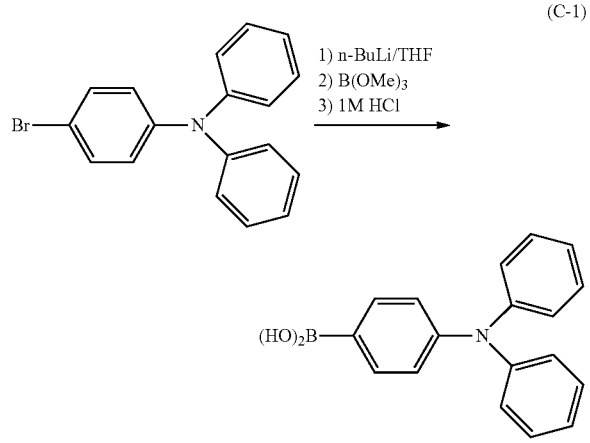
(C-1)

A solution in which 10 g (31 mmol) of 4-bromotriphenylamine is dissolved in 200 mL of tetrahydrofuran (THF) was put into a 500 mL three-neck flask and stirred. After the solution was degassed under low pressure, the atmosphere in the flask was substituted by nitrogen. The solution was stirred at −78° C. for 20 minutes. After the stirring, 24 mL (37 mmol) of hexane solution of 1.55 mol/L of n-butyllithium was dripped with a syringe, and the solution was stirred at −78° C. for 2 hours. After the stirring, 8.0 mL (72 mmol) of trimethyl borate was added and the mixture was stirred −78° C. for 1 hour, and then was stirred for about 24 hours while the temperature of the mixture was being gradually brought back to room temperature. After the stirring, to this solution was added 50 mL of 1M dilute hydrochloric acid, and the solution was stirred for 30 minutes at a room temperature. After the stirring, to this mixture was added ethyl acetate, and extraction with ethyl acetate was performed. After the extraction, the extracted solution was combined with the organic layer and washed with brine. After the washing, magnesium sulfate was added into the organic layer to dry the organic layer. After the drying, this mixture was subjected to suction filtration to give a filtrate. The obtained filtrate was concentrated and recrystallized with a mixture solvent of toluene and hexane to give 5.5 g of a powdery white solid in a yield of 62%.

(ii) Synthesis of 4-(2'-bromophenyl)triphenylamine

A synthetic scheme of 4-(2'-bromophenyl)triphenylamine is shown in (C-2).

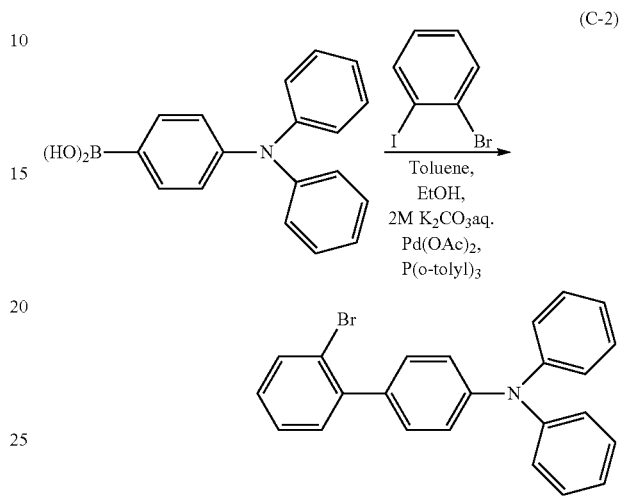
(C-2)

Into a 200 mL three-neck flask were put 5.5 g (19 mmol) of 4-(diphenylamino)phenylboronic acid, 11 g (38 mmol) of 2-bromoiodobenzene, 0.043 g (0.19 mmol) of palladium(II) acetate, and 0.41 g (1.3 mmol) of tri(o-tolyl)phosphine. Into the mixture were added 30 mL of toluene, 5 mL of ethanol, and 15 mL of a 2M aqueous solution of potassium carbonate. After the mixture was degassed under low pressure, the atmosphere in the flask was substituted by nitrogen. The mixture was stirred at 90° C. for 5 hours. After the stirring, toluene was added into the mixture and the organic layer was washed with a saturated aqueous solution of sodium carbonate and brine in this order. After the washing, magnesium sulfate was added into the organic layer to dry the organic layer. After the drying, the mixture was subjected to suction filtration to give a filtrate. The obtained filtrate was concentrated, and purification by silica gel column chromatography was performed. The column chromatography was performed first using hexane as a developing solvent and then using a mixed solvent of hexane and ethyl acetate (hexane:ethyl acetate=20:1) as a developing solvent. The obtained fraction was concentrated and dried to give 4.9 g of colorless oily substance in a yield of 65%.

(iii) Synthesis of 4'-(diphenylamino)biphenyl-2-boronic acid

A synthetic scheme of 4'-(diphenylamino)biphenyl-2-boronic acid is shown in (C-3).

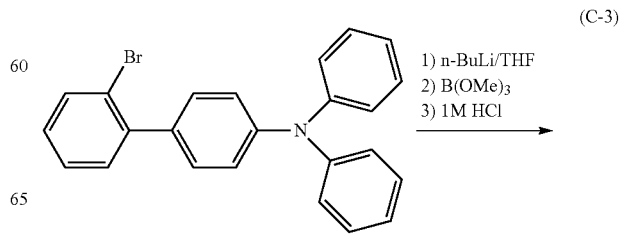
(C-3)

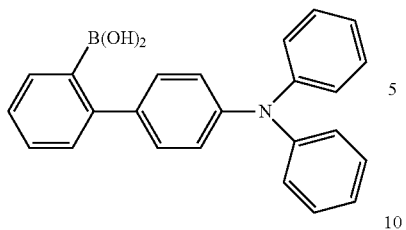

Into a 300 mL three-neck flask were put a mixed solution of 4.9 g (12 mmol) of 4-(2-bromophenyl)triphenylamine and 100 mL of tetrahydrofuran (THF). After the solution was degassed under low pressure, the atmosphere in the flask was substituted by nitrogen. The solution was stirred at −78° C. for 20 minutes. After the stirring, 9.5 mL (15 mmol) of hexane solution of 1.55 mol/L of n-butyllithium was dripped with a syringe, and the solution was stirred at −78° C. for 2 hours. After the stirring, 2.8 mL (25 mmol) of trimethyl borate was added to the mixture and the mixture was stirred at −78° C. for 1 hour, and then was stirred for about 18 hours while the temperature of the mixture was being gradually brought back to room temperature. After the stirring, to this solution was added 50 mL of 1M dilute hydrochloric acid, and the solution was stirred for 30 minutes at a room temperature. After the stirring, to this mixture was added ethyl acetate, and extraction with ethyl acetate was performed. After the extraction, the extracted solution was combined with the organic layer and washed with brine. After the washing, magnesium sulfate was added into the organic layer to dry the organic layer. After the drying, the mixture was subjected to suction filtration to give a filtrate. The obtained filtrate was concentrated and recrystallized with a mixture solvent of toluene and hexane to give 2.4 g of a powdery white solid in a yield of 55%.

Step 2: Synthesis of Z-DPhAO11

A synthetic scheme of Z-DPhAO11 is shown in (E-2).

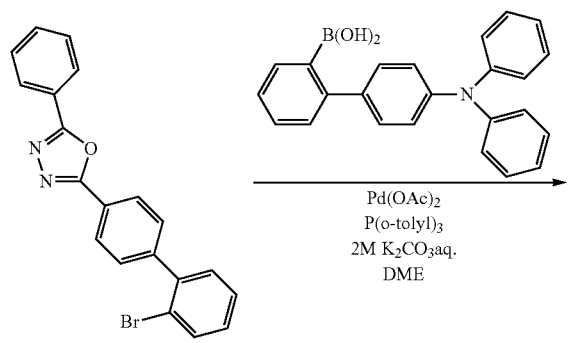

(E-2)

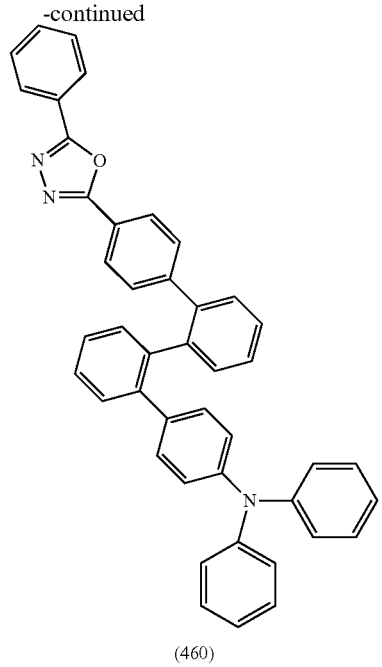

(460)

Into a 100 mL three-neck flask were put 1.0 g (2.7 mmol) of 2-(2'-bromobiphenyl-4-yl)-5-phenyl-1,3,4-oxadiazole which was synthesized in Step 1 of Synthesis Example 1, 0.97 g (2.7 mmol) of 4'-(diphenylamino)biphenyl-2-boronic acid which was synthesized in Step 1 of Synthesis Example 2, 0.010 g (0.045 mmol) of palladium(II) acetate, and 0.10 g (0.33 mmol) of tri(o-tolyl)phosphine. Into the mixture were added 15 mL of 1,2-dimethoxyethane (DME) and 15 mL of a 2M aqueous solution of potassium carbonate. After the mixture was degassed under low pressure, the atmosphere in the flask was substituted by nitrogen. This mixture was stirred at 90° C. for 10 hours. After the stirring, toluene was added into the mixture, the mixture was separated into an aqueous layer and an organic layer, and the organic layer was washed with a saturated aqueous solution of sodium carbonate and brine in this order. After the washing, magnesium sulfate was added into the organic layer to dry the organic layer. After drying, the mixture was subjected to suction filtration to give a filtrate. The obtained filtrate was subjected to suction filtration through Celite (manufactured by Wako Pure Chemical Industries, Ltd., Catalog No. 531-16855) to give a filtrate. The compound obtained by concentrating the obtained filtrate was purified by silica gel column chromatography. The column chromatography was performed first using toluene as a developing solvent and then using a mixed solvent of toluene and ethyl acetate (toluene:ethyl acetate=20:1) as a developing solvent. A solid which was obtained by concentrating the obtained fraction was dissolved in chloroform and purified by high performance liquid chromatography (HPLC). The chromatography was performed using chloroform as a developing solvent. The solid which was obtained by concentrating the obtained fraction was recrystallized with a mixed solvent of chloroform and methanol to give 0.60 g of a powdery white solid in a yield of 37%.

Sublimation purification of 0.60 g of the obtained white solid was performed by a train sublimation method. The sublimation purification was performed under a reduced pressure of 7.0 Pa, with a flow rate of argon at 4 mL/min, at 230° C. for 18 hours. After the sublimation purification, 0.55 g of an objective compound was obtained in a yield of 92%.

The obtained compound was analyzed by nuclear magnetic resonance (NMR) measurement, whereby it was confirmed that the compound was 4-[4"-(5-phenyl-1,3,4,-oxadiazol-2-yl)-[1,1':2',1"]terphenyl-2-yl]triphenylamine (Z-DPhAO11).

Hereinafter, the $^1$H NMR data is shown.

$^1$H NMR (CDCl$_3$, 300 MHz): δ=6.44 (d, J=8.8 Hz, 2H), 6.72 (d, J=8.8 Hz, 2H), 6.86 (d, J=8.8 Hz, 2H), 6.97-7.56 (m, 21H), 7.79 (d, J=8.3 Hz, 2H), 8.09-8.13 (m, 2H)

Figure 51A:
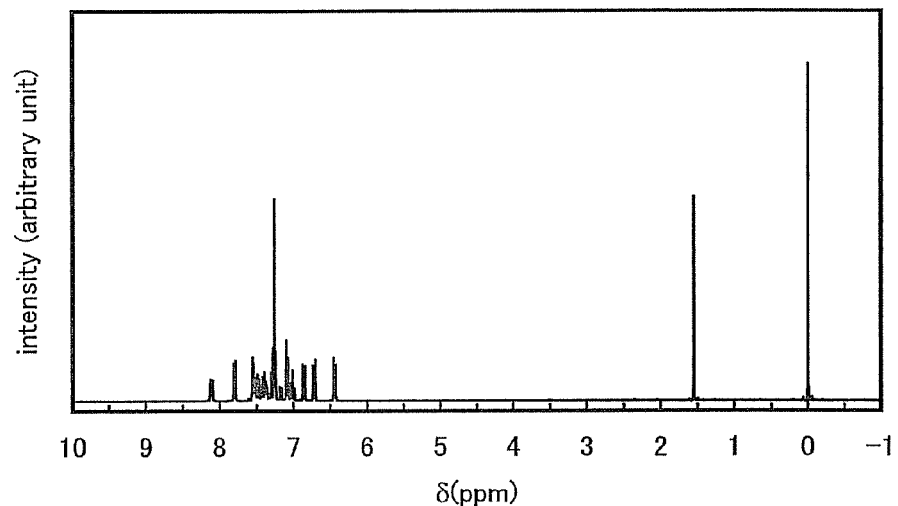
FIGS. 51A and 51B show $^1$H NMR charts of Z-DPhPA11.
Figure 51B:
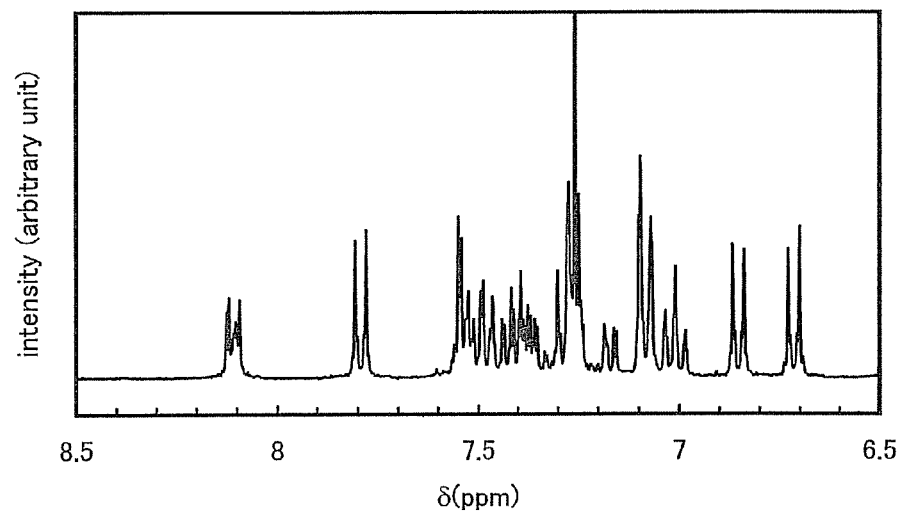

Further, the $^1$H NMR chart is shown in FIGS. 51A and 51B. Note that FIG. 51B shows an enlarged chart showing the range of 6.5 ppm to 8.5 ppm in FIG. 51A.

Thermogravimetry-differential thermal analysis (TG-DTA) was performed on the obtained Z-DPhAO11. The measurement performed using a thermogravimetric/differential thermal analyzer (TG/DTA 320, manufactured by Seiko Instruments Inc.) revealed that the 5% weight loss temperature was 395° C. The glass transition temperature of Z-DPhAO11, which was measured using a differential scanning calorimetry (Pyris 1 DSC, manufactured by Perkin Elmer Co., Ltd.), was 99° C. From these results, it was found that Z-DPhAO11 was a material having favorable heat resistance.

Synthesis Example 3

Z-CzPBOx

A synthesis method of 9-[4'"-(benzoxazol-2-yl)-[1,1':2', 1":2",1'"]quaterphenyl-4-yl)]-9H-carbazole (Z-CzPBOx) represented by Structural Formula (101) which is one of benzoxazole derivatives described in Embodiment 2 will be described.

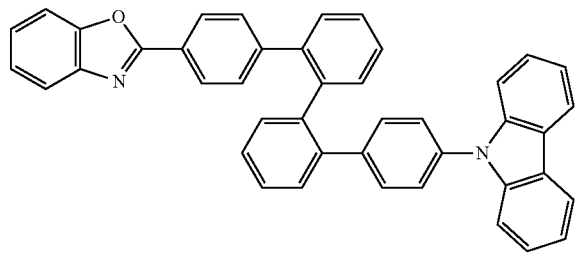

(101)

Step 1: Synthesis of 2-(2'-bromobiphenyl-4-yl)benzoxazole (i) Synthesis of 4-iodobenzoylchloride A synthesis scheme of 4-iodobenzoylchloride is shown in (D-1).

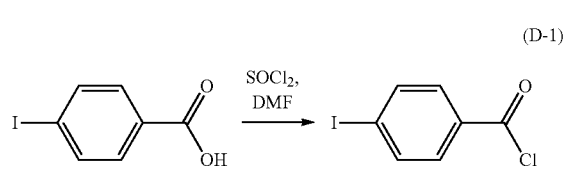 [SMILES: O=C(O)c1ccc(I)cc1 ; O=C(Cl)c1ccc(I)cc1]

(D-1)

Into a 200 mL three-neck flask was put 25 g (0.10 mol) of 4-iodobenzoate and were added 70 mL of thionyl chloride and 3 drops of N,N-dimethylformamide (DMF). The mixture was stirred under a nitrogen gas stream at 80° C. for 3 hours. After the stirring, thionyl chloride in the reaction solution was distilled under a reduced pressure and removed to give a light-yellow oily substance.

(ii) Synthesis of 4-iodo-N-(2-hydroxyphenyl)benzamide

A synthetic scheme of 4-iodo-N-(2-hydroxyphenyl)benzamide is shown in (D-2).

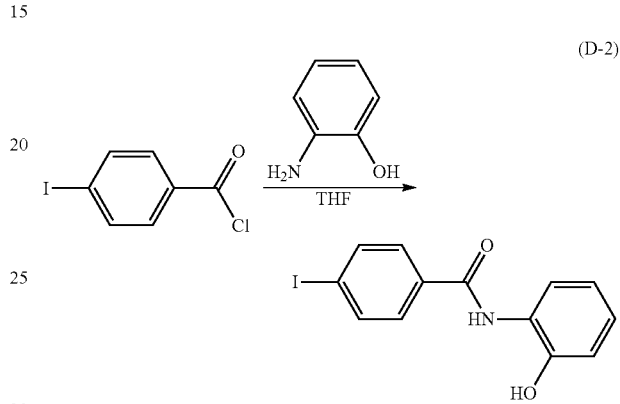

(D-2)

In a 300 mL three-neck flask were put 10 g (92 mmol) of 2-aminophenol and 7.0 mL of triethylamine and was added 100 mL of tetrahydrofuran (THF). The solution was stirred at 0° C. for 20 minutes. After the stirring, a solution in which 0.10 mol of 4-iodobenzoyl chloride was dissolved in 100 mL of tetrahydrofuran (THF) was dropped. The solution was stirred at 0° C. for 5 hours under a nitrogen stream. After the stirring, the solution was added to about 300 mL of water and an aqueous layer of the obtained mixture was extracted with ethyl acetate. After the extraction, the extracted solution was combined with the organic layer and washed with 1 M hydrochloric acid, a saturated aqueous solution of sodium hydrogen carbonate and brine in this order. After the washing, magnesium sulfate was added into the organic layer to dry the organic layer. After the drying, the mixture was subjected to suction filtration through Celite (manufactured by Wako Pure Chemical Industries, Ltd., Catalog No. 531-16855) to give a filtrate. The solid, which was obtained by condensation of the obtained filtrate, was recrystallized with a mixed solvent of ethyl acetate and hexane to give 30 g of a powdery white solid in a yield of 97%.

(iii) Synthesis of 2-(4-iodophenyl)benzoxazole

A synthetic scheme of 2-(4-iodophenyl)benzoxazole is shown in (D-3).

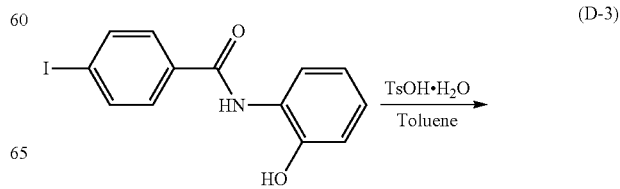

(D-3)

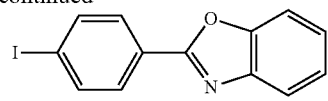

Into a 300 mL three-neck flask were put 15 g (44 mmol) of 4-iode-N-(2-hydroxyphenyl)benzamide and 24 g (0.14 mol) of para-toluenesulfonic acid monohydrate and the atmosphere in the flask was substituted by nitrogen. 300 mL of toluene was added to the mixture. The mixture was stirred at 110° C. for 4 hours under a nitrogen gas stream. After the stirring, the reaction mixture was added to about 300 mL of water, and then the aqueous layer of the mixture was extracted with ethyl acetate. After the extraction, the extracted solution was combined with the organic layer and washed with a saturated aqueous solution of sodium hydrogen carbonate and brine in this order. After the washing, magnesium sulfate was added into the organic layer to dry the organic layer. After the drying, the mixture was subjected to suction filtration through Celite (manufactured by Wako Pure Chemical Industries, Ltd., Catalog No. 531-16855) to give a filtrate. The solid which was obtained by concentrating the obtained filtrate was recrystallized with a mixed solvent of ethyl acetate and hexane to give 11 g of a powdery white solid in a yield of 75%.

(iv) Synthesis of 2-(2'-bromobiphenyl-4-yl)benzoxazole

A synthetic scheme of 2-(2'-bromobiphenyl-4-yl)benzoxazole is shown in (D-4).

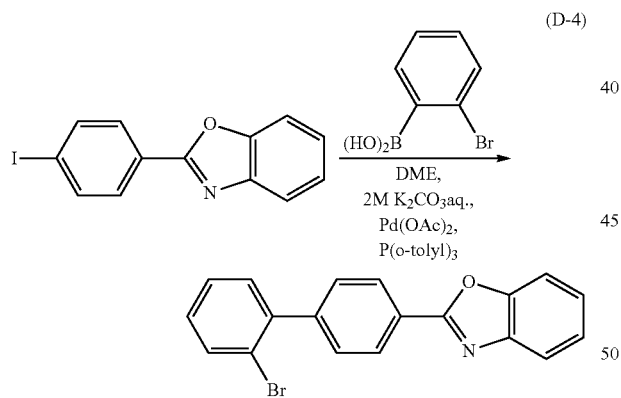

Into a 100 mL three-neck flask were put 7.0 g (22 mmol) of 2-(4-iodophenyl)benzoxazole, 4.4 g (22 mmol) of 2-bromophenylboronic acid, 0.049 g (0.22 mmol) of palladium (II) acetate, and 0.46 g (1.5 mmol) of tri(o-tolyl)phosphine. Into the mixture were added 60 mL of 1,2-dimethoxyethane (DME) and 30 mL of a 2M aqueous solution of potassium carbonate. After the mixture was degassed under low pressure, the atmosphere in the flask was substituted by nitrogen. This mixture was stirred at 90° C. for 10 hours. After the stirring, toluene was added into the mixture and the organic layer was washed with a saturated aqueous solution of sodium carbonate and brine in this order. After the washing, magnesium sulfate was added into the organic layer to thy the organic layer. After the drying, the mixture was subjected to suction filtration to give a filtrate. The obtained filtrate was subjected to suction filtration through Celite (manufactured by Wako Pure Chemical Industries, Ltd., Catalog No. 531-16855) to give a filtrate. The obtained filtrate was concentrated, and purification by silica gel column chromatography was performed. The column chromatography was performed first using a mixed solvent of chloroform and hexane (chloroform:hexane=1:4) as a developing solvent and then using a mixed solvent of chloroform and hexane (chloroform:hexane=1:1) as a developing solvent. An obtained fraction was concentrated to give a solid. The obtained solid was recrystallized with a mixed solvent of chloroform and hexane to give 2.2 g of a powdery white solid in a yield of 29%.

Step 2: Synthesis of Z-CzPBOx

A synthesis scheme of Z-CzPBOx is shown in (E-3)

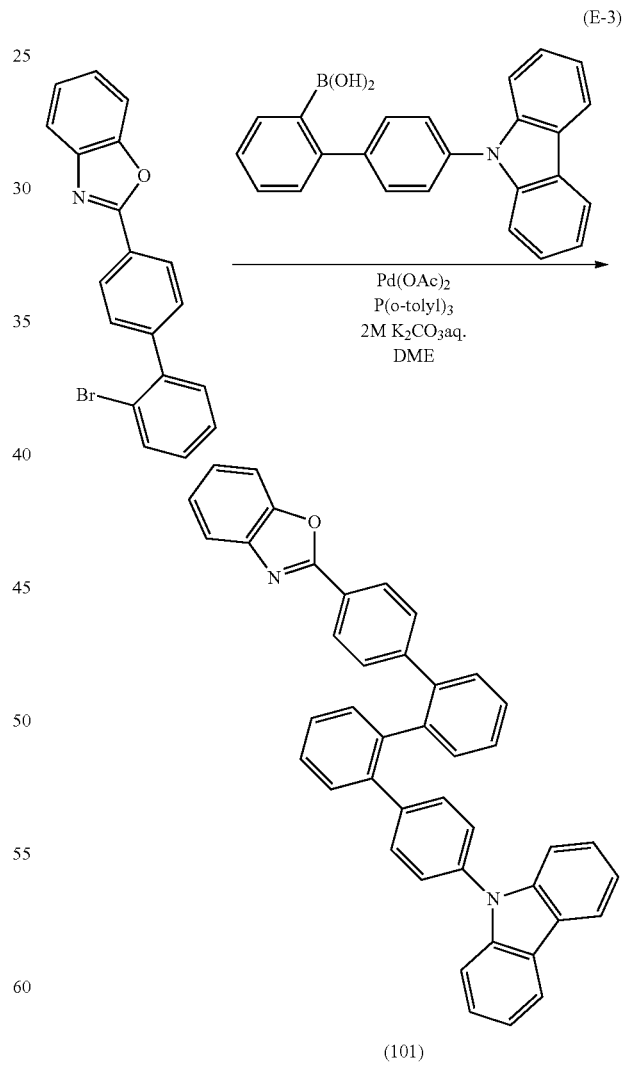

Into a 200 mL three-neck flask were put 2.1 g (5.7 mmol) of 2-(2'-bromobiphenyl-4-yl)benzoxazole which was synthesized in Step 1 of Synthesis Example 3, 2.0 g (5.7 mmol)

of 4'-(9H-carbazol-9-yl)biphenyl-2-boronic acid which was synthesized in Step 2 of Synthesis Example 1, 0.020 g (0.089 mmol) of palladium(II) acetate, and 0.20 g (0.65 mmol) of tri(o-tolyl)phosphine. Into the mixture were added 30 mL of 1,2-dimethoxyethane (DME) and 30 mL of a 2M aqueous solution of potassium carbonate. After the mixture was degassed under low pressure, the atmosphere in the flask was substituted by nitrogen. The mixture was stirred at 90° C. for 10 hours. After the stirring, chloroform was added into the mixture, and the organic layer was washed with a saturated aqueous solution of sodium carbonate and brine in this order. After the washing, magnesium sulfate was added into the organic layer to dry the organic layer. After the drying, the mixture was subjected to suction filtration to give a filtrate. The obtained filtrate was subjected to suction filtration through Celite (manufactured by Wako Pure Chemical Industries, Ltd., Catalog No. 531-16855) to give a filtrate. The obtained filtrate was concentrated, and purification by silica gel column chromatography was performed. The silica gel column chromatography was performed by using toluene as a developing solvent. A solid which was obtained by concentrating the obtained fraction was dissolved in chloroform and purified by high performance liquid chromatography (HPLC). The chromatography was performed using chloroform as a developing solvent. The solid which was obtained by concentrating the obtained fraction was recrystallized with a mixed solvent of chloroform and methanol to give 2.6 g of a powdery white solid in a yield of 77%.

Sublimation purification of 2.6 g of the obtained white solid was performed by a train sublimation method. The sublimation purification was performed under a reduced pressure of 7.0 Pa, with a flow rate of argon at 4 mL/min, at 250° C. for 15 hours to give 2.3 g of an objective compound in a yield of 88%.

The obtained compound was analyzed by nuclear magnetic resonance (NMR) measurement, whereby it was confirmed that the compound was 9-[4''''-(benzoxazol-2-yl)-[1,1':2',1'':2'',1'''-]quaterphenyl-4-yl)]-9H-carbazole (Z-CzPBOx).

Hereinafter, the $^1$H NMR data is shown.

$^1$H NMR (CDCl$_3$, 300 MHz): δ=6.78 (d, J=8.3 Hz, 2H), 6.87 (d, J=8.3 Hz, 2H), 7.15-7.62 (m, 19H), 7.72-7.77 (m, 1H), 7.95 (d, J=8.3 Hz, 2H), 8.16 (d, J=7.8 Hz, 2H)

Figure 52A:
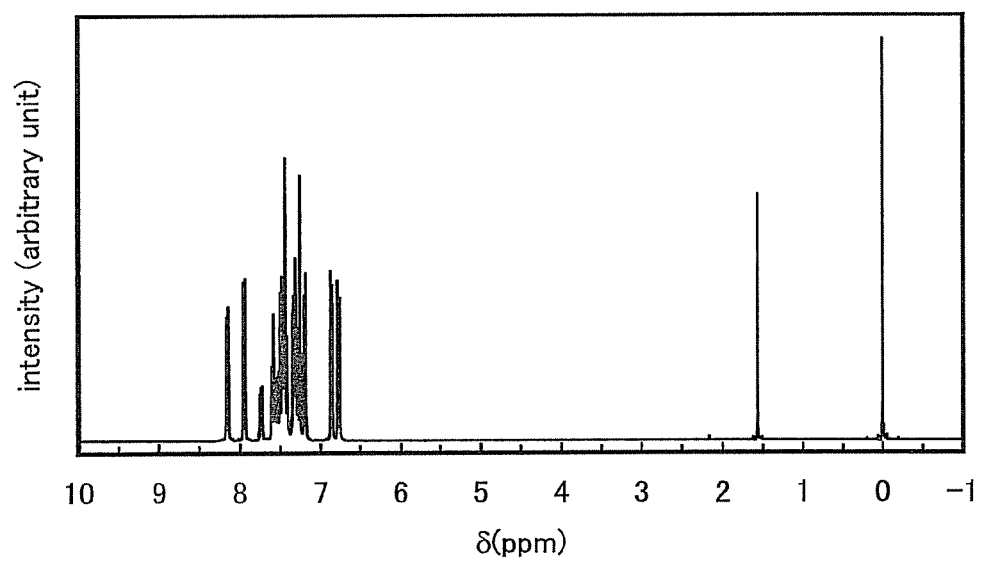
FIGS. 52A and 52B show $^1$H NMR charts of Z-CzPBOx.
Figure 52B:
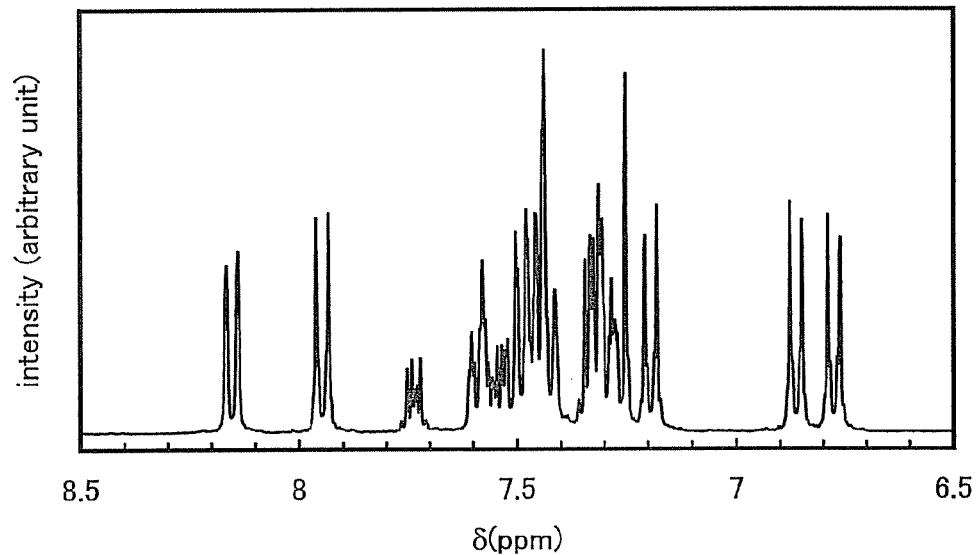

Further, the $^1$H NMR chart is shown in FIGS. 52A and 52B. Note that FIG. 52B shows an enlarged chart showing the range of 6.5 ppm to 8.5 ppm in FIG. 52A.

Thermogravimetry-differential thermal analysis (TG-DTA) was performed on the obtained Z-CzPBOx. The measurement was conducted by using a high vacuum differential type differential thermal balance (manufactured by Bruker AXS K.K., TG/DTA 2410SA). When the measurement was carried out under a nitrogen stream (flow rate: 200 mL/min) under a normal pressure at a temperature rising rate of 10° C./min, it was found, from the relationship between weight and temperature (thermogravimetry), that the 5% weight loss temperature was 395.2° C.

In addition, a thermal property of Z-CzPBOx was measured using a differential scanning calorimeter (DSC, manufactured by PerkinElmer, Inc., Pyris 1). First, a sample was heated from −10° C. up to 350° C. at a temperature rising rate of 40° C./min, and then it was cooled down to −10° C. at 40° C./min. After that, Z-CzPBOx was heated up to 290° C. at a temperature rising rate of 10° C./min, thereby obtaining a DSC chart. The peak showing the glass transition temperature of Z-CzPBOx was observed in the DSC chart and it was found that the glass transition temperature (Tg) was 110° C. From the result, it was found that Z-CzPBOx has a high glass transition temperature. Accordingly, it was confirmed that Z-CzPBOx in this synthesis example has high heat resistance.

Synthesis Example 4

Z-DPhABOx

A synthesis method of 4-[4''-(benzoxazol-2-yl)-[1,1':2',1'']quaterphenyl-2-yl]triphenylamine (Z-DPhABOx) which is represented by following Structural Formula (201) and which is one of the benzoxazole derivatives described in Embodiment 2 will be described.

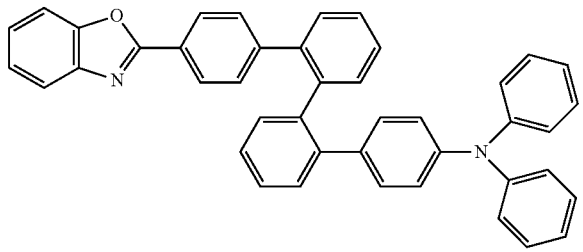

(201)

Step 1: Synthesis of Z-DPhABOx

A synthesis scheme of Z-DPhABOx is shown in (E-4).

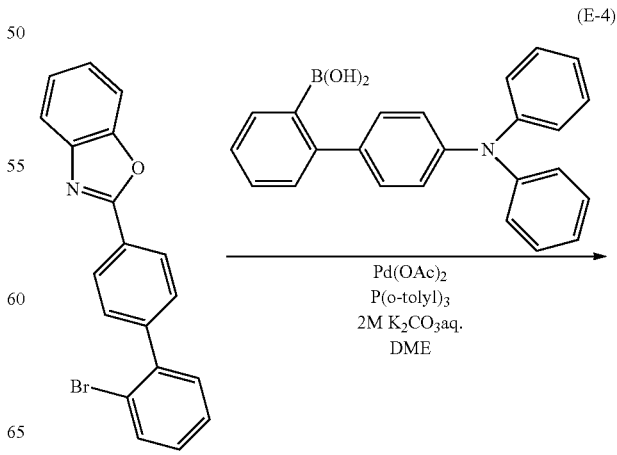

(E-4)

-continued

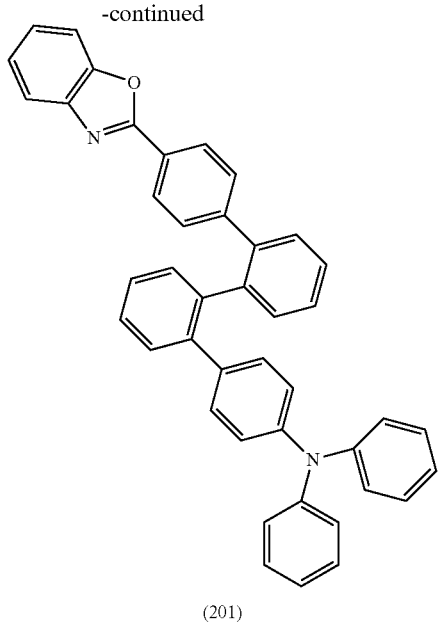

(201)

Into a 100 mL three-neck flask were put 1.0 g (2.9 mmol) of 2-(2'-bromobiphenyl-4-yl)benzoxazole which was synthesized in Step 1 of Synthesis Example 3, 1.0 g (2.9 mmol) of 4'-(diphenylamino)biphenyl-2-boronic acid which was synthesized in Step 1 of Synthesis Example 2, 0.010 g (0.045 mmol) of palladium(II) acetate, and 0.10 g (0.33 mmol) of tri(o-tolyl)phosphine. Into the mixture were added 15 mL of 1,2-dimethoxyethane (DME) and 15 mL of a 2M aqueous solution of potassium carbonate. After the mixture was degassed under low pressure, the atmosphere in the flask was substituted by nitrogen. The mixture was stirred at 90° C. for 10 hours. After the stirring, toluene was added into the mixture, and the organic layer was washed with brine. After the washing, magnesium sulfate was added into the organic layer to dry the organic layer. After the drying, the mixture was subjected to suction filtration to give a filtrate. The obtained filtrate was subjected to suction filtration through Celite (manufactured by Wako Pure Chemical Industries, Ltd., Catalog No. 531-16855) to give a filtrate. The obtained filtrate was concentrated, and purification by silica gel column chromatography was performed. The column chromatography was performed first using a mixed solvent of toluene and hexane (toluene:hexane=1:1) as a developing solvent and then using toluene as a developing solvent. The solid which was obtained by concentrating the obtained fraction was recrystallized with a mixed solvent of chloroform and methanol to give 1.0 g of a powdery white solid in a yield of 61%.

Sublimation purification of 1.0 g of the obtained white solid was performed by a train sublimation method. The sublimation purification was performed under a reduced pressure of 7.0 Pa, with a flow rate of argon at 4 mL/min, at 230° C. for 20 hours to give 0.84 g of an objective compound in a yield of 84%.

The obtained compound was analyzed by nuclear magnetic resonance (NMR) measurement, whereby it was confirmed that the compound is 4-[4''-benzoxazol-2-yl)-[1,1':2',1'']quaterphenyl-2-yl]triphenylamine (Z-DPhABOx).

Hereinafter, the $^1$H NMR data is shown.

$^1$H NMR (CDCl$_3$, 300 MHz): δ=6.45 (d, J=8.3 Hz, 2H), 6.71 (d, J=8.3 Hz, 2H), 6.85 (d, J=8.3 Hz, 2H), 6.98-7.17 (m, 7H), 7.23-7.57 (m, 14H), 7.71-7.75 (m, 1H), 7.92 (d, J=7.8 Hz, 2H)

Figure 53A:
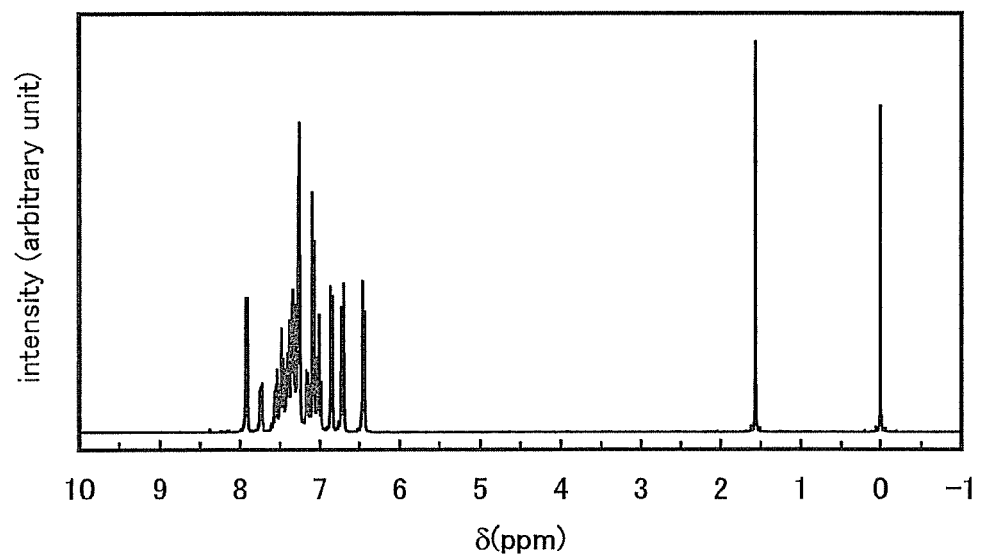
FIGS. 53A and 53B show $^1$H NMR charts of Z-DPhA-BOx.
Figure 53B:
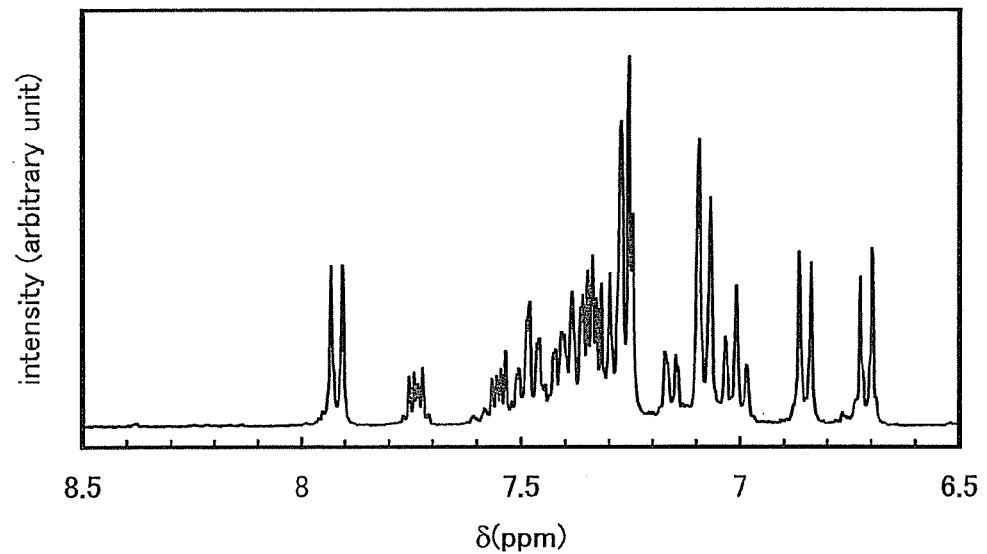

Further, the $^1$H NMR chart is shown in FIGS. 53A and 53B. Note that FIG. 53B shows an enlarged chart showing the range of 6.5 ppm to 8.5 ppm in FIG. 53A.

In addition, a thermal property of Z-DPhABOx was measured using a differential scanning calorimeter (DSC, manufactured by PerkinElmer, Inc., Pyris 1). First, a sample was heated from −10° C. up to 350° C. at a temperature rising rate of 40° C./min, and then it was cooled down to −10° C. at 40° C./min. After that, Z-DPhABOx was heated up to 290° C. at a temperature rising rate of 10° C./min, thereby obtaining a DSC chart. The peak showing the glass transition temperature of Z-DPhABOx was observed in the DSC chart and it was found that the glass transition temperature (Tg) was 98.4° C. From the result, it was found that Z-DPhABOx has a high glass transition temperature. Accordingly, it was confirmed that Z-DPhABOx in this synthesis example has high heat resistance.

This application is based on Japanese Patent Application serial no. 2008-229129 filed with Japan Patent Office on Sep. 5, 2008, the entire contents of which are hereby incorporated by reference.

The invention claimed is:

1. A compound represented by a following formula:

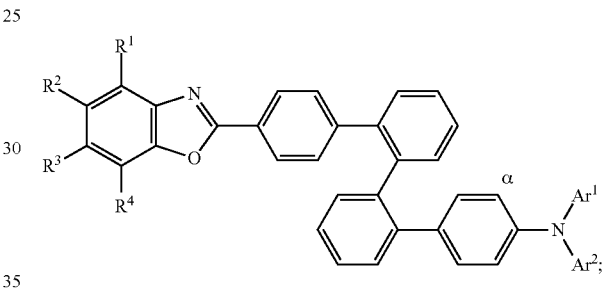

Ar$^1$ represents an unsubstituted aryl group having 6 to 13 carbon atoms or aryl group having 6 to 13 carbon atoms substituted by an alkyl group having 1 to 4 carbon atoms;

Ar$^2$ represents an unsubstituted aryl group having 6 to 13 carbon atoms or aryl group having 6 to 13 carbon atoms substituted by an alkyl group having 1 to 4 carbon atoms or an aryl group having 6 to 13 carbon atoms;

R$^1$ to R$^4$ each independently represent any of hydrogen, an alkyl group having 1 to 4 carbon atoms, or halogen; and Ar$^1$ and a carbon of α are bonded to each other directly or through sulfur, oxygen, or nitrogen.

2. The compound according to claim 1, wherein:

the compound is represented by a following formula:

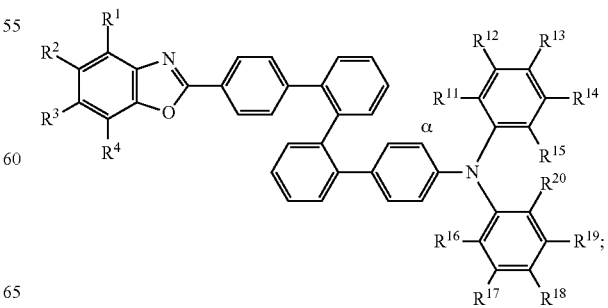

$R^{11}$ to $R^{15}$ each independently represent any of hydrogen or alkyl group having 1 to 4 carbon atoms;

$R^{16}$ to $R^{20}$ each independently represent any of hydrogen, alkyl group having 1 to 4 carbon atoms, or an unsubstituted aryl group having 6 to 13 carbon atoms; and an ortho-carbon with respect to the nitrogen atom in the above formula, which is directly bonded to $R^{11}$, and a carbon of α are bonded to each other directly or through sulfur, oxygen, or nitrogen.

3. A compound represented by a following formula:

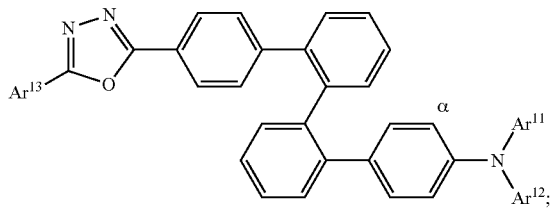

$Ar^{11}$ represents an unsubstituted aryl group having 6 to 13 carbon atoms or aryl group having 6 to 13 carbon atoms substituted by an alkyl group having 1 to 4 carbon atoms;

$Ar^{12}$ represents an unsubstituted aryl group having 6 to 13 carbon atoms or aryl group having 6 to 13 carbon atoms substituted by an alkyl group having 1 to 4 carbon atoms or an aryl group having 6 to 13 carbon atoms; and $Ar^{13}$ represented by any one of following formulae:

(15-4)
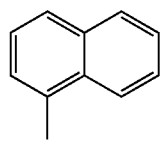

(15-5)
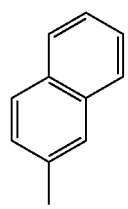

(15-9)
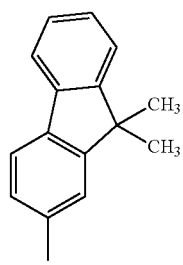

(15-10)
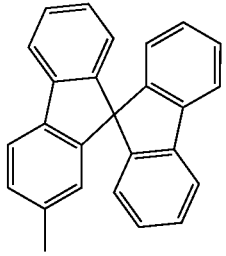

(15-11)
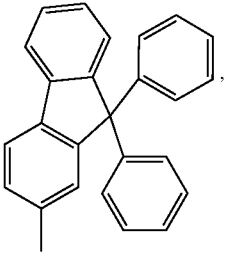

and $Ar^{11}$ and a carbon of α are bonded to each other directly or through any of oxygen, sulfur, or nitrogen.

4. The compound according to claim 3, wherein:

the compound is represented by a following formula:

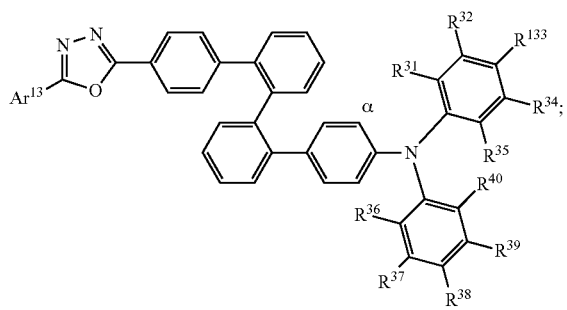

$R^{31}$ to $R^{35}$ represent any of hydrogen or an alkyl group having 1 to 4 carbon atoms;

$R^{36}$ to $R^{40}$ each independently represent any of hydrogen, alkyl group having 1 to 4 carbon atoms, or an unsubstituted aryl group having 6 to 13 carbon atoms; and an ortho-carbon with respect to the nitrogen atom in the above formula, which is directly bonded to $R^{31}$, and a carbon of α are bonded to each other directly or through sulfur, oxygen, or nitrogen.

5. A light-emitting element comprising a compound according to claim 1 between a pair of electrodes.

6. A lighting device comprising the light-emitting element according to claim 5.

7. An electric device having a display portion, the display portion comprising the light-emitting element according to claim 5.

8. A light-emitting element comprising a compound according to claim 3 between a pair of electrodes.

9. A lighting device comprising the light-emitting element according to claim 8.

10. An electric device having a display portion, the display portion comprising the light-emitting element according to claim 8.

11. The compound according to claim 1, wherein Ar¹ is represented by any one of the following formulae:
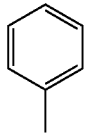 (11-1)
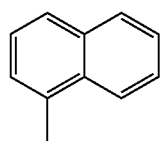 (11-2)
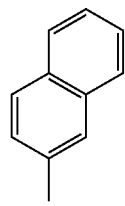 (11-3)
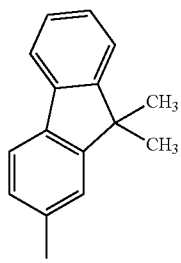 (11-10)
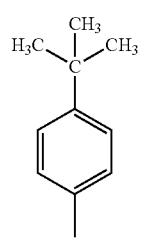 (11-18)
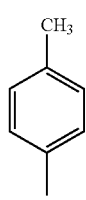 (11-19)
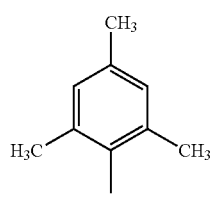 (11-21)
-continued
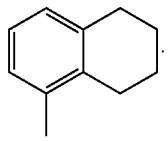 (11-22)
12. The compound according to claim 11, wherein Ar² is represented by any one of the following formulae:
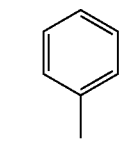 (11-1)
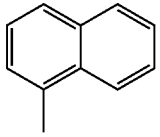 (11-2)
 (11-3)
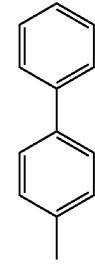 (11-4)
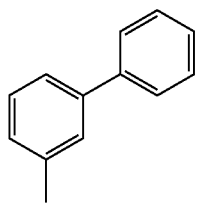 (11-5)
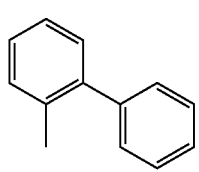 (11-6)

(11-7) 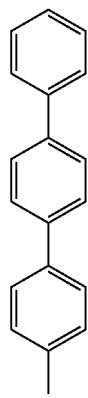
(11-8) 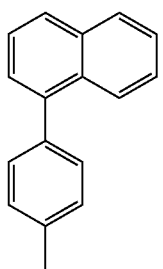
(11-9) 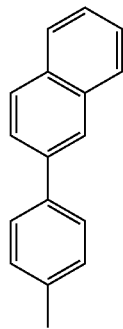
(11-10) 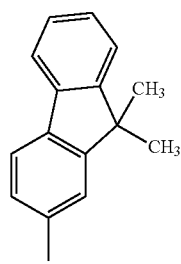
(11-11) 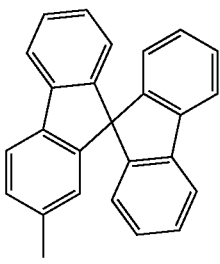
(11-12) 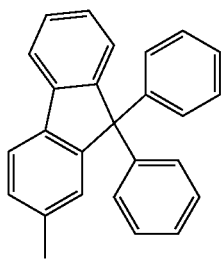
(11-13) 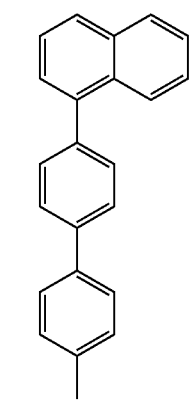
(11-14) 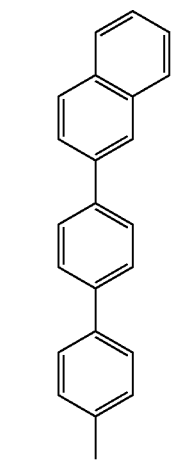
(11-15) 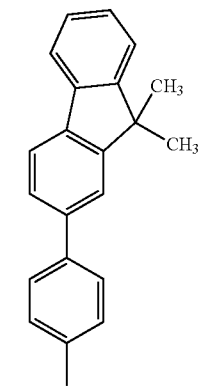

-continued
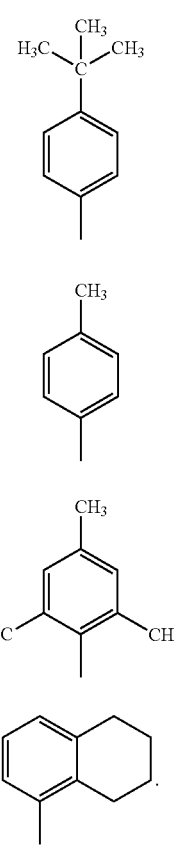
(11-18)
(11-19)
(11-21)
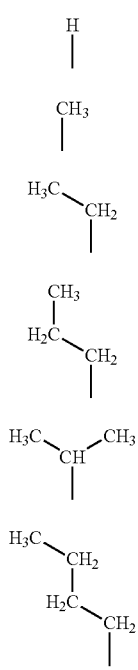
(11-22)
13. The compound according to claim 1, wherein $R^1$ to $R^4$ each is independently represented by any one of the following formulae:
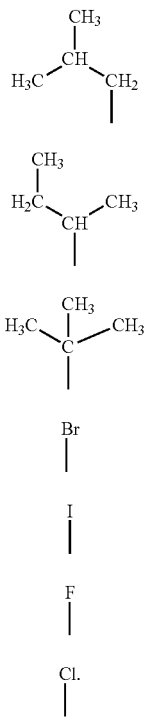
(13-1)
(13-2)
(13-3)
(13-4)
(13-5)
(13-6)
-continued
(13-7)
(13-8)
(13-9)
(13-13)
(13-14)
(13-15)
(13-16)
14. The compound according to claim 2, wherein $R^1$ to $R^4$ each is independently represented by any one of the following formulae:
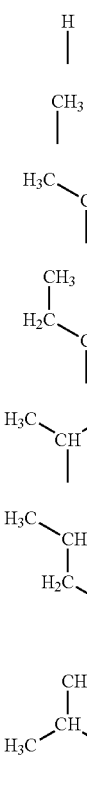
(13-1)
(13-2)
(13-3)
(13-4)
(13-5)
(13-6)
(13-7)

-continued
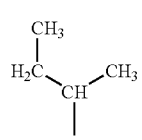
(13-8)
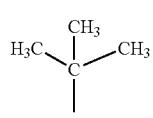
(13-9)
Br
|
(13-13)
I
|
(13-14)
F
|
(13-15)
Cl.
|
(13-16)
15. The compound according to claim 14, wherein $R^{16}$ to $R^{20}$ each is independently represented by any one of the following formulae:
H
|
(13-1)
CH₃
|
(13-2)
(13-3)
(13-4)
(13-5)
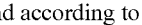
(13-6)
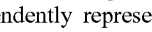
(13-7)
(13-8)
-continued
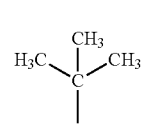
(13-9)
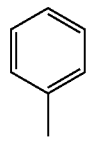
(13-10)
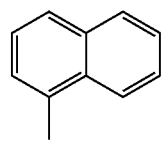
(13-11)
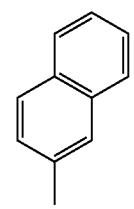
(13-12)
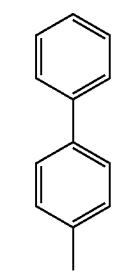
(14-13)
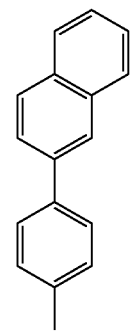
(14-14)
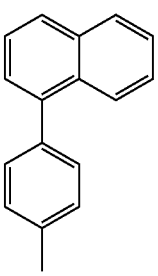
(14-15)

(14-16)
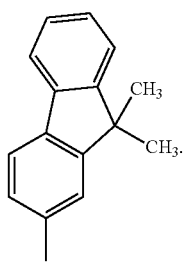
16. The compound according to claim 3, wherein $Ar^{11}$ is represented by any one of the following formulae:
(15-1)
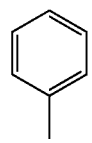
(15-4)
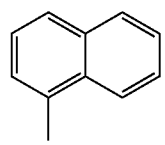
(15-5)
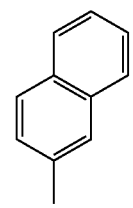
(15-9)
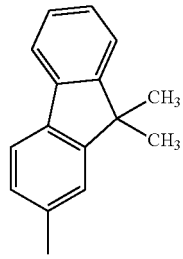
(15-12)
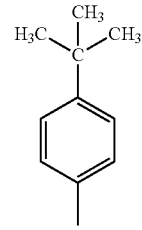
(15-13)
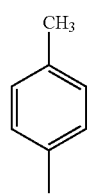
(15-14)
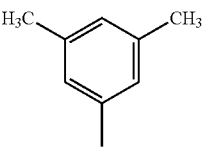
(15-15)
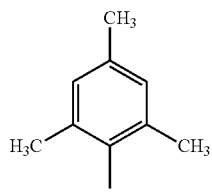
(15-16)
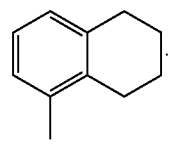
17. The compound according to claim 16, wherein $Ar^{12}$ is represented by any one of the following formulae:
(15-1)
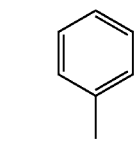
(15-2)
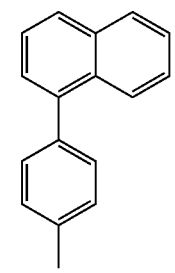
(15-3)
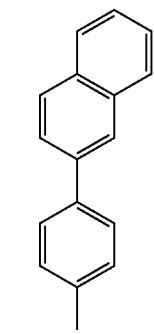
(15-4)
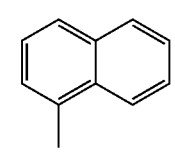

(15-5) 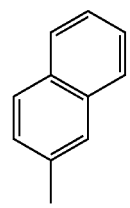
(15-6) 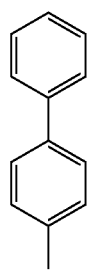
(15-7) 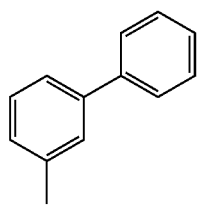
(15-8) 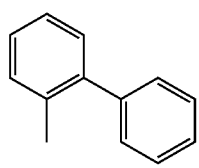
(15-9) 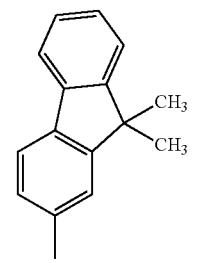
(15-10) 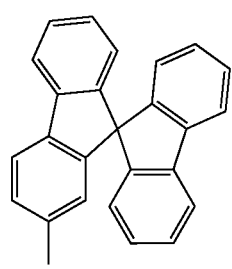
(15-11) 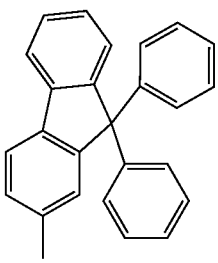
(15-12) 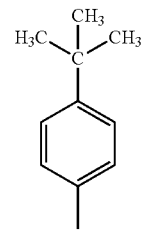
(15-13) 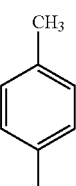
(15-14) 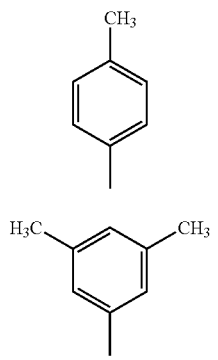
(15-15) 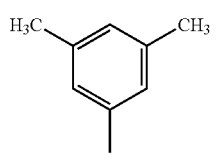
(15-16) 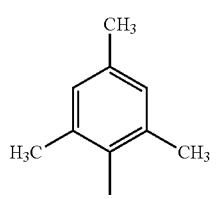
18. The compound according to claim 4, wherein $R^{32}$ to $R^{35}$ each is independently represented by any one of the following formulae:
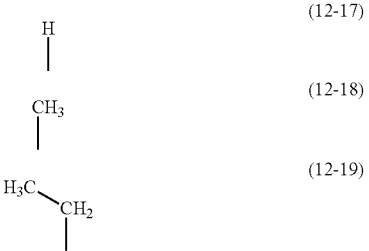
(12-17)
(12-18)
(12-19)

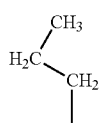 (12-20)
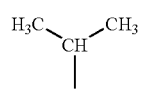 (12-21)
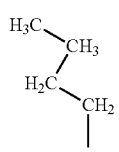 (12-22)
(12-23)
(12-24)
(12-25)
19. The compound according to claim 18, wherein $R^{36}$ to $R^{40}$ each is independently represented by any one of the following formulae:
(12-1)
(12-2)
(12-3)
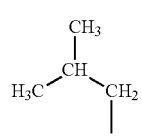 (12-4)
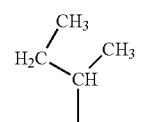 (12-5)
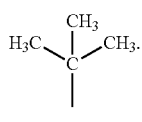 (12-6)
(12-7)
(12-8)
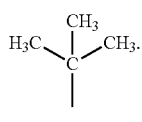 (12-9)

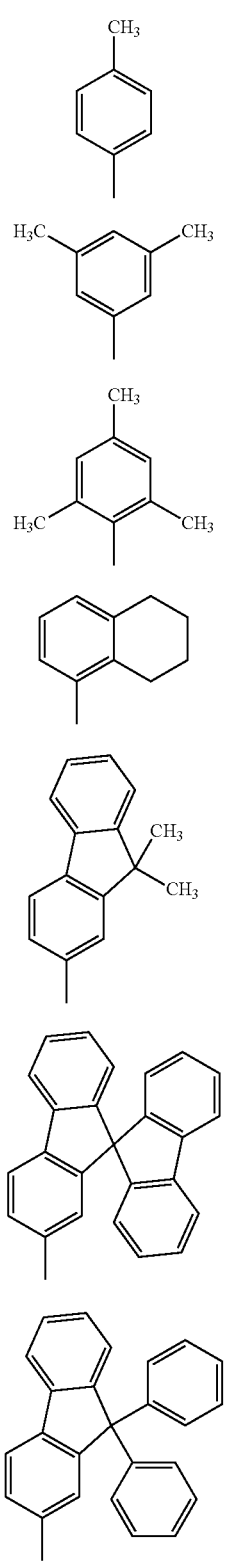
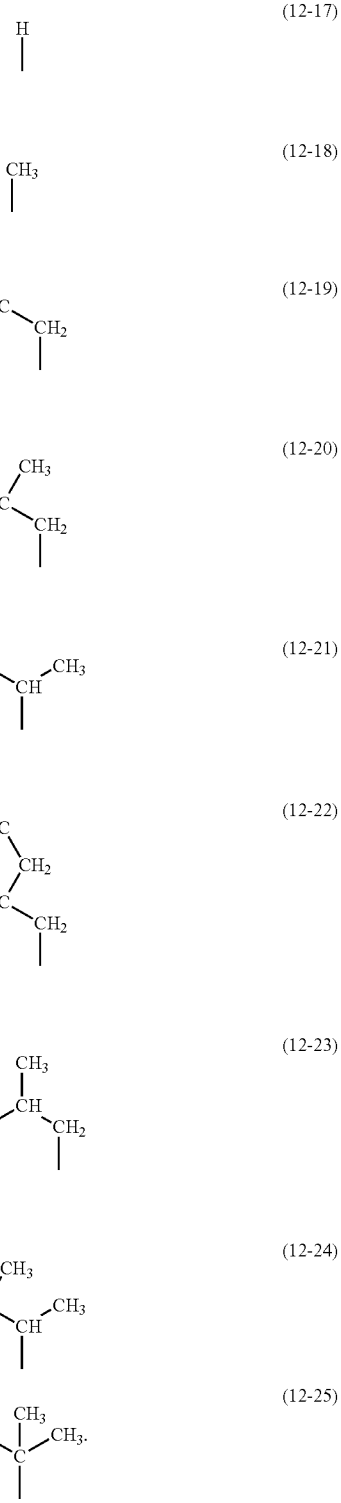
* * * * *

UNITED STATES PATENT AND TRADEMARK OFFICE
CERTIFICATE OF CORRECTION

PATENT NO. : 9,620,723 B2
APPLICATION NO. : 13/728313
DATED : April 11, 2017
INVENTOR(S) : Seo et al.

Page 1 of 3

It is certified that error appears in the above-identified patent and that said Letters Patent is hereby corrected as shown below:

In the Specification

Column 7, Line 2; Change "allyl" to --alkyl--.

Column 15, Line 10; Change "(II))." to --(11)).--.

Column 15, Line 11; Change "(II))," to --(11)),--.

Column 106, Lines 23 to 32; Change

" 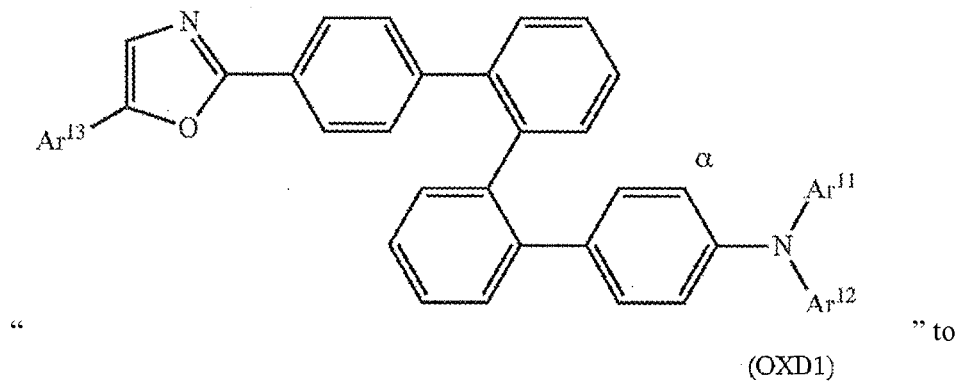 " to

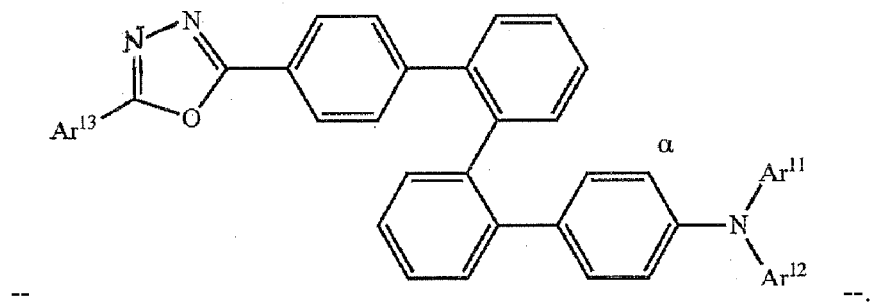

-- --.

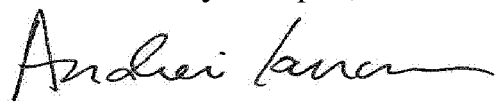

Signed and Sealed this
Tenth Day of April, 2018

Andrei Iancu
*Director of the United States Patent and Trademark Office*

CERTIFICATE OF CORRECTION (continued)

Column 156, Line 37; Change "trio-tolyl)" to --tri(o-tolyl)--.

Column 163, Line 35; Change "irridium" to --iridium--.

Column 163, Line 62; Change "europiom" to --europium--.

Column 163, Line 63; Change "(2-thenyl)" to --(2-thenoyl)--.

Column 165, Line 31; Change "TPBI)," to --(TPBI),--.

Column 171, Line 25; Change "Mimed" to --formed--.

Column 171, Line 53; Change "table; i.e.," to --table, i.e.,--.

Column 172, Line 25; Change "passive-matrix" to --a passive-matrix--.

Column 185, Line 8; Change "(am)" to --(nm)--.

Column 186, Lines 13 to 14; Change "(-237)" to --(-2.37)--.

Column 191, Line 26; Change "faulted" to --formed--.

Column 197, Lines 1 to 10; Change

"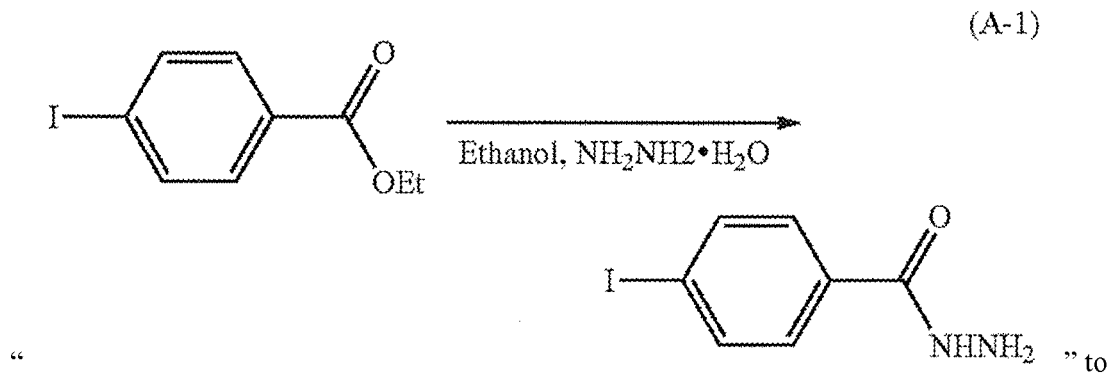 to

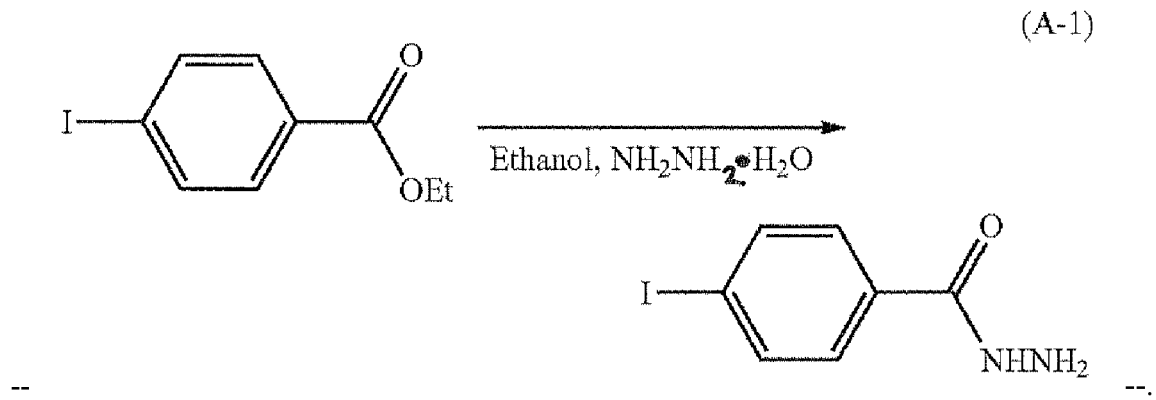 --.

CERTIFICATE OF CORRECTION (continued)
U.S. Pat. No. 9,620,723 B2

Column 197, Line 67; Change "oxadiazoe" to --oxadiazole--.

Column 199, Line 3; Change "Wako." to --Wako--.

Column 209, Line 67; Change "thy" to --dry--.